(12) United States Patent
Wojdacz et al.

(10) Patent No.: US 8,911,937 B2
(45) Date of Patent: Dec. 16, 2014

(54) METHOD FOR DETECTING METHYLATION STATUS BY USING METHYLATION-INDEPENDENT PRIMERS

(75) Inventors: Tomasz Kazimierz Wojdacz, Arhus N (DK); Lise Lotte Hansen, Risskov (DK); Alexander Dobrovic, Eltham (AU)

(73) Assignees: Brainreader ApS, Aarhus C (DK); Peter MacCallum Cancer Centre, East Melbourne (AU)

( * ) Notice: Subject to any disclaimer, the term of this patent is extended or adjusted under 35 U.S.C. 154(b) by 981 days.

(21) Appl. No.: 12/219,378

(22) Filed: Jul. 21, 2008

(65) Prior Publication Data

US 2009/0155791 A1 Jun. 18, 2009

Related U.S. Application Data

(60) Provisional application No. 60/950,751, filed on Jul. 19, 2007, provisional application No. 60/950,760, filed on Jul. 19, 2007.

(51) Int. Cl.
*C12Q 1/68* (2006.01)
*C12P 19/34* (2006.01)

(52) U.S. Cl.
USPC ............................ 435/6.1; 435/6.12; 435/91.2

(58) Field of Classification Search
USPC ........................................ 435/6.1, 6.12, 91.2
See application file for complete search history.

(56) References Cited

U.S. PATENT DOCUMENTS 5,786,146 A 7/1998 Herman et al.
7,855,053 B2 * 12/2010 Hagerman et al. ........... 435/6.12

FOREIGN PATENT DOCUMENTS

WO WO 2006034879 A2 * 4/2006

OTHER PUBLICATIONS

Shen et al. MGMT Promoter Methylation and Field Defect in Sporadic Colorectal Cancer. Journal of the National Cancer Institute (2005) 97(18): 1330-1338.*
Monis et al. Comparison of SYTO9 and SYBR Green I for real-time polymerase chain reaction and investigation of the eVect of dye concentration on amplification and DNA melting curve analysis. Analytical Biochemistry (2005) 340: 24-34.*
Kristensen et al. PCR-Based Methods for Detecting Single-Locus DNA Methylation Biomarkers in Cancer Diagnostics, Prognostics, and Response to Treatment. Clinical Chemistry (2009) 55(8): 1471-1483.*
Nosho et al. Comprehensive Biostatistical Analysis of CpG Island Methylator Phenotype in Colorectal Cancer Using a Large Population-Based Sample. PLoS ONE (2008) 3(11): e3698.*
Chalitchagorn et al. Distinctive pattern of LINE-1 methylation level in normal tissues and the association with carcinogenesis. Oncogene (2004) 23: 8841-8846.*
Akey et al. Assaying DNA Methylation Based on High-Throughput Melting Curve Approaches. Genomics (2002) 80(4): 376-384.*
Grunau et al., Nucleic Acids Research, vol. 29, No. 13, (2001), e65, pp. 1-7.*
Adorjan P. et al. (2002), Tumor class prediction and discovery by microarray-based DNA methylation analysis, Nucleic Acids Res., 30, e21, p. 1-9.
Aggerholm A. et al (1999), Extensive intra- and interindividual heterogeneity of p15INK4B methylation in acute myeloid leukemia, Cancer Res., 59, 436-441.
Bestor T.H. et al (1992), Targeted mutation of the DNA methyltransferase gene results in embryonic lethality, Cell, 69, 915-926.
Bird A. (1992), The essentials of DNA methylation, Cell, 70, 5-8.
Boyd V. L. et al (2004), Bisulfite conversion of genomic DNA for methylation analysis: protocol simplification with higher recovery applicable to limited samples and increased throughput, Anal. Biochem., 326, 278-280.
Cedar H. (1988), DNA methylation and gene activity, Cell, 53, 3-4.
Clark S. J. et al (1994), High sensitivity mapping of methylated cytosines, Nucleic Acids Res., 22, 2990-2997.
Colella S. et al (2003), Sensitive and quantitative universal Pyrosequencing methylation analysis of CpG sites, Biotechniques, 35, 146-150.
Cottrell, S. E. et al (2003), Sensitive detection of DNA methylation, Ann. NY. Acad. Sci., 983, 120-130.
Dobrovic A. (2005), Methods for Analysis of DNA Methylation, In Coleman W. B., Tsongalis G. J. (eds.), Molecular diagnostics for the clinical laboratorian, Humana Press, Totowa, NJ, 149-160.
Dobrovic A. et al (2002), Screening for and analysis of methylation differences using methylation-sensitive single-strand conformation analysis, Methods, 27, 134-138.
Estelier M. et al (2000), Inactivation of the DNA-repair gene MGMT and the clinical response of gliomas to alkylating agents, N. Engl. J. Med., 343, 1350-1354.

(Continued)

*Primary Examiner* — Ardin Marschel
(74) *Attorney, Agent, or Firm* — Gifford, Krass, Sprinkle, Anderson & Citkowski, P.C.

(57) ABSTRACT

A reliable and highly sensitive method is provided for detecting methylation status of CpG-containing nucleic acids by nucleic acid amplification and melting curve analysis of amplification products. The methods and compositions employs a novel design of primers, CpG-containing methylation-independent oligonucleotide primers, wherein both unmethylated and methylated alleles of a CpG-containing nucleic acid can be detected by use of only one set of primers after the CpG-containing nucleic acid has been subjected to cytosine to thymine conversion of unmethylated Cytosine. The method is useful for detection of methylation status in for example cancer genes and other disease related genes, wherein methylation influences gene expression.

61 Claims, 46 Drawing Sheets
(37 of 46 Drawing Sheet(s) Filed in Color)

(56) References Cited

OTHER PUBLICATIONS

Esteller M. et al (2002), Hypermethylation of the DNA repair gene O(6)-methylguanine DNA methyltransferase and survival of patients with diffuse large B-cell lymphoma, J. Natl. Cancer Inst., 94, 26-32.
Esteller, m. et al. (2001), A gene hypermethylation profile of human cancer, Cancer Res., 61, 3225-3229.
Frommer M. et al (1992), A genomic sequencing protocol that yields a positive display of 5-methylcytosine residues in individual DNA strands, Proc. Natl. Acad. Sci. U.S.A., 89. 1827-1831.
Gardiner-Garden M. and Frommer M. (1987), CpG islands in vertebrate genomes, J. Mol. Biol., 196, 261-282.
Gotoh O. et al (1983), Prediction of meting profiles and local helix stability for sequenced DNA, Adv. Biophys., 16, 1-52.
Guldberg P. et al (2002), Profiling DNA methylation by melting analysis, Methods, 27, 121-127.
Hegi M. E. et al (2005), MGMT gene silencing and benefit from temozolomide in glioblastoma. N. Engl. J. Med., 352, 997-1003.
Herman J. G. et al (1996), Methylation-specific PCR: a novel PCR assay for methylation status of CpG islands, Proc. Natl. Acad. Sci. U.S.A., 93, 9821-9826.
Jones, P.A. and Baylin, S.B. (2002), The fundamental role of epigenetic events in cancer, Nat. Rev. Genet, 3, 415-428.
Klimasauskas S. et al (1994), HhaI methytransferase flips its target base out of the DNA helix, Cell, 76, 357-369.
Laird P. W. et al (1994), DNA methylation and cancer, Human Mol. Genet., 3, 1487-1495.
Miller S. A. et al (1988), A simple salting out prochedure for extracting DNA from human nucleated cells, Nucleic Acids Res., 16, 1215.
Murai M. et al (2005), Aberrant DNA methylation associated with silencing BNIP3 gene expression in haematopoietic tumours, Br. J. Cancer, 92, 1165-1172.
Murai M. et al (2005), Aberrant methylation and silencing of the BNIP3 gene in colorectal and gastric cancer, Clin. Cancer Res., 11, 1021-1027.
Okami J. et al (2004), Silencing of the hypoxia-inducible cell death protein BNIP3 in pancreatic cancer, Cancer Res., 64, 5338-5346.
Paz M. F. et al (2003), A systematic profile of DNA methylation in human cancer cell lines, Cancer Res., 63, 1114-1121.
Teodoridis J.M et al. (2004). Epigenetic silencing mediated by CpG island methylation: potential as a therapeutic target and as a biomarker, Drug Resist. Updat., 7, 267-278.
Trinh B. N. et al (2002), DNA methyltransferase deficiency modifies cancer susceptibility in mice lacking DNA mismatch repair, Mol. Cell. Biol., 22, 2906-2917.
Virmani A. K. et al (2002), Hierarchical clustering of lung cancer cell lines using DNA methylation markers, Cancer Epidemiol. Biomarkers Prev., 11, 291-297.
Warnecke P.M. et al (1997), Detection and measurement of PCR bias in quantitative methylation analysis of bisulphite-treated DNA, Nucleic Acids Res., 25, 4422-4426.
Wittwer C. T et al (2003), High-resolution genotyping by amplicon melting analysis using LCGreen, Clin. Chem., 49, 853-860.
Wodacz T. et al (2006), Techniques used in studies of age-related DNA methylation changes, Ann. NY. Acad. Sci., 1067, 479-487.
Wojdacz T. el al (2007), Methylation-sensitive high resolution melting (MS-HRM): a new approach for sensitive and high-throughput assessment of methylation, Nucleic Acids Research, vol. 35. No. 6, e41.
Wojdacz T. et al (Sep. 2006), Reversal of PCR bias for improved sensitivity of the DNA methylation melting curve assay, Biotechniques, 41, 274-278.
Wojdacz T. et al (Sep. 2006), Supplementary material for: Reversal of PCR bias for improved sensitivity of the DNA methylation melting curve assay, Biotechniques, 41, 274-278.
Worm J. et al (2001), In-tube DNA methylation profiling by flourescence melting curve analysis, Clin. Chem., 47, 1183-1189.
Boyd, V. et al., Bisulfite conversion of genomic DNA for methylation analysis: protocol simplification with higher recovery applicable to limited samples and increased throughput, *Analytical Biochemistry*, 326: 278-280, 2004.
Genereux, D. et al., Errors in the bisulfite conversion of DNA: modulating inappropriate- and failed-conversion frequencies, *Nucleic Acids Resarch*, 36(22): 1-19, 2008.
Shiraishi, M. et al., High-Speed Conversion of Cytosine to Uracil in Bisulfite Genomic Sequencing Analysis of DNA Methylation, *DNA Research*, 11: 409-415, 2004.
Life Technologies product page, Cells-to-CpG™ Bisulfite Conversion Kit, downloaded Apr. 2, 2014.
NEB product page, Bisulfite Conversion, downloaded Mar. 31, 2014.
Diagenode product page, Bisulfite Conversion, downloaded Mar. 31, 2014.
Wang, R. et al., Comparison of bisulfite modification of 5-methyldeoxycytidine and deoxycytidine residues, *Nucleic Acids Research*, 8(20): 4777-90, 1980.

\* cited by examiner

Genomic sequence:

5'-GGGCTCCGGAGGGGTGTAGACAGAGCCCGGGCCGGCAGCCTCCCAGAGACAGCAGCCACCCGGACCCCGSTTTCTGCTGCACCTGGTCAGGTGCCTGGCCGTC-3'  SEQ ID NO: 44

Unmethylated allele:

5'-GGGTTTCGAGGGGGTGTAGATAGAGTCGGGCCGGTAGTTATTTCGATTCCGAGAGTAGTTATTTCGATTCCGGTAGAGTAGTTATTCGATTCGGAGAGTAGTTGGTTGGTTTTT-3'  SEQ ID NO: 45

Methylated allele: SEQ ID NO: 140

F1 - GAGGGGTGTAGATAGAGT

5'-GGGTTCCGAGGGGTGTAGATAGAGTCGGGCCGGTAGTTTCGAGAGTAGTTATTCGATTCGGAGAGTAGTTATTCGATTCGGAGAGTAGTTGGTTTTTGTATTTGGTTAGGTGTTGGTTCGTT-3'  SEQ ID NO: 141

F2 - TCGGAGGGGTGTAGATAGAGT

SEQ ID NO: 142

R1 - CATAAACCAATCCACAACCA

R2 - CATAAACCAATCCACAACCAGCA  SEQ ID NO: 143

Figure 2

Figure 6
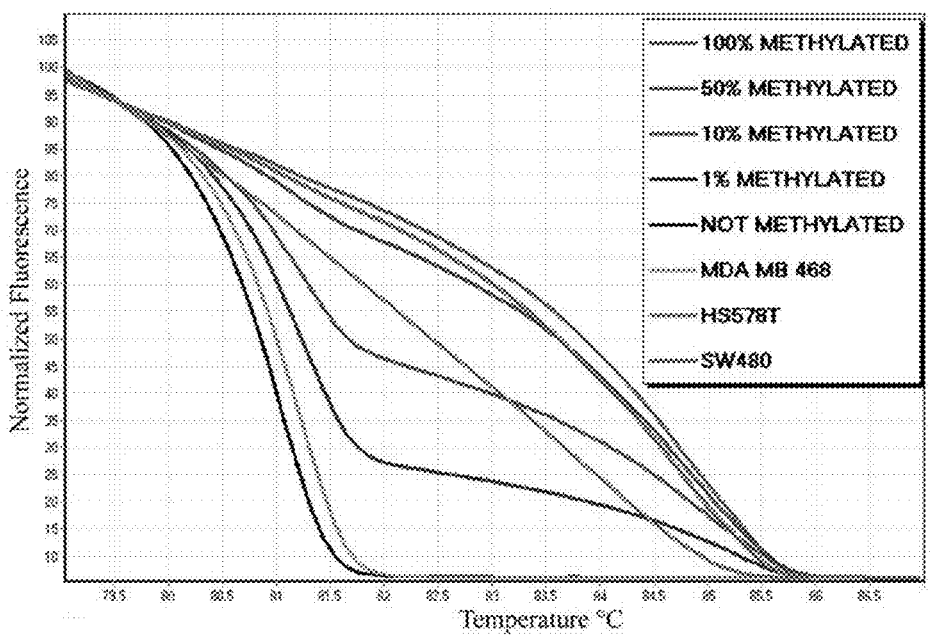
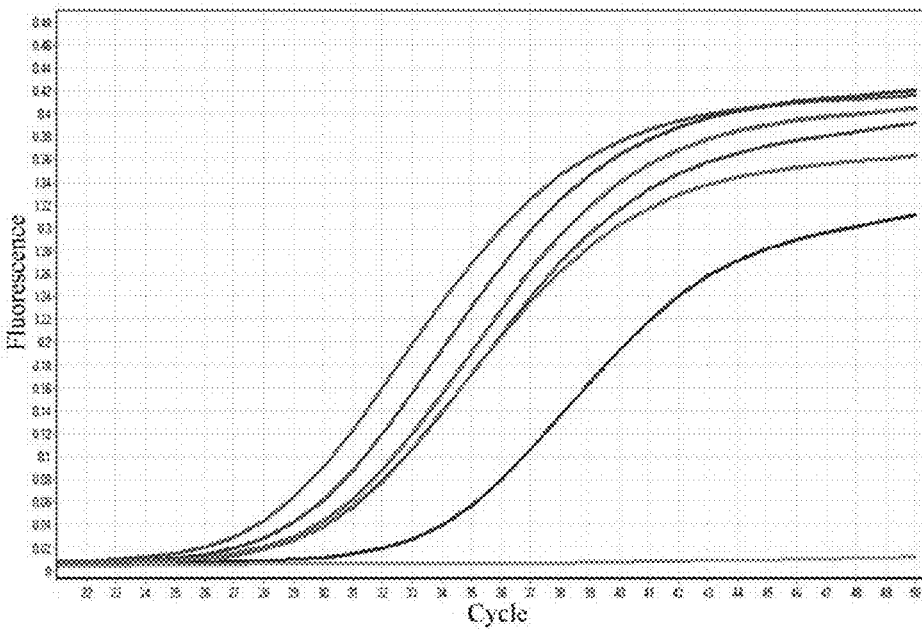

Figure 8

Target sequence genomic top (SEQ ID NO: 255)
After bisulfitemodification bottom (SEQ ID NO: 256)

```
GGCGGGGCCCTGTGCCCCACTGCGGAGTGCGGGTCGGGAAGCGGAGAGAGAAGCAGCTGT
| |++| | :::|||| ::::|:||++||||||++||||++||||++||||||||||:||:|||
GGCGGGGTTTTGTGTTTTATTGCGGAGTGCGGGTCGGGAAGCGGAGAGAGAAGTAGTTGT

GTAATCCGCTGGATGCGGACCAGGGCGCTCCCCATTCCCGTCGGGAGCCCGCCGATTGGC
|||||:++:||||||++|:::|||||++:|::::|||::++|++||||::++:++|||| :
GTAATTCGTTGGATGCGGATTAGGGCGTTTTTTATTTTCGTCGGGAGTTCGTCGATTGGT

TGGGTGTGGGCGCACGTGACCGACATGTGGCTGTATTGGTGCAGCCCGCCAGGGTGTCAC
||||||||||++:|++|||:++:||||||:|||||||||:|::++::|||||||: ::
TGGGTGTGGGCGTACGTGATCGATATGTGGTTGTATTGGTGTAGTTCGTTAGGGTGTTAT
```

```
PRIMERS
APCMSHRMF1 (SEQ ID NO: 185)
GCG GAG AGA GAA GTA GTT GTG TAA TT
TM 65
APCMSHRMR1 (SEQ ID NO: 186)
TAC GCC CAC ACC CAA CCA ATC
TM 63
```

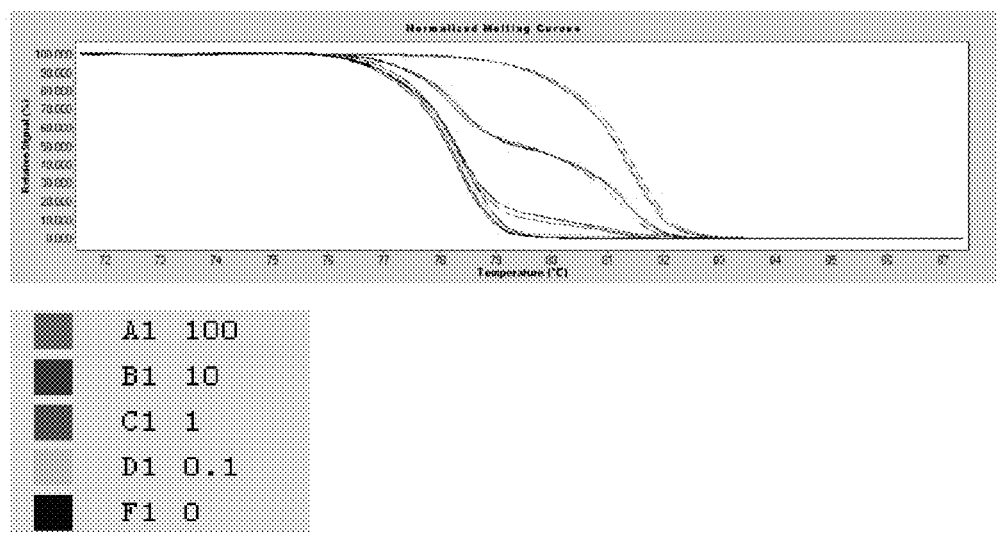

Target sequence genomic top (SEQ ID NO: 257)
After bisulfitemodification bottom (SEQ ID NO: 258)

```
AGACTTGGAGGGGCGGGGATGAGGAGGGCGGGGAGGACGACGAGGGCGAAGAGGGTGGGT
| | | : | | : | | | | | | ++ | : | | | | | | | | | | ++ | | | | | | ++ | ++ | | | | ++ | | | | | | | | | |
AGATTTGGAGGGGCGGGGATGAGGAGGGCGGGGAGGACGACGAGGGCGAAGAGGGTGGGT

GAGAGCCCCGGAGCCCGAGCCGAAGGGCGAGCCGCAAACGCTAAGTCGCTGGCCATTGGT
| | | | | : : : ++ | | | : : ++ | | : ++ | | | | ++ | | : ++ : | | | ++ : | | | | ++ : | | | : | | | | | |
GAGAGTTTCGGAGTTCGAGTCGAAGGGCGAGTCGTAAACGTTAAGTCGTTGGTTATTGGT

GGACATGGCGCAGGCGCGTTTGCTCCGACGGGCCGAATGTTTTGGGGCAGTGTTTTGAGC
| | | : | | | | ++ : | | | ++++ | | | | : | : ++ | ++ | | : ++ | | | | | | | | | | : | | | | | | | | | | +
GGATATGGCGTAGGCGCGTTTGTTTCGACGGGTCGAATGTTTTGGGGTAGTGTTTTGAGC
```

```
primers
ATMMSHRMF1 (SEQ ID NO: 187)
CGA AGA GGG TGG GTG AGA GTT T
Tm 64

ATMMSHRMR1 (SEQ ID NO: 188)
ACGCCATATCCACCAATAACCAAC
Tm64
```

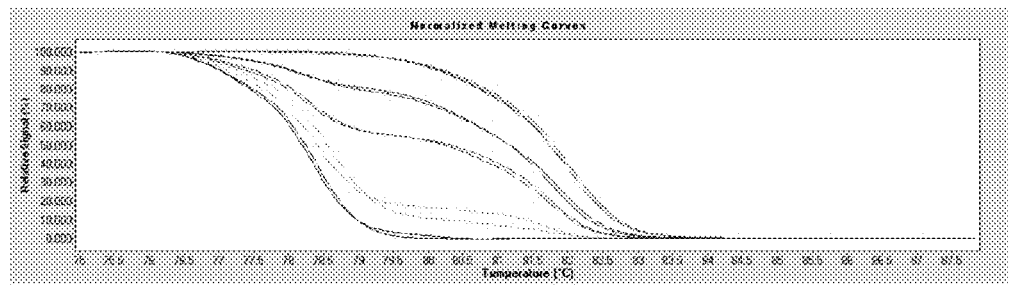

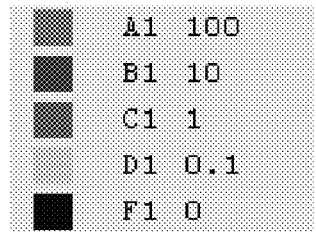

Target sequence genomic top (SEQ ID NO: 259)
After bisulfitemodification bottom (SEQ ID NO: 260)

```
TGGGGAGACAGAGGACGCAAACCTAAGAGGGCACCCAGAGCGCCGGGGAACGCAGCCTGG
||||||||:|||||||++:|||::||||||||:|:::|||++:++||||++:||::|||
TGGGGACATACAGGACGTAAATTTAAGAGGGTATTTAGAGCGTCGGCGAACGTAGTTTGG

GGACCTCGAAGCCCCTCGAAAGCGCTCCTCTAGAGGTGACAGCACCAGATCCTGGCGAAG
|||::|++||:::|++|||++:|::|:||||||||:||:|::|||::|||++|||
GGATTCGAAGTTTTTCGAAAGCGTTTTTTAGAGGTGATAGTATTAGATTTTGGCGAAG
```

BIN1MSHRMF2 (SEQ ID NO: 189)
GGACGTAAATTTAAGAGGGTATTTAGAG
TM 64

BIN1MSHRMR2 (SEQ ID NO: 190)
CTTCGCCAAAATCTAATACTATCACCT
TM 64

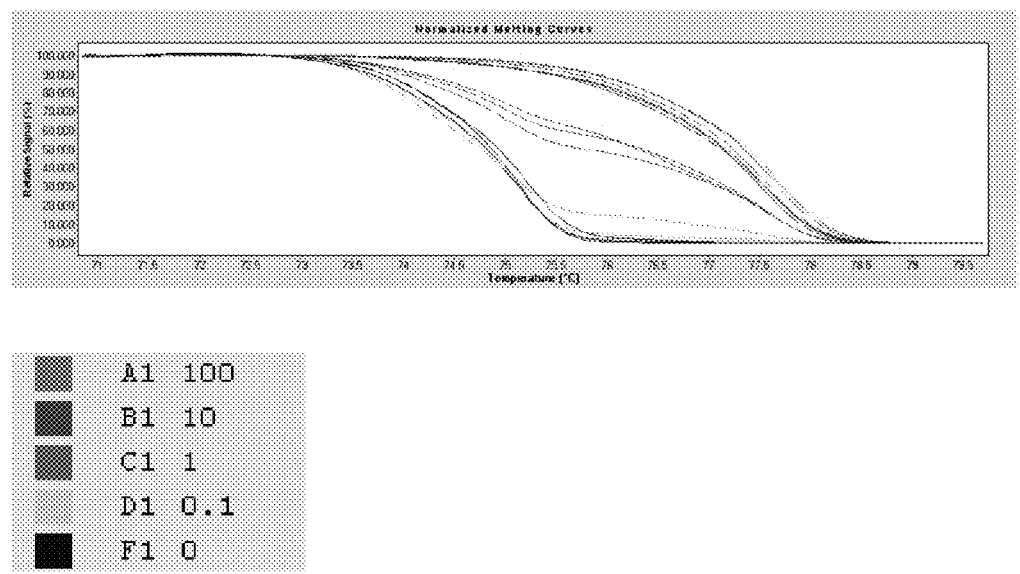

Figure 11

Target sequence genomic top (SEQ ID NO: 261)
After bisulfitemodification bottom (SEQ ID NO: 262)

```
481 CGTATTCTGAGAGGCTGCTGCTTAGCGGTAGCCCCTTGGTTTCCGTGGCAACGGAAAAGC
    ++| | | :| | | | | | :| | :| :| | | |++ | | | :::: | | | | | |:++| | | :| |++ | | | | |+
481 CGTATTTTGAGAGGTTGTTGTTTAGCGGTAGTTTTTTGGTTTTCGTGGTAACGGAAAAGC

541 GCGGGAATTACAGATAAATTAAAACTGCGACTGCGCGGCGTGAGCTCGCTGAGACTTCCT
    +++| | | | | | :| | | | | | | | | | | :| |++| : | |++++|++| | | | :|++:| | | | :| | ::|
541 GCGGGAATTATAGATAAATTAAAATTGCGATTGCGCGGCGTGAGTTCGTTGAGATTTTTT

601 GGACGGGGGACAGGCTGTGGGGTTTCTCAGATAACTGGGCCCCTGCGCTCAGGAGGCCTT
    | | |+-| | | | |:| | | :| | | | | | | | |:|:| | | | | |:| | | |::::| |++:|:| | | | | |::||
601 GGACGGGGGATAGGTTGTGGGGTTTTTTAGATAATTGGGTTTTTGCGTTAGGAGGTTTT
```

BRCA1MSHRMF2(SEQ ID NO: 191)
GGA AAA GCG CGG GAA TTA TAG ATA AAT
TM 64

BRCA1MSHRMR2(SEQ ID NO: 192)
ATCCCCCGTCCAAAAAATCTCAAC
TM 64

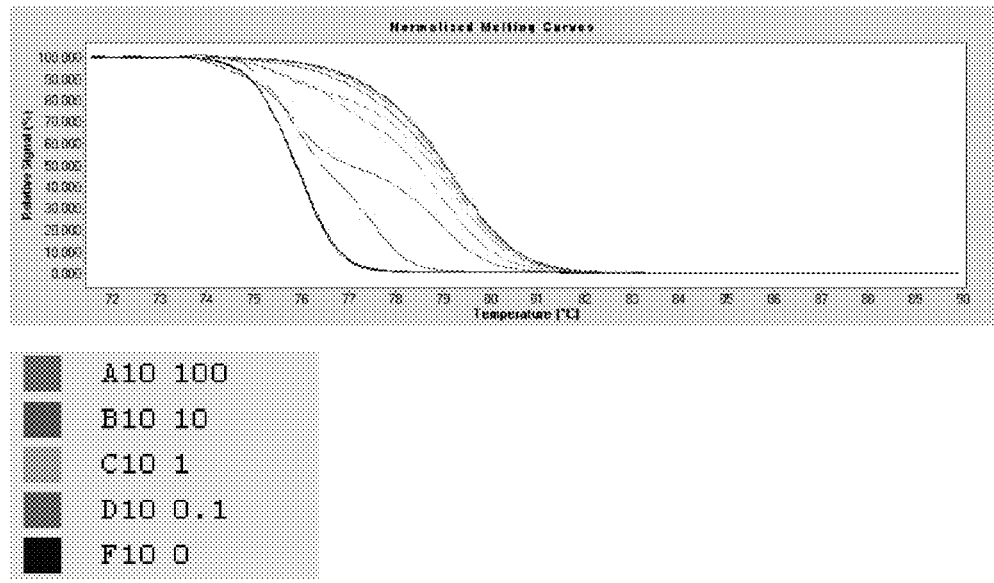

Figure 12

Target sequence genomic top (SEQ ID NO: 263)
After bisulfitemodification bottom (SEQ ID NO: 264)

```
GGGGGGTGGACCGCCTAAGAGGGCGTGCGCTCCCGACATGCCCCGCGGCGCGCCATTAAC
+|:|||||||:++::|||||||||++||+-:|::++:|||::+++:|+++:|:||||:
GGGGGGTGGATCGTTTAAGAGGGCGTGCGTTTCGATATGTTTCGCGGCGCGTTATTAAT

CGCCAGATTTGAATCGCGGGACCCGTTGGCAGAGGTGGCGGCGGCATGGGTGCCCCG
++::|||||||||||++++|||::++|||:|||||||||++|++|++:|||||||:::++
CGTTAGATTTGAATCGCGGGATTCGTTGGTAGAGGTGGCGGCGGCGGTATGGGTGTTTCG
```

```
BIRC5MSHRMR1 (SEQ ID NO: 193)
CGCCGCCACCTCTACCAAC
TM 64

BIRC5MSHRMF2 (SEQ ID NO: 194)
GGGGTGGATCGTTTAAGAGGG
Tm 63
```

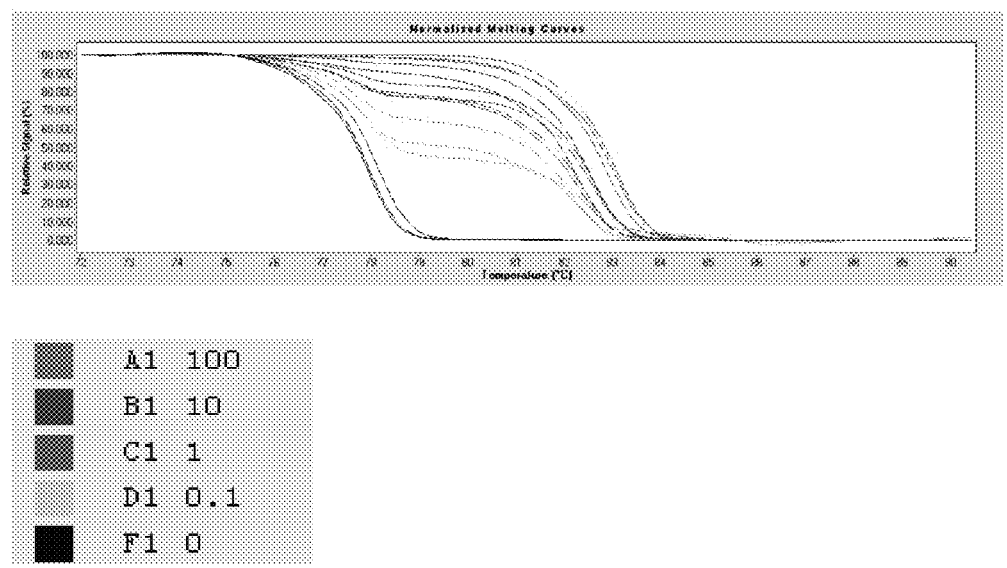

Target sequence genomic top (SEQ ID NO: 265)
After bisulfitemodification bottom (SEQ ID NO: 266)

```
CACCCACGGAGCCTCCGGGGCTGGTGAGGAGCGGGTAGGGGCGGGGGTGCGGTCCTGCA
: |::: |++| |::: |:+-| |:| | | | | |:| |++| | | | | | |++| | | | |++|::| |:|
TATTTACGGAGTTTTCGGGGTTGGTGAGGAGCGGGTAGGGGCGGGGGTGCGGTTTTGTA

GGGGCCGGGAATGGAGGCCGCGGTGCCGACCCGAAGCCGACGGGAGCCTGGGGCCTCGGC
| | | |:++| | | | | | | | |:++++| | |:++|::++| | |:++|++| | | |::| | | | |::|++|+
GGGGTCGGGAATGGAGGTCGCGGTGTCGATTCGAAGTCGACGGGAGTTTGGGGTTTCGGC

GCGGGGCGGCCTGGGGTGCGAAAGGCCGGCCCGGGGGCTTCCCGCGCCAGCATGGAGCT
++|| |++|:: | | | | | |++| | | |:++|:::++| | |:| |::++++::| |:| | | | |:|
GCGGGGCGGTTTGGGGTGCGAAAGGTCGGTTTCGGGGTTTTCGCGTTAGTATGGAGTT
``` primers

BSCMSHRMR1 (SEQ ID NO: 195)
CGCCGAAACCCCAAACTCCC
TM 65

BSCMSHRMF2 (SEQ ID NO: 196)
GGT TTT GTA GGG GTC GGG AAT G
Tm 64

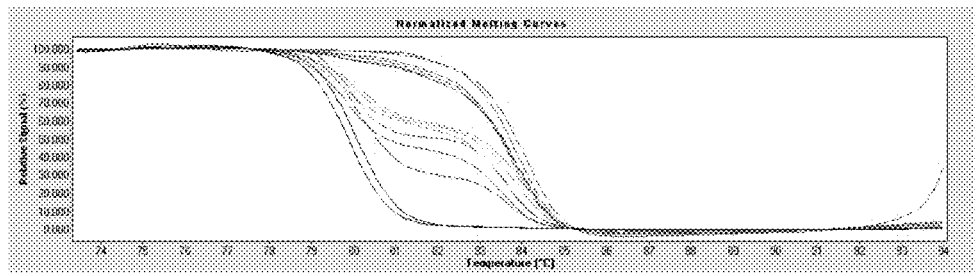

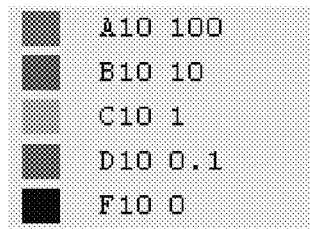

Target sequence genomic top (SEQ ID NO: 267)
After bisulfitemodification bottom (SEQ ID NO: 268)

```
1981 GATGGCGAGCTTCACGCTCGGGAACAGTCAGTAATCGGAAGGGGAAGTGGACAGGGGAAC
     +||||++||:||:|++:|++||||:|||:||||||++||||||||||||:||||||||:
1981 GATGGCGAGTTTTACGTTCGGGAATAGTTAGTAATCGGAAGGGGAAGTGGATAGGGGAAT

2041 TTCAAGAGGCGAGCCTGCCACGCGGGAAGCGCCCGAACTTGCGGGTCTCCATGAATGCAG
     ||:||||||++||::||::|++++|||||++::++||:|||++|||:|::||||||:||
2041 TTTAAGAGGCGAGTTTGTTACGCGGGAAGCGTTCGAATTTGCGGGTTTTTATGAATGTAG

2101 AGGGCGCCGGGAAGGGGGGCATCCGGCCGCGACCCTCTCTGCCCCTCCCATTCGCTGCC
     ||||++:++|||||||||||:|||:++|:++++|:::|:|:||::::|::|||++:||::
2101 AGGGCGTCGGGAAGGGGGGGTATTCGGTCGCGATTTTTTTGTTTTTTTATTCGTTGTT

CCND2MSHRMF1 (SEQ ID NO: 197)
GAA GTG GAT AGG GGA ATT TTA AGA GG
TM 65
CCND2MSHRMR1 (SEQ ID NO: 198)
CGACGCCCTCTACATTCATAAAAAC
TM 64
```

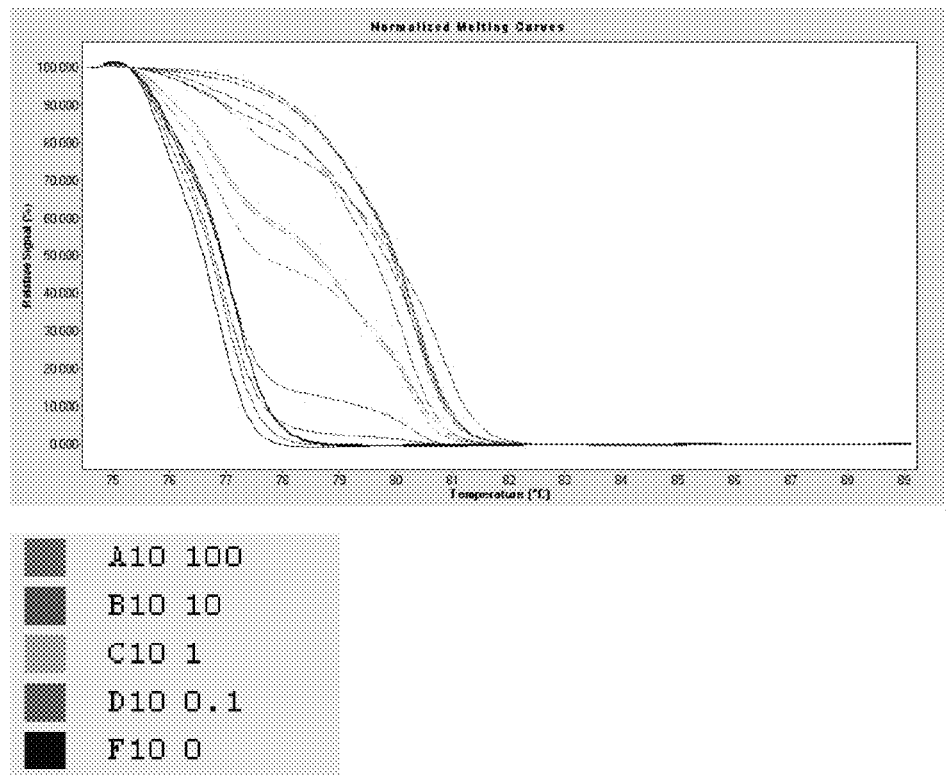

Figure 15

Target sequence genomic top (SEQ ID NO: 269)
After bisulfitemodification bottom (SEQ ID NO: 270)

```
241 CCCTGGGGAGGGGTCCGCGCTGCTGATTGGCTGTGGCCGGCAGGTGAACCCTCAGCCAAT
    :::|||||||||||:++++:||:||||||||:|:||||:++|:||||||||:::|:||::|||
241 TTTTGGGGAGGGGTTCGCGTTGTTGATTGGTTGTGGTCGGTAGGTGAATTTTTAGTTAAT

301 CAGCGGTACGGGGGGCGGTGCCTCCGGGGCTCACCTGGCTGCAGCCACGCACCCCCTCTC
    :||++||++||:||++|||::|:++|||:|::::|||:||:||::++::::::|:|:
301 TAGCGGTACGGGGGGCGGTGTTTTCGGGGTTTATTTGGTTGTAGTTACGTATTTTTTTT
``` primers

CDH1MSHRMF1 (SEQ ID NO: 199)
GTTGTGGTCGGTAGGTGAATTTTTAG
TM 65

CDH1MSHRMR1 (SEQ ID NO: 200)
TACGTAACTACAACCAAATAAACCCC
TM 63

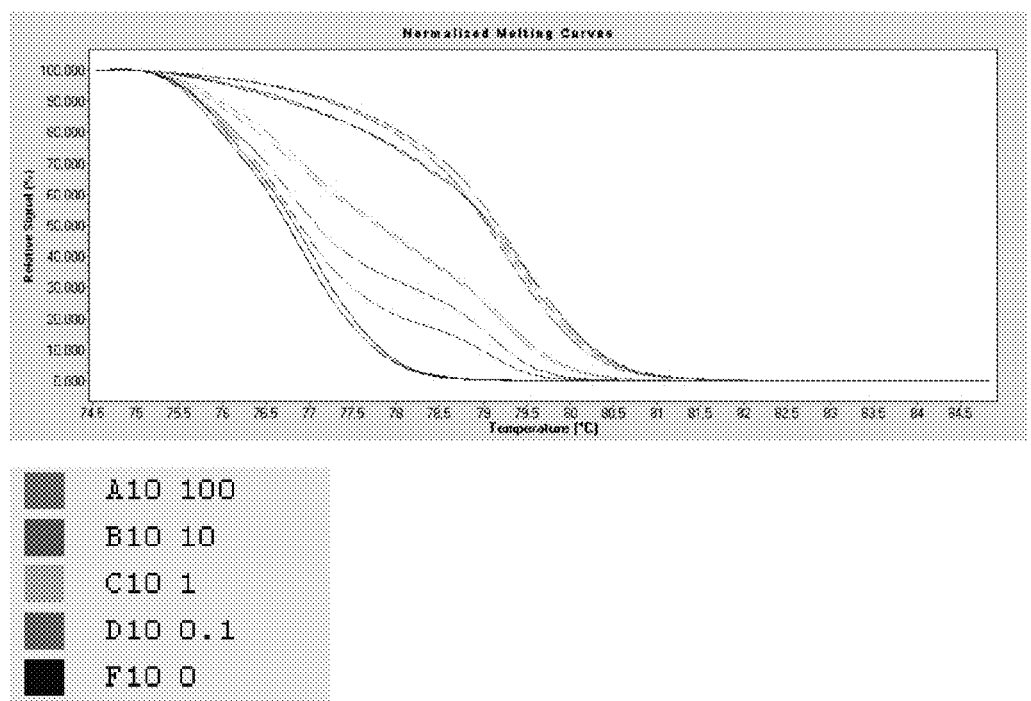

Figure 16
Target sequence genomic top (SEQ ID NO: 271)
After bisulfitemodification bottom (SEQ ID NO: 272)

```
GAAAACCCTCACTCGCGGCGGGCCGCACGCGCGCCGAATCCGGAGGGTCACCAAGAACCT
+:|||:::|:|:|++++|++||:++:|++++++:++||::++|||||:::||||::|
GAAAATTTTTATTCGCGGCGGGTCGTACGCGCGTCGAATTCGGAGGGTTATTAAGAATTT

GCGCACCATGTTCTCGCCGCCTCCAGGGCCGAGCTCGGCAGCCGCTGCGCCGCCCTTTGG
|++:|::|||||:|++:++::|::||||:++||:|++:||:++:|++:++::||||
GCGTATTATGTTTCGTCGTTTTAGGGTCGAGTTCGGTAGTCGTTGCGTCGTTTTTTGG

CACCAGAGGTGAGCAGCGCCACTCCTGCCCCTTAACTGCAGACTGGGACCCACGCACCG
:|::||||||||:|++:|:|::|::::||||:|:|||:|||||::|++:|:++
TATTAGAGGTGAGTAGCGTTATTTTGTTTTTTAATTGTAGATTGGGATTACGTATCG
```

PRIMER SEQUENCE
p16MSHRMF1 (SEQ ID NO: 201)
TCG AAT TCG GAG GGT TAT TAA GAA TTT G
Tm 64
p16MSHRMR1 (SEQ ID NO: 202)
ACGCTACTCACCTCTAATACCAAAA
TM 63

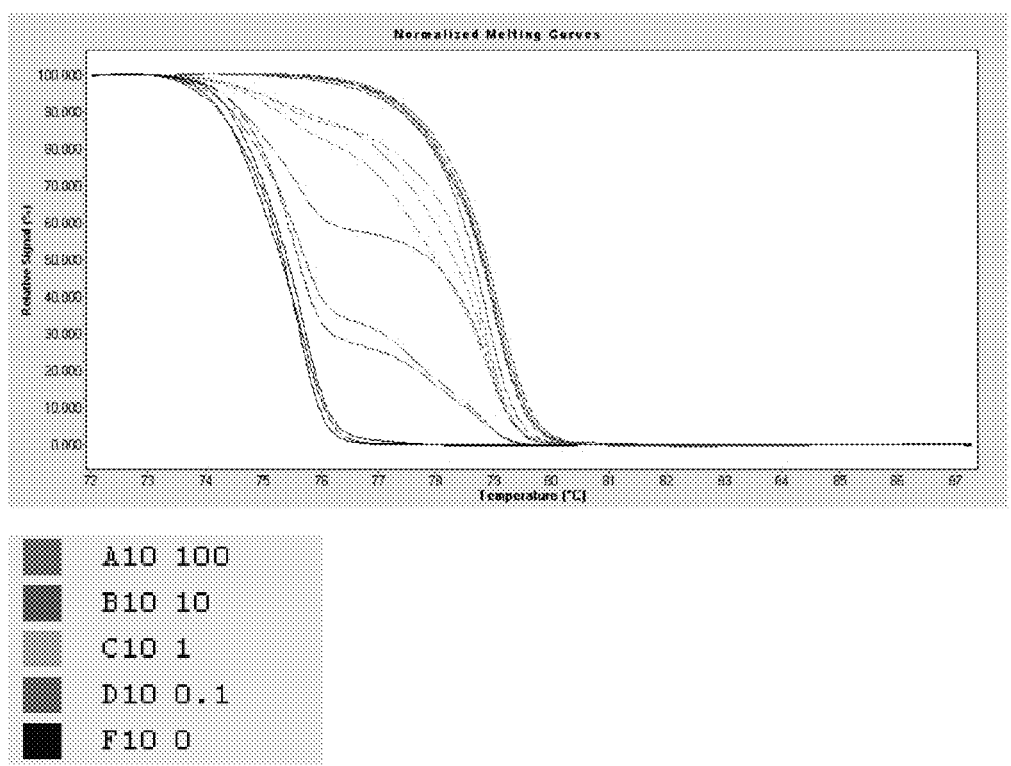

Figure 17

Target sequence genomic top (SEQ ID NO: 273)
After bisulfitemodification bottom (SEQ ID NO: 274)

```
GCTCGGCACTCACGGCTCTGAGGGCTCCGACGGCACTGACGGCCATGGCGCGTTCGAACC
: :|++|:|:|:|++|:|:|||||:|:++|++|:|:|||++|::||||++-|++|::
GTTCGGTATTTACGGTTTTGAGGGTTTCGACGGTATTGACGGTTATGGCGCGTTCGAATT

TCCCGCTGGCGCTGGGCCTGGCCCTGGTCGCATTCTGCCTCCTGGCGCTGCCACGCGACG
|::++:||++:|||::|||:::|||++:|||:|::|::||++:|:::|++++|++
TTTCGTTGGCGTTGGGTTTGGTTTTGGTCGTATTTGTTTTTGGCGTTGTTACGCGACG
```

PRIMERS
CST6MSHRMF1 (SEQ ID NO: 203)
GTT CGG TAT TTA CGG TTT TGA GGG TTT
TM 65

CST6MSHRMR1 (SEQ ID NO: 204)
CAAAATACGACCAAAACCAAACCCAAC
TM 65

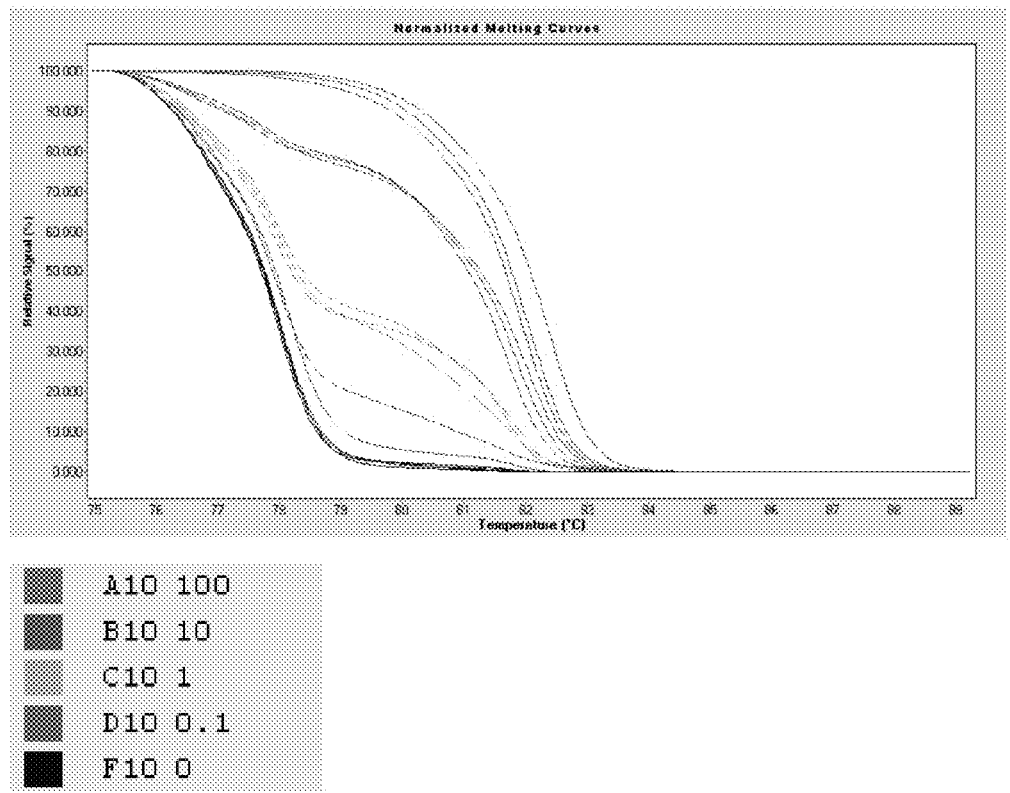

Figure 18

Target sequence genomic top (SEQ ID NO: 275)
After bisulfitemodification bottom (SEQ ID NO: 276)

```
        GGAGCGCGGAGCTGGGAGGAGCAGCGAGCGCCGCGCAGAACCCGCAGCGCCGGCCTGGCA
        +||| ++++ ||| : ||||||||||| : | | ++ | | ++ : ++++ : ||| : : ++ : || ++ : -+ | : : ||| : |
        GGAGCGCGGAGTTGGGAGGAGTAGCGAGCGTCGCGTAGAATTCGTAGCGTCGGTTTGGTA

GGGCAGCTCGGAGGTGGGTGGGCCGCGCCGCCAGCCCGCTTGCAGGGTCCCCATTGGCCG
        ||| : || : | ++ |||||||||||| : -+++ : ++ : : || : : ++ : || : ||||| : : : : ||||| : ++
        GGGTAGTTCGGAGGTGGGTGGGTCGCGTCGTTAGTTCGTTTGTAGGGTTTTTATTGGTCG
```

```
Primers
DAPK1MSHRMF1 (SEQ ID NO: 205)
GCGCGGAGTTGGGAGGAGT
TM 64

DAPK1MSHRMR1 (SEQ ID NO: 206)
CTCCGAACTACCCTACCAAACC
TM 64
```

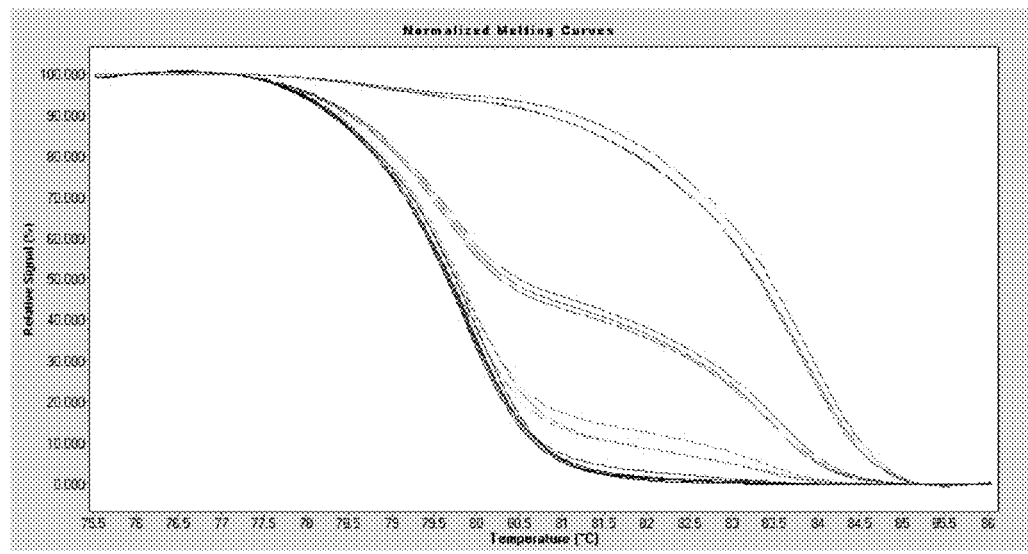

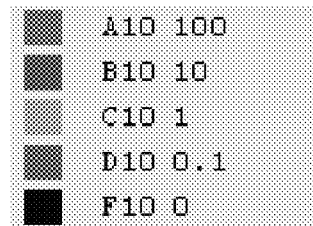

Figure 19

Target sequence genomic top (SEQ ID NO: 277)
After bisulfitemodification bottom (SEQ ID NO: 278)

```
CCCGGGAGCCCAGGAGCTGGCGGAGGGCGTTCGTCCTGGGACTGCACTTGCTCCCGTCGG
::++:|||:::;||||:|||++||||:-+||++:::||||:|::|:|||:|::++|++|
TTCGGGAGTTTAGGAGTTGGCGGAGGGCGTTCGTTTTGGGATTGTATTTGTTTTCGTCGG

GTCGCCCGGCTTCACCGGACCCGCAGGCTCCCGGGGCAGGGCCGGGGCCAGAGCTCGCGT
||++:;++|:|:|:++||::++:|||:|::++||:|||||:++|||::||||:|+-++|
GTCGTCGGTTTTATCGGATTCGTAGGTTTTCGGGGTAGGGTCGGGGTTAGAGTCGCGT
```

Primers

ESR1MSHRMF2 (SEQ ID NO: 207)
GCG TTC GTT TTG GGA TTG TAT TTG TTT
TM 64

ESR1MSHRMR2 (SEQ ID NO: 208)
TCT AAC CCC GAC CCT ACC CC
TM 65

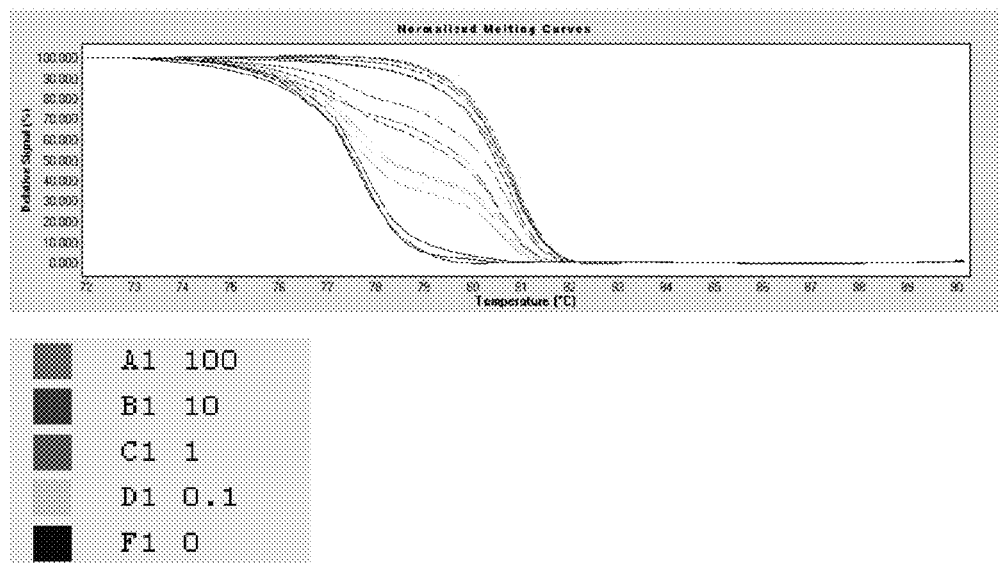

Target sequence genomic top (SEQ ID NO: 279)
After bisulfitemodification bottom (SEQ ID NO: 280)

```
GCACCGCAGACCGCCGGCGGGCAAGGCGGGCCAGGCTCTCTTGGAGTGTCTCCTCATCGG
|:|:++:||::++:++|++|:|||||++:|::|||:|:|||||||:|:::|:|++|
GTATCGTAGATCGTCGGCGGGTAAGGCGGGTTAGGTTTTTTTGGAGTGTTTTTTTATCGG

CGTCCCGGACGCCCGGGCCGGGAAAGAGTTGCTGCACCAGGTGGTAACGAGCTGCATCCC
++|::++||++::++||:++|||||||||:|:|::|||||||||++|::||:|:::
CGTTTCGGACGTTCGGGTCGGGAAAGAGTTGTTGTATTAGGTGGTAACGAGTTGTATTTT
```

```
Primers

FANCFMSHRMF1 (SEQ ID NO: 209)
GCGGGTTAGGTTTTTTTGGAGTGTT
TM 64

FANCFMSHRMR1 (SEQ ID NO: 210)
AATACAACTCGTTACCACCTAATACAA
TM 62
```

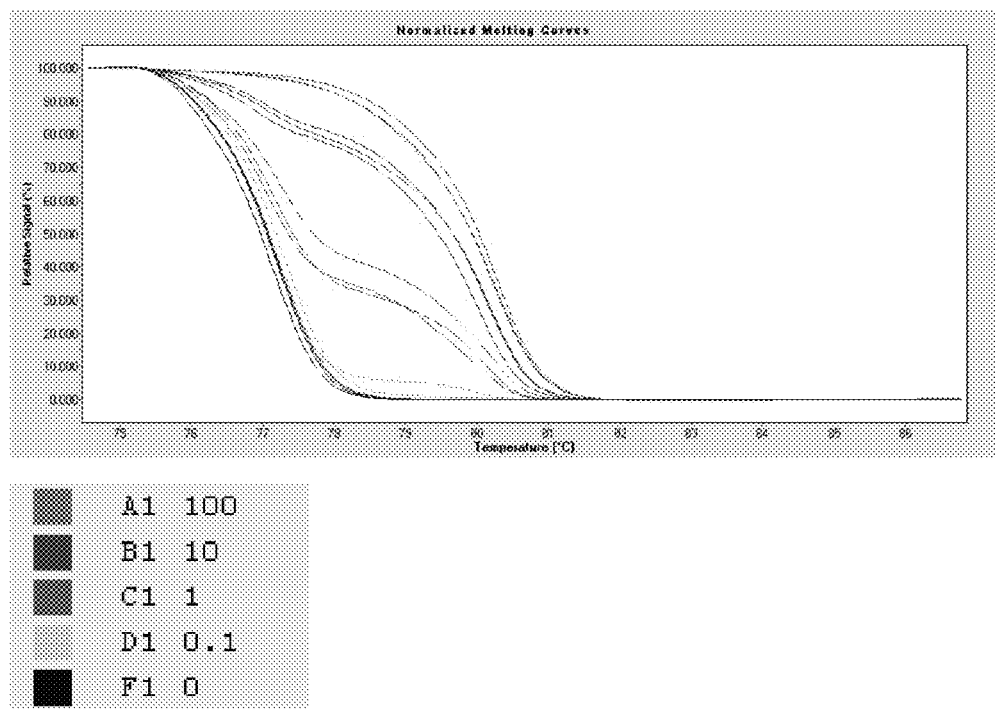

Figure 21

Target sequence genomic top (SEQ ID NO: 281)
After bisulfitemodification bottom (SEQ ID NO: 282)

```
CCTGATCTGCCAGCAGCATGCGCAGGGCCGCGCAGCGGCCTGCGGGGAGGGAGAAGTACG
::|||:|::||:|||:|||++:|||:+++:|++|::|++||||||||||||||++
TTTGATTTGTTAGTAGTATGCGTAGGGTCGCGTAGCGGTTTGCGGGGAGGGAGAAGTACG

AGATGTGGGGACCGGGCCGACTCCGCCTCGCAGCAACCCGGGGAGGGGTCAGGAGTGCAG
||||||||||:++||:++|:|:++:;|+|:|;|::+||||||||:|||||:||
AGATGTGGGGATCGGGTCGATTTCGTTTCGTAGTAATTCGGGGAGGGGTTAGGAGTGTAG
```

Primers
GSTP1MSHRMF6 (SEQ ID NO: 211)
GAGAAGTACGAGATGTGGGGAT
Tm 63

GSTP1MSHRMR6 (SEQ ID NO: 212)
TACACTCCTAACCCCTCCCC
Tm 63

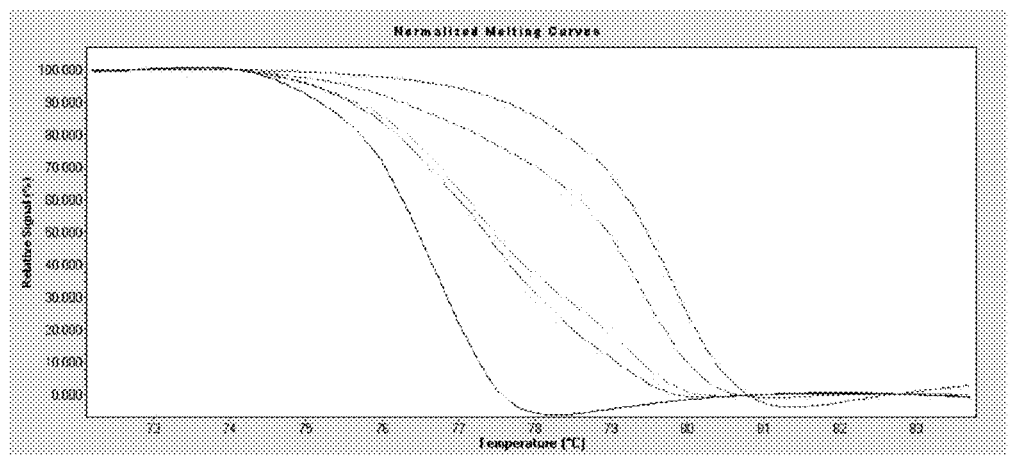

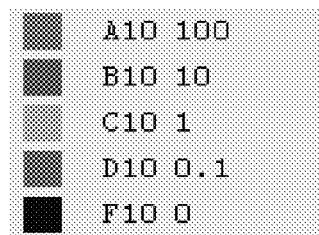

Figure 22

Target sequence genomic top (SEQ ID NO: 283)
After bisulfitemodification bottom (SEQ ID NO: 284)

```
CCTGGGGCGGGGCCAGGCGTCGGTGGCCGTGACTGGAGACTGTTACTGAGGGCGGCCCGG
::|||||++||::|||++|++||||:++||:|||||:|||||:|||||++|::++|
TTTGGGGCGGGGTTAGGCGTCGGTGGTCGTGATTGGAGATTGTTATTGAGGGCGGTTCGG

GCAGTAAGCAGTCTAGAGCCAAGGTGCCGGCGCGCTGTCCGGGCGGGGTGCCCGGTCGC
|:|||||:||::||||::|||||:++|+-++:|||:++||++||||:::++||+:
GTAGTAAGTAGTTAGAGTTAAGGTGTCGGCGCGTTGTTCGGGCGGGGTGTTTCGGTCGT

CCCGGCTGCCCCGGCTGGGGGCTCTGCTGCTCCGCCTCCCCTGCGTCTCCCGCCCTGCCC
:;++|:||::;++|:|||||:|:|:||:|:++::|:::||++|;|:++:::||:::
TTCGGTTGTTTCGGTTGGGGGTTTTGTTGTTTCGTTTTTTTGCGTTTTTCGTTTTGTTT
```

Primers 2
HIC1MSHRMF2 (SEQ ID NO: 213)
GGC GGT TCG GGT AGT AAG TAG TT
Tm 65
HIC1MSHRMR2 (SEQ ID NO: 214)
AACGAAACAACAAAACCCCAACC
TM 64

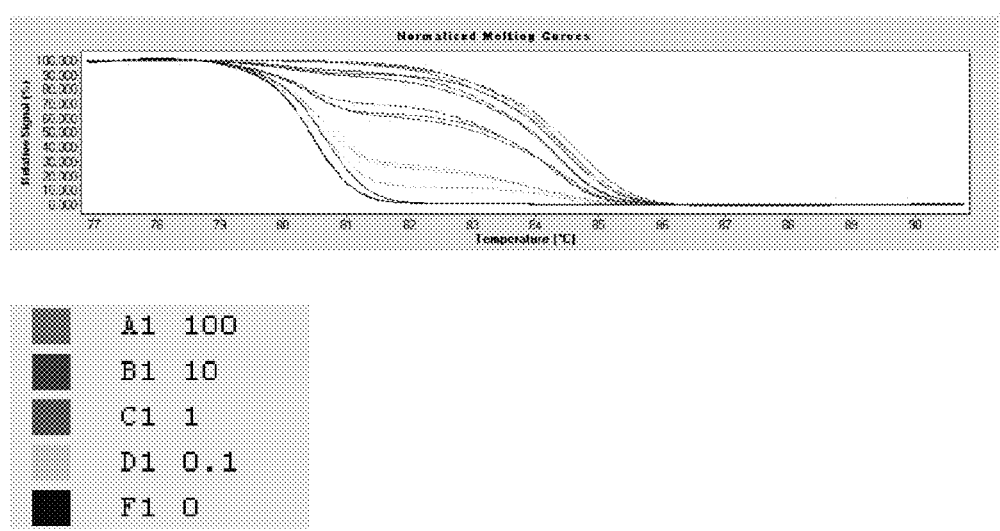

Figure 23

Target sequence genomic top (SEQ ID NO: 285)
After bisulfitemodification bottom (SEQ ID NO: 286)

```
GGCGAGGCTGGAAGGACCTGGGATCCACGATCGGCGCAGGCAGCGGCGGGGGCGCAGCGG
||++||:|||||||::||||||::|++||++|++:|||:|++|-+|||++:||++|
GGCGAGGTTGGAAGGATTTGGGATTTACGATCGGCGTAGGTAGCGGCGGGGGCGTAGCGG

GCGCCGAGGCCTCAGGCCCCACCGTGCGCGCCAGGAGCCCGGGGCGCTCACCGGAGCTGC
|++:++||:::|:|||::::::++||++++:|||||::++||++:|:|++||:||:
GCGTCGAGGTTTTAGGTTTTATCGTGCGCGTTAGGAGTTCGGGGCGTTTATCGGAGTTGT
```

Primers
HIN1MSHRMchr5F1 (SEQ ID NO: 215)
CGAGGTTGGAAGGATTTGGGATT
Tm 63

HIN1MSHRMchr5R1 (SEQ ID NO: 216)
CGCACGATAAAACCTAAAACCTC
Tm 61

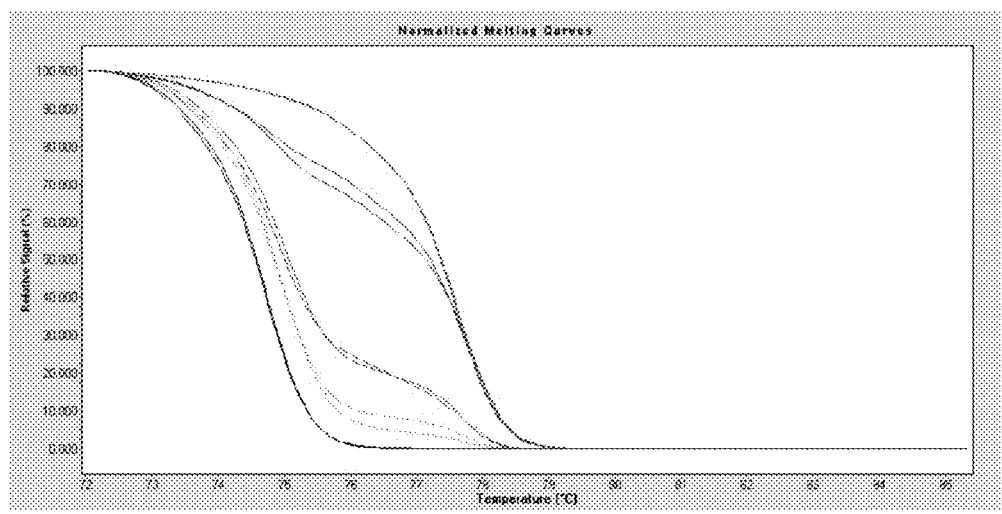

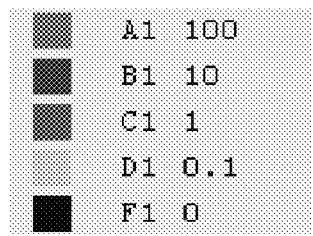

Target sequence genomic top (SEQ ID NO: 287)
After bisulfitemodification bottom (SEQ ID NO: 288)

```
CCGACGAAGCCGCTCCAGGGCTGCTCTCAGAGGACGCGCGGCAGGCAAAGAGAATGAACC
:++|++|||:++:|::|||:||:|:|:||||||+++++|:|||:||||||||||||::
TCGACGAAGTCGTTTTAGGGTTGTTTTAGAGGACGCGCGGTAGGTAAAGAGAATGAATT

TGAGCGTCCACGAAACGTCCTGCACGGCTCCCGGGAGCTGGGAGAAACAGGTGCCTTTCT
|||:|++|::|++||||++|::||:|++|:|::++|||:|||||||||:||||::|||:|
TGAGCGTTACGAAACGTTTTGTACGGTTTCGGGAGTTGGGAGAAATAGGTGTTTTTTT

CCGACGTCCGCGGGCGACGCCTGCCGCACCTTGCCCGCTGCCGCGCCCTCCCGGGCACC
:++|++|:++++||++|++::||:++:|::|||:++:||:++++::::|::++|:|::
TCGACGTTCGCGGGCGACGTTTGTCGTATTTTGTTCGTTGTCGCGTTTTTTCGGGTATT
``` primers:
KLMSHRMF1 (SEQ ID NO: 217)
GCG GTA GGT AAA GAG AAT GAA TTT GA
Tm 63

KLMSHRMR1 (SEQ ID NO: 218)
CGTCGAAAAAAACACCTATTTCTCC
TM 63

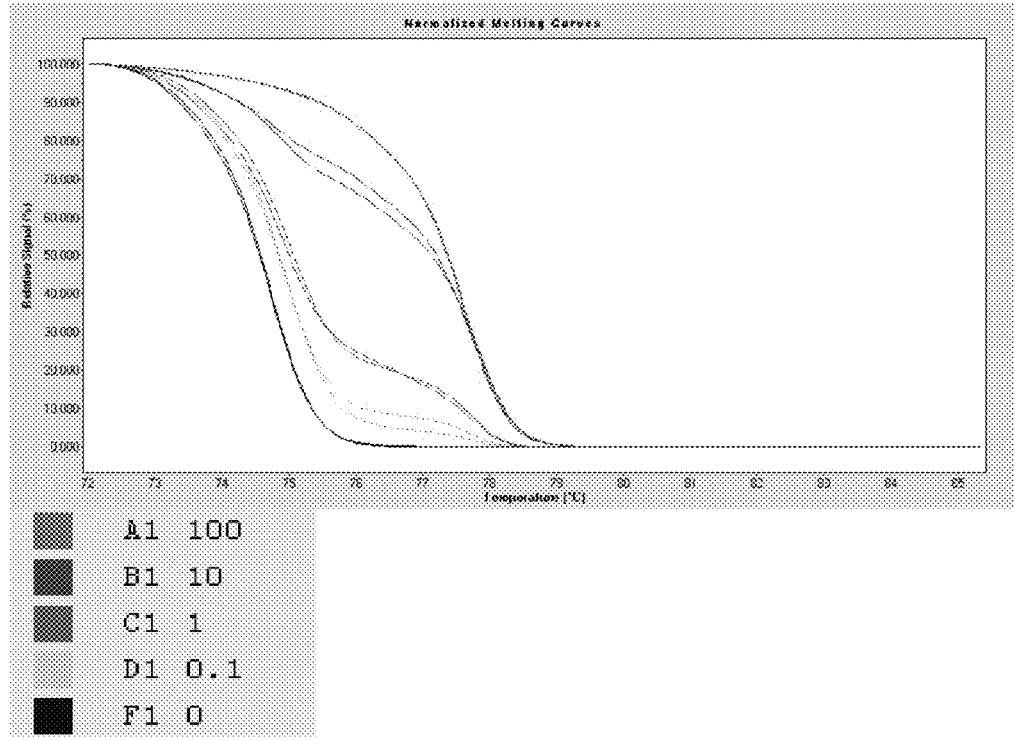

Target sequence genomic top (SEQ ID NO: 289)
After bisulfitemodification bottom (SEQ ID NO: 290)

```
301  CGTGAGCAAACTCGCAGAGTTGGCGCGGCAGCCGGCCGGGAGACGCCGAGCAGGGCCTGG
     ++|||:|||:|++:||||||||-+++|:||:++|:++||||||++:++|:|||::|||
301  CGTGAGTAAATTCGTAGAGTTGGCGCGGTAGTCGGTCGGGAGACGTCGAGTAGGGTTTGG

361  CCGCCCGCAGCCCGGGAGGAACGGCGCCCCAGGGTCCGGTGGCCTCTGAGGGGCTGACT
     :++::++:||::++|||||||-+|++::::||||:++||||::|:||||||:||:|
361  TCGTTCGTAGTTCGGGAGGAACGGCGTTTTAGGGTTCGGTGGTTTTTGAGGGGTTGATT

421  GGCCCGTGAGCCGGCGGCGCGGCCGCGGGGAACGGGGTGGGAACCGCGCGGCAGTGGGTG
     ||::++|||:++|++|++++:-+++||||++|||||||:+++++++:|||||||
421  GGTTCGTGAGTCGGCGGCGCGGTCGCGGGGAACGGGGTGGGAATCGCGCGGTAGTGGGTG
``` primers

LATS2MSHRMF1 (SEQ ID NO: 219)
F-GAGACGTCGAGTAGGGTTTGGT
TM 64

LATS2MSHRMR1 (SEQ ID NO: 220)
R-TCACGAACCAATCAACCCCTCAAAAA
TM 65

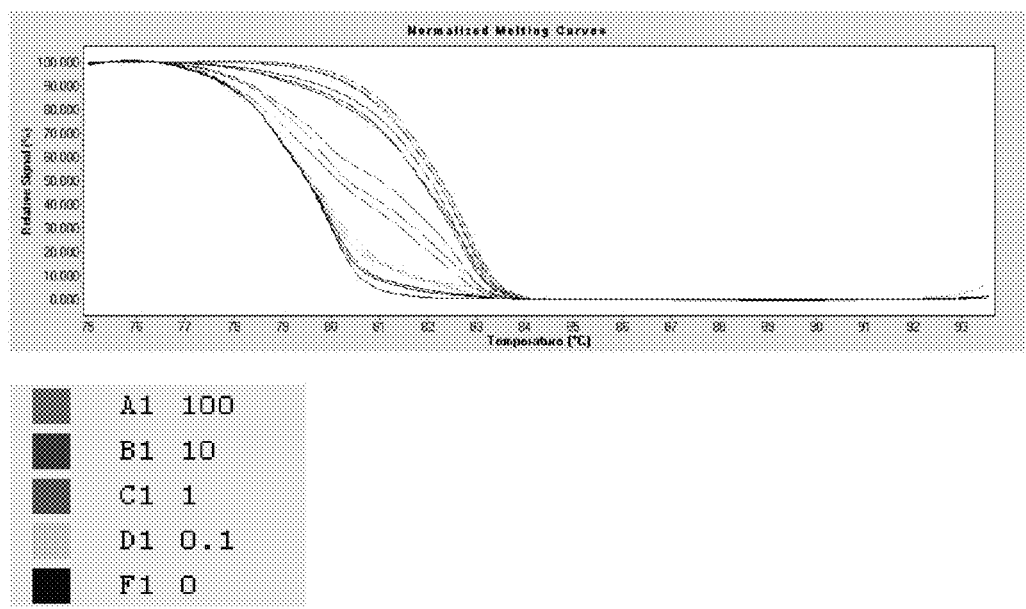

Target sequence genomic top (SEQ ID NO: 291)
After bisulfitemodification bottom (SEQ ID NO: 292)

```
TTATCCAGCGGCCAGCTAATGCTATCAAAGAGATGATTGAGAACTGGTACGGAGGGAGTC
||||::||++|::||:||||:||:||||||||||||||||:||||++|||||||+
TTATTTAGCGGTTAGTTAATGTTATTAAAGAGATGATTGAGAATTGGTACGGAGGGAGTC
```

```
GAGCCGGGCTCACTTAAGGGCTACGACTTAACGGGCCGCGTCACTCAATGGCGCGGACAC
+||:++|:|:|:|||||||:||+-|:||||++|:+++|:|:|:|||:++++|:|+
GAGTCGGGTTTATTTAAGGGTTACGATTTAACGGGTCGCGTTATTTAATGGCCGCGATAC
```

```
GCCTCTTTGCCCGGGCAGAGGCATGTACAGCGCATGCCCACAACGGCGGAGGCCGCCGGG
+:::|:|||::+-||:||||:||||:||++:|||:::|:||++|++|||:++:+-||
GTTTTTTTGTTCGGGTAGAGGTATGTATAGCGTATGTTTATAACGGCGGAGGTCGTCGGG
```

PRIMERS

MLH1MSHRMF1 (SEQ ID NO: 221)
GTC GAG TCG GGT TTA TTT AAG GGT TA
TM 65

MLH1MSHRMR1 (SEQ ID NO: 222)
ACATACGCTATACATACCTCTACCC
TM 64

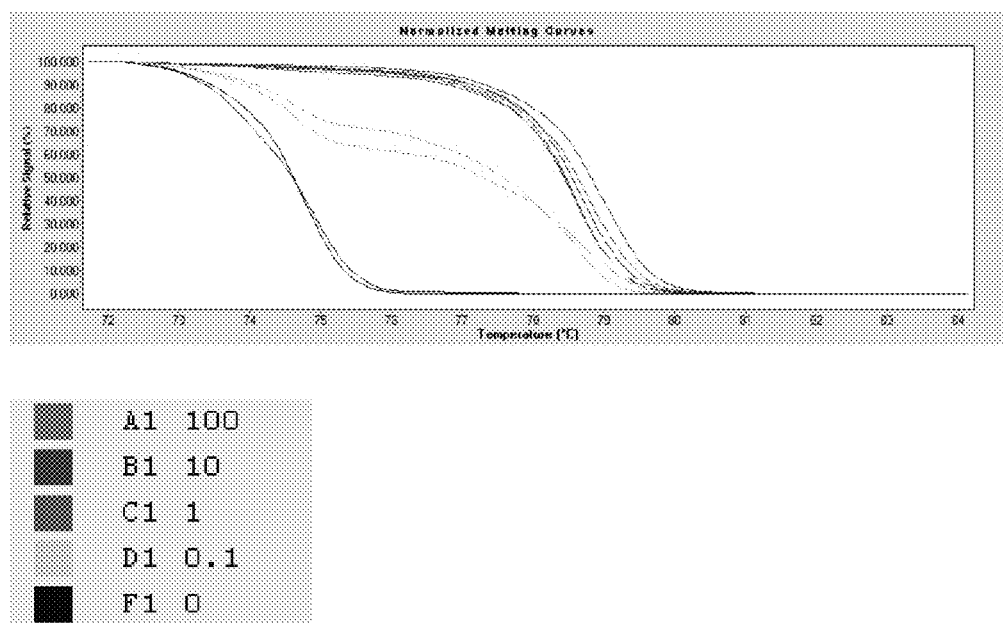

Target sequence genomic top (SEQ ID NO: 293)
After bisulfitemodification bottom (SEQ ID NO: 294)

```
721 AACTGGACCGGCGGCAGAAGCCGTGGAAGAGCTGGGCTGCCTGGCGCCGGAGGAGGGTGC
    ||:||||:++|++|:||||||:++|||||||:||||:||::||++:++||||||||||+
721 AATTGGATCGGCGGTAGAAGTCGTGGAAGAGTTGGGTTGTTTGGCGTCGGAGGAGGGTGC

781 GCGCGGCGGCTCCGGGCCGCGAGGAGCGCTGCGCCTGTGGGGTGTGCAGGCGCAAGTGTG
    ++++|++|:|:++||:++++||||++:||++::|||||||||||:|||+-:||||||
781 GCGCGGCGGTTTCGGGTCGCGAGGAGCGTTGCGTTTGTGGGGTGTGTAGGCGTAAGTGTG
```

Primers
PITX2MSHRMF1 (SEQ ID NO: 223)
F- AAGTCGTGGAAGAGTTGGGTTGTT
TM 64
PITX2MSHRMR1 (SEQ ID NO: 224)
R- CTTACGCCTACACACCCCACAAA
TM-65

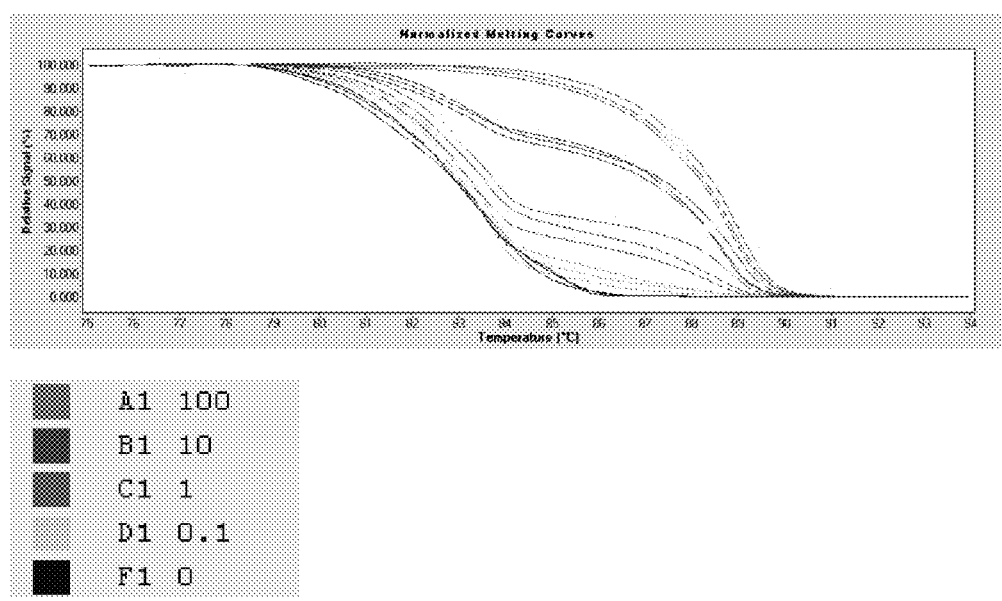

| | A1 | 100 |
| | B1 | 10 |
| | C1 | 1 |
| | D1 | 0.1 |
| | F1 | 0 |

Figure 28

Target sequence genomic top (SEQ ID NO: 295)
After bisulfitemodification bottom (SEQ ID NO: 296)

```
241 GGGTCTATTCTTTGCCAAAGGGGGGACCAGAATTCCCCCATGCGAGCTGTTTGAGGACTG
    ||||:||||:||||::|||||||||||::||||::::::||++|::|||||||||:||
241 GGGTTTATTTTTTGTTAAAGGGGGGATTAGAATTTTTTTATGCGAGTTGTTTGAGGATTG

301 GGATGCCGAGAACGCGAGCGATCCGAGCAGGGTTTGTCTGGGCACCGTCGGGTAGGATC
    ||||:++|||++++|++|:++|:||||||||:||||:|||:++|++||||||||:
301 GGATGTCGAGAACGCGAGCGATTCGAGTAGGGTTTGTTTGGGTATCGTCGGGTAGGATT

361 CGGAACGCATTCGGAAGGCTTTTTGCAAGCATTTACTTGGAAGGAGAACTTGGGATCTTT
    ++|||++:||++|||||:|||||||:||:|||:|||||||||||||:||||||:|||
361 CGGAACGTATTCGGAAGGTTTTTTGTAAGTATTTATTTGGAAGGAGAATTTGGGATTTTT
``` primers:
RARbeta2MSHRMF1 (SEQ ID NO: 225)
CGA GTT GTT TGA GGA TTG GGA TGT
Tm 64

RARbeta2MSHRMR1 (SEQ ID NO: 226)
AATACGTTCCGAATCCTACCCC
Tm 62

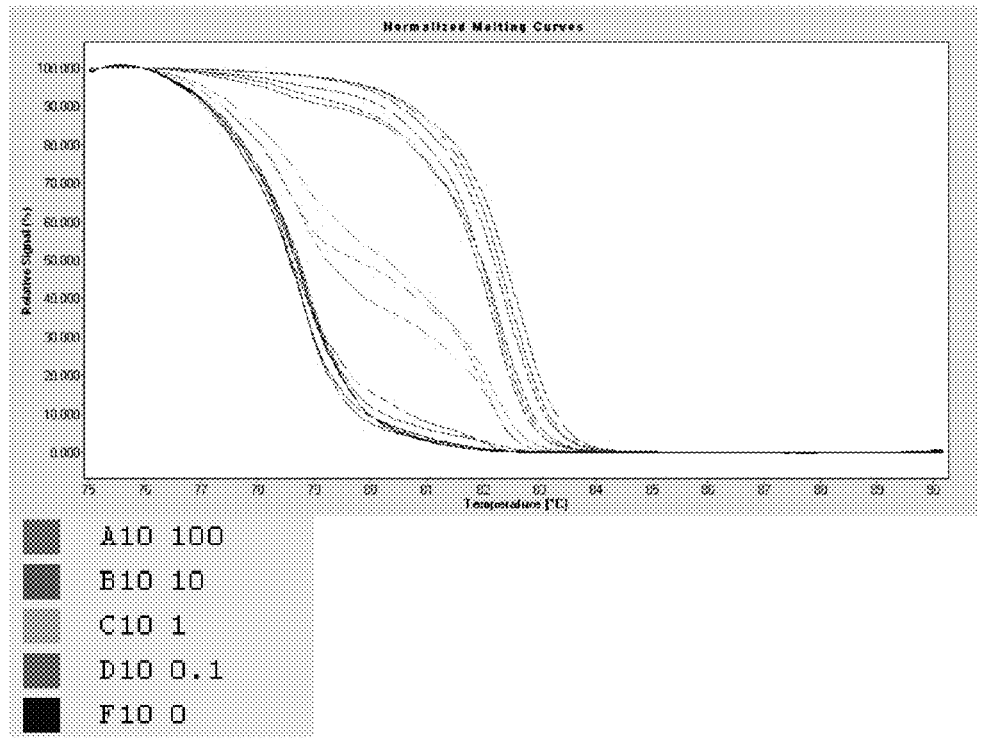

Target sequence genomic top (SEQ ID NO: 297)
After bisulfitemodification bottom (SEQ ID NO: 298)

```
361 AGGCGCGCGGGGCCACTACTCACGCGCGCACTGCAGGCCTTTGCGCACGACGCCCAGAT
    | | | +++++++ | | | :: | : | | | : | : | ++++++ : | : | | : | | | :: | | | | ++ : | ++ | ++ ::: : | | | |
361 AGGCGCGCGGGGTTATTATTTACGCGCGTATTGTAGGTTTTTGCGTACGACGTTTTAGAT

421 GAAGTCGCCACAGAGGTCGCACCACGTGTGCGTGGCGGGCCCCGCGGGCTGGAAGCGGTG
    | | | | | ++ :: | : | | | | | ++ : | :: | ++ | | | ++ | | ++ | ::: +++ | : | | | | | ++ | | |
421 GAAGTCGTTATAGAGGTCGTATTACGTGTGCGTGGCGGGTTTCGCGGTTGGAAGCGGTG

481 GCCACGGCCAGGGACCAGCTGCCGTGTGGGGTTGCACGCGGTGCCCCGCGCGATGCGCAG
    | :: | ++ :: | | | | | :: | : | | : | ++ | | | | | | | | | : | ++++ | | | ::: ++++++ | | ++ : | |
481 GTTACGGTTAGGGATTAGTTGTCGTGTGGGGTTGTACGCGGTGTTTCGCGCGATGCGTAG
```

```
primers:
RASSF1AMSHRMF1 (SEQ ID NO: 227)
GTT TTA GAT GAA GTC GTT ATA GAG GT
Tm 62

RASSF1AMSHRMR1 (SEQ ID NO: 228)
CCC CAC ACG ACA ACT AAT CCC TAA
Tm 65
```

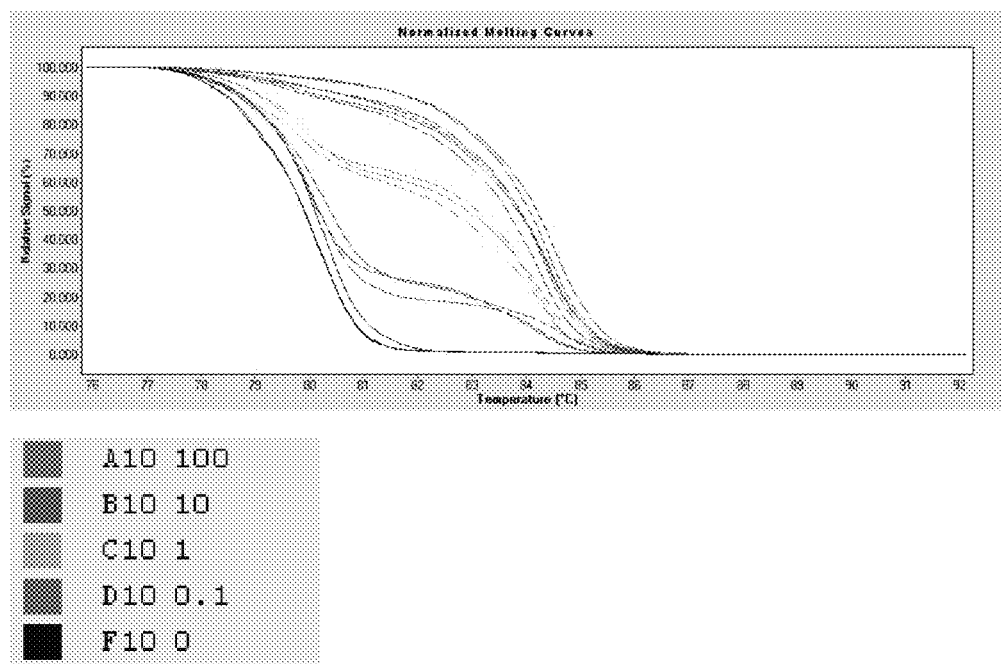

Target sequence genomic top (SEQ ID NO: 299)
After bisulfitemodification bottom (SEQ ID NO: 300)

```
601 CAGGTTCTCCAGCGCATCCAGGATGGCGTCGCGCGCGCCCCATGGCTCCAGGATCCCC
    :|||||:|::||++:||::|||||||-+|++++++++++::::||:|:|::|||||:::+
601 TAGGTTTTTTAGCGTATTTAGGATGGCGTCGCGCGCGTTTTATGGTTTTAGGATTTTC

661 GGCCGCTGCCGCCGCTCACCCCGCTGCAGCCGCCGACCAGGAGGAAGTCGGCTCCGGGGC
    +|:++:||:++:++:|:|:::+:|:|||:++:++|::|||||||||:|++:|:++|||+
661 GGTCGTTGTCGTCGTTTATTTCGTTGTAGTCGTCGATTAGGAGGAAGTCGGTTTCGGGGC
```

TMS1MSHRMF2 (SEQ ID NO: 229)
GCGCGCGTTTTATGGTTTTAGGATTTT
TM 65

TMS1MSHRMR2 (SEQ ID NO: 230)
CCGAAACCGACTTCCTCCTAATC
TM 65

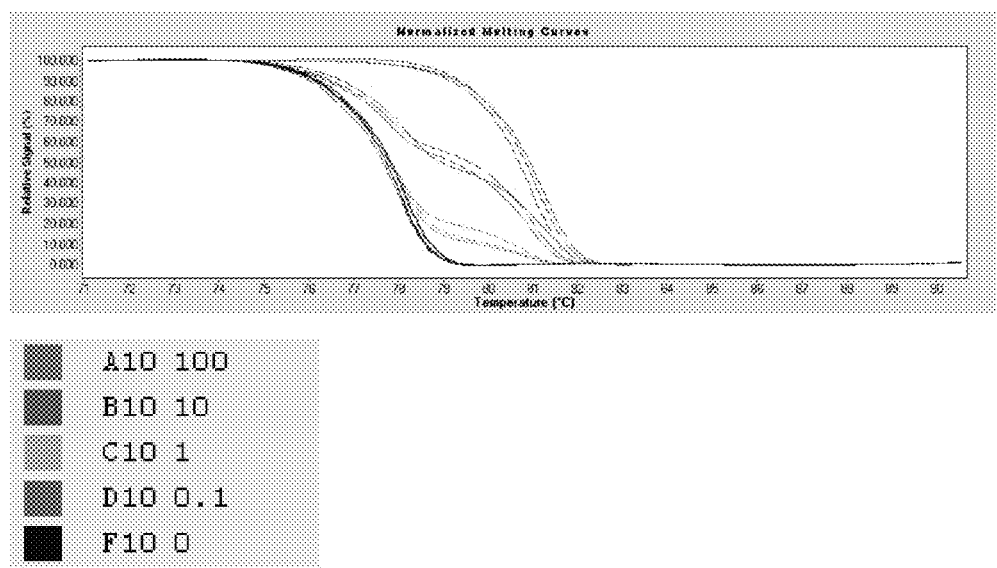

Figure 31

Target sequence genomic top (SEQ ID NO: 301)
After bisulfitemodification bottom (SEQ ID NO: 302)

```
TTGCTCAGCTTGTCCGAGGGCAGCGTGGGGATGATCTTCCGCAGCGCGGCGAACGCCTCG
|||:|:|||:||||:++||||:||++|||||||||||:||:++:||++++|++||++::|++
TTGTTTAGTTTGTTCGAGGGTAGCGTGGGGATGATTTTTCGTAGCGCGGCGAACGTTTCG

TTCAGCGACTGGGTGCGCTGGCGCTCCCGCACGTTGGCCATGACCCGCTGCGTCTGCAGC
||:||++:|||||||++:|||++:|::++:|++||||::||||::++:||++|||:|||:
TTTAGCGATTGGGTGCGTTGGCGTTTTCGTACGTTGGTTATGATTCGTTGCGTTTGTAGT
```

PRIMERS

TWIST1MSHRMF1 (SEQ ID NO: 231)
GAGGGTAGCGTGGGGATGATTTTT
TM 65

TWIST1MSHRMR1 (SEQ ID NO: 232)
CTACAAACGCAACGAATCATAACCAAC
TM 65

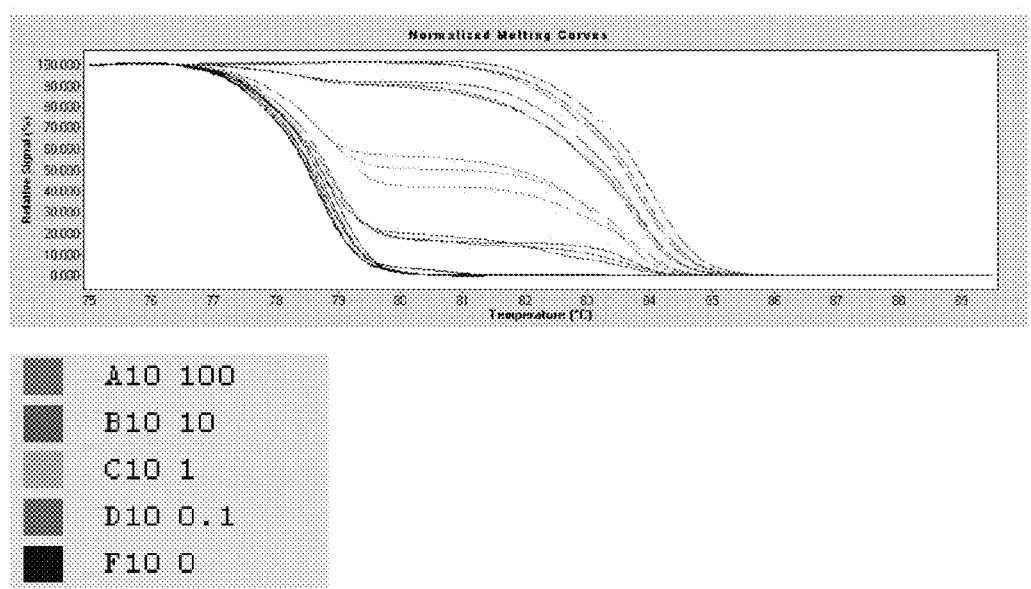

Figure 32

Target sequence genomic top (SEQ ID NO: 303)
After bisulfitemodification bottom (SEQ ID NO: 304)

```
301 GAGCGCTGCAAGACAGGGGAGGGAGCCGGGCGGGAGAGGGAGGGGCGGCGCCGGGCGGG
    |||++:||:||||:|||||||||||:++|:++|||||||||||||++|++:++|||++||
301 GAGCGTTGTAAGATAGGGGAGGGAGTCGGGCGGGAGAGGGAGGGGCGGCGTCGGGGCGGG

361 CCCTGATATAGAGCAGGCGCCGCGGGTCGCAGCACAGTGCGGAGACCGCAGCCCCGGAGC
    :::|||||||||||:|||++:++++||:++:||:|:|||++||||:++:|||::++|||:
361 TTTTGATATAGAGTAGGCGTCGCGGGTCGTAGTATAGTGCGGAGATCGTAGTTTCGGAGT

421 CCGGGCCAGGGTCCACCTGTCCCCGCAGCGCCGGCTCGCGCCCTCCTGCCGCAGCCACCG
    :++|::||||||::|::|||:::++:|++:++|:|++++:::|::||:++:|::|:++
421 TCGGGTTAGGGTTTATTTGTTTTCGTAGCGTCGGTTCGCGTTTTTTGTCGTAGTTATCG
```

PRIMERS

UPAMSHRMF1 (SEQ ID NO: 233)
GGG CGG GTT TTG ATA TAG AGT AGG
TM 65

UPAMSHRMR1 (SEQ ID NO: 234)
CTACGAAAACAAATAAACCCTAACCC
TM 65

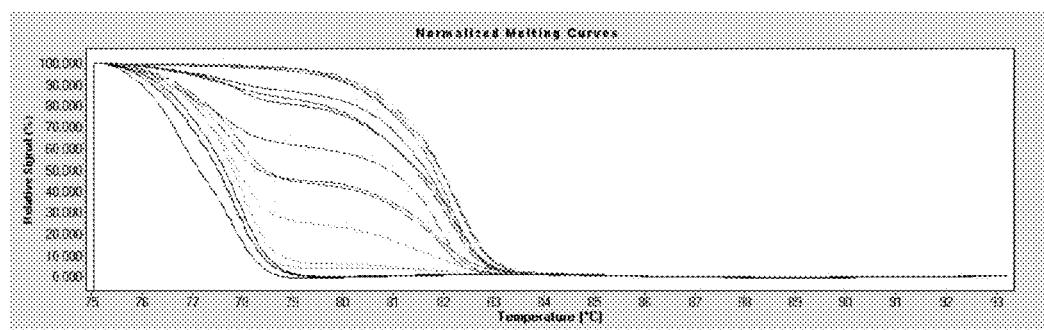

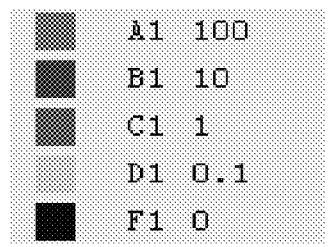

Figure 33

Target sequence genomic top (SEQ ID NO: 305)
After bisulfite modification bottom (SEQ ID NO: 306)
Primers in bold

```
TCGGGGCGGCGGGCGGCGCGGGCCGGGAGGGGGCGCCTCGGGCTCACCCCGCCCCAGGGC
|++|||++|++||++|++++||:++|||||||++::|++|:|:|:::++::::||||:
TCGGGGCGGCGGGCGGCGCGGGTCGGGAGGGGGCGTTTCGGGTTTATTTCGTTTTAGGGT

CGCCGGGCGGAAGGCGGAGGCCGAGACCAGACGCGGAGCCATGGCCGAGGTGTTGCGGAC
++:++||++|||||:||||:++|||::|||++++||::||||:++||||||++||+
CGTCGGGCGGAAGGTGGAGGTCGAGATTAGACGCGAGTTATGGTCGAGGTGTTGCGGAC

GCTGGCCGGTGAGTGCAGGCCTCGGCCCCGGGTGCCCGCGAGGGAGCCGCTACCG
+:|||:++|||||||:|||::|++|:::++|||::++++|||||:++:||:++
GTTGGTCGGTGAGTGTAGGTTTCGGTTTCGGGTGTTCGCGAGGGAGTCGTTATCG
```

PRIMERS
ABO MSHRMF pe59.9 (SEQ ID NO: 235)
TTCGGGTTTATTTCGTTTTAGGGT
TM 59.9
ABO bisa64mod pe59.5 (SEQ ID NO: 236)
GCAACACCTCGACCATAACTCC
TM 59.5

*The performance of the MS-HRM assay tested on the*
*mixes on methylated template (percentage*
*indicated in the legend) in 'normal' template background.*

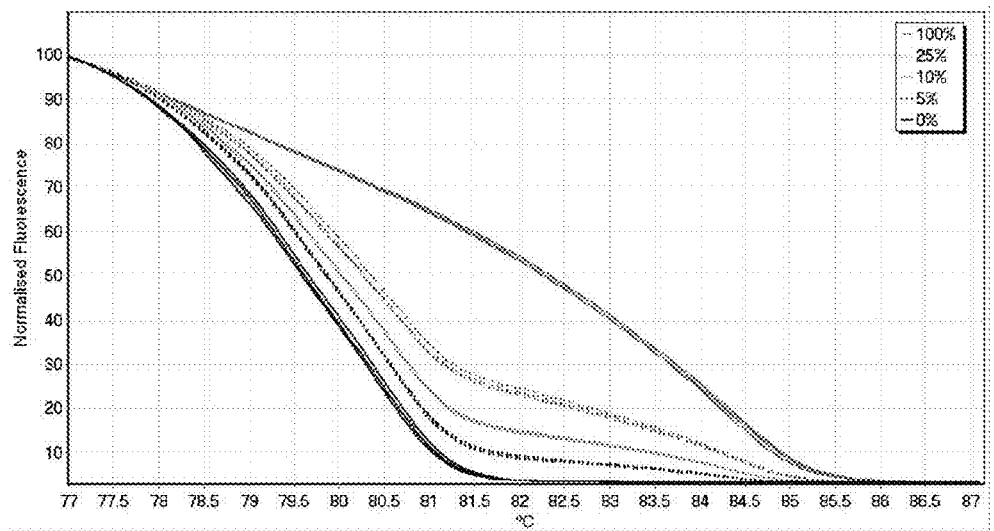

Figure 34

Target sequence genomic top (SEQ ID NO: 307)
After bisulfite modification bottom (SEQ ID NO: 308)
Primers in bold

```
TGCGGCCAGAGCGGCTTTGAGCTCGGCTGCGTCCGCGCTAGGCGCTTTTTCCCAGAAGCA
||++|::|||||++|:|||||:|++|:|++|:+++:||||++:|||||:::|||||:|
TGCGGTTAGAGCGGTTTTGAGTTCGGTTGCGTTCGCGTTAGGCGTTTTTTTTAGAAGTA

ATCCAGGCGCGCCCGCTGGTTCTTGAGCGCCAGGAAAAGCCCGGAGCTAACGACCGGCCG
||::|||++++:+:++:|||||:||||++::||||||||::++||:|||++|:++|:++
ATTTAGGCGCGTTCGTTGGTTTTTGAGCGTTAGGAAAAGTTCGGAGTTAACGATCGGTCG

CTCGGCCACTGCACGGGGCCCCAAGCCGCAGAAGGACGACGGGAGGGTAATGAAGCTGAG
:|++|::|  ||:|++|||:::::|||:++:||||||++|||||||||||||:|||
TTCGGTTATTGTACGGGGTTTTAAGTCGTAGAAGGACGACGGGAGGGTAATGAAGTTGAG
```

PRIMERS
p15MSHRMF3 (SEQ ID NO: 237)
gTtaggcgTtttttTTTagaagTaatTTagg
TM 59.7
p15MSHRMR3 (SEQ ID NO: 238)
tAcgActtAAAAccccgtAcaAtAAcc
TM 60.5

*The performance of the MS-HRM assay tested on the mixes on methylated template (percentage indicated in the legend) in 'normal' template background.*

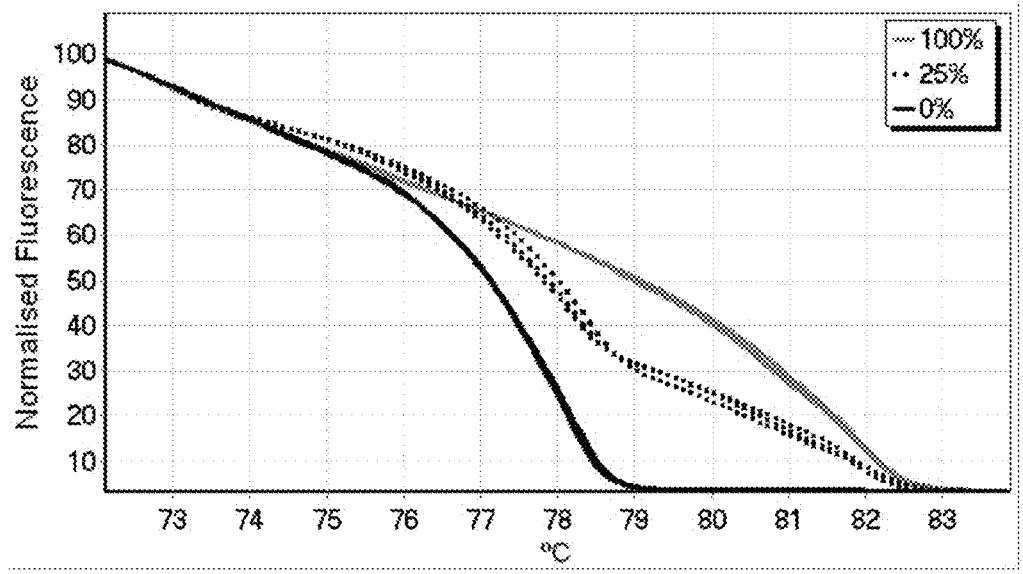

Figure 35

Target sequence genomic top (SEQ ID NO: 309)
After bisulfite modification bottom (SEQ ID NO: 310)

```
TCGGGCCCCACAGTCCCTGCACCCAGGTTTCCATTGCGCGGCTCTCCTCAGCTCCTTCCC
|++|::::|:|||:::|:|:::||||||::|||++++|:|:|::|:|:|::||::+
TCGGGTTTTATAGTTTTTGTATTTAGGTTTTTATTGCGCGGTTTTTTTAGTTTTTTTC

CCCGCCCAGTCTGGATCCTGGGGCAGG
+:++:::|||:||||:::||||||||
GTCGTTTAGTTTGGATTTTGGGGGAGG
```

PRIMERS
RASSF1A MSHRM F2 60 (SEQ ID NO: 239)
TCGGGTTTTATAGTTTTTGTATTTAGGTTTT
TM 60

RASSF1A MSHRM R2 60 (SEQ ID NO: 240)
CCTCCCCCAAAATCCAAACTAA
TM 60

The performance of the MS-HRM assay tested on the mixes on methylated template in unmethylated template background

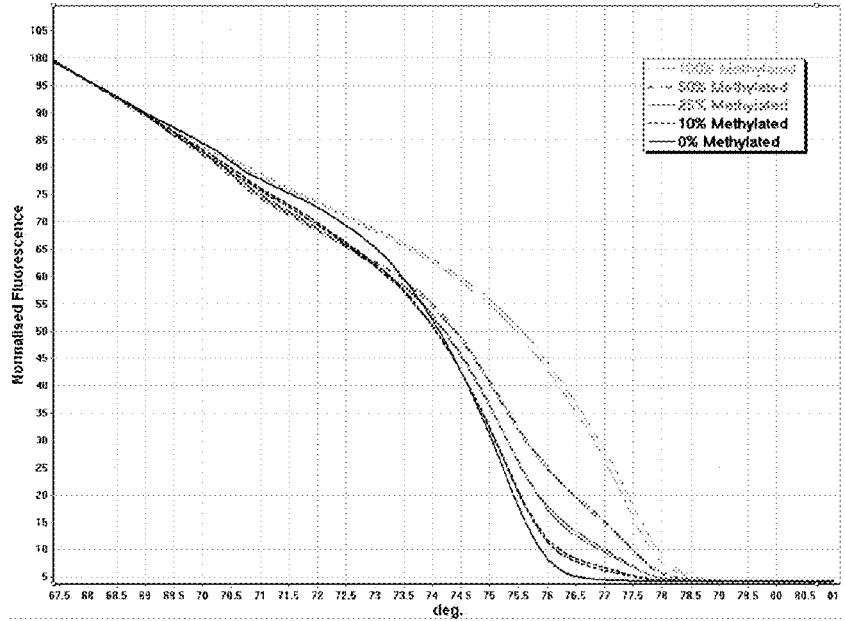

Figure 36
Target sequence genomic top (SEQ ID NO: 311)
After bisulfite modification bottom (SEQ ID NO: 312)

```
CGGGGCTTTAAAAATGTTGGTGCCCACCACCTCCCCGGAACAGGGCCCGCTCTA
++|||:||||:||||||||||||||::::|::|::|:::++||:||||::++:|:||
CGGGGTTTTAAAAATGTTGGTGTTTATTATTTTTTCGGAATAGGGTTCGTTTTA

CCTCGGTCGGGGAGCGCGGGACCTCAGCGTTCCCTTAACGCCACCGTCCGCGGGTCCGCT
::|++||++||||||++++|||::|:||++||:::||||++:|:++|:++++|||:++:|
TTTCGGTCGGGGAGCGCGGGATTTTAGCGTTTTTTAACGTTATCGTTCGCGGGTTCGTT

TTGCGCAGGCGCGGCGCCCCACTCAGTACCCGCTCCGGCGTGGCATGGTGCGCAGGCG
|||++:|||++++|++:::::|:|:||||::+:|:++||++||:||||||++:||++
TTGCGTAGGCGCGGCGTTTTATTTAGTATTCGTTTCGGCGTGGTATGGTGCGTAGGCG

CGATGTCCCCACTGCAGCCCCGCTCGACTCCGGCGTGGTGCGCAGGCGCGGTATCCCCC
++|||::::::|:||:||::++:|++:|:++|++||||++:|||++++||||:::::
CGATGTTTTTATTGTAGTTTCGTTCGATTTCGGCGTGGTGCGTAGGCGCGGTATTTTTT

CTCCCCCGCCAGCTCGACCCCGGTGTGGTGCGCAGGCGCAGTCTGCGCAGGGACTGGCGG
:|::::++:|||++|::++|||||||++:|||++:|:::|++:||||:|||++|
TTTTTCGTTAGTTCGATTCGGTGTGGTGCGTAGGCGTAGTTTGCGTAGGGATTGGCGG

GACTGCGCGGCGGCAACAGCAGACATGTCGGGGGTCCG
|||:||++++|++|:||:||:|||:|||++|||||:++
GATTGCGCGGCGGTAATAGTAGATATGTCGGGGGTTCG
```

SDHA MSHRM F 60.9 (SEQ ID NO: 241)
cggggTtttaaaaatgttggtgTT
TM 60.9
SDHA MSHRM R 61.8 (SEQ ID NO: 242)
cgAaccccegacatAtctActAttAcc
TM 61.8

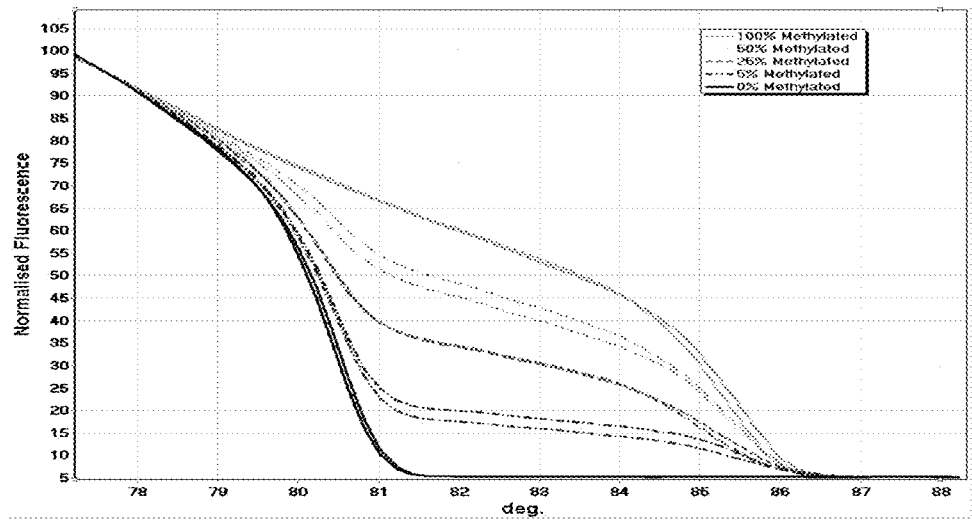

Figure 37

Target sequence genomic top (SEQ ID NO: 313)
After bisulfite modification bottom (SEQ ID NO: 314)

```
CGGGGGAAGCCAAATGGGCATGCGCCGCTACTGCGCTATTGCGCACGCTCGCTGTGCTTG
++:|||||||::|||||||:|||++:++:||:||++:||||||++:|++:|++:|||:|||
CGGGGGAAGTTAAATGGGTATGCGTCGTTATTGCGTTATTGCGTACGTTCGTTGTGTTTG

CCCCGCCTTCCCTCCGCCCACCCGGGAAACCGGAAGCCGCCTCCCACTTGGTTGCTCGTA
:::++::||:::|:++::|::++||||:++||||:++::|:::|:||||||:|++||
TTTCGTTTTTTTTCGTTTATTCGGGAAATCGGAAGTCGTTTTTATTTGGTTGTTCGTA

CGCGGCTAGTGGGTCCTCAGTGGATGTAGGCTGGGCG
++++|:|||||||||::|:||||||||||||:|||++
CGCGGTTAGTGGGTTTTAGTGGATGTAGGTTGGGCG
```

PRIMERS
SDHB MSHRM F pe60.2 (SEQ ID NO: 243)
cgggggaagTTaaatgggTatg
TM 60.2

SDHB MSHRM R pe59.8 (SEQ ID NO: 244)
CGCCCAACCTACATCCACTAAA
TM 59.8

The performance of the MS-HRM assay tested on the mixes on methylated template in unmethylated template background

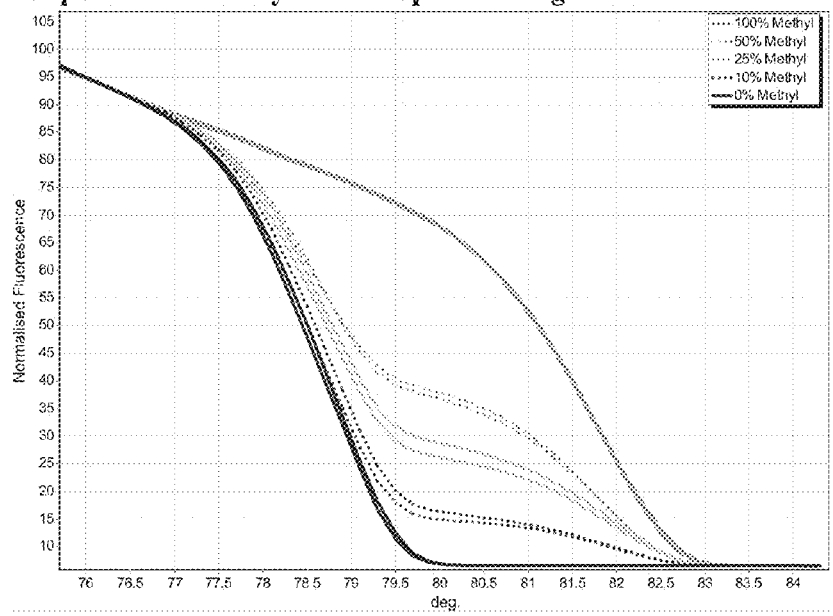

Figure 38

Target sequence genomic top (SEQ ID NO: 315)
After bisulfite modification bottom (SEQ ID NO: 316)

```
TCGTCACATGACACCCCAACCCCGACCCCAGCCGGCGCGCCTCCGCCCTCGGGTGGCG
|++|:::|:|||:|:::::||:::++|:::::||:++|++++::::++::::|++||||++
TCGTTATATGATATTTTTAATTTCGATTTTAGTCGGCGCGTTTTCGTTTTCGGGTGGCG

GGGCCGCCTGGCGTCACTTCCGTCCAGACCGGAACCCAAGAT
|||:++:::|||++|:|:||:++|:::|||:++||:::|||||
GGGTCGTTTGGCGTTATTTTCGTTTAGATCGGAATTTAAGAT
```

PRIMERS
SDHC MSHRM f58.8 (SEQ ID NO: 245)
tcgtTaTatgaTaTTTTTaaTTTcgaTTTTTagT
TM 58.8

SDHC MSHRM r58.9 (SEQ ID NO: 246)
atcttAAAttccgAtctAAacgAaaAtAac
TM 58.9

The performance of the MS-HRM assay tested on the mixes on methylated template in unmethylated template background

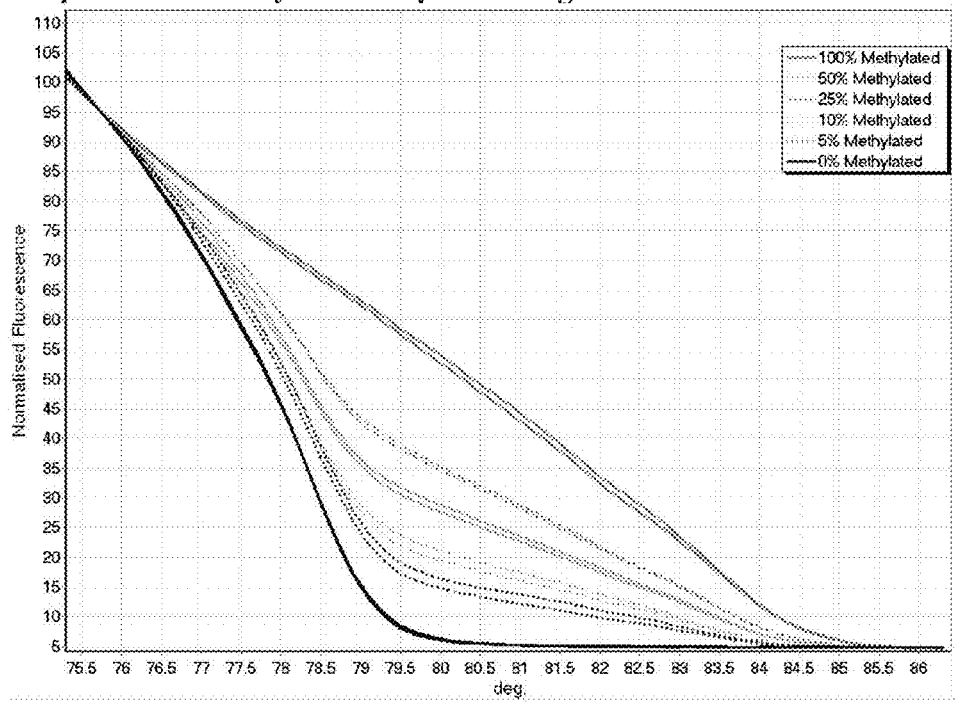

Figure 39

Target sequence genomic top (SEQ ID NO: 317)
After bisulfite modification bottom (SEQ ID NO: 318)

```
CGGGTTGGTGGATGACCTTGAGCCCTCAGGAACGAGATGGCCGGTTCTCTGGAGGCTGAGT
++|||||||||||||::||||:::|:||||++|||||||++|||:|:||||||:|||||
CGGGTTGGTGGATGATTTTGAGTTTTTAGGAACGAGATGGCCGGTTTTTTGGAGGTTGAGT

GCCGTTTGCGGTGCCCTAGGAGGCCGAGGTGAGG
|:++||||++|||:::||||||||:++|||||||
GTCGTTTGCGGTGTTTTAGGAGGTCGAGGTGAGG
```

PRIMERS
SDHD_MSHRM f62.2 (SEQ ID NO: 247)
cgggttggtggatgaTTttgag
TM 62.2

SDHD_MSHRM r61.1 (SEQ ID NO: 248)
cctcacctcgAcctcctaAAAcac
TM 61.1

The performance of the MS-HRM assay tested on the mixes on methylated template in unmethylated template background

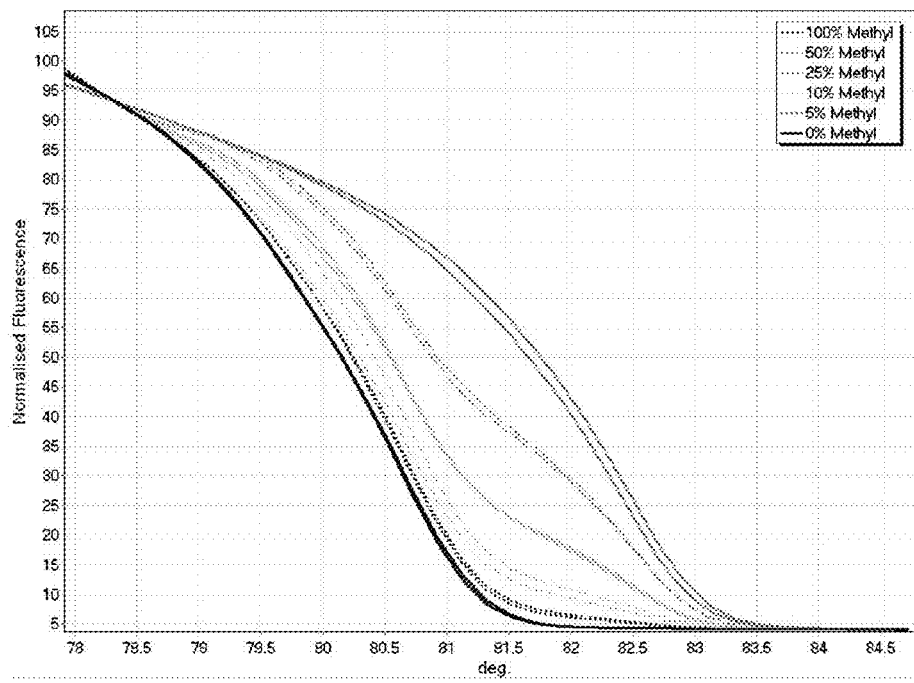

Figure 40

Bisulfite translated sequence
Target sequence genomic top (SEQ ID NO: 319)
After bisulfite modification bottom (SEQ ID NO: 320)

```
CGCGTGAGGACAGCGGCCGCACCCCGACACTGCTGTGGGCCCTCGGTGTGGAGGCCTGTG
+++|||||:||-+|:+-:|::++|:|:|||||||:::|++|||||||::|||
CGCGTGAGGATAGCGGTCGTATTTCGATATTGTTGTGGGTTTTCGGTGTGGAGGTTTGTG

GGCGTCCAGGCCACGCCCGAGACCAGCCCCTCCGCCGGCGCCGCTGCAGCGACCCTCGAA
||++|::|||::|++:|++|||::||::::|:++:++|++:+:|||+|:::|++||
GGCGTTTAGGTTACGTTCGAGATTAGTTTTTCGTCGGCGTCGTTCTAGCCATTTTCGAA

CCCGGGCAAGGTCTCCACCGCCGTGGCACCGGGTGCGGGAGGCGTTTCCCCCCTCCCAG
::++|::|||::::|:-+:++||:|:++|||++||||++||::::::|::::|
TTCGGGTAAGGTTTTTATCGTCGTGGTATCGGGTGCGGGAGGCGTTTTTTTTTTTTTAG
```

Primers sequence

LIT1MSHRM-R (SEQ ID NO: 249)
CCACGACGATAAAAACCTTACCC

LIT1MSHRM-F (SEQ ID NO: 250)
GTTTAGGTTACGTTCGAGATTAGTTTTTT

*The performance of the MS-HRM assay tested on the mixes on methylated template in unmethylated template background.*

*Normal tissue - dotted line*
*Fully methylated control – solid line*

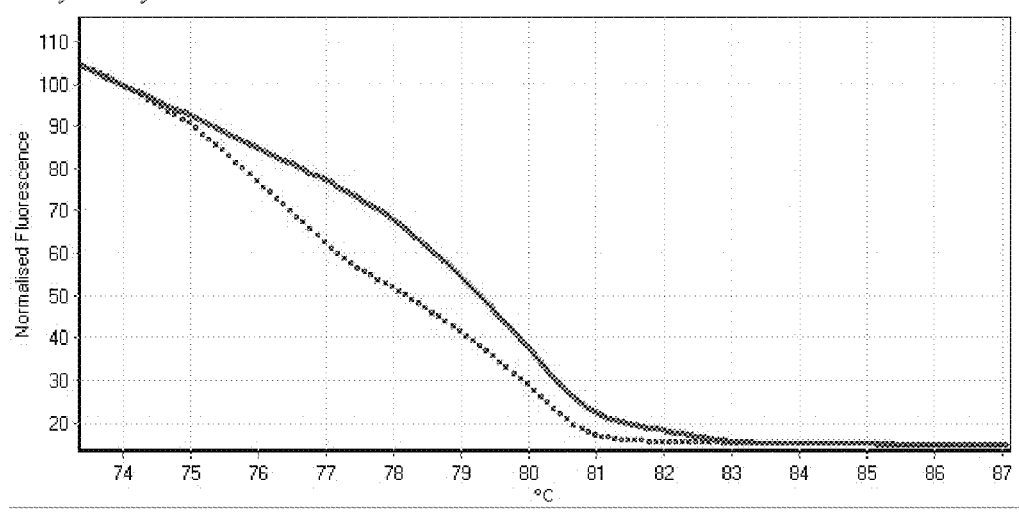

Figure 41

GENOMIC SEQUENCE (forward strand) SEQ ID NO: 251
CGTTTGCGACTTGGTGAGTGTCTGGGTGCCTCCTCCCGGAAGAGTGCGGAGCTCTCCTCGGGACGGTGGCAGCTCGAGTGGTCCTGCAGG
METHYLATED STRAND           SEQ ID NO: 252
CGTTTGCGATTTGGTGAGTGTTTGGGTCGTTTCGTTTCGGAAGAGTGCGGAGTTTTTTTCGGGACGGTGGTAGTTTCGAGTGGTTTTGTAGG
UNMETHYLATED STRAND         SEQ ID NO: 253
CGTTTGTGATTTGGTGAGTGTTTGGGTTGTTTTGTTTTGGAAGAGTGTGGAGTTTTTTTTGGGATGGTGGTAGTTTTGAGTGGTTTTGTAGG Figure 43
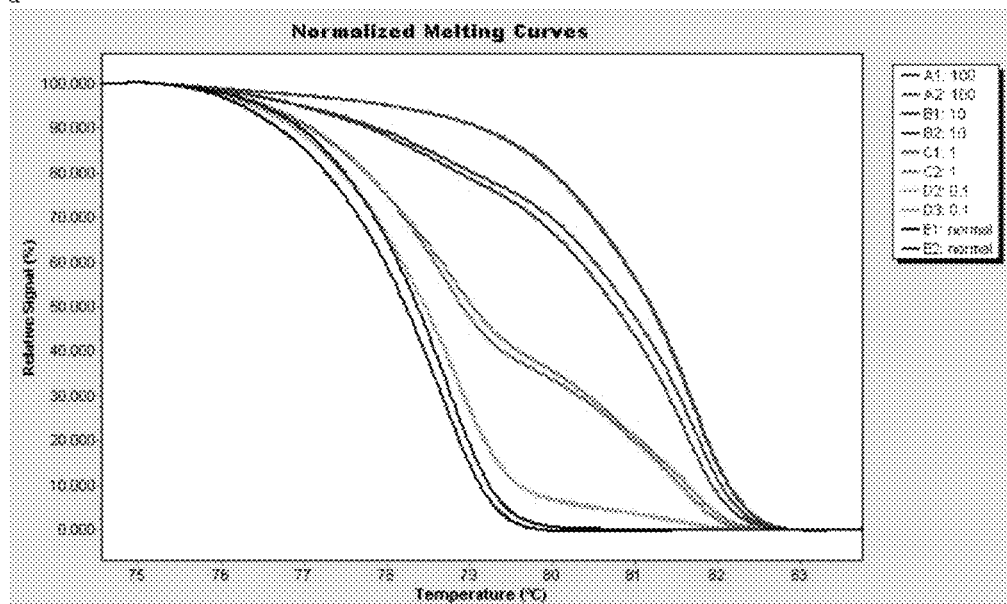
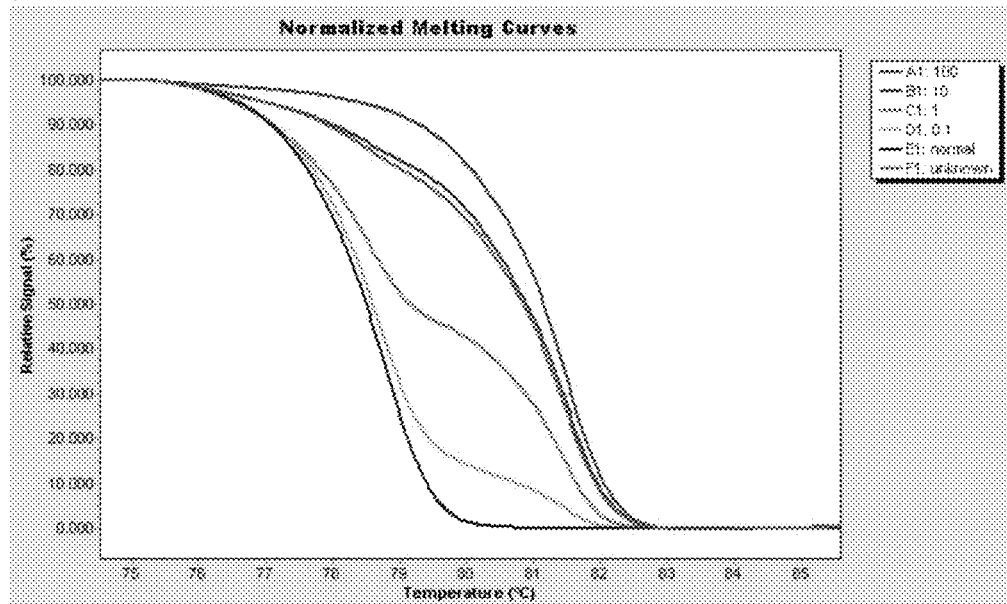

SEQUENCE LISTING

```
<160> NUMBER OF SEQ ID NOS: 320

<210> SEQ ID NO 1
<211> LENGTH: 1710
<212> TYPE: DNA
<213> ORGANISM: Homo sapiens

<400> SEQUENCE: 1
tgaaagagtg agacccatc tccaaaacga acaaacaaaa aatcccaaaa aacaaaagaa      60
ctcagccaag tgtaaaagcc ctttctgatc ccaggtctta gtgagccacc ggcggggctg     120
ggattcgaac ccagtggaat cagaaccgtg caggtcccat aacccaccta gaccctagca    180
actccaggct agagggtcac cgcgtctatg cgaggccggg tgggcgggcc gtcagctccg    240
```

```
ccctggggag gggtccgcgc tgctgattgg ctgtggccgg caggtgaacc ctcagccaat      300
cagcggtacg gggggcggtg cctccggggc tcacctggct gcagccacgc accccctctc      360
agtggcgtcg gaactgcaaa gcacctgtga gcttgcggaa gtcagttcag actccagccc      420
gctccagccc ggcccgaccc gaccgcaccc ggcgcctgcc ctcgctcggc gtccccggcc      480
agccatgggc ccttggagcc gcagcctctc ggcgctgctg ctgctgctgc aggtaccccg      540
gatcccctga cttgcgaggg acgcattcgg gccgcaagct ccgcgcccca gccctgcgcc      600
ccttcctctc ccgtcgtcac cgcttccctt cttccaagaa agttcgggtc ctgaggagcg      660
gagcggcctg gaagcctcgc gcgctccgga ccccccagtg atgggagtgg ggggtggggtg     720 gtgaggggcg agcgcggctt cctgcccccc tccagcgcag accgaggcgg ggcgtctgg       780 ccgcggagtc cgcggggtgg gctcgcgcgg cggtggggg cgtgaagcgg ggtgtagggg        840
gtggggtgtg agaagggggt gccctggtgc aagtcgaggg ggagccagga gtcgtgggga     900
cgatcttcga gggaaggaga ggggcatccg tagaaataaa ggcacctgcc atgccaagaa      960
aggtcgtaaa taggagtgag ggtcccgggg ataagaaagt gaggtcggag gaggtgggag      1020
cgcccctcgc tctgaggagt ggtgcattcc cggtctaagg aaagtggggt actggagaat      1080
aaagacatct ccaataaaat gagaaaggag actgaaaggg aacggtgggc taggtcttga     1140
gggggtgact cggcggcccc ctcccggag ttcctggggg ctcggcggcc gtaggtttcg       1200
gggtggggga gggtgacgtc gctgcccgcc cgtcccgggg ctgcgggctg ggtcctccc      1260 ccaatcccga cgccgggagc gagggagggg cggcgctgtt ggtttcggtg agcaggaggg     1320
aaccctccga gtcacccggt tccatctacc tttcccccac cccaggtctc ctcttggctc     1380
tgccaggagc cggagccctg ccaccctggc tttgacgccg agagctacac gttcacggtg    1440
ccccggcgcc acctggagag aggccgcgtc ctgggcagag gtgagggcgc gctgccggtg    1500
tccctgggcg gagtagggag ggggttggaaa ggggccgaga aattgcactc ccacacccct   1560
gggttgcaat gggcaagctc cctccttggc tcaaacgaca ccccttggaa tttacgcaga    1620
tttggggatc caaacgttta cgactgaaca ctgtggtgga gggggtaacc ctgcctggtt    1680
gttgactatg ttataaagaa gaggaggttg                                         1710

<210> SEQ ID NO 2
<211> LENGTH: 1171
<212> TYPE: DNA
<213> ORGANISM: Homo sapiens

<400> SEQUENCE: 2
agtatcatct atccctattt aggaggtgag agtgtctcag atcggttaag taactggctc      60
ataatgatca gtgcttgtgg gaaagctgga atatccacgg agttctttcg aactctagcg      120
gtccaagctc tttcccaagt cacgtagctt ctctattcgg agagaagtcg gagtactggg     180
atagacccag gaggtcagag cggaaactct gcccgggtgc gtggaaccgg agtccccggt    240
gcgcggcgcc aggtactcac ctgtatggct gagcgccagg accgcgcaca gcagcagggc   300
gcgggcgagc atcgcagcgg cgggcagggc gcggcgcggg ggtaggcttt gctgtctgag   360
ggcgtctggc tgtggagctg aaggaggcgc tgctgaggag ttcctggacg tgctcctgac   420
gctcactgca agtcgtatga caattggtcg ctaaccgaga gaaccttcct ttttataaga   480
ctgaaaacca agcccatgtg acgaaatgac tgtttctttc cgccttttcg taccccccac    540
aaatttttcc ctcctctccc cttaaaaaaa ttgcgtaagc ccggtggggg cagggttttt    600
```

| | |
|---|---|
| tacccacgga aatgagaaaa tcggaaaccc aggaagctgc cccaatttgg gagcagaggg | 660 |
| ggtagtcccc actctcctgt ctgatccctc cctctcctcc ccgagttcca ccgccccagg | 720 |
| cgcacaggtt tccgccagat gtcttttctt cttcgcagtc tttgcccgag cgcttccgag | 780 |
| agccagttct ggactgatcg ccttggatgg gataccgggg gagggcagaa ggacacttgg | 840 |
| cttcctctcc aggaatctga gcggccctga ggtccggggg cgcagggaat cccctctccc | 900 |
| gccgccgccg ccgtgtctgg tctgtacgtc tttagagggt cgaggaagtc acgtcgggac | 960 |
| agactggggc gagtaaggtt aagaaaggct gacatgtttt atgttttagt gacgacgctt | 1020 |
| aataggctgt atatctgctc tatatgcagc acatacatac atagcttttt aaaaaactct | 1080 |
| tattttgtgg aatgaaatag ctaccttcag tgtacatagc tgtaatttat ctttgtagct | 1140 |
| aagttgcttt caacagaaga aatactgttc t | 1171 |

<210> SEQ ID NO 3
<211> LENGTH: 1041
<212> TYPE: DNA
<213> ORGANISM: Homo sapiens

<400> SEQUENCE: 3

| | |
|---|---|
| aacactcttc agagccacag cctgtgctcg ggctcctcgc cgcctcccag gccctgcgat | 60 |
| ctctttgcat cccaggaggt cccggttggt tgcagtcctc ctgggtgact caggaaccag | 120 |
| cctctcctga agcacacagc ctaggagtt cctggggcca gagacatctc caagggaagg | 180 |
| tcaagggcct ggaggatgtg cggacctgac gacagatgcc ccgcacgctg gccgggaccg | 240 |
| ggaagggcg tcaagtgtgg aaagggtctg gcggctgcca ggcctggcag agtggagcgg | 300 |
| ggcggggcgc agcggggcgg ggcgggcctg gagctgcacc cgcttctggg tggacgcact | 360 |
| tggcgagcgc gcgggatgc agacggctgc gaggcgctgg gcacaggtca gacgtcagta | 420 |
| cccgcagggg gcttgaaact ggaggagggc tcgaagggag agggagcccc gccaaggagc | 480 |
| ggggctgtga tggagagggg gttccgactc gcatgggacc tgcggggag ggtacgcgga | 540 |
| cagggagggg ataccgactg ggaggggctc agggacaggg atggaggctc ctctagggga | 600 |
| ggacgggagg ggatgagggg ccctggtgtc gcagaagccc acctgggggcc cctccgggc | 660 |
| tgcggcaccg atgcgcacac tactcccacc gcccccgagt gcctatgtcc ggctggccgc | 720 |
| ggccctggaa tgaatattgc tcagtccccc gcgagtcagg tctgccgcgt tgcagggtga | 780 |
| ggggaaggtg tgaagccccg ggcctccgtc tgccccgtga gtccgggaac gcgcgccccc | 840 |
| gtggatgcca cctggcccct gagctgtgtc cagtcacagc tcacatagct ctgggcactg | 900 |
| gtaccccgac tgcctttcct tgttagctgc gatacacaaa tacatgagcc agatcctttc | 960 |
| ctgaggccag gaagcctgga atctaataac attgggcggt ggataaagtc ccccgatcca | 1020 |
| gtgcttagct tccgttaatg g | 1041 |

<210> SEQ ID NO 4
<211> LENGTH: 1121
<212> TYPE: DNA
<213> ORGANISM: Homo sapiens

<400> SEQUENCE: 4

| | |
|---|---|
| ccaagccgtg cctgccctgc cctgccctgc cctggttgcg ggagcacaga tgcaggctgt | 60 |
| gcaggagtgc ggtggggccg ggctgggtgt ggaggcctca cctggcttgg ctgccgactg | 120 |
| aggagggggcc tggatcccag ctggcgcggc tccagagcct ggaaggatat gggccaagtg | 180 |
| atccccttcc cttcccttcc cgccgtgggg ccggggtccc gttggtcggt aggccaagcg | 240 |

-continued

| | |
|---|---|
| tggggagcct cctttccggt agagcagctt tgtttagggg taggaggaac agaaagcgga | 300 |
| agagcccgcg gggtaagcgc tggtgtgggt ggaggggaaa gacggggtgg aggggaacgg | 360 |
| gggcggctca ccctggtgcg tggccgcctg cagctgcccg gccatctcct gcaggcccat | 420 |
| gtcgcgcagc acgttagcgg tgagctcggc gccgtaggtc tccaggtaga agctgaccag | 480 |
| cttgtcggtg aggtccaagg cgtccatgga cagcagcgcg ccccgcggga tgcgcccgta | 540 |
| gccctcgcgc agcggcaccg acagcagctt cagcttgaac ttcttgagct cctcggcggt | 600 |
| caggttctcc agcgcatcca ggatggcgtc gcgcgcgcgc ccatggctc caggatcccc | 660 |
| ggccgctgcc gccgctcacc ccgctgcagc cgccgaccag gaggaagtcg gctccggggc | 720 |
| ggaacctgga ctccccgcct tcctcccact ctggtctccc gactcccgc cccggtccgt | 780 |
| tgccctccag caaaaggcgc ttccttacta caccccttggt cccctcccac ccaggcctct | 840 |
| ggattgggc cccaggccgt cggggacgc caggatcgcg ccctccagct ggcctgcgag | 900 |
| gtgggacccg ggaggggcc gcagaggggc tcatgggtgg cgcctgcttg tctctgggct | 960 |
| tgcaccagcg ggtacagacc ggaaacctgg gctggctctc actgggttta ttggagcacc | 1020 |
| taggcttaga acctcggatt tctagaaccc cgaaacctcc gcggttcccc gaaccttagg | 1080 |
| atcctctccc acatgtcgta gaatcttgga atcatgacag c | 1121 |

<210> SEQ ID NO 5
<211> LENGTH: 2046
<212> TYPE: DNA
<213> ORGANISM: Homo sapiens

<400> SEQUENCE: 5

| | |
|---|---|
| agattctgca atctcagatt tcagagttgg agtcgtcagg ggaagtggcg tcagcagctg | 60 |
| gcgtgatcca attcaataaa ccagaggtgg cttgggatag acaactgacc gggtgcagac | 120 |
| ccccgcccct caatctctgc atttcctgca cgctctgggc accctgggag gccccggctc | 180 |
| catccccat tccagctctc cgcgaggagg ggtcgggttt cctgtggcgc cttccacgcg | 240 |
| cctcctccag gccagctccc cacccggccg tgggctccca agccagtgc cgccacccgc | 300 |
| tccccggccg ccggaaacgc taagcccctg ctggggcgag ggcacctcct tgcggggtgc | 360 |
| gtagccctgg gctcccggtg gggcgggct gggcgggagc ttccaggccg caggcacctc | 420 |
| tcgggaaagg aaacccaatc cctccttcgg cccacggaga acgaaagtgg agaagcagtg | 480 |
| ggaaggaagg aactgtgggt gccggttcga gaagcagcct tgggagtccg ggggaatagt | 540 |
| gtccccaggg gcagagggac atactccctc tcgccccgag cgccggccca gcctaggttg | 600 |
| cctgcatggg cctggagagc tgagggtcac cacctggcct cccagcctcc cggcccttgg | 660 |
| cctccaaagc ggggtagcct ggagcgcgcg cctgagaaga gcctggagca gggccggcca | 720 |
| ctgctgtgca gccgagccac gaaggtgcaa agcggggccc tgtcctgccc cggccgggtg | 780 |
| tggggagaca gaggacgcaa acctaagagg gcacccagag cgccgggaa cgcagcctgg | 840 |
| ggacctcgaa gcccctcgaa agcgctcctc tagaggtgac agcaccagat cctggcgaag | 900 |
| gaccaggccc cggggtcgga ggatagggg acaggtggcc ggggctccgc ggcggctggg | 960 |
| actccgcggc tgctggggct ccggctcgct caccttctcc tgcgcgcggg tgagcttctt | 1020 |
| ctgcacgttg ctggcgatct ttcccgccgt cacccctta ctgcccatct ctgccatcgc | 1080 |
| ggcgcaggcc tcgcccggtg gcaggggccg ctctcgcgcg gggagatctt gcgcgccgcg | 1140 |
| ctcccagccc ccagccccgg ccgcgcgtcc agaccggctg ccgctccacg ccgcgcaccc | 1200 |

```
gacagcggag ccaactgacg gaggcggagc gtgcgccgga cgggcgagcg agccagcgag   1260
ctagccagcg agcgacgcgg ggacagaggg agggagaggg gaggggccgg gcctcaggcc   1320
gcggtcggcg ccccccgccc gcccccctccg dacaataagc tgcctttta agggccactc   1380 cgggcgccgg caccgccagg tccgcgagga gggaggggcg cgcgcggcgc tggggctgcg   1440
gcgagcggga ctcccctgac gctccagctg caccgccccg gggcggggac taatccgccg   1500
gcctggcgtc ttggtcttcc ccgcaagcag taatctcctg caacccagga aaggagacta   1560
ggtggaggag aggagtgctt tcgaaatcaa agagaaagtg cggcgaaggg ggcgcggccc   1620
tgaacagagg agccgcggct gctgggagaa cgcgcccgga gccccctcct tttccagggg   1680
ctcacctccc gcccggtgcc cggtgcccgg tgcccgacgc tccgcctcct cccagccttc   1740
ggccctcggg ttttcgcccg gatacccctag gcgcctccgg gacatctcca catctttgcc   1800
tacggcgcct agcccagtac caaccggtgc ttggtcttcc cgttcgctaa aaatttatta   1860
taataacaac aacctagcat tactgagtgc ttactgtgta ctaagtgact tgacaggcat   1920
tatttcattc ggtctccgtg gccctagagg taggtgctat tactgttcct actttacaac   1980
caacgcgccg ggatcgagga acgagatctc tgcctctgtc tcccaggtgc tccaccacca   2040
tacgcc                                                              2046

<210> SEQ ID NO 6
<211> LENGTH: 726
<212> TYPE: DNA
<213> ORGANISM: Homo sapiens

<400> SEQUENCE: 6
tctcacggaa atccagtgga tagattggag acctgtgcgc gcttgtactt gtcaacagtt    60
atggactgga gtgttatgtt ttcgtatttt gaaagcagaa actaggcctt aaaaagatac   120
gtacaactct ttagggagac tacaattccc atccagcccc aggagtctgg ggcaagtagt   180
cttgtaaggt cagtggcctg cggggacgca gtgagcgccg aatttgcctg ggcaggggaa   240
aatgcgctct ggcccatgtc tgcgcactcg tagttccacc cctcagcccc agtgtttgtt   300 attttttcggg ttcagcttgc ttttgccccg ctccgtcga cgcaatcgcc accagtcaat   360
ggggtggtcg ttttgaggga caagtggtaa gagccaatct tcttggcgaa aacgcggaga   420
aacgggacta gttactgtct ttgtccgcca tgttagattc accccacaga gatagcggca   480
gagctggcag cggacggtct ttgcattgcc gcctccccag ggggcgggaa gctggtaagg   540
aagcagcctg ggttagctag gggtgggggtc acgtcacact aagagggttt ggagaagttc   600
aagggaggaa tcctgcaaag aagaggggcg acttttttccg tgtctccgga cagctaatcg   660
ttttagtgac aggatgagag agcccttcgt gttctgaggg accgagtggg cgaaaagcgc   720
cggaga                                                              726

<210> SEQ ID NO 7
<211> LENGTH: 1788
<212> TYPE: DNA
<213> ORGANISM: Homo sapiens

<400> SEQUENCE: 7
actggagact tgcatttcac aaacgggttt gctccaggcc gcactccatc cccgagggaa    60
agctccccag aagttctgga gttgggctga aggatgtgat ggcaagatgt gaatgatgtc   120
agaatcccca tctccagagt ccggctgggg agctaagcgc aggtgagctt acatcagaag   180
agaaagccaa accccccaca cgtcgctaaa ctagggcacg ggaatggcgt gttatgcaac   240
```

| | | | |
|---|---|---|---|
| ggccgccgtt | cgcgtggcca | cgaaagcgct cctgcgcctc | gggccgcgtc cgccaagac | 300 |
| cgtgagcaaa | ctcgcagagt | tggcgcggca gccggccggg | agacgccgag cagggcctgg | 360 |
| ccgcccgcag | cccgggagga | acggcgcccc caggtccgg | tggcctctga ggggctgact | 420 |
| ggcccgtgag | ccggcggcgc | ggccgcgggg aacggggtgg | gaaccgcgcg gcagtgggtg | 480 |
| aggcggcgca | gccaccgggg | gctgagggc ggcgcggcct | cgactgcggc accgccgtgg | 540 |
| gtccgtcggc | tcgcgggacg | acggggcggc cggcgggggc | caacagggcg ggctctgaag | 600 |
| gactgattgg | cccgtgggac | gatggcgcgg ccgggaggat | ggccccggat ccgtgggacc | 660 |
| gctgcgccgc | cggaccgggg | gtcccgaggc tgtcaggggc | gcccggccgg gcgtctagtg | 720 |
| aaaagccgat | cccccggaga | cagcggaagc agaggcgcgc | ccggcgctac ggcctttcgg | 780 |
| gtctaggaca | ccgcccccgg | cccgcgccgc ccctgccccg | ccgggatccc ggccgccccg | 840 |
| gtcgccgcac | aacaaagcgg | cgcagccccg ctgcccccgc | ccgacgccgg cctccaactt | 900 |
| ccccggctcc | tctggaaccg | gctccgcggg ctccgtacgg | cctggactac gagccgccgg | 960 |
| gcggggggcgg | ctccgggcgg | gcgcggaccg tgggggcagg | gcgcagggct ccgtccggac | 1020 |
| aaacttcctc | ggccgccccg | ccgggcgccc ttcccggagc | ctcggcacca cagtaggtgc | 1080 |
| gcggagccgc | agggctcgac | cgcttcgcgg aaactctcgc | caccctccga gctgccgccc | 1140 |
| cgaccccagc | tccagccccc | ctcacctcca ggggcgcggt | ctacaccctc ggggcgtcc | 1200 |
| tggccggcgg | ctcccgggcc | tctcgcgccg ggagaccggg | cactggtggc tggagctgct | 1260 |
| gctggccccg | cagggacggg | ggagccccgg gcggcggcgg | tggcgtggac ggcgactgct | 1320 |
| ccatcttccc | ggggcgctca | cgccgcggtt ccaaagcgca | gacccaagtg ggacattcgc | 1380 |
| tacattgttg | gcattccacg | ggcgtcacgt gaccccgcct | ccgcgtcac tctcggccgc | 1440 |
| ataccagtcc | gggcggggcg | cctgcggccc ctgctcctcc | gcggccgctc cgcccagccc | 1500 |
| cgccggccg | tgcttcctgc | ctccggcctc gaccgccacc | tgcccacggc ctccctgctg | 1560 |
| gcctgcggta | gctcgccagg | gcctctcgga cctatttgac | tggctgctat ctgcccccaa | 1620 |
| acttgagtat | ttgccctctc | gactgcattt gtattaaaag | ttggtaactg tcgttaaagc | 1680 |
| cactattctt | aagtatctca | taccagtctt ggtgaaagaa | aaaaaaaagt tagcaggcct | 1740 |
| gaaggagcca | ccaagttacc | aactagtggc tggacactaa | aaatagg | 1788 |

<210> SEQ ID NO 8
<211> LENGTH: 2802
<212> TYPE: DNA
<213> ORGANISM: Homo sapiens

<400> SEQUENCE: 8

| | | | |
|---|---|---|---|
| agctgggcca | gggccgggac | aaaggtttcc cagggagggc | caactcttcc gtgtctctgg | 60 |
| cgggttttcc | ttgttaaagg | ctcacaggtt ggagcctgtt | cgcggctctt ggcctggtag | 120 |
| ggattttatt | agctctgctc | tggcaactgc aagccaggaa | cacaatgtcc tgtgcagggg | 180 |
| attgcccatg | cagcccagct | cgtgagatcg cgggatggcg | gggcagtgag ccggtgccgc | 240 |
| tctgggagcc | tgagccaggg | cggcagtcct gtcggcctcg | gagagggaac tgtaatctcg | 300 |
| caaccaggcc | gccgcgaggc | cttctgcctt tgcaaagctg | cgcccaccg gcgccctccc | 360 |
| aggcggcgct | gccttccaca | ttctctcctg gtctacttgg | cctgtacctc cacaacatcc | 420 |
| tcccccatc | cctcccagac | tccgtgctgg ctcctacccg | gactcgggct tccgtaaggt | 480 |
| tggtccacac | agcgatttct | tcgcgtgtgg acatgtccgg | gtagcggttc ctctggaaag | 540 |

```
tggcctccag ctcctggagc tgctggctgg taaagtgagt ccgctgccgc ctttgccgct      600
tcttcttaga cgggtcctcg gcgcccacgt cctcattctt ccctgctgg cttttatctt       660 tctctgaaaa cgaaacacac acactttccc gtcagcatgc ccacctgcaa cgcggacgcc      720
aactggaccg gcggcagaag ccgtggaaga gctgggctgc ctggcgccgg aggagggtgc      780
gcgcggcggc tccgggccgc gaggagcgct gcgcctgtgg ggtgtgcagg cgcaagtgtg      840
ggtgtccgcg ccccatttcc tccctcccc cagcgccgca cgttttattt acatgtttat       900
ctcactgcag cggcacattc acttttatag cctgtgcttt caagtatatt tatacacctc     960
tgcgcagaca caccaaatct cctgggacgc gcacacgcgc gtggtttaca gaccccctc      1020 ccctcgcag aaagctcaga tttccatgcg gtttgggaag gctaggaaaa gatgtgggga     1080
ttcggttggg caccgaagtt cgccggcccct tcccaaaaa aaaaaaaaa atgcctcttc    1140 gcgaagggca tttctgagtg gtttcaggca atttcctaac gagtggagct cctcgggagc   1200
tgaaagccga gaggaaaaca gggacagagg tcggcggcct ctgaaggtcc tcgaatcaag  1260
atgctgggat ttttgtgacc caggaaacag aaggaggcc agggtacgaa tagagagggc  1320
ggcagaattg ctcgcgccct tagcgcccca ggagccgggc cggtcgaggg agaactaaag   1380
ggatgcgggg tagtcaaaat tccggctccc ggaagttctg cggggagcca ggcgaacgac  1440
cactcccacc acgcctcccc ccggaggggc tgacttcctt ggggcgagag ggagcgggtg   1500
gcgcagagca gctgagcggg aatgtctgca gggcggcgcg cgccttacc tgcggcctcc    1560 gggctggagg tgtcggagat ggtgtgcacc tccagcctgt gcttggagga gtccagcgac  1620
cggggctgac cgggagccag aaccgaagcc atggctaacg gctggggatg gtgacaggaa  1680
gatgaggaga cggccgacag cttggtcccc gctgctcggt gctccaagtg aagcgggcct  1740
ttcatgcagt tcatggacga gggagcgcga cgctctacta gtccttggct actgccccgc  1800
cgagcccccg tagccgccgc tgcccgctcc gggtcgcgct ctaggcgcgg agtttccccg   1860
ctgcggggag agccagggga cgcaaccccc gccgagttct caagccaagc tgccccgtc    1920 tcctccggaa ggctcaagcg aaaaagtccg gagacggaaa gtcagcgggc aaacgaagac   1980
atgggatgtg ggcagaaggg caccactcag agcgtcttta gggagcaggc ttccaagctc   2040
caaagcgaaa caagagtggg caaagacccc cttcttctct ccctccctcc cccaagaacc   2100
cctccaataa ggaaagctaa cgccgaccgc gctctgcccg cccccccccc acgcggcagc   2160
cctgacagag aagtgtcaag agtgacaggg acaggtaggt gatattagat cccctgcggc   2220
ggcagcagcc gctgcagcca cgacgcggcc ctctgagcgc accctccgca acgcgcacac   2280
gcacacccct cgggcggtcg aacaggagcc gggccttgcc gcagctcagc tccaggcacc   2340
caggcgagcg acggaccaga tctgcggctc cgcgcttccc tgttggccta acatcttaaa   2400
accagaggcg ggcttcctgg tgccgagacg tcactccgcc gcggccctcc ccagccctct   2460
ccgcctccgc ctcctcccag acccttctcc gggtgcgact gacgtggctc cgcaccaatc   2520
aggacgcccc gagccgcggt ggagggactg tcctgcctgc acctatcagc agtgcggggc   2580
cgggctactg cctcgccgtg cgcactgggt ctacacaggc aagctcccgg gaattcagct    2640
cctgcccagc ccaaggcgat ccggcttttta gtacgaaccc aaaggtgaag agatgaggct   2700
aggagtcgaa ggcttgggag aagagagtgg aatggtcaag aagagaaagg tacaaggatc   2760
aacaagacac ccactctttg tgtctcacta catccatttc ca                       2802
```

<210> SEQ ID NO 9
<211> LENGTH: 2065

<212> TYPE: DNA
<213> ORGANISM: Homo sapiens

<400> SEQUENCE: 9

```
acagcatgat cctctgtcaa gtttcctttt tgtaaaacca aaacaaatgc ataaggcaac      60
gatcccatca atcttcagca ctctccagtt atagctgatt tgaaacttcc caatgaatca     120
ggagtcgcgg ggagagggag taaaaattag gaggatttcc agatcgattc ccagacttct     180
gcttcacaga aatgtcaatc cgcaggaatc ccaaccggag atctcaagag ctcgagaaaa     240
aaaaaaggca gcggcggcgg cagatgaatt acaattttca gtccggtatt cgcagaagtc     300
ctgtgatgtt ttcccttct cggcaattta cacgcgcgca cacacgcgcg gcacaggca      360
tgaatctcta tccacgggac cgcttcacgc ctccccagga gagagacagg ggagagggga     420
cgatgaagga gccggggacg gaggcaggaa tcctcttctg attaaactcc gaacagcaaa     480
tgcatttttcc gaaaagctgc tggataaatg aaggcaggac gcgcctggcc cgccggtgcc     540
gagcgctaga agcccgcgct gtgtgtggtg cggcgagggg tggggagaag gaggtggtgg     600
gggagggttt tattttttcc ctctttcct aaaaaggatg actgctacga agttctcccc      660
cctggacccc ctcttccgct gcaccccacc ggcgcacccc gcctccgggc tgcgcaccct     720
ttctcctcct cctggtcctg cgcggcggcg ctggctacgg ccgcctcccg gagctcccgc     780
cgcgcagccc gctccgagcg ctgacggcc ccggcaggga gggcccggag ccccggcacc      840
ttcgctggca gcggcggcgg cggcagcgcg gcggggccac ggagagcggc gggcgggagc     900
gcggcgggcg ggcgggcagg cggcgcgag gggcgggcgc gggaggaagg gggcgggagc      960
ggggctgtgg tgcctgtcct cttacttcat tctctgcaca gcccgaccgg tttcctgtgc    1020
gtaacgtcac acggttcatt caaaaaaaga agaaagaaag agccctcctc tgagccaccc    1080
gaccgccccc tccgccccgc tccctggccc gggttaaagg cgccgcggca ggcccgggag    1140
tggcgcgtcc cgccggggc acatggcgcg cggggccgcg gccggggagg gcgcgtccgg    1200
gccggccacc cgcccgctcc gctgcgcccg cggggcccgg ccagtgggtg gcgcgggcgg    1260
cacaggcctc ccgcgcggcc gcggcgcggt gggtgtgcgc ggggccttct gctcaggcct    1320
gcggcaggcc gcgtgcggac ttggtggtcg ctggggtccg cgacggggtg ggggctcccg    1380
gggaaccgca cgcggccggg ccgggcggac gacggagtgc ggaggggggc ggctggcggg    1440
agggtgcgcc atgaaaacaa gggctggaaa agcgccggga accgcctgga ccctttctgg    1500
ccgtgtgagt gtgtgtggag tgtgtgtgtg tgtgtgtgtg tgtgtgtgtg tctcgcctgg    1560
accttttcta gccgtgtatg tgggagtgtg tgtgtcgcct ggacccttc tagccgtgta    1620
tgagagtgtg tacacgcgcc tacacacaca cacgttgtgt taccggcgct cggccgccgg    1680
gggaagaccc aggccaatgc cgcccccac cgccccagc agtgggacct cagcgctgcc     1740
ctgctgtgaa gacaggtgac tctgcacgtt ttaagcaatg tctagggacg ccccgagcgt    1800
ggtgtttact ttcaagtagc ttcctaggtg tccgcgcact acacacgcac gcgcatcccc    1860
gccccgtgtcc acctgaacac ctagtccgtg gcccaggcca tgcagaactc agcgctccag    1920
ggaaggggtt tatcaaggc tttacgacag tttaagtcaa tgttttccct ctgtccctaa    1980
cacctttta c actggtttag tgctacacga tgaggacttc catatagtaa ctttcaggcc    2040
caccgtccta acgctggggt gggtg                                        2065
```

<210> SEQ ID NO 10
<211> LENGTH: 1900
<212> TYPE: DNA

<213> ORGANISM: Homo sapiens

<400> SEQUENCE: 10

```
gtcagaaaaa gcgccccagt ctggtctggg ttggttttta tttcacgttg ttgcaagtag      60
gcgaagtccc ttctgtctcc tcccttgggg taagtggaaa ggagtccggc agggggcccg     120
cagtggcctg cacaggggaa ctgggtagcg agagagttcc aggcaattcc ggggctgcc     180
ccacagaagc aggtggggat cgacagtggc tctccggccc agggaggaga gcgcggtcgc     240
gggtccctcc cctcagcctg gaggctgcag ccgctcgagt cggcccgggt gggggcgggg     300
tgggggcggc gcggagggca cggagattac ggcggcgcca cccgggacat ccagggcccc     360
gaggccctgg gcggtcccca cgcgagatcg caaaccatga caataggcag tcacccgagg     420
tcaaataaaa acggagtggg tccccgcgc gccgccgccc ccgcgtccc tggcggcctc      480
ccccgaggcc cccggcggcc tcacgagccc gcagtagccg gtggcgacgt cgcccccgcc     540
ccacctccct gcgcaagtgc gaggctgccg gcagcgcggc gcacgctccg gccgttcccg     600
gcttccgcgc aaaacttcca tcctgtccac gtgaagttgt cgctgcctta gagaggggga     660
aagagctgcg ggaaaagccg gggagtgacg actgcggcgg ctgggcgcgc tctctcattt     720
tcttttcttc tccttttcccc cctgtcgcag tccggagttt tggctcctct cctttcctcc     780
tccccctcgg agccggcttc tccctccgcc ccgcttctcc cccgcttgtg tacgctattt     840
gttgtggggt ggccgaaggg gatgtcctgt tttcaccaga ggcacagcgc gaaggggaaa     900
cttcgacact ggaaggaacg agaataaata cttaattacg gacgcactga accgcggctg     960
ggacagacac ttcgggaacc cgaggcggac cgggcgacga ggtgagtgac ccttcttcc    1020
aacccccgcc ccagggctcc cggggagcc tgagttgaga gaaccccaa actttccggg     1080
aaagtgcgcg aggctccgcc ggggacgccg agcgctgggt actgaggacg cgcagctgga    1140
cggtgcgtgg gcgcctgcgt cccggggggg cgcttggagg ccgggtgccc cacgcctgag    1200
ggcccgggcc gctcggaccg cagcggtgct ctctgcccta aagacgtcc ccaagcccca     1260
agggtccctt ccgagcctgc ctgtcccttc cggggtcggc gcggagcctg cgcgtaacgg    1320
agttcatcca gcagtccagc gcgcggcttc tacctgcacc ccgcctccac ctggcagagg    1380
cgcgagcatc ggggtctccc ccacatcttt cttatgacgt gtattacttt ctgatgaccc    1440
cctagatggt ccaggcgcga ggatgctgac ccagagtcct tcggagggtc acaggcgcct    1500
gggctttccc ggtgccgggt gcgtgtgtac tttaaaggct cgcgttctaa tctccaggca    1560
ctgatcgggc ttttcaactg cggcgatccc actttaatag tttttatgtg gcgtggactg    1620
aatgtctcct gcagtttgcc agggtcggtg aaattagagg cgccttgtca gagcagtcgc    1680
gttcattggc tcgagtagcg ggtgccatgg aaggcttata acttctccaa aggaagggac    1740
ctggctgggt agagcaggtt tttctctcct tccaagcctg ctgggtctgg ggaggcagtg    1800
gaacttgaaa tggctcggat ttttagcgtg gtgaagcgag gtttggaagt agacgtgtgt    1860
gtgcttgttt tattctgcgc cgcacagcaa cccgaacttt                          1900
```

<210> SEQ ID NO 11
<211> LENGTH: 2274
<212> TYPE: DNA
<213> ORGANISM: Homo sapiens

<400> SEQUENCE: 11

```
gagggcaaat cctaaaaaaa tatgtatcac gtgaaacggg ggcaaatact tgattgaaaa      60
tgagtacttc gaatattata ttttcctcgg ggatttttttt tccgagtcaa tgaagaaggg    120
```

```
aagcggcgga aggatcacga gtctcacgct tgaagagaaa gggggatggg taggagggag    180
ggagagggag ggaggggtg gctcggagat gcgacgggaa acgctgcagc tccggcaagc      240
cgcgggatcc ggcgggctga cggcaggggc ccggcgaact agagggcggc ggagtcgcga    300
gtcagtcaga ggcgggcggt ggcggtggcg gcggctcctc tcctcattgc gccaggagca    360
gctgcaggcg gcggctggat ccagcggcca tggcggtggc ggaggcagct cccttcagac    420
cccaggcagc ggctcctcga ctgttcccca ttcgccgggg acatgggaac ccggcaaccg    480
cttccgtccc tcggggcccc ctccccgtc cgcggcaaca gctcggccgc cctcccgccc     540
ctcggctctg ctcggtgccc gctcaggaag tgtccgcgct ttgccccagc ccagagccct    600
gtcagcggct gcggggccgg ctcctcctcg cttccttcct tcctttgtca cttggcccgg    660
gcggcggcgg cggcggcggc ggcacaagcc cgcattcgcc cgggtcagga gctgctctgt    720
gtgaggagcg ctgtctgcgc agccgccttg cacttcccca ctcctcctcc ccctcctac    780 tcgtcctcca cctccttcct cccccaccca gccttacacc gccagcgcc ccgccgcccg     840 cgtaacaggc gtctgggaat cgccggccga gccccacgct cgcccgcttc ggctgggagc    900
cgaagcccga acggagccaa tcacggacgt cgtttgtttg cggctcctcc cggaaaaagc    960
cgatcagcct gagaaaccaa ttagaaagtg acgctgggaa gccacgccca aagagcggaa   1020
aatgccgaag gtagccgaac ggaaagggtg aattcgcctt gttcggtggc tggctggagg    1080
agacattcga caatggcaac agtggccaat cagagtcgcc ggcccttacg aagaggcttg   1140
aagagttgag gacggtgaaa cccagagacg ctggtgaaac tgcacggctg ggcgccgccg   1200
ccgctttgtg attggctgga aaactccgct gggagcgtac ctccttcggt gattggtgaa   1260
gagaaggggg cttccgagga cagtctggcc agtcaggact tcccctcccct ctccaaggtg   1320 gggagaagaa agcgaaggga gggcgtctat aaagcgctgt ctcattggcc tgaagcttag   1380
gcgctggagt tggggcaaaa gggagaggga gggagcccga aactcgcggc ggcggccaat   1440
cggctctcac tgccgtccaa tcgcaagacc tagctgcagt gtgattggcc ttcggccccg   1500
gtcccaggag cggggagatg cctgactcgg gtcgtggctg acgacccgac ggttcgcctg   1560
cggccgcctc caacaacggt ggaaaccgca cacagggacc gcgggccctc ggtgcagcaa   1620
atcggaaagt gctgcggtcg gcggccctgg gctctgagcg ctcaagcgag cagaggggtg   1680
gaggggctct cccacccac aggaggctct cggcggggcg cagccaattc tgcgcgccca    1740
aggctcccct ctgccgtgga tcgcgtgtgc cgagtgttgg cctcttcccc gaaagggcca   1800
gacggaccaa gggggccttc ccagccggct gcaagctctc agacgctaaa atgggaacaa    1860
agcttccaga aaggcagcgc ctttgggcgg ccgcgccccg cccagccgcg ggggccattg    1920
atacagaggc ttgctgcgct tggtgtgcgc ggcccggccg ggcctctgga aacgccatg     1980 agaaatgagc tcatgctgga tgcgcgcgct ccttgggcgc aactgcccag cgcaaaacgg    2040
gccccgaaag caggtgaggg gaaatgccgt caggccggat atcctgaagc ctccgaggaa    2100
atgggggggt cagaggagcc cgtggtagct ttggatcttt tggaactagg gtgatctata    2160
aaagtgcagc ttgagaagat ttcatacata agaccagcgt ccattgttct accatagaac    2220
cagttccttt ggtctgcttt agaacagtga ggtatggcta cgtcaagata acag          2274
```

<210> SEQ ID NO 12
<211> LENGTH: 1528
<212> TYPE: DNA
<213> ORGANISM: Homo sapiens

<400> SEQUENCE: 12

```
gtccaaggca agagaatagg ctttaaagtc cctggctcgg ttaaaaagct ggttgcgtag        60
attcctgtca atgctcagga tcctctgcct tgtgatatct ggagataagt caacgccttg       120
caggacgctt acatgctcgg gcagtacctc tctcagcaac acctccatgc actggtatac       180
aaagtccccc tcaccccagc cgcgacccct caaggccaag aggcggcaga gcccgaggcc       240
tgcacgagca gctctctctt caggagtgaa ggaggcacg ggcaagtcgc cctgacgcag        300
acgctccacc agggccgcgc gctcgccgtc cgccacatac cgctcgtagt attcgtgctc       360
agcctcgtag tggcgcctga cgtcgcgttc gcgggtagct acgatgaggc ggcgacagac       420
caggcacagg gccccatcgc cctccggagg ctccaccacc aaataacgct gggtccactc       480
gggccggaaa actagagcct cgtcgacttc catcttgctt cttttgggcg tcatccacat       540
tctgcgggag gccacaagag cagggccaac gttagaaagg ccgcaagggg agaggaggag       600
cctgagaagc gccaagcacc tcctccgctc tgcgccagat cacctcagca gaggcacaca       660
agcccggttc cggcatctct gctcctattg gctggatatt tcgtattccc cgagctccta       720
aaaacgaacc aataggaaga gcggacagcg atctctaacg cgcaagcgca tatccttcta       780
ggtagcgggc agtagccgct tcaggagggg acgaagagac ccagcaaccc acagagttga       840
gaaatttgac tggcattcaa gctgtccaat caatagctgc cgctgaaggg tggggctgga       900
tggcgtaagc tacagctgaa ggaagaacgt gagcacgagg cactgaggtg attggctgaa       960
ggcacttccg ttgagcatct agacgttttcc ttggctcttc tggcgccaaa atgtcgttcg      1020
tggcaggggt tattcggcgg ctggacgaga cagtggtgaa ccgcatcgcg gcggggaag       1080
ttatccagcg gccagctaat gctatcaaag agatgattga gaactggtac ggagggagtc      1140
gagccgggct cacttaaggg ctacgactta acgggccgcg tcactcaatg gcgcggacac      1200
gcctctttgc ccgggcagag gcatgtacag cgcatgccca caacggcgga ggccgccggg      1260
ttccctgacg tgccagtcag gccttctcct tttccgcaga ccgtgtgttt ctttaccgct      1320
ctcccccgag acctttaaag ggttgtttgg agtgtaagtg gaggaatata cgtagtgttg      1380
tcttaatggt accgttaact aagtaaggaa gccacttaat ttaaaattat gtatgcagaa      1440
catgcgaagt taaagatgt ataaaagctt aagatgggga gaaaacctt ttttcagagg        1500
gtactgtgtt actgttttct tgcttttc                                         1528
```

<210> SEQ ID NO 13
<211> LENGTH: 1287
<212> TYPE: DNA
<213> ORGANISM: Homo sapiens

<400> SEQUENCE: 13

```
gtttgggtct ttctcctctg tgcctgctct ctccagagaa actggagggg tagcagttag        60
cattcccccg ctggttccac caagcacagt caaggtctct aggacatggc caccctcac        120
ctgtggaagc ggtcctgctg gggtgggtgg gtgttagttg gttctggttt gggtcagaga       180
cacccagtgg cccaggtggg cgtggggcca gggcgcagac gagaagggc acgagggctc        240
cgctccgagg acccagcggc aagcaccggt cccgggcgcg cccagcccca cccactcgcg       300
tgcccacggc ggcattattc cctataagga tctgaacgat ccgggggcgg cccgccccg       360
ttaccccttg cccccggccc cgccccctttt ttggagggcc gatgaggtaa tgcggctctg       420
ccattggtct gaggggcgg gccccaacag cccgaggcgg gtccccggg gcccagcgc         480
tatatcactc ggccgcccag gcagcggcgc agagcgggca gcaggcaggc ggcgggcgct       540
```

```
cagacggctt ctcctcctcc tcttgctcct ccagctcctg ctccttcgcc gggaggccgc    600
ccgccgagtc ctgcgccagc gccgaggcag cctcgctgcg ccccatcccg tcccgccggg    660
cactcggagg gcagcgcgcc ggaggccaag gttgccccgc acggcccggc gggcgagcga    720
gctcgggctg cagcagcccc gccggcggcg cgcacggcaa cttttggagag gcgagcagca   780 gccccggcag cggcggcagc agcggcaatg acccccttggc tcgggctcat cgtgctcctg   840
ggcagctgga gcctggggga ctgggcgcc gaggcgtgca catgctcgcc cagccacccc     900
caggacgcct tctgcaactc cgacatcggt aagcgctcct ggtgccccgc ccgagcccca    960
cgctgcagcc aggactgcag cgctgcttag ggaggcaggg cgagcccac tcctttcctc    1020 tgccccagga gagggcaga cggggttggg gcggagtgga gaaactcgat gtccttgggc    1080
gggggcgctg gcatagctga gaggggaaga tgccctgcag aggaaactca cagtggctga   1140
gggagcccct ggccgccttt gctttcctaa cttaggtcgt gaggttccta ccggtccttt    1200
tgacatctgg aaaatgtccc cattcactac taacggagga agggctagaa gagaagggtg    1260
gggaaagggt tcccaaaact tggaatg                                        1287

<210> SEQ ID NO 14
<211> LENGTH: 2035
<212> TYPE: DNA
<213> ORGANISM: Homo sapiens

<400> SEQUENCE: 14
atttagttac cagatgtaaa atgctgggat cagtgcctgg caaaggaaaa ctttgtacag     60
ctgcaggctt tcaccataca caacagcatc gctaacgaat gctattacaa tattcattta    120
gcgtttacca agtgcctact ctatacaaat cttgagaata aacgtgaag gtgaactgct    180 gactaaagtt tggtcccttt cgctccgtct ccttgcgaaa atgctctaac ggcaggaggt    240
cacgcgagcg ctggacgcgt ttctccccgc gagccccttt ccgaggcctt tcgggtcccc    300
ccggttatcc ccgcccgggc ggtgcgcgcc cccgctgttc ccgcttccgc tccagagagg    360
cagggctttc cgagcctgct agcccgcgg ccgcaactaa ccccgggtcg gagtgttccg     420
gcccggccag ccccgcggcg tgagggaagg ggagctcagc agttcccgc gcggggccca    480 ggcgtcggcg gcagggcggg cccctcaccg ccagcgtgcc agccccgccc ctacccacca    540
gtgtgccagc cccgcccttc cccacgtcgc cgcgcgcccg ggggcgggc ctggcgcgca    600 ccgcccgcgc acggcgaggc gcctgttgat tggccactgg ggcccgggtt cctccggcgg    660
agcgcgcctc cccccagatt tcccgccagc aggagccgcg cggtagatgc ggtgcttta    720 ggagctccgt ccgacagaac ggttgggcct tgccggctgt cggtatgtcg cgacagagca    780
ccctgtacag cttcttcccc aagtctccgg cgctgagtga tgccaacaag gcctcggcca    840
gggcctcacg cgaaggcggc cgtgccgccg ctgccccgg ggcctctcct tccccaggcg     900
gggatgcggc ctggagcgag gctgggcctg ggccaggcc cttggcgcgc tccgcgtcac    960
cgcccaaggc gaagaacctc aacggagggc tgcggagatc ggtagcgcct gctgccccca   1020
ccaggtagcg gggtgggggt ggggtcgaag gcggggcat agcggcgggg cgcttggaac    1080
ccggcgaggg gaggctcgca caggggttg gggggtgca cggcctggcc ctgggctcgg    1140
aggaggcggg gccgcagagt tggcttgaat gagtgcaggg gtcgagtctg gagcatttgg    1200
gggtgtagct tgtaaacagg gtcggaggag agaggctgtg caggaagagg gctgcagggg   1260
agacgcggag agttcgggcc ttttggaggg aggagacgcg tcccgccagg tgggggtgct   1320
```

| | |
|---|---|
| gggctaagga aggggcgacg cgcgcagctc cgggtgggga gggggcctgg gaggtgggag | 1380 |
| cactgggggt ggggcgagaa ggggaaggcg cccggcccac ttggtgggcg gggcgggggg | 1440 |
| cggggtggcg ggaaggagga atgcctgcgg gaggccgaac ggggagagtc cggtggtgtg | 1500 |
| gggtgcgaaa ggaggttcct cggccggcgc ggagatagtg agttggggct ccagtagtcg | 1560 |
| atcgaggtag acacttagag gtagttaaga gccgcggtcg ccgagacgcc ttggggacgg | 1620 |
| tgggccttcg gcctaggtga ggggccgccg aggggtggg ccacgagctg cgagcgcggg | 1680 |
| ggggtgtgtc accatgggga ccgcggggcc taattgggcg gggcggggcc gtgggagcc | 1740 |
| gaagtgctgg gatccggctg ggtccttcgg taggtaggct gcacgtgcac cgagacgaag | 1800 |
| atagaatatt ttgacgtatg tggaaattcg tgtcgagtgg aaaatatttt attttatgaa | 1860 |
| atagtgtaat ttttatgggg caccactggg cttttagagg ccttaatcgg gcgctggaca | 1920 |
| aagatgtgtg gacgtgagtg actccgggga agcctgtcgg gagttgtcct cactttatgg | 1980 |
| gcagttaagt gctttttttt tttttccctt tttgagagag agtttcgctc aagtc | 2035 |

<210> SEQ ID NO 15
<211> LENGTH: 1504
<212> TYPE: DNA
<213> ORGANISM: Homo sapiens

<400> SEQUENCE: 15

| | |
|---|---|
| ctctttcccc agttccctga gacaggaccg gtgtcctgcc tggggtatcc ccagagtttg | 60 |
| gcacacggtg atagccaaca ttcactgagc gccaaagggc caggtgctgc cactctctca | 120 |
| aaataagcct ctgccactta ctgaacaact agtctgcgcc aagcactggg atactaagcc | 180 |
| tacgactccc agaaaggtcc cggcggaccc ccgtgcgcag cgggacgcag tgggcgccag | 240 |
| ggaccgcagt gccccgggcc cagcgctctt ctccaggtga tcgccgggga ggcaggttta | 300 |
| aaaggcagga gccggaagcc gtctcggcgc ccaggtggcc gagaatccag tcaccaggtc | 360 |
| actgagtcac cgatggggc gaggacacgg gcctgggccg gtcagagggg cgggatcgtc | 420 |
| acccctggct caggggcccc tccgtccagg cagggagcca aagtcagtct tcgcttgagg | 480 |
| gttggcggtc gctggaagtg gtagccattg ggagttacac taatcccgcg aagggtgcgc | 540 |
| aagggaggcg gcagcccccc ccaagaagag aggcaggccg gcctccagcg ctccccgccc | 600 |
| acaagcacgt ccttgccccc gggaggttgt ttgccggctc caggatctcc ctcccggcga | 660 |
| ccccggcctc gccgtcactc accctccagt cccgggtgac tcagaacgct cggccgccgg | 720 |
| ccgcaccact gtggccgctg caggggcggg gaacgcagtg aaggggcgcg cgcaggtgt | 780 |
| caggttgctg gagaggcggg cctacagggc ggaaaccacc ggcgcgggtg accggaagcc | 840 |
| ccgcccccaa catggccgtg cccacaggtc tcgttggagg ccgtgccttt atcgtcatgt | 900 |
| gacgcgagtc ctcgccccac ccgtctgcag ccactcctgg tctcagtccc agagctcgag | 960 |
| agggccacgt gaccgtcccg gggccagtca cgtgaggcgc agatcctggc tgggaggggg | 1020 |
| ttggtagagg ggtccagagt ggcagtaaag gaggaagatg gcggggtgca gggggtctct | 1080 |
| gtgctgctgc tgcaggtggt gctgctgctg cggtgagcgt gagacccgca ccccgagga | 1140 |
| gctggtaaga agccggcgga gtcggcctgg ggaggggggcg gttgctaagg gactgagaga | 1200 |
| ggcgttgccg ggggtggggc cgggccaatc tgggcccgca ggtggcagcg ggtggggcct | 1260 |
| ggggaccgca gccagggctc tcgaagcgtc taccctgctt cacgtgccta agtctggggt | 1320 |
| ctttctcat aaccccctcct ggaatctgag ggagaatcca ggccagctcc agtaaatccc | 1380 |
| acccatgttt cctttatttt ccatctgaaa agagtttgga atgaaacaag cgttttcaga | 1440 |

```
atgagcttcc tcacaggact ttgtgcttat catgctgctg ttttagcttc tccagtcctt    1500
tctc                                                                 1504

<210> SEQ ID NO 16
<211> LENGTH: 2756
<212> TYPE: DNA
<213> ORGANISM: Homo sapiens

<400> SEQUENCE: 16
gaaccaaaag ggttcaccct aagcggcagg gcatcagcga tggagaggcc cgagagccct      60
agcgcccagc tccttttccc acgtttggga aggcgcagaa taggtcgatg tagagcaagg     120
agtgagtctc aggtctcagt cctttggctt gctcttaggg tagcaggcga ggagtggcac     180
cagtttgggg actctctccc cgcgttctgt aagaatcggc ggcagccagc aggcggggag     240 gcggggcac gtgtttggat gtgggtgctt gtgtaaccag ttccccaagc gccagccccg      300
acagcgctcc ttcgggaggc tggtccgagc ccctgtttcc gccgcggcgc aggaagggtt     360
ggggttccgc tgcctgcacc aggcaagagc accccgagca aggaagaag acgacttgcc     420 tccggagcta tcactgggga gtgggaattt ggaaagttcc ccaactaggg acacacgtga     480
cctccttcgg aaagtagttc cgactgtggc ccgtgtatcc ttccacctcc ttttgaaccc     540
tcctaggtct cctcgcccg cccactcgct gggctgcagc ttcctaccgt tccgtacttt      600
ccactcaacc cggtaacccc aaacgtgcac ggtccggccg gggcgcgcgg agcctggccc     660
cgggcgatcc atcctgccgg gttttcacgg cggccaaggg ggggcggggc taggtggtct     720
ctgagaaccg agcttgactc cgacgccgcg aaccgacctg agcccgagg ggaaagatgc      780 tcgactctct tgggggcacc ggagcgggcg caggagaggc ctgcggggtg cgtcccactc     840
acagggatcc tctttcagtt catttagata ggtgcccttt gggcccttga aattcaacgg     900
ctatgtgttc acgttcagca cgctcggctg agagctttca tttttagggc aaacgagccg     960
agttaccggg gaagcgagag gtggggcgct gcaagggagc cggatgaggt gatacacgct    1020
ggcgacacaa tagcaggttg ctctttgtgc taagactgac accatgagga cacagatttg    1080
ggggaagggg gaatctctag gcaaaggctg ttacagtcaa atctctgcga acgattgtga    1140
tccgacagcg gtgcaaaagg aaagagcgaa tgcagtccac gccgcggaaa tctagggta    1200 gaggcaaggg gggagggtat tccccttgca gggaccgtcc ctgcatttcc ctctacactg    1260
agcagcgtgg tcacctggtc ctttttcacct gtgcacaggt aacctcagac tcgagtcagt    1320
gacactgctc aacgcaccca tctcagcttt catcatcagt cctccacccc cgccccacaa    1380
cagcctaccc tgcctccggc tgggtttctg ggcagaggcc gaggcttagc tcgttatcct    1440
cgcctcgcgt tgctgcaaaa gccgcagcaa gtgcagctgc aggctggcgg ctgggaaccg    1500
gcccgagcaa gccccaggca gctacactgg gcatgctcag tagagcctgc ggcttgggga    1560
ctctgcgctc gcaccagag ctaccgctct gccccctcct accgcccct gccctgccct      1620 gccctcccct cgccggcgc ggtcccgtcc gcctctcgct cgcctcccgc ctcccctcgg     1680
tcttccgagg cgcccgggct cccggcgcgc cggcggaggg ggcgggcagg ccggcgggcg    1740
gtgatgtggc gggactcttt atgcgctgcg gcaggatacg cgctcggcgc tgggacgcga    1800
ctgcgctcag ttctctcctc tcggaagctg cagccatgat ggaagtttga gagttgagcc    1860
gctgtgaggc gaggccgggc tcaggcgagg gagatgagag acggcggcgg ccgcggcccg    1920
gagcccctct cagcgcctgt gagcagccgc ggggcagcg ccctcgggga gccggccggc     1980
```

```
ctgcggcggc ggcagcggcg gcgtttctcg cctcctcttc gtcttttcta accgtgcagc     2040
ctcttcctcg gcttctcctg aaagggaagg tggaagccgt gggctcgggc gggagccggc     2100
tgaggcgcgg cggcggcggc ggcacctccc gctcctggag cgggggggag aagcggcggc     2160
ggcggcggcc gcggcggctg cagctccagg aggggtct gagtcgcctg tcaccatttc     2220
cagggctggg aacgccggag agttggtctc tccccttcta ctgcctccaa cacggcggcg     2280
gcggcggctg gcacatccag ggacccgggc cggttttaaa cctcccgtgc cgccgccg     2340 caccccccgt ggcccgggct ccggaggccg ccggcggagg cagccgttcg gaggattatt     2400
cgtcttctcc ccattccgct gccgccgctg ccaggcctct ggctgctgag gagaagcagg     2460
cccagtcgct gcaaccatcc agcagccgcc gcagcagcca ttacccggct gcggtccaga     2520
gccaagcggc ggcagagcga ggggcatcag ctaccgccaa gtccagagcc atttccatcc     2580
tgcagaagaa gccccgccac cagcagcttc tgccatctct ctcctccttt tcttcagcc     2640 acaggctccc agacatgaca gccatcatca aagagatcgt tagcagaaac aaaaggagat     2700
atcaagagga tggattcgac ttagacttga cctgtatcca tttctgcggc tgctcc       2756

<210> SEQ ID NO 17
<211> LENGTH: 616
<212> TYPE: DNA
<213> ORGANISM: Homo sapiens

<400> SEQUENCE: 17
gccagtctga tccagaaggc caagctggca gagcaggccg aacgctatga ggacatggca      60
gccttcatga aaggcgccgt ggagaagggc gaggagctct cctgcgaaga gcgaaacctg     120
ctctcagtag cctataagaa cgtggtgggc ggccagaggg ctgcctggag ggtgctgtcc     180
agtattgagc agaaaagcaa cgaggagggc tcggaggaga aggggcccga ggtgcgtgag     240
taccgggaga aggtggagac tgagctccag ggcgtgtgcg acaccgtgct gggcctgctg     300
gacagccacc tcatcaagga ggccggggac gccgagagcc gggtcttcta cctgaagatg     360
aagggtgact actaccgcta cctggccgag gtggccaccg tgacgacaa gaagcgcatc     420 attgactcag cccggtcagc ctaccaggag gccatggaca tcagcaagaa ggagatgccg     480
cccaccaacc ccatccgcct gggcctggcc ctgaactttt ccgtcttcca ctacgagatc     540
gccaacagcc ccgaggaggc catctctctg gccaagacca ctttcgacga ggccatggct     600
gatctgcaca ccctca                                                    616

<210> SEQ ID NO 18
<211> LENGTH: 821
<212> TYPE: DNA
<213> ORGANISM: Homo sapiens

<400> SEQUENCE: 18
ttttgcgcgc gtgtgcgtgc gtgtgtgtgt gcgtgtgtgt gtgtgccgtt tctctaaaat      60
tctgactcat agtctggagg acaatgattg acttttttcc acttcacata gttgctatga     120
atttctcctc acaaggatgg gcctgtttac tcaccctggg catcgttggt agagcgctag     180
tgtaaacagc ctgaggaacc cggtgggccg gggaagtggg cgcgctctgt tctccgcggc     240
cagctgggac gccgggccag gtggggccgc ctgcgtttag caactgcttt ctcaccccct     300
ggatttgcga tgtttgccac agcagcgaga agcgccattg taatgggat gggaggggtg     360 gagcctccaa gtcctgtctc aatttagatc tctcactctg ctgttaggcg cgcccatttc     420
agattactaa actcgaatta agagggaaaa aaaatcaggg aggaggtggc aagccacacc     480
```

```
ccacggtgcc cgcgaacttc cccggcagcg gactgtagcc caggcagacg ccgtcgagat      540
gcagggccca ccgctcctga ccgccgccca cctcctctgc gtgtgcaccg ccgcgctggc      600
cgtggctccc gggtaggaac gtgggcgcgc ggggggcgcg cgggcgcgcg ggcctgggcc      660
gctctgcggc tctgggccag ggcttcgggg aggtggcggc tgctgtgcag cagcgggtgg      720
gaaatgccct cgcggctgca gtccccagcc tggtactggc ctggaggttt gaccatatgt      780
agcttcagcg tggctctcca tgggacagtt aactttctcc a                         821

<210> SEQ ID NO 19
<211> LENGTH: 1349
<212> TYPE: DNA
<213> ORGANISM: Homo sapiens

<400> SEQUENCE: 19
tccagcagcg acgacaagta aagtaaagtt cagggaagct gctctttggg atcgctccaa      60
atcgagttgt gcctggagtg atgtttaagc caatgtcagg gcaaggcaac agtccctggc      120
cgtcctccag caccttttgta atgcatatga gctcgggaga ccagtactta aagttggagg     180
cccgggagcc caggagctgg cggagggcgt tcgtcctggg actgcacttg ctcccgtcgg      240
gtcgcccggc ttcaccggac ccgcaggctc ccggggcagg gccggggcca gagctcgcgt      300
gtcggcggga catgcgctgc gtcgcctcta acctcgggct gtgctctttt tccaggtggc      360
ccgccggttt ctgagccttc tgccctgcgg ggacacggtc tgcaccctgc ccgcggccac      420
ggaccatgac catgaccctc cacaccaaag catctgggat ggccctactg catcagatcc      480
aagggaacga gctggagccc ctgaaccgtc cgcagctcaa gatcccctg gagcggcccc       540 tgggcgaggt gtacctggac agcagcaagc ccgccgtgta caactacccc gagggcgccg      600
cctacgagtt caacgccgcg gccgccgcca acgcgcaggt ctacggtcag accggcctcc      660
cctacgcccc cgggtctgag gctgcggcgt tcggctccaa cggcctgggg ggtttcccc       720 cactcaacag cgtgtctccg agcccgctga tgctactgca cccgccgccg cagctgtcgc      780
ctttcctgca gccccacggc cagcaggtgc cctactacct ggagaacgag cccagcggct      840
acacggtgcg cgaggccggc ccgccggcat tctacaggta cccgcgcccg cgccgcccgt      900
cggggtggcc gccgcgcccg gcaggaggga gggagggagg gagggagaag ggagagccta     960
gggagctgcg gagccgcgg gacgcgcgac ccgaggtgc gcgcagggag cccggggcgc      1020
gcggcccagc ccgggggttc tgcgtgcagc ccgcgctgcg ttcagagtca agttctctcg     1080
ccgggcagct gaaaaaaacg tactctccac ccacttaccg tccgtgcgag aggcagaccc     1140
gaaagcccgg gcttcctaac aaaacacacg ttggaaaacc agacaaagca gcagttattt    1200 gtggggaaa acacctccag gcaaataaac acggggcgct tgagtcact tgggaaggtc      1260 tcgctcttgg catttaaagt tggggtgtt tggagttagc agagctcagc agagttttat     1320
ttatcctttt aatgttttg tttaatgtg                                         1349

<210> SEQ ID NO 20
<211> LENGTH: 2366
<212> TYPE: DNA
<213> ORGANISM: Homo sapiens

<400> SEQUENCE: 20
gcccaactca aggacccctt acttagacct caacctggag acaggggtgc tgtacgtgaa      60
cgagaaaata gaccgcgaac aaatctgcaa acagagcccc tcctgtgtcc tgcacctgga     120
```

| | |
|---|---|
| ggtctttctg agaaccccc tggagctgtt ccaggtggag atcgaggtgc tggacattaa | 180 |
| tgacaacccc ccctctttcc cggagccaga cctgacggtg gaaatctctg agagcgccac | 240 |
| gccaggcact cgcttcccct tggagagcgc attcgaccca gacgtgggca ccaactcctt | 300 |
| gcgcgactac gagatcaccc ccaacagcta cttctccctg gacgtgcaga cccagggggga | 360 |
| tggcaaccga ttcgctgagc tggtgctgga gaagccactg gaccgagagc agcaagcggt | 420 |
| gcaccgctac gtgctgaccg cggtggacgg aggaggtggg ggaggagtag agaaggagg | 480 |
| gggaggtggc gggggagcag gcctgccccc ccagcagcag cgcaccggca cggccctact | 540 |
| caccatccga gtgctggact ccaatgacaa tgtgcccgct ttcgaccaac ccgtctacac | 600 |
| tgtgtcccta ccagagaact ctcccccagg cactctcgtg atccagctca acgccaccga | 660 |
| cccggacgag ggccagaacg tgaggtcgt gtactccttc agcagccaca tttcgccccg | 720 |
| ggcgcgggag cttttcggac tctcgccgcg cactggcaga ctggaggtaa gcggcgagtt | 780 |
| ggactatgaa gagagcccag tgtaccaagt gtacgtgcaa gccaaggacc tgggccccaa | 840 |
| cgccgtgcct gcgcactgca aggtgctagt gcgagtactg gatgctaatg acaacgcgcc | 900 |
| agagatcagc ttcagcaccg tgaaggaagc ggtgagtgag ggcgcggcgc ccggcactgt | 960 |
| ggtggcccttt ttcagcgtga ctgaccgcga ctcagaggaa aatgggcagg tgcagtgcga | 1020 |
| gctactggga gacgtgcctt tccgcctcaa gtcttccttt aagaattact acaccatcgt | 1080 |
| taccgaagcc cccctggacc gagaggcggg ggactcctac accctgactg tagtggctcg | 1140 |
| ggaccggggc gagcctgcgc tctccaccag taagtcgatc caggtacaag tgtcggatgt | 1200 |
| gaacgacaac gcgccgcgtt tcagccagcc ggtctacgac gtgtatgtga ctgaaaacaa | 1260 |
| cgtgcctggc gcctacatct acgcggtgag cgccaccgac cgggatgagg gcgccaacgc | 1320 |
| ccagcttgcc tactctatcc tcgagtgcca gatccagggc atgagcgtct tcacctacgt | 1380 |
| ttctatcaac tctgagaacg gctacttgta cgccctgcgc tccttcgact atgagcagct | 1440 |
| gaaggacttc agttttcagg tggaagcccg ggacgctggc agcccccagg cgctggctgg | 1500 |
| taacgccact gtcaacatcc tcatagtgga tcaaaatgac aacgcccctg ccatcgtggc | 1560 |
| gcctctacca gggcgcaacg ggactccagc gcgtgaggtg ctgccccgct cggcggagcc | 1620 |
| gggttacctg ctcacccgcg tggccgccgt ggacgcggac gacggcgaga acgcccggct | 1680 |
| cacttacagc atcgtgcgtg caacgaaat gaacctcttt cgcatggact ggcgcaccgg | 1740 |
| ggagctgcgc acagcacgcc gagtcccggc caagcgcgac ccccagcggc cttatgagct | 1800 |
| ggtgatcgag gtgcgcgacc atgggcagcc gcccctttcc tccaccgcca ccctggtggt | 1860 |
| tcagctggtg gatggcgccg tggagcccca gggcgggggc gggagcggag cggagggtc | 1920 |
| aggagagcac cagcgcccca gtcgctctgg cggcggggaa acctcgctag acctcacccct | 1980 |
| catcctcatc atcgcgttgg gctcggtgtc cttcatcttc ctgctggcca tgatcgtgct | 2040 |
| ggccgtgcgt tgccaaaaag agaagaagct caacatctat acttgtctgg ccagcgattg | 2100 |
| ctgcctctgc tgctgctgct gcggtggcgg aggttcgacc tgctgtggcc gccaagcccg | 2160 |
| ggcgcgcaag aagaaactca gcaagtcaga catcatgctg gtgcagagct ccaatgtacc | 2220 |
| cagtaacccg gcccaggtgc cgatagagga gtccgggggc tttggctccc accaccacaa | 2280 |
| ccagaattac tgctatcagg tatgcctgac ccctgagtcc gccaagaccg acctgatgtt | 2340 |
| tcttaagccc tgcagccctt cgcgga | 2366 |

<210> SEQ ID NO 21
<211> LENGTH: 1703

<212> TYPE: DNA
<213> ORGANISM: Homo sapiens

<400> SEQUENCE: 21

```
ttattatcta tctgtcccac cagaatgcag gtttccggaa ggcagggatt taaaaaaatc    60
tgttttgttc tatgtgattt tcccatacca agcaccgtgc ccggcacaag ctgggatccc   120
agtacacatc tcgggacgga agaaccgtgt ttccctagaa cccagtcaga gggcagctta   180
gcaatgtgtc acaggtgggg cgcccgcgtt ccggcggac gcactggctc cccgccggc    240
gtgggtgtgg ggcgagtggg tgtgtgcggg gtgtgcgcgg tagagcgcgc cagcgagccc   300
ggagcgcgga gctgggagga gcagcgagcg ccgcgcagaa cccgcagcgc cggcctggca   360
gggcagctcg gaggtgggtg ggccgcgccg ccagcccgct tgcagggtcc ccattggccg   420
cctgccggcc gccctccgcc caaaaggcgc caaggagccg agaggctgct tcggagtgtg   480
aggaggacag ccggaccgag ccaacgccgg ggactttgtt ccctccgcgg aggggactcg   540
gcaactcgca gcgcagggt ctggggccgg cgcctgggag ggatctgcgc cccccactca   600
ctccctagct gtgttcccgc cgccgccccg gctagtctcc ggcgctggcg cctatggtcg   660
gcctccgaca gcgctccgga gggaccgggg gagctcccag gcgcccgggt gagtagccag   720
gcgcggctcc ccggtccccc cgaccccgg cgccagcttt tgctttccca gccagggcgc   780
ggtgggttt gtccgggcag tgcctcgagc aactgggaag gccaaggcgg agggaaactt   840
ggcttcgggg agaagtgcga tcgcagccgg gaggcttccc cagccccgcg ggccgggtga   900
gaacaggtgg cgccggcccg accaggcgct ttgtgtcggg gcgcgaggat ctggagcgaa   960
ctgctgcgcc tcggtgggcc gctcccttcc ctcccttgct ccccgggcg gccgcacgcc  1020
gggtcggccg ggtaacgag agggagtcgc caggaatgtg gctctgggga ctgcctcgct  1080
cggggaaggg gagagggtgg ccacggtgtt aggagaggcg cgggagccga gaggtggcgc  1140
gggggtgcca ccgttgccgc aggctggaga gagattgctc ccagtgaggc gcgtaccgtc  1200
tgggcgaggg cttcattctt ccgcggcgtc cctggaggtg ggaaagctgg gtgggcatgt  1260
gtgcagagaa agggagggcg gggaggccag tcacttccgg agccggttct gatcccaaca  1320
gaccgcccag cgtttgggga cgccgacctc ggggtgccgt ggtgcccggc ccacgcgcg   1380
cgcggggctg aggggtcggg ggcgtccctg gccgcccagc tttaacaaag ggtgctcctc  1440
tccaccccgc gaggaggggc agctccggag acccggtctt cagcgagcgg ggtcttagcg  1500
ccggggaggt ctacttcctt ttggggttgc cattttacta ttattattgc cttttttttt  1560
tcttcaaaag gactggagac tgatgcatga gggggctacg gaggcgcagg agcggtggtg  1620
atggtctggg aagcggagct gaagtgccct gggctttggt gaggcgtgac agtttatcat  1680
gaccgtgttc aggcaggaaa acg                                         1703
```

<210> SEQ ID NO 22
<211> LENGTH: 1021
<212> TYPE: DNA
<213> ORGANISM: Homo sapiens

<400> SEQUENCE: 22

```
tgtaagaaag tccgaccaag taccgatgag ttctcccaca acaataaatt cgatgcctct    60
ttgcctgttt ttgaagtagt aatgtaaaat tatctcccaa aatgctgcct tctctatact   120
ccggtttgct cctgtcctgg gcacgtgttc agcaaccct taggggaatc cagagctgcg   180
tgtttaacac agacctgttg ggacggattt tcgctacttg tctatgaaac tgacgaacca   240
```

```
tcccaaaacg gcgggtgccg actacacccc cagagccaag agctgtggcg tccccggacc    300
cgctggcgtg gccccgtgcc tcagtttccc caatgtataa acacggtgga ggaggaacgg    360
gttagggcta gggtcggtgc ttgggaattg gggggcccga gtccccaccc tgagaccctc    420
gtggggcgga agagtactcg ggacagaagc ccaccgcccc gtgagcggcg ccggccccac    480
tgggctccgg ggtgatgacc tgacgcgcgt ggaaacccag acccgcgccc cagaaacagt    540
attccacttg ggcttgcctc cccgccccta ccttccagga tgttgacagc tgggaatgaa    600
aggcagaggg agggagcgcg gggccggagc gccgcctggg agtgtgccca ctgggtggcc    660
gcctgaggga cccgggaaca gagggcaaaa agtcctgtga ccggacagag cagagcgggg    720
actgcaattc ccagaagacc ccacggtagg ggcgggaccc aagatggccg cttgtctggg    780
gacaggagcg gaggccaata cgcgcagagc atgcgcctac gccgggccaa ttgaaagcca    840
tagtgacagt aaccctgatt caggggcggg aaacactgac cacagaagac aagttgaggt    900
gagaatcccc ttacaagggg gtttgggggca taaatcgcac aatctttggc ttttctaac    960 tagaaaaaga aacatgattc ttttcacgtg taacgaaagg ctgtaccgca cttttgcttt    1020
t                                                                    1021

<210> SEQ ID NO 23
<211> LENGTH: 1128
<212> TYPE: DNA
<213> ORGANISM: Homo sapiens

<400> SEQUENCE: 23
ttttgtatct gataaagagc atacttccat ctaatacaaa tatgttcccc ccttcagatc     60
ttctcagcat tcgagagatc tgtacgcgcg tggctcctca ttcctcttcc ttggcttccc    120
aagcccccag ggcgtcgcca ggaggaggtc tgtgattaca aacccttct gaaaactccc     180 caggaagcct cccctttttc cggagaatcg aagcgctacc tgattccaat tccctgcaa    240 acttcgtcct ccagagtcgc ccgccatccc ctgctcccgc tgcagaccct ctacccacct    300
ggatcggcct ccgaccgtaa ctattcggtg cgttgggcag cgccccgcc tccagcagcg    360 cccgcacctc ctctacccga cccgggcgcg ggccgtggc cagccagtca gccgaaggct    420
ccatgctgct ccccgccgcc ggctccatgc tgctccccgc cgcccgctgc ctgctctccc    480
cctctccgca gccgccgagc gcacgcggtc cgccccaccc tctggtgacc agccagcccc    540
tcctcttcct tcctccggtg ctggcggaag agccccctcc gaccctgtcc ctcaaatcct    600
ctggagggac cgcggtatct ttccaggcaa ggggacgccg tgagcgagtg ctcggaggag    660
gtgctattaa ctccgagcac ttagcgaatg tggcaccct gaagtcgccc caggttgggt     720
ctcccccggg ggcaccagcc ggaagcagcc ctcgccagag ccagcgttgg caaggaagga    780
ggactgggct cctccccacc tgcccccac accgccctcc ggcctccctg ctcccagccg    840
cgctcccccg cctgccagca aaggcgtgtt tgagtgcgtt cactctgtta aaagaaatc    900 cgccccgcc ccgtttcctt cctccgcgat acaaccttcc taactgccaa attgaatcgg    960
ggtgtttggt gtcataggga aagtatggct tcttctttta atcataagaa aaagcaaaac    1020
tattctttcc tagttgtgag agccccaccg agaatcgaaa tcacctgtac gactagaaag    1080
tgtcccccta cccctcaac ccttgattt caggagcgcg gggttcac                   1128

<210> SEQ ID NO 24
<211> LENGTH: 1041
<212> TYPE: DNA
<213> ORGANISM: Homo sapiens
```

<400> SEQUENCE: 24

```
aacactcttc agagccacag cctgtgctcg ggctcctcgc cgcctcccag gccctgcgat    60
ctctttgcat cccaggaggt cccggttggt tgcagtcctc ctgggtgact caggaaccag   120
cctctcctga agcacacagc ctagggagtt cctggggcca gagacatctc caagggaagg   180
tcaagggcct ggaggatgtg cggacctgac gacagatgcc ccgcacgctg gccgggaccg   240
ggaagggcgt tcaagtgtgg aaagggtctg gcggctgcca ggcctggcag agtggagcgg   300
ggcggggcgc agcggggcgg ggcgggcctg gagctgcacc cgcttctggg tggacgcact   360
tggcgagcgc cgcgggatgc agacggctgc gaggcgctgg gcacaggtca gacgtcagta   420
cccgcagggg gcttgaaact ggaggagggc tcgaagggag agggagcccc gccaaggagc   480
ggggctgtga tggagagggg gttccgactc gcatgggacc tgcggggag ggtacgcgga    540
cagggagggg ataccgactg ggaggggctc agggacaggg atggaggctc ctctagggga   600
ggacgggagg ggatggaggg ccctggtgtc gcagaagccc acctggggcc cctccgggc    660
tgcggcaccg atgcgcacac tactcccacc gcccccgagt gcctatgtcc ggctggccgc   720
ggccctggaa tgaatattgc tcagtccccc gcgagtcagg tctgccgcgt tgcagggtga   780
ggggaaggtg tgaagccccg ggcctccgtc tgccccgtga gtccgggaac gcgcgccccc   840
gtggatgcca cctggcccct gagctgtgtc cagtcacagc tcacatagct ctgggcactg   900
gtaccccgac tgcctttcct tgttagctgc gatacacaaa tacatgagcc agatcctttc   960
ctgaggccag gaagcctgga atctaataac attgggcggt ggataaagtc ccccgatcca  1020
gtgcttagct tccgttaatg g                                            1041
```

<210> SEQ ID NO 25
<211> LENGTH: 1137
<212> TYPE: DNA
<213> ORGANISM: Homo sapiens

<400> SEQUENCE: 25

```
gtggtaattt cccttcaccc taaaggttct ggaggggggtc atgagtgttt gagaagaggc    60
aagcctggga agatggactc cgaggacagt aggcacaaac cctttctcaa gaagggccaa   120
ggcattttaa agataagaaa cttaaaatca gcgtattttt acatataagc agccacctct   180
gctcatctgt ggcccagata cgagtggagt gcgacaaggg ataaaccatt tcgcgcact    240
cttcagcgat ggggcgaaag taacggacct agtcctcggg agctgtcccc gccgacccc    300
tctgccgcga cttgacccgc ggcgactgcg ctgcccttg gctgccccctt ccgctctcgt   360
aggcgcgcgg ggccactact cacgcgcgca ctgcaggcct ttgcgcacga cgccccagat   420
gaagtcgcca cagaggtcgc accacgtgtg cgtggcgggc ccgcgggct ggaagcggtg    480
gccacggcca gggaccagct gccgtgtggg gttgcacgcg gtgccccgcg cgatgcgcag   540
cgcgttggca cgctccagcc gggtgcggcc cttccagcg cgcccagcgg gtgccagctc    600
ccgcagctca atgagctcag gctcccccga catggcccgg ttgggcccgt gcttcgctgg   660
ctttgggcgc tagcaagcgc gggcgggcg gggccacagg gcgggcccg acttcagcgc    720
ctccccccagg atccagactg ggcggcggga aggagctgag gagagccgcg caatggaaac   780
ctgggtgcag ggactgtggg gcccgaaggc ggggctgggc gcgctctcgc agagcccccc   840
ccgccttgcc cttccttccc tcctttcgtcc cctcctcaca cccaccccg gacgccaca    900
acgacggcga ccgcaaagca ccacgcggag atacccgtgt ttctggaggc cagctttact   960
```

| | |
|---|---|
| gtgctagagg aagagggtcc ccacatccgg ccctggccct cctggtccgg tttgctgaag | 1020 |
| caacacactt ggcctaccca ctgggtgggg caggaagtct cgagccttca cttggggtga | 1080 |
| ggaggaggga gatcggtcag cagctttacc gcccgctctg ctctccactg cggagac | 1137 |

<210> SEQ ID NO 26
<211> LENGTH: 1121
<212> TYPE: DNA
<213> ORGANISM: Homo sapiens

<400> SEQUENCE: 26

| | |
|---|---|
| ccaagccgtg cctgccctgc cctgccctgc cctggttgcg ggagcacaga tgcaggctgt | 60 |
| gcaggagtgc ggtggggccg ggctgggtgt ggaggcctca cctggcttgg ctgccgactg | 120 |
| aggaggggcc tggatcccag ctggcgcggc tccagagcct ggaaggatat gggccaagtg | 180 |
| atcccctccc cttccctccc cgccgtgggg ccggggtccc gttggtcggt aggccaagcg | 240 |
| tggggagcct cctttccggt agagcagctt tgtttagggg taggaggaac agaaagcgga | 300 |
| agagcccgcg gggtaagcgc tggtgtgggt ggaggggaaa gacggggtgg aggggaacgg | 360 |
| gggcggctca ccctggtgcg tggccgcctg cagctgcccg gccatctcct gcaggcccat | 420 |
| gtcgcgcagc acgttagcgg tgagctcggc gccgtaggtc tccaggtaga agctgaccag | 480 |
| cttgtcggtg aggtccaagg cgtccatgga cagcagcgcg ccccgcggga tgcgcccgta | 540 |
| gccctcgcgc agcggcaccg acagcagctt cagcttgaac ttcttgagct cctcggcggt | 600 |
| caggttctcc agcgcatcca ggatggcgtc gcgcgcgcgc ccatggctc caggatcccc | 660 |
| ggccgctgcc gccgctcacc ccgctgcagc cgccgaccag gaggaagtcg gctccggggc | 720 |
| ggaacctgga ctccccgcct tcctcccact ctggtctccc gactcccgc ccggtccgt | 780 |
| tgccctccag caaaaggcgc ttccttacta caccccttggt cccctcccac ccaggcctct | 840 |
| ggattggggc cccaggccgt cggggacgc caggatcgcg ccctccagct ggcctgcgag | 900 |
| gtgggacccg ggaggggcc gcagagggc tcatggtgg cgcctgcttg tctctgggct | 960 |
| tgcaccagcg ggtacagacc ggaaacctgg gctggctctc actgggttta ttggagcacc | 1020 |
| taggcttaga acctcggatt tctagaaccc cgaaacctcc gcggttcccc gaaccttagg | 1080 |
| atcctctccc acatgtcgta gaatcttgga atcatgacag c | 1121 |

<210> SEQ ID NO 27
<211> LENGTH: 1083
<212> TYPE: DNA
<213> ORGANISM: Homo sapiens

<400> SEQUENCE: 27

| | |
|---|---|
| cttttttaaaa agcacttatc tcattcattt ttcacctcaa aacgagacac caaactttt | 60 |
| aagacacaaa agtgtgctca cttccaggat ccatagtttc ttggacccac gctacggacc | 120 |
| tggctctccc tccctctgca ccgggttttg tgggagggag aacgctttcc aacctcctcc | 180 |
| accaaggact ctcacaaact cgcaatcggg ctcccggagt gctggaacgc ccctgtgtga | 240 |
| cgtccgcccg cgccggggga actccgcaga dacaggtgca gcccgcgagg cccgagcgac | 300 |
| cctactgtgg gtgcggtgtc ttcccagaga gtggtgaagt taggaaggta cgaccccta | 360 |
| ggccgaacag cctgtgggct agctggcgcc tcctgccgca gtaaacacaa agtggggtac | 420 |
| agaaacgaaa actccgggaa gaaacggcca gcacgggcct cgccgtgccg gctactcaac | 480 |
| acgccttcct gagagcacag aacatccaca gccctataca gcgcgccatc cagagagctc | 540 |
| cggactccca gctcggcgca ggggcgggac ttccgctcaa gtcagacttc cgggcgaggc | 600 |

```
ggtgagggc ttccggttgg ggtggcaggg tggtggatct gtcggtcccg tttcccgtc      660
gcacgtggtg gccactgttg gcttctgaat ggtttgcaag gcggatatcc acgccaaggc    720
ctttggatcg gccgtgggta catccgtctg agccgttcct ttccatcgca gagcggcggc    780
ctccggcggc gctctccagt catggactac cggcggcttc tcatgagccg ggtggtcccc    840
gggcaattcg acgacgcgga ctcctctgac aggtaggcgg ccgtacagtg ccctggctct    900
gggtacggct ctctccttga ccgcccctt ggggtgtgga ctcttgtttg cggtttagag     960
ggagactagt ggttcatcac tcagcgtctc tcttgacaac cctttgcctg tttctgcatc   1020
ccagctgggt ttttctccca gttcacgcgg cagagttaag tgaaagctac ttgtcaaggg   1080
agt                                                                 1083
```

<210> SEQ ID NO 28
<211> LENGTH: 2014
<212> TYPE: DNA
<213> ORGANISM: Homo sapiens

<400> SEQUENCE: 28

```
aaataaaaac taatgtcttt tctattttt tcctactggc aatcacattg gggtggtggg      60
ggcgtgtggt acaatctcag tcaagaggtc ctctcttgtg tgggtgctgg cataacactg    120
gccgtataca atggccaagc aaagcgacat tctgtcctgc tgtgctttac acgtaaatag    180
agaatggatg aggttctcag cgcccagggg tccgcggctt ccgcgagggt agcgtcgggg    240
gccgctgcag agattggaag agtacccgcc gggaatggga gggaagacgc ggggaaggtg    300
gagaatagga atcatgtgtg ttcctcgagt gtacaaccca catttgagtg acaaatcacg    360
aggacaatcg acaaaaacaa ctaagcgcaa agccgcccga atccatctcc ctctctgtgc    420
gtgtgccttt tcaactaact ttgggaactc gtatagaccc agcgtcgctc cccgcgccgc    480
ctcgcctcca ctttggtttc ccgcgtcctg cccgccctct tcggtgcctc ctcttcctcc    540
gggacaagga tggaggatct cttagcccc tcaattctgc cgccggcgcc caacattcc      600
gtgcccatct tgctgggctg gggtctcaac ctgaccttgg ggcaaggagc ccctgcctct    660
gggccgccca gccgccgcgt ccgcctggtg ttcctggggg tcatcctggt ggtggcggtg    720
gcaggcaaca ccacagtgct gtgccgcctg tgcggcggcg cgggccctg ggcgggcccc     780
aagcgtcgca agatggactt cctgctggtg cagctggccc tggcggacct gtacgcgtgc    840
ggggcacgg cgctgtcaca gctggcctgg gaactgctgg gcgagccccg cgcggccacg     900
ggggacctgg cgtgccgctt cctgcagctg ctgcaggcat ccgggcgggg cgcctcggcc   960
cacctcgtgg tgctcatcgc cctcgagcgc cggcgcgcgg tgcgtcttcc gcacggccgg  1020
ccgctgcccg cgcgtgccct cgccgccctg ggctggctgc tggcactgct gctggcgctg  1080
ccccgggcct tcgtggtgcg cggggactcc ccctcgccgc tgccgccgcc gccgccgcca  1140
acgtccctgc agccaggcgc gcccccggcc gccgcgccct ggccggggga gcgtcgctgc  1200
cacgggatct tcgcgcccct gccgcgctgg cacctgcagg tctacgcgtt ctacgaggcc  1260
gtcgcgggct tcgtcgcgcc tgttacggtc ctgggcgtcg cttgcggcca cctactctcc  1320
gtctggtggc ggcaccggcc gcaggccccc gcggctgcag cgcccggtc ggcgagccca   1380
ggtcgagccc ctgcgcccag cgcgctgccc cgcgccaagg tgcagagcct gaagatgagc  1440
ctgctgctgg cgctgctgtt cgtgggctgc gagctgccct actttgccgc ccggctggcg  1500
gccgcgtggt cgtccgggcc cgcggagac tgggagggag agggcctgtc ggcggcgctg   1560
```

| | |
|---|---:|
| cgcgtggtgg cgatggccaa cagcgctctc aatcccttcg tctacctctt cttccaggcg | 1620 |
| ggcgactgcc ggctccggcg acagctgcgg aagcggctgg gctctctgtg ctgcgcgccg | 1680 |
| cagggaggcg cggaggacga ggaggggccc cggggccacc aggcgctcta ccgccaacgc | 1740 |
| tggccccacc ctcattatca ccatgctcgg cgggaaccgc tggacgaggg cggcttgcgc | 1800 |
| ccaccccctc cgcgcccag accctgcct tgctcctgcg aaagtgcctt ctaggtgctt | 1860 |
| ggtggtcaga cacgggtcat ctgtcgctaa ggcgcaacct ccaggaact cgaggcctgc | 1920 |
| cagggtctgt ccagatcaca aggggcagga gagtctgtga gagagtgaca ctgaagttgt | 1980 |
| cccccttcctc cactctccta ttcccttctc atgt | 2014 |

<210> SEQ ID NO 29
<211> LENGTH: 1078
<212> TYPE: DNA
<213> ORGANISM: Homo sapiens

<400> SEQUENCE: 29

| | |
|---|---:|
| agactctgca taaacagacc tcgctgtggt ggcggtttta actggcttgg gtcttctggg | 60 |
| tcctgttctc tcctttgtag gatgcgtgcg tcttggtacc tggaacaccc aggacttgcg | 120 |
| tgttctatgc aagtggcatg tctctagctc aaaattcaca aggcacatct agcatggcag | 180 |
| gggagagaag gggctggtgg cggggagagg gacgggaccc cgggcaggcg gcaggacggg | 240 |
| gatcccaggc tgcgggggga ctccgcgcca gagccgctgg gacctgaccc gggagcgcct | 300 |
| tcgtccccgc gcgcacctcc ccgggtcggg cgacttacgt gcgggcgtcg ggtatgtgga | 360 |
| agtccacggc gtagccgaag tagctgccct tggggccgct gtacactgtg agctttccca | 420 |
| cgtccaggtt gaacgcctga caggcggggg accacagcaa catccccagc gcggccgcgg | 480 |
| cgcagcagag gggcgcgatc agcggcgcct ggcttcccg gggaccgcgg ctggccccgg | 540 |
| gcgacatctc cctccgcccc ggtgggtggc tgctacccag gagcgcgagc cgaggacccc | 600 |
| tgcgggggcaa gggggggctgg tggaatctgg cggtccccag ctgcccgtgt cccgggtcgg | 660 |
| tgcgctcggc gcacccgtgg tgacagtgcc cggcgtctgc tcccaccgc ccgcccgccc | 720 |
| agccggctcg gggggctggc ccaggggctc tagccctcct ccggccgcgg gcagggacca | 780 |
| gctctctcgc ggcgcctcct cgcggctggt ctagagccag ggactcccgg gcggcccagc | 840 |
| tggtggctgg agcgctgggt gcctcttcgg gctgccgga tttctattgc agtcccatct | 900 |
| caaggacaat cagtttcgtc tctgtcacct caagctattt attgctttag aagcaatgcc | 960 |
| ccaggtggag cgagagcttg ctccagttgt gtcaaaggcg cagcttggat ggagaatgtg | 1020 |
| aaaaccaacc ccaccaccag gaggggcaaa gcaattatct cttcatcacc tctgcagc | 1078 |

<210> SEQ ID NO 30
<211> LENGTH: 1387
<212> TYPE: DNA
<213> ORGANISM: Homo sapiens

<400> SEQUENCE: 30

| | |
|---|---:|
| agccaggtgg gtgaactgag agtccaccga gacgcccagc acttcacagc ccagcttgcg | 60 |
| gaagtcctct gcacggttgc tgaacgcgat gatctcggtg gggcacacaa agtgaagtc | 120 |
| cagagggtag aaaaagagga ccacgtactt ccctggggag gagggacaca gaggagttag | 180 |
| ggcccagctt ctctcatgca cggccccgct tctacctggg cccctccgg gcggcgctca | 240 |
| cctttgtagt ccgacagctt cacctctttg aaggcgccat caaccaccgc tgtggccttg | 300 |
| aagtcagggg ctggcttttcc gatgcgcgcg ttaccggagg ccatgactga aagctgagac | 360 |

```
cccccgcccgg tcagtgcgcc cgggaagaca ctttgtcctc ccaacccaag gtcgcgctgc    420
gtgctgggcc ctatgactga gtcagcacgg cggaggcgac agcactaacc ctcaccctcc    480
cgggtacccg gtctacgagg cccggaggct gccggagacc cgctctcctg accagagcac    540
gagtgaccca gccactgcca ccagcacccc acgagcgagt cggccggagg gcggtgtcgc    600
aagcccccag cccagaagga gacagtgagg cccgcacgag caggggcgg gaagtcgggc     660 gatcaggcct cgcgctgcaag gctgtggcct cggtttcccc cgcaaggaca aaggaggcca   720
ctatagcgga tggaaagcaa aggcggccag cactaaagtc aggatcgggc caaagcagcc    780
tgaagggggt cctcccgcca ggtgcactcc gggtgttcat acctgcgtgg caaaggcta    840 gacgcacgga cgatcacacg cgtggacccg cgttctcagc gccaagtgag ccctgggccg    900
cgaagccttt tatgcccggc ccgaaccaag acgtgcacgg cgcgggggag ggagcggacg    960
agcggagcgg tcgggtccac tgcgcccgca ggtgcggggg agcgtgcggc cgggtccatg   1020
cgcctgcggg cggcgggggg agacgcgttg ccttcggccg ggaccactgc acctgcccgc   1080
gtgggtaatg cgcccgccgc agactccgcg cacgactccg cctgggagcg cgttggggc    1140 cgttggagtc cagcatggcg cggacccgg gggcgctgct gctggcgcct ctgctactcc    1200
tgcagctggc gacccctgcc ctggtctacc aggactatca gtacttaggg cagcagggcg   1260
aaggtgacag ctgggagcag ctgaggctgc agcatctaaa gggtaacctc aggcggcggg   1320
gatgacgatg cccaaaggct ccccgttgcc ctacttctcc tgctggctgc aaagggacct   1380
tcctcgg                                                            1387
```

<210> SEQ ID NO 31
<211> LENGTH: 1171
<212> TYPE: DNA
<213> ORGANISM: Homo sapiens

<400> SEQUENCE: 31

```
tggtgttcac ctacagggtc cctctcagca ctgcccaggc ctcccgagtg ctccagcaca     60
gtagcttgga gcttgttggt ttggtgacca agatacactc cagggaatat gccatgcagt   120
ggagtctctt ccccggcact gcatagcaaa aggaaagggc cgctgggtgt ctgtgggtcc   180
tgggcagtca cagaagccac cgcgctggcg gggaggaggg ggaccgatgc ggtccatgtc   240
ccgggcagcc ccaccttctc tgcctgcgaa gggcccttgt ccggcgggag gagagaggcg   300
cgccccaccc gggctcctct acacctgccg ccgcctgggc cgattccgcg ggcctcgccc   360
ggcgcttcag ccgattcccg cccagctccg ggctcatggg cgcggtcagc agggcgggcc   420
agggcggcgg ggcgcgacac tgggaggaag tgcgggccgc ctgcccgggc gcgttaagga   480
agttgcccaa aatgaggaag agccgcgggc ccggcggctg aggccacccc ggcggcggct   540
ggagagcgag gaggagcggg tggccccgcg ctgcgcccgc cctcgcctca cctggcgcag   600
gtaggtgtgg ccgcgtcccc taccggccg ggactttctg gtaaggagag gaggttacgg    660
ggaacgacgc gctgctttca tgccctttct tgttctacct tcatcggccg aggtaaaagt   720
gctgaaacca tgtgaataaa atacaggtgg gttccgccag cttcgctcct gaacctaccc    780
gcgctcggga tccagaagct gcgcggggag agagggctc aggcctgggc ggaggggacg    840
gaggtcagac cgtgcggaaa gtgacccggg caccccaggg cgcccaggcc cccagggagc   900
gcggaaagtg cggtcgcggc ccggccctcg ggagacgcgg gattgggatc aggcacagcg   960
cgaggaagtc gatcttggag ctagaacatt ttcctttggc catttacacg aatccactgg   1020
```

```
aaaatgccgc agtgtttatc aaagttactc aaagtagaaa tgtccagacg tcttatgagc    1080
ttagacaaat cttttactac aaaaagaaac agcagttgca ttcaaacaac aaccottctg    1140 aaccactact aaaatttagc ataattactc t                                   1171

<210> SEQ ID NO 32
<211> LENGTH: 3438
<212> TYPE: DNA
<213> ORGANISM: Homo sapiens

<400> SEQUENCE: 32
agccaggagc cttttaacgt agtaaaggag ctctctgtcc ctgacccagc tctcaggcct      60
gccgtacccg gagcacccct cacccggagg agtgccagag ccctaccagc cggctgcttc     120
taagccactg tgcagccagg aagcagcgcc gcagcaggcc cgagtgctcc actgtcccca     180
cagaaggcat ccattgagac cgcgggacca gccttggctt tcacatttcg ctgcagcctt     240
gtcccgcgcc gcactgtttc ctccggccac tgtgggtca ctaagcgacc tgcagaactc      300
gctgaggccc aggctcctgc agctcccgcc gaagactcaa agccagagtg acataaacg      360 ccgtgggcag gaccccggtg aggcctcggt gccttcttg ggggttctca gcgttggccc      420
agaagcctca gcccgggtct aagaacttgg gactctcctc gactttggcg atcggccggg     480
tcatccggct cagggcctca gcggcagcgg gcaaaactct agtaggagtc tcttgccgag     540
ggcgtgtttc gacgtcagag ccaaactcgg gacagactag ccaagcgcgg acggcgcgag     600
agtggctggc agcgccagca cgcagcctgg gttcagagca aggctgggcg ctctcagcaa     660
agggcggcct ggggctgcgc gggcggcgga ctgcaggcgg gagaagagcg aggtgcgcca     720
ggctctgggg cgcgcaactg cccagcctcg tgaaagatcg cgccgcagat ggggcgcagc     780
tgcgcgctca ctcgtgtgga ctggaaacgc tccgagccgg ttattttaaa aaccgggaaa     840
taaggcgggt tccctcttcg cccgccactt cccaccaagt aggctgtgcg gccctgggg      900 ctgactgtcc tcaagcagcc aggctccacc gcgcgccgcg ctgcgccgag gtccgctctg     960
ccgcagggac gctggcagcc cgttgaacac cggcaagagc gccagaggct agcggccgcc    1020
aggatctcta ccaggctctg ctcgcacccg cctgcctccc tttcgtttgg cctgtcctcc    1080
gttcaactga atcgttaat tttcttaccc ccttgttctc attttgatat attctacgct    1140
ttaaacatgc tccgttttct tttgtttagt ctgctccctc cctctttgtc ctttccccct    1200
tctctagtta tccgtttcgt tcgatcttgc tcctgctttt tttattcgtt cgttcctcat    1260 ttattcatttt tagttcatcc cagctcgccg actgccattt accctctcgt tctcgccgcg    1320
ctctccgttg ttttgttcaa tttcccttcc ccttttcttg gttgtcgctc gctttctttg    1380
gttttctttc tcggtatttc gttgtcaagg ccaccttgc cgtcggatcc cggggtgctg     1440
ggtttctccc ggccgctcgt tccgcaccag cgctctctgc agttcgcgcg gcaccggtgt    1500 ggtccgggg cccgagctgt cggtgccgga tgcggcgcgc ctagcaggga cgcgggcctg     1560 gggggtggc tcctgcccga cgcggagcgc tgagccaggc cgggtacctg tctctggcgg     1620
tgctcaccgc actgcgcggc ctctgccgtc tggctgggat cagaggagcc aggccaactg    1680
cttctcatta agtcccaact gtggtttta tcaggaaagc ctctttcaaa gggcacagac     1740
acgaagctcc gcggactcgt tcatttcctc cgttgaccca cacacacctc cccgccctcc    1800
cctacacatt cccaccgccc cggctgggcg aaagccggag atgcccgcc actccgtgga    1860 ggcccgcgag gcgccagccg ggcggcggca gggggttgag gcggatcttg gaggatccag     1920
ttctgggcct aggctgcggg atatggcagc gcagataagg tgggtgcagt gcggaagccg    1980
```

```
agacgcctta caggtcatag ggtgcggcgg acggccgcag agctgccgat cagcctgcca    2040 ggccccctgcc ttcaggcgca ttctcggatg ccggcgcggt ccagccggcc ttagcacagg   2100
gcaccggccc gtgagcccgc ggcgccaggg ggttaggctg cccagggctg ctcctgactg    2160
cccagcggtg atgatccagc gcggggaagc caagactgcc agaagggcgg ctatcatagt    2220
gcataacggc agggaggcca gcttagtatg agaaataaga atacagttat tccgtcttga    2280
ggacagccct ggcattgcac gaccagtcgc ggccagactg tgccagtctg ccgcacaggc    2340
agcacccttc ctgtgaaggc taggcccggg gaggagagac gggccaagac caggccgcag    2400
tccccagccg accccgattt gaccactcta ggttgaggcc cagcctcagg gccctcaaag    2460
ggcgccagac acaaaagccg cgcttcttcg tcaggtctca gtgtggctcc acagccctcg    2520
gccgggtctg ggcttcaggg taggtggcag ttccagtcca acttcggcag agcatgctct    2580
ctccttccca ggtccaactg ctttcgggcc ccgactggac tccgggccgt cgccactgca    2640
ccttccctcg acctcccgcc ttccattccc gccgccgagg aacggtggtt caccctcccg    2700
ccccacactg gcctttgcct ggcccgggcc agcgccaacc cggcttccgt ggaagccgtg    2760
gcgaaaggcg agaggggcaa aaagttgaga aataggcgag cggagagat aagcaggaag     2820 gcccgggtgg gcccgggtaa ggaagaagaa gagagggtcg ggctgcgcgc tacgccccgc   2880
gccgcgcgtt accttccgcg gggccctcgt agaagtggcc gccgttgagg gccgggccgg    2940
gcccgaggtc ctgcaggtac ttggcgggcg gcttggccgg ctctgggagg tagggctcca    3000
ggggcccgca ggccggaaag cgggtcagcc gcggccgcg gggcggcgcg gggtgcaggt     3060
gaggcgcagc ggcgggggtt ccctgcgggc ccggaggctc gtcccccgag gccacatagg    3120
ggccgggtgc aggcccccacg cggaaaggcg cgcagtgctc ggggtccatg ccggctcagg   3180
gcgcacaggc ctccggggct ccggggctcg cgctgcccgc gccgctgtg agcgcccgcc     3240 aaggggggagg gacctgggcg cggggcgcg gagcccccgg gagcggcgcg cgccgcgggg   3300 ggcgggggc gggggcagg ggagggggcc gcgcctctga cttaatgctg gaaccatcca     3360
cgtcacgtgt ggccccgtgc gggttaaccc ctcggagccc gggaacccc tccccccatt    3420 cacccagagc ccagtccc                                                 3438
```

<210> SEQ ID NO 33
<211> LENGTH: 999
<212> TYPE: DNA
<213> ORGANISM: Homo sapiens

<400> SEQUENCE: 33

```
gggtggggtt cggaacctca caccctcaca cctagttcct agcttctagg gagcctggag     60
ccggggcttc ccccctctg ctcgctgctt ctctcccttc cccttcctc ccctcttcc       120 ccctccttcc tcctccccgc cggcctcggt ccgcgtactt aaagcggcgc gggagggcgg    180
acgcgggcgg gcgccccgtt cgggcggtgg cagatgcgcc cagcggtgac agcggccagc    240
ggcgcgcagg tgaccggcct gaggcgcagc ctggtcaggg agcgcccggg gagagctggc    300
ggcagagggc agccgatccg ccccccagcgc gcgcgtctcg gcgccaggag ccgtcccggg    360
gcgtgttggc gagcgttgat atagatataa ggacatttct cttcatggcg tcacgtgaca    420
taattaccac cagaatcaat caagatgaat tgcacgtcag cgcccggtgg ggattttttgc   480 ttagttgatc ctggcccaag cctcttgtgc aatcgatggc tcaggttggc tgcgcgggga    540
gcggccagag gctcgctggc gcgcacgccg cggagtcatg aacgactttg acgagtgcgg    600
```

| | |
|---|---|
| ccagagcgca gccagcatgt acctgccggg ctgcgcctac tatgtggccc cgtctgactt | 660 |
| cgctagcaag ccttcgttcc tttcccaacc gtcgtcctgc cagatgactt tcccctactc | 720 |
| ttccaacctg gctccgcacg tccagcccgt gcgcgaagtg gccttccgcg actacggcct | 780 |
| ggagcgcgcc aagtggccgt accgcggcgg cggcggcggc ggcagcgcgg ggggcggcag | 840 |
| cagcggggc ggcccggcg ggggcggcgg cggcgcgggg ggctacgctc cctactacgc | 900 |
| ggcggcggcg gcggcggctg cggcggccgc ggcggccgag gaggcggcca tgcaacgcga | 960 |
| gcttctcccg cccgcgggcc gccggccgga cgtgctctt | 999 |

<210> SEQ ID NO 34
<211> LENGTH: 983
<212> TYPE: DNA
<213> ORGANISM: Homo sapiens

<400> SEQUENCE: 34

| | |
|---|---|
| ctggattgct caagagaggt cagggaaacc cctcagaact cctgagaccc agagattgag | 60 |
| ggaggggttg aggcggagtc tgcaatgggg gctgtccagc agtagcaagc agcgggccga | 120 |
| tcctggtgga gggttgggag gctgctgtca ttttatgggt cggcagccag agtgagagtg | 180 |
| tccctgctgc cagaggacta cggcgggctg gcgcgcgggg ccccgcctct cgctcaccac | 240 |
| acagaccccg cgcctcctct ggcagccgcg gtggtggcgg cggcagagcc tcgcccactc | 300 |
| caatccccac cctctccatc cttagtcatt aaagaacagc agcgcctggc acgttcttgg | 360 |
| aggaccccgg gcgcagagga ggaaagggag caggcgcagg gggactggaa aggcagcatg | 420 |
| cgctcgccag gagcaacctc ggcgcccagg gtctgaggct gcagcccag ttcgccattg | 480 |
| tgagccgccg ccggggagt ccgctagcgc agccgtgccc ccgagtcccc gtccgcgcag | 540 |
| cgatgggca cctgcccacg gggatacacg gcgcccgccg cctcctgcct ctgctctggc | 600 |
| tctttgtgct gttcaaggta ggggagctcc tccaccccctt tttcccagcg gtccgggcgg | 660 |
| cagccgcgct ccggcgccct cgctctgccg ttgggagcgg cgcgcccag ggcacgatgg | 720 |
| cccagccgcg ggaagcgcct gccgtgcagc ctgggcgcac gctttgttgt cctcgcgtgt | 780 |
| gcgtgttcct ggtggtcttg agaggtaggg ggcgggggga agaataaggg aagtttgctc | 840 |
| cctccggctt tcgcccttttg tgctcttttta tcgctgctga aatccacatc aaaggtgggc | 900 |
| ttgttggatc gtgctttctc aggcaaaatg aggtcacttt cttttctggt ttccactgca | 960 |
| ccccaacgct gcttaacctt tcc | 983 |

<210> SEQ ID NO 35
<211> LENGTH: 1292
<212> TYPE: DNA
<213> ORGANISM: Homo sapiens

<400> SEQUENCE: 35

| | |
|---|---|
| tgaaagaaag ttctctaaaa ccaggaaatc aggaatcagc agttttaagt tctccaggtt | 60 |
| atattttaac attgtgttca tatgcaaaac aaaggttgtg aatcagcacg aatgctggca | 120 |
| agccctggaa ggtttgtgat cacggacttt cacgagaccc caaggcaagg agagacagaa | 180 |
| gcccaggaca cagcatggg cgccgctttt tagtcgggcg ccgcttttg gtcaggcgcc | 240 |
| acctggacta catttcccat atccaattgc cgggctcctg caggattggc cagaacaacg | 300 |
| cggaagtgat tacgggtcgc ccagcaacgg gcggagtcct ggcccgaaac tggatgcgca | 360 |
| cgccccttcc ctgcgcgggg gaggctgaca aggctccgct ctatctctag cgcctcggag | 420 |
| cgctctccgg ctttgctgtc tagcccggcg gcagcgcgat ctcttaggca ctttcaccgc | 480 |

| | |
|---|---|
| cttcctctcc aggccctgcc cctttgacgc cggccgtcgc gatattgcgg agactggatt | 540 |
| tcagcttcgt ggtcggcgga gcggcccctg gagggcgcag tgcgcaggcg tgagcggtcg | 600 |
| ggccccgacg cgcgcgggtc tcgtttggag cgggagtgag ttcctgagcg agtggacccg | 660 |
| gcagcgggcg ataggggggc caggtgcctc cacagtcagc catggcagcg ctgcgctacg | 720 |
| cggggctgga cgacacggac agtgaggacg agctgcctcc gggctgggag gagagaacca | 780 |
| ccaaggacgg ctgggtttac tacgccaagt aaggggggccg cagtggggcc gcggacgcac | 840 |
| ctgggaccct gcacagccca cggacgccac ctgcgcgggg aggacgcgca ctccagcgca | 900 |
| gcgcgtgcgg tgcaaagtga aagtaactgt taaggagctt cagggaaaag ggtccagggt | 960 |
| tcccagtagg ggccggcccc cttggtgggc ctcgggtcca gcggggtca cctggtggct | 1020 |
| tcccggcgcg ccctctgctg ttcaggatgc agcactgcgc ggcgcggcga gggcaaagcg | 1080 |
| gcctcatccc cgccaaaaaa taaagatgtt ttaaaaagcg cacatgctca gctccctcct | 1140 |
| gcaggctctg ggttgcaggg ataggagttt tgttgtgttt tgttttgttt tgtccagacc | 1200 |
| ggtattgctc agtcatccag gctggagtgc agggtgcca tcatagccca ctgtagcctc | 1260 |
| tacctactgg gttcagacaa tcctctcatc tc | 1292 |

<210> SEQ ID NO 36
<211> LENGTH: 955
<212> TYPE: DNA
<213> ORGANISM: Homo sapiens

<400> SEQUENCE: 36

| | |
|---|---|
| ttcagggcct agggatcctg ggtatgctgg ctcagtaccc ctatccccat ctatgttcag | 60 |
| cttgtcccga tctatacagc cctcctccct gcctcttggg agcccaagct ccacctgccc | 120 |
| ccgagtcccg tgggcctcag gccccctgcc ccagacgtac cagttctcag ggaagccgtg | 180 |
| cagaaacagc atgaggggtc cgttacctcg tccagccgag acatagtgca gacgcaggcc | 240 |
| cgagctctag ggggagggca cagcctgaag cctggggaac cctctctccc gaggcttgaa | 300 |
| ccgtctcgac cccacgcgac cccgcagccc cgatagcgcc cccgtgcgat caccttgagg | 360 |
| ttcaggaaac cgtgctcacc cagcgagggg tcgctcaggc aggcggggga cgcgctccga | 420 |
| cggcgcccgc agcagccgcg ccggggccgg cacagcacgt gcgtgagcgc tatgcagccg | 480 |
| tagaccgccg cggccaccag cgccaccgag aacaccaggc tccacatgaa ggcgcgcagc | 540 |
| agcttcagcg acaggcgcga cggcgccagc agcgcggtca ccaccagctc cggcatgtcg | 600 |
| ccgcgctccg gaccacggc ggcgctgccg gccagggca cctgcagcag cggcgaagcg | 660 |
| gtgtcagggc tcaggggccc atcgcccttg gcctgggcc cctccgtgcc gtcgggattt | 720 |
| gtgggacgcg ctgaaggaag aggcgggcgg ctccgacaga aaacagccag agcgcaccac | 780 |
| tcacctgagt gccaggtaaa cacctgggcg cgacagggac aggaaacaag ggtagggtgc | 840 |
| ggaggctggg gaggaagagg ttggaaaggg gggaaataaa tgggcggggc ctagcaggtc | 900 |
| ctgtgcgggg cttagggccg gggcggggcc caggaagact cagcagcggg tgggt | 955 |

<210> SEQ ID NO 37
<211> LENGTH: 2432
<212> TYPE: DNA
<213> ORGANISM: Homo sapiens

<400> SEQUENCE: 37

| | |
|---|---|
| gatgtgaaat gtacctaaag gttcctagcc gtctttcatc cctccctctg tgaaacaggg | 60 |

```
agacacatgt gttttaaggc agagatggaa cttgggcgat gggcgggggg tgggggaggt      120
gggaagggac ggcttaggac agggcaggat tgtggattgt ttctgccgcc ttggttgccc      180
atactgggca tctctgcagg cgcgtcggct ccctccaccc ctgctgagat gatgcactgc      240
gaaaacattc gctctccccg ggacgcctct cggtggttca gagcagggaa aatgttgcct      300
caggtttaaa ataatctgcc caagcacccc agcgcgggag aaacgttctc actcgctctc      360
tgctcgctgc gggcgctccc cgccctctgc tgccagaacc ttggggatgt gcctagaccc      420
ggcgcagcac acgtccgggc caaccgcgag cagaacaaac ctttggcggg cggccaggag      480
gctccctccc agccaccgcc cccctccagc gcctttttt cccccatac aatacaagat        540 cttccttcct cagttcccctt aaagcacagc cagggaaaac ctcctcacag ttttcatcca    600
gccacgggcc agcatgtctg ggggcaaata cgtagactcg gaggtaggca tccgtggggg      660
ggcgccggct cgggcgtgcg gggagtgtcc gcttctgcta tctgcctctc caaatatccc      720
gactgctgcc ctggcccccag ccctctctcc acttcggagc actcctctgg cgttggcacc    780
gctgaggaat gggcctgggc ggggaggtga agagaagcca ggaatgtttt atgttttcct     840
aatggagagg gggcctaggg agcccctgag ctaggaggac acggaaaagg ggattggggt     900
cctgagattg ggtctgttgg gcccaggacg cgttttctgg atgggtctag gatgctccct    960
tgtcgcggga cccccgcggt ccggccctgc ctgctggggg ttcgaagagg tggagtgcag    1020
ggtggaggtg ttatttaccc gagtcctggg gacagtcccc gggactctcc gccaggcgcc    1080
cagaccggca ggtcccgcag gcggcgcgcg gtgtgtttgc actttccaaa gttcttgaac    1140
catctcaaga actccttctg catcttggcg tctggcaggg gtgttccgag agaggtagac    1200
ctcccctccc caaactgcca ccatcacttc caacgccctc cacgcgctgg agctctgccc    1260
gggtgtggaa acctcgtctt ccaacacgta gctgccttc agccacccgc ccgcagcctg    1320
ggagtgccct gagggtgggt cggggggagct gcgcaggtga gactgagttc taggacattt    1380 aggggggtctg gtgcctggct ccgccaaaaa tggggacttt cgggattgtg atcatcacgg    1440
cggattgagc agggagagcc gtggagggac aagagagggc cgaggcaggg tggggggcgc    1500
gggcaggtgc gaggggatg cggccaagaa gcagcgataa agggaacatt ccacgggtcg      1560
ggcggctgct gttggatctt agataaagct ggaagggatt accggggcag gggtaatagg    1620
gaccggggac gggaacgcga aacaggtgaa gcgctcaggg cgagagcgac tcggcttagg    1680
gagtccggga gaagcctgcg gctgccccct cgccgccgag gtcctgcggg tcctgcgggt    1740
cctgcgtgct gagccgggc gtgcgcggc ggggccttc ggaccgcgcg gcggggcctg        1800
ccctgacccc tggcggcggg cggggggaggc aggcgcgccc tgcagagtac agaggggtgt    1860
ggtgtcctct gcgagatcct cttaaaaagc tggctacgcg caggcggttt ctgtgcacgg    1920
agccgtagct gtcggagcgg ttagttcgat ttcgagctcg aggtttcccc cgccgccagg    1980
ctgacttctc atcgcttgtt tttctttttg cattttttcct cccaccgccg ttgccgccct   2040
ccccgtcctg gccgtccgcc ctccgccctc tgcagggaca tctctacacc gttcccatcc    2100
gggaacaggg caacatctac aagcccaaca acaaggccat ggcagacgag ctgagcgaga    2160
agcaagtgta cgacgcgcac accaaggaga tcgacctggt caaccgcgac cctaaacacc    2220
tcaacgatga cgtggtcaag gtaagccaag gcgaccaaca gggaagggct gggacagctc    2280
tcctctggca gttagcccgt gcatccttct ttagcattgc cgtgtacgca cccccacccc    2340
cgccccctac acgcgcacac acacacacac acagagtttt gtgggtttga tgtgtgggag    2400
ctcccgcagt cggcagaaac gttacatctc cc                                   2432
```

<210> SEQ ID NO 38
<211> LENGTH: 1728
<212> TYPE: DNA
<213> ORGANISM: Homo sapiens

<400> SEQUENCE: 38

| | | | | | | |
|---|---|---|---|---|---|---|
| tttctctcct | cttccctctt | cttcccccca | cttcctcttc | acttttctt | cactttttct | 60 |
| tcttcttctc | tttccttccc | ccatgccttt | ctcaaccttg | tttccacttc | ttgtcgctct | 120 |
| tcttgcttca | acaaacgtcg | atgcagtcac | agttcctggg | ctgaggctgg | gggatgggag | 180 |
| gaagtcctga | gggcagcccc | cgcccccttc | cccgccccgt | cactccctct | gccccgcctg | 240 |
| cacagcttct | tgccaattca | ttcccgcccc | taccgcccct | ataagccacc | aggtcgctcc | 300 |
| agtttggtgc | cagcgcctgg | agggagaggc | gtggcgaggg | ctgtgctgcc | taggatccac | 360 |
| tgagtggctc | ttgctggcgt | gtcagctgcg | cgcgaaccag | ggctgggagg | ctcggctgga | 420 |
| ggtgtgacca | gggcagggac | tgacctggcc | cggaacagaa | gcgcgcagag | tcccatcctg | 480 |
| ccacgccacg | aggagagaag | aaggaaagat | acagtgttag | gaaagagacc | tccctcgccc | 540 |
| ctacgccccg | cgcccctgcg | cctcgcttca | gcctcaggac | agtcctgccg | ggacggtgag | 600 |
| cgcattcagc | accctggaca | gcaccgcggt | tgcgctgcct | ccagggcggc | cccgggctgc | 660 |
| tcctgctccg | cagagctacg | ccctccccc | gggtgccccg | gacctgcac | ttgccgccgc | 720 |
| tttcctcgcg | ctgctctgga | ccttgctagc | cggctctgca | cctcccagaa | gccgtgggcg | 780 |
| cgccgctcag | ctgctccatc | gcctcacttt | cccaggctcg | cgcccgaagc | agagccatga | 840 |
| gaaccccagg | gtgcctggcg | agccgctagc | gccatgggcc | ccggcgaggc | gctgctggcg | 900 |
| ggtctcctgg | tgatggtact | ggccgtggcg | ctgctatcca | acgcactggt | gctgctttgt | 960 |
| tgcgcctaca | gcgctgagct | ccgcactcga | gcctcaggcg | tcctcctggt | gaatctgtct | 1020 |
| ctgggccacc | tgctgctggc | ggcgctggac | atgcccttca | cgctgctcgg | tgtgatgcgc | 1080 |
| gggcggacac | cgtcggcgcc | cggcgcatgc | caagtcattg | gcttcctgga | caccttcctg | 1140 |
| gcgtccaacg | cggcgctgag | cgtggcggcg | ctgagcgcag | accagtggct | ggcagtgggc | 1200 |
| ttcccactgc | gctacgccgg | acgcctgcga | ccgcgctatg | ccggcctgct | gctgggctgt | 1260 |
| gcctggggac | agtcgctggc | cttctcaggc | gctgcacttg | gctgctcgtg | gcttggctac | 1320 |
| agcagcgcct | tcgcgtcctg | ttcgctgcgc | ctgccgcccg | agcctgagcg | tccgcgcttc | 1380 |
| gcagccttca | ccgccacgct | ccatgccgtg | ggcttcgtgc | tgccgctggc | ggtgctctgc | 1440 |
| ctcacctcgc | tccaggtgca | ccgggtggca | cgcagacact | gccagcgcat | ggacaccgtc | 1500 |
| accatgaagg | cgctcgcgct | gctcgccgac | ctgcacccca | ggtattggcc | cagtgcatgc | 1560 |
| cgacaggccc | aggccaggga | cttgggcgct | ccctgggcag | ttggcttgag | gagcctgtgg | 1620 |
| gcatcaccac | cgttactccg | cccagagttc | accagccaca | gcactgcccc | tgcacgctgc | 1680 |
| tcacaggggt | ttcctgttgg | ttcattggtg | cagacactgc | gggggcct | | 1728 |

<210> SEQ ID NO 39
<211> LENGTH: 1425
<212> TYPE: DNA
<213> ORGANISM: Homo sapiens

<400> SEQUENCE: 39

| | | | | | | |
|---|---|---|---|---|---|---|
| ccactgcact | ccagcctggg | ccacagcgtg | agactacgtc | ataaaataaa | ataaaataac | 60 |
| acaaaataaa | ataaaataaa | ataaaataaa | ataaaataaa | ataaaataaa | ataaaataaa | 120 |

| | |
|---|---|
| aaaataaaat aaaataaaat aaaataaagc aatttccttt cctctaagcg gcctccaccc | 180 |
| ctctcccctg ccctgtgaag cgggtgtgca agctccggga tcgcagcggt cttagggaat | 240 |
| ttcccccgc gatgtcccgg cgcgccagtt cgctgcgcac acttcgctgc ggtcctcttc | 300 |
| ctgctgtctg tttactccct aggccccgct ggggacctgg gaaagaggga aaggcttccc | 360 |
| cggccagctg cgcggcgact ccggggactc cagggcgccc tctgcggcc gacgcccggg | 420 |
| gtgcagcggc cgccggggct ggggccggcg ggagtccgcg ggaccctcca agagcggc | 480 |
| cggcgccgtg actcagcact ggggcggagc ggggcgggac cacccttata aggctcggag | 540 |
| gccgcgaggc cttcgctgga gtttcgccgc cgcagtcttc gccaccagtg agtacgcgcg | 600 |
| gcccgcgtcc ccggggatgg ggctcagagc tcccagcatg gggccaaccc gcagcatcag | 660 |
| gcccgggctc ccggcagggc tcctcgccca cctcgagacc cggacgggg gcctagggga | 720 |
| cccaggacgt ccccagtgcc gttagcggct ttcaggggc ccggagcgcc tcggggaggg | 780 |
| atgggacccc gggggcgggg agggggggca gactgcgctc accgcgcctt ggcatcctcc | 840 |
| cccgggctcc agcaaacttt tctttgttcg ctgcagtgcc gccctacacc gtggtctatt | 900 |
| tcccagttcg aggtaggagc atgtgtctgg cagggaaggg aggcagggc tgggctgca | 960 |
| gcccacagcc cctcgcccac ccggagagat ccgaacccc ttatccctcc gtcgtgtggc | 1020 |
| ttttaccccg ggcctccttc ctgttccccg cctctcccgc catgcctgct ccccgcccca | 1080 |
| gtgttgtgtg aaatcttcgg aggaacctgt ttccctgttc cctccctgca ctcctgaccc | 1140 |
| ctccccgggt tgctgcgagg cggagtcggc ccggtcccca catctcgtac ttctccctcc | 1200 |
| ccgcaggcc ctgcgcggcc ctgcgcatgc tgctggcaga tcagggccag agctggaagg | 1260 |
| aggaggtggt gaccgtggag acgtggcagg agggctcact caaagcctcc tgcgtaagtg | 1320 |
| accatgcccg ggcaagggga gggggtgctg ggccttaggg ggctgtgact aggatcgggg | 1380 |
| gacgcccaag ctcagtgccc ctccctgagc catgcctccc ccaac | 1425 |

<210> SEQ ID NO 40
<211> LENGTH: 9809
<212> TYPE: DNA
<213> ORGANISM: Homo sapiens

<400> SEQUENCE: 40

| | |
|---|---|
| gttggggacc cttcttatcc tcctagctca gagggaaaga ttcaagagtt tactcttcgc | 60 |
| ccaatgccca cttcagctag gggttcctgg aagaacgggg ctgtggagta tctcagaaaa | 120 |
| ctttcctccc tctactgtct tcaggcccca ggagacaaac ctccttccaa gcctcctggt | 180 |
| cccagtggct tccctctcac cgaaatcgaa agaacccgag tcccagcccg accccttctc | 240 |
| tcgccgagcc ctggctggga taccttggcc gggaggacag gacggcctca ggctggccgc | 300 |
| cagacgcact ccgcaggacg cgcgcgctcg agcctcggtg gactcagccg ccggccccgg | 360 |
| gaggccgcct ccctgcgcag cacctcctgc caccgcgcg gcacgtgggg atcttgactc | 420 |
| gccgcccccg cctccttctg ctccgcgtcc ccagcccgcg gctcggggcg cggcgtggcg | 480 |
| cggcgcgtgg gcgtgctgcg gggcgaccat ggctgtagac tgttacctcc agttcccaca | 540 |
| gtaacaatcg aaagccacgg ttgccctgga gacgcgggg cggggcgcgc ggacggcgcc | 600 |
| ggcgcggggc gggctgacgt cagggccgcg ggggggcggg cggggcggcg ggggctgagg | 660 |
| agcgcgcgtg ggccaccgcc cctcgcagcc cctaggggacc cggacggggc ggcccgatgg | 720 |
| cggcgcctgc gttgatcagc accgcggaca gcggcggcgc aggcagcggg ccggggggcgg | 780 |
| ggccctgagg gacggggact ggggggtcccc gggcgcggcg gcggcggccg gggccgcggt | 840 |

```
cctggggcgg ggccaggcgt cggtggccgt gactggagac tgttactgag ggcggcccgg      900
gcagtaagca gtctagagcc aaggtgccgg cgcgctgtcc gggcggggtg ccccggtcgc      960
cccggctgcc ccggctgggg gctctgctgc tccgcctccc ctgcgtctcc cgccctgccc     1020
cgcccggcgc tcgcgaccag gcacgcggcc cctgacgtca gagggccgtg acgtcaaaga     1080
tgtcccagag ggggcacttc cggcgggggc gtggggcgg ggcgggacct gggaggcccc      1140 gccccccgg tcctgagagg acagctccgc tcgcagaggc gggaagccgt gggcgccgcg      1200
ggacccgctg acgggacct gccgggaagg ggcgcccgac gccatgcggg gcggggtcc       1260 caggagggcc ggggaagcgg gggtggcgt ccgtctctcg cctgcacccc cgctcagccg      1320
gcccgggcag cgaggctgag tcaccgcgcc gcagggaggg agaggagggg gcgcgtctcc     1380
tggggcgcca gcaccttcgc ctcactttcc tgggagaatg gcgcaggagc cccaagaaag     1440 ccggggggg gtctccgagg tcggtcctcc actcgatgct cctccgaagt agctgcgtgt      1500
ccatcgggcg ccggcaggtg ctgcgcgggc tcgtgtcgtc tctggccccg gctccgcagc     1560
cgcgagggga ccccggtgcc ccccgtccgc ccccatcccc accccggagg ggccgcccca    1620
cccgccgcct gcccgtcccc tcctcgtcct cccgtccgtg tccgcacatc tgtccctccg    1680
cggctggtcc gtcccgctta cctggcgggc cgcgtcgcca ctgcccggtc gcctcccgca    1740
gcctggccgg cgcggcggct tttataggcg cgcgtagtac tcgtgcggcg gctcattcat    1800
gcggccgcgg ctcctacaca ctgacgcgct gccgacgtca gcgggaatt taggaaatgg     1860 gaaaagggc tatttatagt ggcgaggcgg ggggtgggga ccgaggcgac cgggagggga     1920 ggaggggcg cggaagcggc ggcggggtag ggggagccgc gccctgccc agccgacaag      1980 gggttaactt tccggaaccg cgggcctggg gccggggagg cggcgcggag gggcgcggcg    2040
ggcccttcga gcttattcac gctctccttc cggagccccg cggctcctgg gggtcttcac    2100
gtggcagccc cttccccctc ctcagttcct ggacctgacg tttctgccgt cacacccgc     2160 aaggccactg cggtgtcgcc accctctcgt cctgcagggt gggcaggaga ggaagctgga    2220
ctcccgtggg ggcctgggc gcagcgaggg ctgtggcgtc gggggccggg agaagaagag     2280
taggggagcc caaagtagcc caggagtctt tagcggagga acctgggcct gggagggaag    2340
gcccagcggg gattcaggta ccacccagga gctggagacc cgaggacgg cagagaagtt     2400 ggggaaggtg ggccaacctc cccagaaatg atgagcaacg ggatcctcta tgagggagct    2460
gggggaacgc gccagaggta ggggtgagag gaatgggcag cctcagcaag ggagagagga    2520
aaggctgtca gtgccacgct ccagagcctg gcatccagga cccaccttcg gaccatttgt    2580
ggcacgatgg acgctcccag agctcacgtt agggtaatag agagtgaagg agaccagcag    2640
cttggccaag aggggcccc aggggatgag gaggacggtt tcctggagaa gttaatgttc     2700
ccggagacca gaattggcag ggagagccca tgacttgtgg ggcagttccc ctggttggga    2760
gcggggaaat gcatggtcct ggcccagcct ggctccatcg agatggagga agggtctaaa    2820
tgagaggagt gtgttcagac gaggagctgg accaggatgg ggagggctgt gcaaggcatg    2880
gccggaagag cggggcaggg agagaaaggt cgaagagtga agtgcacagg agggcaaggc    2940
ggtcctcacc ctgcctgggc tggggcaggg ctgtgagacc ctcccttaca gaagcaatga    3000
gggcttgagg agggggttag gggcctgggc tggggcaggg ctgtgagacc ctcccttaca    3060
gaagcaatga gggcttgagg aggggttag gggcctgggc tggggcaggg ctgtgagacc    3120
ctcccttaca gaagcaatga gggcttgagg atggggttag gggcctgggc tggggcaggg    3180
```

```
ctgtgagacc ctcccttaca gaagcaatga gggcttgagg aggggggttag gggcctgggc    3240
tggggcaggg ctgtgagacc ctcccttaca gaagcaatga gggcttgagg aggggggttag    3300
gggcctgggc tggggcaggg ctgtgagacc ctcccttaca gaagcaatga gggcttgagg    3360
aggggggttag gggcctgggc tggggcaggg ctgtgagacc ctcccttaca gaagcaatga    3420
gggcttgagg atggggttag gggcctgggc tggggcaggg ctgtgagacc ctcccttaca    3480
gaagcaatga gggcttgagg atggggttag gggcctgggc tggggcaggg ctgtgagacc    3540
ctcccttaca gaagcaatga gggcttgagg atggggttag gggcctgggc tggggcaggg    3600
ctgtgagacc ctcccttaca gaagcaatga gggcttgagg atggggttag ggcagtaag     3660
ttaacttggg gagcggatgt gggggaacgc tgaagaataa agactgtggg cacagcagac    3720
ccctggggca ggttagcaat gcacagactc cactgcacaa gatacatggg gcggaggggc    3780
tctttggaag tcggggggtgg gggatctgac tctatcaaaa agagaaaaga taaaagagat   3840
ggggtcagag aggccctgca tagtctggat ttggcctact agagctccag ttttcttgcc    3900
gctagccttt gttccaggga ttctgttatt cacaaatgcc ttcctgctcg gtagaagaac    3960
tcctattcat ccgtcaaagc ccagctctag gagcacttat gaggagcctc tccacctccc    4020
ctcaacactc cgtaacttcc acctcaggcc gcagcacgtc cctcgggcga gatgtcgggg    4080
tccgccttcc ctagagaccg gcagctccgg aggcctccgt tttcctcttt gggacctcac    4140
tgcttctaaa gtgaggatgc tatggggaga catgggagag ggagtgggta agatggatcc    4200
agaacatggg gcggactcag gcagcggcgg gaatcaggcg gactcgtttg gaccgaagcc    4260
tccgccaggc accgaagccg tgaagtcgcc tgcgcagcaa agggagcctc cggggggcgc    4320
ccgagacctt ggtgtcgctc gggggccgct ggtagccgcg cccgctgccc ctcgccggt     4380
gactcagccg gtacctctgg cggggccatg ggggccagag gacagcgcgg ggggcggcga    4440
gcgcggttgc taagctctcc aaggcctcgg agggacagga tctgggcgca cctcaccggt    4500
tgccatggta acgcagcgcc ccagcccctc gcgctccgcg gtggagggag gcgcagccaa    4560
tcggaagcgg cggagttctc ggggacccccc ccccccccg ctccacgccg tgtgtgggcg    4620
ggggtcagga ggtgcgggc ggaggcggag cgtgggccgc ggagatccgg cgttcgcagg     4680
aggcttggtg cgcggcgggg ctgcacgggg ccacttccgg agtagtactg cgagcagcgg    4740
cgcgacagtg cggggtcccc tttctcccag aagagacgtc acccacacaa acctgacctt    4800
cacgtgggc gcgggacctt gcggggtccc agccgcaggc gcccctgttg tttccttcgg    4860
gcgggtgggt tggagaagaa gtccacgcgg gattcttcaa aacggcgtac agggggattc    4920
tagggcccca tggttacttc tttggacccc ccggaggcgc tgtccagcca cttccagtcg    4980
ccctgatgac tcgtcgtggg ttcctttagg agacccgaaa gttcagggcg gctgtgtgg    5040
gtaacacctc tgcccaggtt cccggagggc cctacgtggc tgcccctgga gtatcccaga    5100
gcgctagggc tgcgggaagg ggcgggtgtg cttctggaaa catgagcgcc tgttagtatc    5160
agtgcctgga tagggctggg gacaaatcag tttatgccgc gcacaccgaa tccatgcgcc    5220
tgagtgaggg tgggtgtgtt ggggagtgcg tccaagtgga cagtgccgta cagtaatgtc    5280
tacggggagt tccaggagag ctcggctact cctgcgcagg ataacctctc ccccaccacc    5340
cgagtcccgt gctcgcgggc aggactttc cgaactgggg ctgtgtgcct agaaatacgt     5400
acatgggagc gctcagctca aagccccagg gtttctggga ctcgcgtgtc cggggtcggg    5460
gtcccaggtg ggtacaggtg ggagggcgaa cctgcgggta gggtgggccc ctcccgcgcg    5520
gctcagcatc tgtgcgcctc cagctcaggt gcgcgggagg aaggcagcgg cctgccgcgc    5580
```

```
agagccctgc gcgcccgcga ggtggcgcca tagccgcagc agcgcccgcc ggcccgggcc    5640
gctccagata agagtgtgcg gaaagcgcgg cggggctgag acgcgaccag gacgcgggga    5700
ggacggacca gcaggacaga ccgaccgggg gcccggcggg cggagggcag cgcagccacg    5760
tcccccctgg atccgccgtc agccgggccc ggggctttcg acatgccccc caggtgggtc    5820
ctcgagccgg ggaccgggag ggacggggga cccgggacag cccggtcctc gtgcgtcggc    5880
cgcctcgggt gcatcttctg gcgcgggtgc cccatcgcgg ctggcggctg gcgttcaggg    5940
ctccgggtgt cgtccctttc ggactcagga ccaccgggcc gcggctccgc gccgggttca    6000
cggcggggtc agcggcccgg ggccggctct gcccgcacat gggctggaga ggcgagggga    6060
agggaaggga aggggagctg gcgggcgggg ctggcagggg cgctgccctg gcacagctcg    6120
gggcctggca gcggcgggtg gggcatcggc taagagctgc caccgccgcg gggaggggag    6180
cccggcccgc cgggaccgca ggtaacgggc gcgggggccc cgcgggccag gaggggaacg    6240
gggtcgggcg ggcgagcagc gggcagggga gctcagggct cggctccggg ctctgccgcc    6300
ggatttgggg gccgcgagga agagctgcga gccgagggcc tggggccggc gcactcctcc    6360
cgccctgtct gcagttggaa aacttttccc caagtttggg gcggcggagt tccggggag    6420 aaggggccgg gggagccgcg gagggaggcg ccgggcccgc gcgtgtaggg cccaggccga    6480
ggccgggacg cgggtggggc gcaggccgg gtcaggccg cagccggctg tgcgccgtgc    6540
ccgcccgggg cgctgccccc tccctcccct gggagctgcg tggctccccc ctcccccca    6600 cctgcttcct gcctcagcct cctgcccccga tataacgccc tccccgcgcc gggcccggcc    6660
ttcgcgctct gcccgccacg gcagccgctg cctccgctcc ccgcgcggcc gccgcccggg    6720
ccccgaccga gggttgacag ccccccggcca gggcggcgcc agggcgggca ccgcgctccc    6780
ctcctccgta tcacttcccc caactggggc aacttctccc gaggcgggag gcgctggttc    6840
ctcggctccc tttctcccta cttgggtaaa gttctccgcc ctgaatgact tttcctgaag    6900
cggacatttt acttaaatcg ggtaactgtc tccaaaaggg tcactgcgcc tgaacagttt    6960
tcttctcgga agccccagca cccagccagg tgccctgggg cgtgcaggcc gccctggcct    7020
cccctccacc ggcggccgct caccctcctgc tccttctcct ggtccgggcg ggccggcctg    7080
ggctcccact ccagagggca gccggtcctt cgccggtgcc caggccgcag ggctgatgcc    7140
cccgctcagc tgagggaagg ggaagtggag gggagaagtg ccgggctggg gccaggcggc    7200
cagggcgccg cacggctctc acccggccgg tgtgtgtccc cgcaggagag tgtgctgggc    7260
agacgatgct ggacacgatg gaggcgcccg gccactccag gcagctgctg ctgcagctca    7320
acaaccagcg caccaagggc ttcttgtgcg acgtgatcat cgtggtgcag aacgccctct    7380
tccgcgcgca caagaacgtg ctgcggccaa gcagcgccta cctcaagtcc ctggtggtgc    7440
atgacaacct gctcaacctg gaccatgaca tggtgagccc ggccgtgttc gcctggtgc    7500 tggacttcat ctacaccggc cgcctggctg acgcgcaga ggcggctgcg gccgcggccg    7560
tggccccggg ggctgagccg agcctgggcg ccgtgctggc cgccgccagc tacctgcaga    7620
tccccgacct cgtggcgctg tgcaagaaac gcctcaagcg ccacggcaag tactgccacc    7680 tgcggggcg cggcggcggc ggcggcggct acgcgcccta tggtcggccg ggccggggcc    7740
tgcgggccgc cacgccggtc atccaggcct gctaccgtc cccagtcggg cctccgccgc    7800
cgcctgccgc ggaccgcccc tcgggcccag aggccgcggt caacacgcac tgcgccgagc    7860
tgtacgcgtc gggaccccggc ccggccgccg cactctgtgc ctcggagcgc cgctgctccc    7920
```

```
ctctttgtgg cctggacctg tccaagaaga gcccgccggg ctccgcggcg ccagagcggc   7980
cgctggctga gcgcgagctg cccccgcgcc cggacagccc tcccagcgcc ggccccgccg   8040
cctacaagga gccgcctctc gccctgccgt cgctgccgcc gctgcccttc cagaagctgg   8100
aggaggccgc accgccttcc gacccatttc gcggcggcag cggcagcccg ggaccccgagc  8160
cccccggccg ccccgacggg cctagtctcc tctatcgctg gatgaagcac gagccgggcc   8220
tgggtagcta tggcgacgag ctgggccggg agcgcggctc cccagcgag cgctgcgaag    8280
agcgtggtgg ggacgcggcc gtctcgcccg gggggccccc gctcggcctg gcgccgccgc   8340
cgcgctaccc tggcagcctg gacgggcccg gcgcgggcgg cgacggcgac gactacaaga   8400
gcagcagcga ggagaccggt agcagcgagg accccagccc gcctggcggc cacctcgagg   8460
gctacccatg cccgcacctg gcctatggcg agcccgagag cttcggtgac aacctgtacg   8520
tgtgcattcc gtgcggcaag ggcttcccca gctctgagca gctgaacgcg cacgtggagg   8580
ctcacgtgga ggaggaggaa gcgctgtacg gcagggccga ggcggccgaa gtggccgctg   8640
gggccgccgg cctagggccc ccttttggag gcggcgggga caaggtcgcc ggggctccgg   8700
gtggcctggg agagctgctg cggccctacc gctgcgcgtc gtgcgacaag agctacaagg   8760
accccggcca gctgcggcag cacgagaaga cgcactggct gacccggccc tacccatgca   8820
ccatctgcgg gaagaagttc acgcagcgtg ggaccatgac gcgccacatg cgcagccacc   8880
tgggcctcaa gccttcgcg tgcgacgcgt cggcatgcg gttcacgcgc cagtaccgcc    8940
tcacggagca catgcgcatc cactcgggcg agaagcccta cgagtgccag gtgtgcggcg   9000
gcaagttcgc acagcaacgc aacctcatca gccacatgaa gatgcacgcc gtgggggcg    9060
cggccggcgc ggccggggcg ctggcgggct gggggggct cccccggcgtc cccggccccg    9120
acggcaaggg caagctcgac ttccccgagg gcgtctttgc tgtggctcgc ctcacggccg   9180
agcagctgag cctgaagcag caggacaagg cggccgcggc cgagctgctg gcgcagacca   9240
cgcacttcct gcacgacccc aaggtggcgc tggagagcct ctaccgctg gccaagttca   9300
cggccgagct gggcctcagc cccgacaagg cggccgaggt gctgagccag ggcgctcacc   9360
tggcggccgg gcccgacggc cggaccatcg accgtttctc tcccacctag agcgcccctc   9420
gccagcccgc tctgtcgctg ctgcgcggcc ctggcccgca cccagggag cggcggggc     9480
ggcgcgcagg gcccactgtg cccgggacaa ccgcagcgtc gccacagtgg cggctccacc   9540
tctcggcggc ctcacctggc ctcactgctt cgtgccttag ctcggggtc gggggagaac   9600
cccgggacgg gggtgggatg gggtaaggga aatttatatt tttgatatca gctttgacca   9660
aaggagaccc caggcccctc ccgcctcttc ctgtggttcg tcggcccct cccccggctc   9720
cgcgctgctc ttagagggg aggggtgtca ctgtcggggc actcctagcc ctacctccgg    9780
cccttgcgac cacacccatt ctcactgtg                                       9809
```

<210> SEQ ID NO 41
<211> LENGTH: 1171
<212> TYPE: DNA
<213> ORGANISM: Homo sapiens

<400> SEQUENCE: 41

```
agtatcatct atccctattt aggaggtgag agtgtctcag atcggttaag taactggctc     60
ataatgatca gtgcttgtgg gaaagctgga atatccacgg agttctttcg aactctagcg   120
gtccaagctc tttcccaagt cacgtagctt ctctattcgg agagaagtcg gagtactggg   180
atagacccag gaggtcagag cggaaactct gcccgggtgc gtggaaccgg agtccccggt   240
```

```
gcgcggcgcc aggtactcac ctgtatggct gagcgccagg accgcgcaca gcagcagggc        300
gcgggcgagc atcgcagcgg cgggcagggc gcggcgcggg ggtaggcttt gctgtctgag        360
ggcgtctggc tgtggagctg aaggaggcgc tgctgaggag ttcctggacg tgctcctgac        420
gctcactgca agtcgtatga caattggtcg ctaaccgaga gaaccttcct ttttataaga        480
ctgaaaacca agcccatgtg acgaaatgac tgtttctttc cgccttttcg tacccccac         540 aaatttttcc ctcctctccc cttaaaaaaa ttgcgtaagc ccggtggggg cagggttttt        600
tacccacgga aatgagaaaa tcggaaaccc aggaagctgc cccaatttgg gagcagaggg        660
ggtagtcccc actctcctgt ctgatccctc cctctcctcc ccgagttcca ccgccccagg        720
cgcacaggtt tccgccagat gtcttttctt cttcgcagtc tttgcccgag cgcttccgag        780
agccagttct ggactgatcg ccttggatgg gataccgggg gagggcagaa ggacacttgg        840
cttcctctcc aggaatctga gcggccctga ggtccggggg cgcagggaat cccctctccc        900
gccgccgccg ccgtgtctgg tctgtacgtc tttagagggt cgaggaagtc acgtcgggac        960
agactggggc gagtaaggtt aagaaaggct gacatgtttt atgttttagt gacgacgctt       1020
aataggctgt atatctgctc tatatgcagc acatacatac atagcttttt aaaaaactct       1080
tattttgtgg aatgaaatag ctaccttcag tgtacatagc tgtaatttat ctttgtagct       1140
aagttgcttt caacagaaga aatactgttc t                                      1171

<210> SEQ ID NO 42
<211> LENGTH: 3667
<212> TYPE: DNA
<213> ORGANISM: Homo sapiens

<400> SEQUENCE: 42
cgaccgcctc cagcctcacg actccgcaaa caggtcacga attatgcccc acgcatcaaa         60
aactctgcgc ctgccttcgc cacagcggga gccgccaccc gggcgcgcgc ggcgcagctg        120
cccacggcag tggccgggcg ccctcctgcc ggagcgctcc tccccgggaa agccctgctg        180
cttgcaagcg cctccggtgg gccctggagc gcgctgccga gccccggggc ccagcgccga        240
cgcccccggg gggaggcccg accttggtca cccgggcttt gctaggcaag gggaacgcga        300
cgccgcccca atggccagag cgcacaaacg gcgactccgg cgctggcgtc accagccccc        360
ttcctgcctg cagcccccttc ccaggccggt acaggagctc gcacttgacc ccgcaggcgt       420
ggaggagaca cggtccctgg tccctgtggg gttaatgaag gagctccacg gacccactgc        480
ctcgtgggcc agacaatagc gcagtgagag ctacgtccga gcgtcctgga cccctccgc        540 gcgcacacac ttgcgcacag cacctctcca gctccatgca cgccaggggc ctgggaccct        600
gggctccact tctcggcttc tacagccagg ttctgggacc tgcagcgcgc aagaggagct        660
ctcttccacg gggctgcccc gcagggcccg aggcgcccag gactttgcaa cccctgccct       720
gttcgcccca gaatcatcca gagcagcccc cgcccactac ctggccctcc acaccctccc        780
tcccgcctcc gcctcagcct catcctagcg ctgcagccca cccgcgtggg ggcggaatcc       840
gcccggcaca cacgtgtgcg gattattaag cagccgagct agggccgccg cggtctccac        900
gcagcaacct ctgctaattg cggggggaagg cagccggagc gtgcggaact cgagggaacc       960
gagagtgagc tcagaggctg agttgcctgc ctggaaagga ggaagccccg ggcccagtta       1020
ggcttggagt gcaggggaaa gggcgggaag ttttgcggag ttgcgtggca ggtgtttcct       1080
ctccacgcag gggctcggct ggaaaaagcc aggtcctgtc ccttgggctc ctgccctcac       1140
```

```
cccgctgcga cacacacgcc ccagcacacc tcacagggca caaccctctt ttccctagac    1200
tttagctgcc tcgccttcca attcccagcc agtccagtgc tgaccagagg ccgctgccag    1260
tcgggccctg ctcagcaggc gctgcctccg cagccggcaa tgtcagaggc accggccaag    1320
gcatccggac tgagccgggc gggtgggcag agggtcggcg tctgcaagaa gctccccagt    1380
cccgagcgac cacgagcttg ggtgactaag acccactgtt tgcgatcccc gagatctcgg    1440
ggcgcattcc cgcagacacc cccttgtgag ggtggatgcc ggtgaggagg agctggtgct    1500
gagcggtcag ctttcacgga gccctggacg ccccgtggag gcaagtgcag ggaggggaag    1560
cccaggcggc acgtctctcc cccgctctcc aggcagatct ggagtttcct aatgaaccag    1620
atacagtcct ccttcgccct gccaatcact cttccatctg gaccactgga ggaaaaggaa    1680
atgggtggaa aagaagatgg aagaatctag agaggacggg gaaatattat gtagggaaaa    1740
aagcaagtga ccattgaaaa aaaatcgtaa gattggactc caacctttaa aaatgaaacg    1800
aaagaaaaac cctttgtaga tacagatact cccgggaaca tctatggaag tgctgactga    1860
taaagaaagc atctaaggag gctaaaaatg aggacagggg caggtatttc caatgtgaaa    1920
accaatcagt attctctctc tctctgtctc tctccctctt tctcgccctg tctcaaaagg    1980
gagcttatgt tctttcccgg agaataaaca agtacacaag ctattgccag ccttgaggtc    2040
gcagcctgta ggctacttag aagaaaacat tccccaactc attcagggag aaaaccaagc    2100
tcacagagcc caagcccag gagccaccca gagaaactcc ttcccctgac cagcgtagaa    2160
ggaggatacc cgtgcgccca cagtgaatgt atctgacttg aagccggtc cagaactcct    2220 agcctgtttc acgcaccttg ccaacacctt acaacttgca aggagcgaag tccggggag    2280 aggaaagcgg gggcgacctt ctagaggcag ctactcctcg ccggctgagg acgttggaga    2340
gggaaggagg agaggaggaa tggggtgtat gggtgcgagg aggccgggcc ggcggagacc    2400
tttgcctatt ggtaccaaaa ccccgtaga gagcccgaac tttccaggcc ggcttcaccc    2460
gggacgcttt cccaggcgcg tcgggtccgg ggagaaagtc ctgggaactg ccctcagcc    2520 accccgaccc gtggagtcca cgtctcggag gaggcaacac cgccccggcg gagcacagtt    2580
ccagcccaac tcgtattggg ttcctttctc cttgacaccc tgtactgccg agaaaaagag    2640
atctctcctg tgagcccaag agaggggggaa ggaatggcgg ggtggggcgg gggcccagga    2700
gggctgggga gagcgcgatg gaagctccct cccgtgcatc gcgttccccg agcttcggcg    2760
atggagcagc gccgggcaga ggcggccact ccgtaccctg cggtccccaa aacgcacact    2820
cgcgtccgca cacggggcct ccgagggctc taccgcctcc ccggccagga gcaagtccgt    2880
cttacccttc gctgcagtga ggagcctcgc gcacagcacc agcagcccga aagcaggag    2940 cagcgactgg aatctcctcc acgcagtcat gtctgcagat actccacacg cacgcgacac    3000
cgatggctcc tccgaggaag gcagggctat gagcggagcc aaataatcac ccgagggcaa    3060
ggcgagccgg agagagagcc cggtcccaag accgccgcg catccgacgc ctcctgaagg    3120
tctgggcgcc cggctcgctt ccctctcata gcatcgggtc ccgagccact gcagggctga    3180
gctgctccga gcgcggagac ccgggctggc gggggccgggg ccgggacga gcgccggccg    3240 agccgggcag gaaggcacca aggcggcgag gctgcgggag gggagaaagc ggggagagga    3300
gcgcgcgcag ccaggagaga cctggagagg aggcagctgg agagagagcc agcgagtggg    3360
agatgcgggg aggggggcgc ggggggggagg agagatccag tctagagaga aaaggcggag    3420
agcgcagaag aagggctgct agtggcacaa ggagccgctg ccgtggaggc tggactcaac    3480
catccttacc cacagagagg ggaccgaggc tgggcacggc gcagtcccag acagacagag    3540
```

```
cccagcctcg gggcctcggg ctgcccgcac cgtgctgcgc ttcattcggc ctcagcgcag    3600
cagcgcgcag gctggagaaa ggagacttgt tgggcgctcg ggtgggggaa gctcacgccg    3660
cacaccg                                                              3667
```

<210> SEQ ID NO 43
<211> LENGTH: 1093
<212> TYPE: DNA
<213> ORGANISM: Homo sapiens

<400> SEQUENCE: 43

```
atgagtcaac taatgctctt tcattcatac agtcaatctt catgagaatg acaggattct      60
gcaaactaga tcttcagaaa atcttggtct atgatcactt tgggagtctc ataatctgca     120
gaaagctgca aagccaacag acagaccaag acaaaaaatc tatttattag ggacagcagt     180
aggcccaagc tttgcaaact cgggtcgggg cccctcccac gccgctgtct caggtctccc     240
tctgtagagc gcggggtact cctgccgggc ccccaccctc gccccaccc tcgcccttc       300 ttgggccttt tcccgggcgg cggaagtccc cgatcacgtg acgaggcgcg ccactcggcg     360
catgggccgc gctacacggc cgctcaggga gctgagggta tagcgttttc gccttagact     420
ttcttgggtg caggcccaca ccacctcagc agcctgcccg gcagtcctct tttcccaggt     480
tttgcgtttt agacaaccca cctgagtcct cagccttgtc ccacacagca aggtacaagg     540
gaccggacgt ctgcctcctc agcagcgcag cgcacaagct tcctgtcatc ccggcgccca     600
cgatcagcac ctgcgccatg gcgagaggga gcagcgatcc gcgctgagtc tctgcggcgg     660
ggccgttcgg cccgggcttt ctggaaaggc ggccgaaccg gcgctagcgc tctttggttc     720
cgtgctccct gggccgacct gggccctgag cttcctccg gccggcctgc aggggcgga      780 aaggaggcgg ccggagctga gaggcccctc cgtccttgag gagcaaacct ggggctgcgg     840
agaaccgggg ctgtctgtct tctcgctttg ggggccgggc gccctgcccc tcgcccagaa     900
aagcctggaa atggtgtggg ctattgttgg gagaacccgc ctcgcaacag agctgacgtt     960
gaccacagca gagaagcagc ttaacctatc tactgcgata actctcatgc ctgttgggat    1020
ttttgctgtt ttactattct agatttgaaa gtgggaagaa gaatttacca gcgataccac    1080
gggcaaccct tcc                                                       1093
```

<210> SEQ ID NO 44
<211> LENGTH: 98
<212> TYPE: DNA
<213> ORGANISM: Homo sapiens

<400> SEQUENCE: 44

```
gggctcggag gggtgtagac agagccgggc ggcagcctcc gagagcagcc acccggaccc      60
ggcgttttct gctgcacctg gtcaggtgcc tggccgtc                             98
```

<210> SEQ ID NO 45
<211> LENGTH: 98
<212> TYPE: DNA
<213> ORGANISM: Homo sapiens

<400> SEQUENCE: 45

```
gggtttggag gggtgtagat agagttgggt ggtagttttt gagagtagtt atttggattt      60
ggtgtttttt gttgtatttg gttaggtgtt tggttgtt                             98
```

<210> SEQ ID NO 46

```
<211> LENGTH: 25
<212> TYPE: DNA
<213> ORGANISM: artificial
<220> FEATURE:
<223> OTHER INFORMATION: methylation independent oligonucleotide primer

<400> SEQUENCE: 46
tgcggaagtt agtttagatt ttagt                                              25

<210> SEQ ID NO 47
<211> LENGTH: 23
<212> TYPE: DNA
<213> ORGANISM: artificial
<220> FEATURE:
<223> OTHER INFORMATION: methylation independent oligonucleotide primer

<400> SEQUENCE: 47
tacgactcca aaacccata act                                                 23

<210> SEQ ID NO 48
<211> LENGTH: 23
<212> TYPE: DNA
<213> ORGANISM: artificial
<220> FEATURE:
<223> OTHER INFORMATION: methylation independent oligonucleotide primer

<400> SEQUENCE: 48
ttaggatcgc gtatagtagt agg                                                23

<210> SEQ ID NO 49
<211> LENGTH: 22
<212> TYPE: DNA
<213> ORGANISM: artificial
<220> FEATURE:
<223> OTHER INFORMATION: methylation independent oligonucleotide primer

<400> SEQUENCE: 49
ctcaaacaac aaaacctacc cc                                                 22

<210> SEQ ID NO 50
<211> LENGTH: 21
<212> TYPE: DNA
<213> ORGANISM: artificial
<220> FEATURE:
<223> OTHER INFORMATION: methylation independent oligonucleotide primer

<400> SEQUENCE: 50
gggcgggttt ggagttgtat t                                                  21

<210> SEQ ID NO 51
<211> LENGTH: 24
<212> TYPE: DNA
<213> ORGANISM: artificial
<220> FEATURE:
<223> OTHER INFORMATION: methylation independent oligonucleotide primer

<400> SEQUENCE: 51
actaacgtct aacctatacc caac                                               24

<210> SEQ ID NO 52
<211> LENGTH: 22
<212> TYPE: DNA
<213> ORGANISM: artificial
<220> FEATURE:
<223> OTHER INFORMATION: methylation independent oligonucleotide primer

<400> SEQUENCE: 52
```
tgcgtggtcg tttgtagttg tt                                        22

<210> SEQ ID NO 53
<211> LENGTH: 27
<212> TYPE: DNA
<213> ORGANISM: artificial
<220> FEATURE:
<223> OTHER INFORMATION: methylation independent oligonucleotide primer

<400> SEQUENCE: 53
ctaatcaact tctacctaaa aacctac                                   27

<210> SEQ ID NO 54
<211> LENGTH: 25
<212> TYPE: DNA
<213> ORGANISM: artificial
<220> FEATURE:
<223> OTHER INFORMATION: methylation independent oligonucleotide primer

<400> SEQUENCE: 54
gacgtaaatt taagagggta tttag                                     25

<210> SEQ ID NO 55
<211> LENGTH: 24
<212> TYPE: DNA
<213> ORGANISM: artificial
<220> FEATURE:
<223> OTHER INFORMATION: methylation independent oligonucleotide primer

<400> SEQUENCE: 55
tcgccaaaat ctaatactat cacc                                      24

<210> SEQ ID NO 56
<211> LENGTH: 24
<212> TYPE: DNA
<213> ORGANISM: artificial
<220> FEATURE:
<223> OTHER INFORMATION: methylation independent oligonucleotide primer

<400> SEQUENCE: 56
ttcgggttta gtttgttttt gttt                                      24

<210> SEQ ID NO 57
<211> LENGTH: 23
<212> TYPE: DNA
<213> ORGANISM: artificial
<220> FEATURE:
<223> OTHER INFORMATION: methylation independent oligonucleotide primer

<400> SEQUENCE: 57
acgaccaccc cattaactaa taa                                       23

<210> SEQ ID NO 58
<211> LENGTH: 22
<212> TYPE: DNA
<213> ORGANISM: artificial
<220> FEATURE:
<223> OTHER INFORMATION: methylation independent oligonucleotide primer

<400> SEQUENCE: 58
gtgagtaaat tcgtagagtt gg                                        22

<210> SEQ ID NO 59
<211> LENGTH: 23
<212> TYPE: DNA

```
<213> ORGANISM: artificial
<220> FEATURE:
<223> OTHER INFORMATION: methylation independent oligonucleotide primer

<400> SEQUENCE: 59
caaaaaccac cgaaccctaa aaa                                          23

<210> SEQ ID NO 60
<211> LENGTH: 29
<212> TYPE: DNA
<213> ORGANISM: artificial
<220> FEATURE:
<223> OTHER INFORMATION: methylation independent oligonucleotide primer

<400> SEQUENCE: 60
gacgttttat tagtttttgg ttattgttt                                    29

<210> SEQ ID NO 61
<211> LENGTH: 21
<212> TYPE: DNA
<213> ORGANISM: artificial
<220> FEATURE:
<223> OTHER INFORMATION: methylation independent oligonucleotide primer

<400> SEQUENCE: 61
aattacgtcc cctaactctc c                                            21

<210> SEQ ID NO 62
<211> LENGTH: 25
<212> TYPE: DNA
<213> ORGANISM: artificial
<220> FEATURE:
<223> OTHER INFORMATION: methylation independent oligonucleotide primer

<400> SEQUENCE: 62
gtgtgtcgtt tggatttttt ttagt                                        25

<210> SEQ ID NO 63
<211> LENGTH: 27
<212> TYPE: DNA
<213> ORGANISM: artificial
<220> FEATURE:
<223> OTHER INFORMATION: methylation independent oligonucleotide primer

<400> SEQUENCE: 63
cgataacaca acgtatatat atataaa                                      27

<210> SEQ ID NO 64
<211> LENGTH: 21
<212> TYPE: DNA
<213> ORGANISM: artificial
<220> FEATURE:
<223> OTHER INFORMATION: methylation independent oligonucleotide primer

<400> SEQUENCE: 64
tcgagcgttg ggtattgagg a                                            21

<210> SEQ ID NO 65
<211> LENGTH: 21
<212> TYPE: DNA
<213> ORGANISM: artificial
<220> FEATURE:
<223> OTHER INFORMATION: methylation independent oligonucleotide primer

<400> SEQUENCE: 65
taaaacaccc gacctccaaa c                                            21
```

<210> SEQ ID NO 66
<211> LENGTH: 21
<212> TYPE: DNA
<213> ORGANISM: artificial
<220> FEATURE:
<223> OTHER INFORMATION: methylation independent oligonucleotide primer

<400> SEQUENCE: 66
gcgttggagt tggggtaaaa g                                        21

<210> SEQ ID NO 67
<211> LENGTH: 24
<212> TYPE: DNA
<213> ORGANISM: artificial
<220> FEATURE:
<223> OTHER INFORMATION: methylation independent oligonucleotide primer

<400> SEQUENCE: 67
cgaaaccgaa aaccaatcac acta                                     24

<210> SEQ ID NO 68
<211> LENGTH: 24
<212> TYPE: DNA
<213> ORGANISM: artificial
<220> FEATURE:
<223> OTHER INFORMATION: methylation independent oligonucleotide primer

<400> SEQUENCE: 68
cgagtcgggt ttatttaagg gtta                                     24

<210> SEQ ID NO 69
<211> LENGTH: 22
<212> TYPE: DNA
<213> ORGANISM: artificial
<220> FEATURE:
<223> OTHER INFORMATION: methylation independent oligonucleotide primer

<400> SEQUENCE: 69
acatacgcta tacatacctc ta                                       22

<210> SEQ ID NO 70
<211> LENGTH: 22
<212> TYPE: DNA
<213> ORGANISM: artificial
<220> FEATURE:
<223> OTHER INFORMATION: methylation independent oligonucleotide primer

<400> SEQUENCE: 70
cgagttcggg ttgtagtagt tt                                       22

<210> SEQ ID NO 71
<211> LENGTH: 23
<212> TYPE: DNA
<213> ORGANISM: artificial
<220> FEATURE:
<223> OTHER INFORMATION: methylation independent oligonucleotide primer

<400> SEQUENCE: 71
acccgaacca aaaatcatt acc                                       23

<210> SEQ ID NO 72
<211> LENGTH: 23
<212> TYPE: DNA
<213> ORGANISM: artificial
<220> FEATURE:

<223> OTHER INFORMATION: methylation independent oligonucleotide primer

<400> SEQUENCE: 72
tcgttttcgt tttagagagg tag                                          23

<210> SEQ ID NO 73
<211> LENGTH: 22
<212> TYPE: DNA
<213> ORGANISM: artificial
<220> FEATURE:
<223> OTHER INFORMATION: methylation independent oligonucleotide primer

<400> SEQUENCE: 73
cgaaaaacta ctaaactccc ct                                           22

<210> SEQ ID NO 74
<211> LENGTH: 27
<212> TYPE: DNA
<213> ORGANISM: artificial
<220> FEATURE:
<223> OTHER INFORMATION: methylation independent oligonucleotide primer

<400> SEQUENCE: 74
gtcgagaatt tagttattag gttattg                                      27

<210> SEQ ID NO 75
<211> LENGTH: 27
<212> TYPE: DNA
<213> ORGANISM: artificial
<220> FEATURE:
<223> OTHER INFORMATION: methylation independent oligonucleotide primer

<400> SEQUENCE: 75
caaacgaaaa ctaactttaa ctcccta                                      27

<210> SEQ ID NO 76
<211> LENGTH: 24
<212> TYPE: DNA
<213> ORGANISM: artificial
<220> FEATURE:
<223> OTHER INFORMATION: methylation independent oligonucleotide primer

<400> SEQUENCE: 76
cgtcgttgtt aggtttttgg ttgt                                         24

<210> SEQ ID NO 77
<211> LENGTH: 25
<212> TYPE: DNA
<213> ORGANISM: artificial
<220> FEATURE:
<223> OTHER INFORMATION: methylation independent oligonucleotide primer

<400> SEQUENCE: 77
aacttaacga taactaatac ccctc                                        25

<210> SEQ ID NO 78
<211> LENGTH: 20
<212> TYPE: DNA
<213> ORGANISM: artificial
<220> FEATURE:
<223> OTHER INFORMATION: methylation independent oligonucleotide primer

<400> SEQUENCE: 78
tcgggagaag gtggagattg                                              20

```
<210> SEQ ID NO 79
<211> LENGTH: 27
<212> TYPE: DNA
<213> ORGANISM: artificial
<220> FEATURE:
<223> OTHER INFORMATION: methylation independent oligonucleotide primer

<400> SEQUENCE: 79
acgataataa tcacccttca tcttcaa                                              27

<210> SEQ ID NO 80
<211> LENGTH: 22
<212> TYPE: DNA
<213> ORGANISM: artificial
<220> FEATURE:
<223> OTHER INFORMATION: methylation independent oligonucleotide primer

<400> SEQUENCE: 80
tcggtagcgg attgtagttt ag                                                   22

<210> SEQ ID NO 81
<211> LENGTH: 24
<212> TYPE: DNA
<213> ORGANISM: artificial
<220> FEATURE:
<223> OTHER INFORMATION: methylation independent oligonucleotide primer

<400> SEQUENCE: 81
acgatcaaaa acgataaacc ctac                                                 24

<210> SEQ ID NO 82
<211> LENGTH: 26
<212> TYPE: DNA
<213> ORGANISM: artificial
<220> FEATURE:
<223> OTHER INFORMATION: methylation independent oligonucleotide primer

<400> SEQUENCE: 82
acggttagta ggtgttttat tatttg                                               26

<210> SEQ ID NO 83
<211> LENGTH: 23
<212> TYPE: DNA
<213> ORGANISM: artificial
<220> FEATURE:
<223> OTHER INFORMATION: methylation independent oligonucleotide primer

<400> SEQUENCE: 83
aacgcgaata cctataaaat acc                                                  23

<210> SEQ ID NO 84
<211> LENGTH: 21
<212> TYPE: DNA
<213> ORGANISM: artificial
<220> FEATURE:
<223> OTHER INFORMATION: methylation independent oligonucleotide primer

<400> SEQUENCE: 84
atggcgtcgt ggagttttag g                                                    21

<210> SEQ ID NO 85
<211> LENGTH: 26
<212> TYPE: DNA
<213> ORGANISM: artificial
<220> FEATURE:
<223> OTHER INFORMATION: methylation independent oligonucleotide primer
```

```
<400> SEQUENCE: 85
ggggaaattt cgttagattt tatttt                                    26

<210> SEQ ID NO 86
<211> LENGTH: 24
<212> TYPE: DNA
<213> ORGANISM: artificial
<220> FEATURE:
<223> OTHER INFORMATION: methylation independent oligonucleotide primer

<400> SEQUENCE: 86
cgtagtcggg aggttttttt agtt                                      24

<210> SEQ ID NO 87
<211> LENGTH: 22
<212> TYPE: DNA
<213> ORGANISM: artificial
<220> FEATURE:
<223> OTHER INFORMATION: methylation independent oligonucleotide primer

<400> SEQUENCE: 87
caacaattcg ctccaaatcc tc                                        22

<210> SEQ ID NO 88
<211> LENGTH: 25
<212> TYPE: DNA
<213> ORGANISM: artificial
<220> FEATURE:
<223> OTHER INFORMATION: methylation independent oligonucleotide primer

<400> SEQUENCE: 88
aagagtattc gggatagaag tttat                                     25

<210> SEQ ID NO 89
<211> LENGTH: 25
<212> TYPE: DNA
<213> ORGANISM: artificial
<220> FEATURE:
<223> OTHER INFORMATION: methylation independent oligonucleotide primer

<400> SEQUENCE: 89
ctaaaacgcg aatctaaatt tccac                                     25

<210> SEQ ID NO 90
<211> LENGTH: 27
<212> TYPE: DNA
<213> ORGANISM: artificial
<220> FEATURE:
<223> OTHER INFORMATION: methylation independent oligonucleotide primer

<400> SEQUENCE: 90
gtgcgtttat tttgttaaaa agaaatt                                   27

<210> SEQ ID NO 91
<211> LENGTH: 27
<212> TYPE: DNA
<213> ORGANISM: artificial
<220> FEATURE:
<223> OTHER INFORMATION: methylation independent oligonucleotide primer

<400> SEQUENCE: 91
cccgattcaa tttaacaatt aaaaaaa                                   27

<210> SEQ ID NO 92
<211> LENGTH: 23
```

```
<212> TYPE: DNA
<213> ORGANISM: artificial
<220> FEATURE:
<223> OTHER INFORMATION: methylation independent oligonucleotide primer

<400> SEQUENCE: 92
agttgtattc gtttttgggt gga                                          23

<210> SEQ ID NO 93
<211> LENGTH: 23
<212> TYPE: DNA
<213> ORGANISM: artificial
<220> FEATURE:
<223> OTHER INFORMATION: methylation independent oligonucleotide primer

<400> SEQUENCE: 93
tactaacgtc taacctatac cca                                          23

<210> SEQ ID NO 94
<211> LENGTH: 25
<212> TYPE: DNA
<213> ORGANISM: artificial
<220> FEATURE:
<223> OTHER INFORMATION: methylation independent oligonucleotide primer

<400> SEQUENCE: 94
gattgcgttg ttttttggtt gtttt                                        25

<210> SEQ ID NO 95
<211> LENGTH: 23
<212> TYPE: DNA
<213> ORGANISM: artificial
<220> FEATURE:
<223> OTHER INFORMATION: methylation independent oligonucleotide primer

<400> SEQUENCE: 95
tcgtacgcaa aaacctacaa tac                                          23

<210> SEQ ID NO 96
<211> LENGTH: 27
<212> TYPE: DNA
<213> ORGANISM: artificial
<220> FEATURE:
<223> OTHER INFORMATION: methylation independent oligonucleotide primer

<400> SEQUENCE: 96
gttcggttat tttttgtagg tttatgt                                      27

<210> SEQ ID NO 97
<211> LENGTH: 23
<212> TYPE: DNA
<213> ORGANISM: artificial
<220> FEATURE:
<223> OTHER INFORMATION: methylation independent oligonucleotide primer

<400> SEQUENCE: 97
gtagaagttg attagtttgt cgg                                          23

<210> SEQ ID NO 98
<211> LENGTH: 25
<212> TYPE: DNA
<213> ORGANISM: artificial
<220> FEATURE:
<223> OTHER INFORMATION: methylation independent oligonucleotide primer

<400> SEQUENCE: 98
```

<210> SEQ ID NO 99
<211> LENGTH: 24
<212> TYPE: DNA
<213> ORGANISM: artificial
<220> FEATURE:
<223> OTHER INFORMATION: methylation independent oligonucleotide primer

<400> SEQUENCE: 99
accgcctacc tatcaaaaaa atcc                                          24

<210> SEQ ID NO 100
<211> LENGTH: 23
<212> TYPE: DNA
<213> ORGANISM: artificial
<220> FEATURE:
<223> OTHER INFORMATION: methylation independent oligonucleotide primer

<400> SEQUENCE: 100
gcggtggtag gtaatattat agt                                           23

<210> SEQ ID NO 101
<211> LENGTH: 21
<212> TYPE: DNA
<213> ORGANISM: artificial
<220> FEATURE:
<223> OTHER INFORMATION: methylation independent oligonucleotide primer

<400> SEQUENCE: 101
atccgccaaa accaactaca c                                             21

<210> SEQ ID NO 102
<211> LENGTH: 24
<212> TYPE: DNA
<213> ORGANISM: artificial
<220> FEATURE:
<223> OTHER INFORMATION: methylation independent oligonucleotide primer

<400> SEQUENCE: 102
ggaatttggc ggtttttagt tgtt                                          24

<210> SEQ ID NO 103
<211> LENGTH: 24
<212> TYPE: DNA
<213> ORGANISM: artificial
<220> FEATURE:
<223> OTHER INFORMATION: methylation independent oligonucleotide primer

<400> SEQUENCE: 103
aaaaactaaa acccctaaac caac                                          24

<210> SEQ ID NO 104
<211> LENGTH: 25
<212> TYPE: DNA
<213> ORGANISM: artificial
<220> FEATURE:
<223> OTHER INFORMATION: methylation independent oligonucleotide primer

<400> SEQUENCE: 104
ggtgtatttc gggtgtttat atttg                                         25

<210> SEQ ID NO 105
<211> LENGTH: 25
<212> TYPE: DNA
<213> ORGANISM: artificial

```
<220> FEATURE:
<223> OTHER INFORMATION: methylation independent oligonucleotide primer

<400> SEQUENCE: 105
ggtgtatttc gggtgtttat atttg                                           25

<210> SEQ ID NO 106
<211> LENGTH: 23
<212> TYPE: DNA
<213> ORGANISM: artificial
<220> FEATURE:
<223> OTHER INFORMATION: methylation independent oligonucleotide primer

<400> SEQUENCE: 106
gttagatcgt gcggaaagtg att                                             23

<210> SEQ ID NO 107
<211> LENGTH: 22
<212> TYPE: DNA
<213> ORGANISM: artificial
<220> FEATURE:
<223> OTHER INFORMATION: methylation independent oligonucleotide primer

<400> SEQUENCE: 107
cgctatacct aatcccaatc cc                                              22

<210> SEQ ID NO 108
<211> LENGTH: 26
<212> TYPE: DNA
<213> ORGANISM: artificial
<220> FEATURE:
<223> OTHER INFORMATION: methylation independent oligonucleotide primer

<400> SEQUENCE: 108
gttaaattcg ggatagatta gttaag                                          26

<210> SEQ ID NO 109
<211> LENGTH: 23
<212> TYPE: DNA
<213> ORGANISM: artificial
<220> FEATURE:
<223> OTHER INFORMATION: methylation independent oligonucleotide primer

<400> SEQUENCE: 109
aaacgcccaa ccttactcta aac                                             23

<210> SEQ ID NO 110
<211> LENGTH: 23
<212> TYPE: DNA
<213> ORGANISM: artificial
<220> FEATURE:
<223> OTHER INFORMATION: methylation independent oligonucleotide primer

<400> SEQUENCE: 110
taatcgatgg tttaggttgg ttg                                             23

<210> SEQ ID NO 111
<211> LENGTH: 25
<212> TYPE: DNA
<213> ORGANISM: artificial
<220> FEATURE:
<223> OTHER INFORMATION: methylation independent oligonucleotide primer

<400> SEQUENCE: 111
caacccgaca aatacatact aacta                                           25
```

<210> SEQ ID NO 112
<211> LENGTH: 20
<212> TYPE: DNA
<213> ORGANISM: artificial
<220> FEATURE:
<223> OTHER INFORMATION: methylation independent oligonucleotide primer

<400> SEQUENCE: 112
cggcgtttag ggtttgaggt                                          20

<210> SEQ ID NO 113
<211> LENGTH: 23
<212> TYPE: DNA
<213> ORGANISM: artificial
<220> FEATURE:
<223> OTHER INFORMATION: methylation independent oligonucleotide primer

<400> SEQUENCE: 113
atatccccgt aaacaaatac ccc                                      23

<210> SEQ ID NO 114
<211> LENGTH: 25
<212> TYPE: DNA
<213> ORGANISM: artificial
<220> FEATURE:
<223> OTHER INFORMATION: methylation independent oligonucleotide primer

<400> SEQUENCE: 114
gatattgcgg agattggatt ttagt                                    25

<210> SEQ ID NO 115
<211> LENGTH: 22
<212> TYPE: DNA
<213> ORGANISM: artificial
<220> FEATURE:
<223> OTHER INFORMATION: methylation independent oligonucleotide primer

<400> SEQUENCE: 115
actcgctcaa aaactcactc cc                                       22

<210> SEQ ID NO 116
<211> LENGTH: 27
<212> TYPE: DNA
<213> ORGANISM: artificial
<220> FEATURE:
<223> OTHER INFORMATION: methylation independent oligonucleotide primer

<400> SEQUENCE: 116
tcgagaatat taggttttat atgaagg                                  27

<210> SEQ ID NO 117
<211> LENGTH: 25
<212> TYPE: DNA
<213> ORGANISM: artificial
<220> FEATURE:
<223> OTHER INFORMATION: methylation independent oligonucleotide primer

<400> SEQUENCE: 117
cgacataccg aaactaataa taacc                                    25

<210> SEQ ID NO 118
<211> LENGTH: 27
<212> TYPE: DNA
<213> ORGANISM: artificial
<220> FEATURE:
<223> OTHER INFORMATION: methylation independent oligonucleotide primer -continued

<400> SEQUENCE: 118
cgtttttcgt tttttgttgt tagaatt                                    27

<210> SEQ ID NO 119
<211> LENGTH: 23
<212> TYPE: DNA
<213> ORGANISM: artificial
<220> FEATURE:
<223> OTHER INFORMATION: methylation independent oligonucleotide primer

<400> SEQUENCE: 119
cccgccaaaa atttattcta ctc                                        23

<210> SEQ ID NO 120
<211> LENGTH: 22
<212> TYPE: DNA
<213> ORGANISM: artificial
<220> FEATURE:
<223> OTHER INFORMATION: methylation independent oligonucleotide primer

<400> SEQUENCE: 120
ggcggcgttg gatatgtttt tt                                         22

<210> SEQ ID NO 121
<211> LENGTH: 29
<212> TYPE: DNA
<213> ORGANISM: artificial
<220> FEATURE:
<223> OTHER INFORMATION: methylation independent oligonucleotide primer

<400> SEQUENCE: 121
atatccaaaa aaccaataac ttaacatac                                  29

<210> SEQ ID NO 122
<211> LENGTH: 24
<212> TYPE: DNA
<213> ORGANISM: artificial
<220> FEATURE:
<223> OTHER INFORMATION: methylation independent oligonucleotide primer

<400> SEQUENCE: 122
atcgtagcgg ttttagggaa tttt                                       24

<210> SEQ ID NO 123
<211> LENGTH: 26
<212> TYPE: DNA
<213> ORGANISM: artificial
<220> FEATURE:
<223> OTHER INFORMATION: methylation independent oligonucleotide primer

<400> SEQUENCE: 123
cccaacgaaa cctaaaaaat aaacaa                                     26

<210> SEQ ID NO 124
<211> LENGTH: 20
<212> TYPE: DNA
<213> ORGANISM: artificial
<220> FEATURE:
<223> OTHER INFORMATION: methylation independent oligonucleotide primer

<400> SEQUENCE: 124
ggacggggat tgggggtttt                                            20

<210> SEQ ID NO 125

```
<211> LENGTH: 22
<212> TYPE: DNA
<213> ORGANISM: artificial
<220> FEATURE:
<223> OTHER INFORMATION: methylation independent oligonucleotide primer

<400> SEQUENCE: 125
ccgaaccgcc ctcaataaca at                                              22

<210> SEQ ID NO 126
<211> LENGTH: 26
<212> TYPE: DNA
<213> ORGANISM: artificial
<220> FEATURE:
<223> OTHER INFORMATION: methylation independent oligonucleotide primer

<400> SEQUENCE: 126
cggcgttagg tatttatttg tatggt                                          26

<210> SEQ ID NO 127
<211> LENGTH: 24
<212> TYPE: DNA
<213> ORGANISM: artificial
<220> FEATURE:
<223> OTHER INFORMATION: methylation independent oligonucleotide primer

<400> SEQUENCE: 127
accaaacgcc ctcaaacaac aaaa                                            24

<210> SEQ ID NO 128
<211> LENGTH: 21
<212> TYPE: DNA
<213> ORGANISM: artificial
<220> FEATURE:
<223> OTHER INFORMATION: methylation independent oligonucleotide primer

<400> SEQUENCE: 128
gcgaatgggg tagggttgt a                                                21

<210> SEQ ID NO 129
<211> LENGTH: 24
<212> TYPE: DNA
<213> ORGANISM: artificial
<220> FEATURE:
<223> OTHER INFORMATION: methylation independent oligonucleotide primer

<400> SEQUENCE: 129
ttctcgactt ctacaaccaa attc                                            24

<210> SEQ ID NO 130
<211> LENGTH: 26
<212> TYPE: DNA
<213> ORGANISM: artificial
<220> FEATURE:
<223> OTHER INFORMATION: methylation independent oligonucleotide primer

<400> SEQUENCE: 130
tcggagttga gaggtttttt cgtttt                                          26

<210> SEQ ID NO 131
<211> LENGTH: 26
<212> TYPE: DNA
<213> ORGANISM: artificial
<220> FEATURE:
<223> OTHER INFORMATION: methylation independent oligonucleotide primer

<400> SEQUENCE: 131
```

```
caccatttcc aaactttct aaacga                                          26

<210> SEQ ID NO 132
<211> LENGTH: 24
<212> TYPE: DNA
<213> ORGANISM: artificial
<220> FEATURE:
<223> OTHER INFORMATION: methylation independent oligonucleotide primer

<400> SEQUENCE: 132
gcgtttcgga tatgttggga tagt                                           24

<210> SEQ ID NO 133
<211> LENGTH: 25
<212> TYPE: DNA
<213> ORGANISM: artificial
<220> FEATURE:
<223> OTHER INFORMATION: methylation independent oligonucleotide primer

<400> SEQUENCE: 133
cctacaaaac cactcgaaac tacca                                          25

<210> SEQ ID NO 134
<211> LENGTH: 24
<212> TYPE: DNA
<213> ORGANISM: artificial
<220> FEATURE:
<223> OTHER INFORMATION: methylation independent oligonucleotide primer

<400> SEQUENCE: 134
gcgtttcgga tatgttggga tagt                                           24

<210> SEQ ID NO 135
<211> LENGTH: 22
<212> TYPE: DNA
<213> ORGANISM: artificial
<220> FEATURE:
<223> OTHER INFORMATION: methylation independent oligonucleotide primer

<400> SEQUENCE: 135
aacgacccaa acactcacca aa                                             22

<210> SEQ ID NO 136
<211> LENGTH: 22
<212> TYPE: DNA
<213> ORGANISM: artificial
<220> FEATURE:
<223> OTHER INFORMATION: methylation independent oligonucleotide primer

<400> SEQUENCE: 136
cgtttgcgat ttggtgagtg tt                                             22

<210> SEQ ID NO 137
<211> LENGTH: 25
<212> TYPE: DNA
<213> ORGANISM: artificial
<220> FEATURE:
<223> OTHER INFORMATION: methylation independent oligonucleotide primer

<400> SEQUENCE: 137
cctacaaaac cactcgaaac tacca                                          25

<210> SEQ ID NO 138
<211> LENGTH: 23
<212> TYPE: DNA
```

```
<213> ORGANISM: artificial
<220> FEATURE:
<223> OTHER INFORMATION: methylation independent oligonucleotide primer

<400> SEQUENCE: 138
ggttgcggga tgtgttttag ttg                                           23

<210> SEQ ID NO 139
<211> LENGTH: 23
<212> TYPE: DNA
<213> ORGANISM: artificial
<220> FEATURE:
<223> OTHER INFORMATION: methylation independent oligonucleotide primer

<400> SEQUENCE: 139
accccgccct accctataaa ttc                                           23

<210> SEQ ID NO 140
<211> LENGTH: 18
<212> TYPE: DNA
<213> ORGANISM: artificial
<220> FEATURE:
<223> OTHER INFORMATION: methylation independent oligonucleotide primer

<400> SEQUENCE: 140
gaggggtgta gatagagt                                                 18

<210> SEQ ID NO 141
<211> LENGTH: 21
<212> TYPE: DNA
<213> ORGANISM: artificial
<220> FEATURE:
<223> OTHER INFORMATION: methylation independent oligonucleotide primer

<400> SEQUENCE: 141
accaaacacc taaccaaata c                                             21

<210> SEQ ID NO 142
<211> LENGTH: 21
<212> TYPE: DNA
<213> ORGANISM: artificial
<220> FEATURE:
<223> OTHER INFORMATION: methylation independent oligonucleotide primer

<400> SEQUENCE: 142
tcggaggggt gtagatagag t                                             21

<210> SEQ ID NO 143
<211> LENGTH: 24
<212> TYPE: DNA
<213> ORGANISM: artificial
<220> FEATURE:
<223> OTHER INFORMATION: methylation independent oligonucleotide primer

<400> SEQUENCE: 143
acgaccaaac acctaaccaa atac                                          24

<210> SEQ ID NO 144
<211> LENGTH: 21
<212> TYPE: DNA
<213> ORGANISM: artificial
<220> FEATURE:
<223> OTHER INFORMATION: methylation independent oligonucleotide primer

<400> SEQUENCE: 144
gcgaataggg tagggttgt a                                              21
```

<210> SEQ ID NO 145
<211> LENGTH: 24
<212> TYPE: DNA
<213> ORGANISM: artificial
<220> FEATURE:
<223> OTHER INFORMATION: methylation independent oligonucleotide primer

<400> SEQUENCE: 145
ttctcgactt ctacaaccaa attc                                          24

<210> SEQ ID NO 146
<211> LENGTH: 28
<212> TYPE: DNA
<213> ORGANISM: artificial
<220> FEATURE:
<223> OTHER INFORMATION: methylation independent oligonucleotide primer

<400> SEQUENCE: 146 gagatttta ttatagggtt ttagtaat                                       28

<210> SEQ ID NO 147
<211> LENGTH: 27
<212> TYPE: DNA
<213> ORGANISM: artificial
<220> FEATURE:
<223> OTHER INFORMATION: methylation independent oligonucleotide primer

<400> SEQUENCE: 147
aaaaaccaac cgtactaatt ttccgtc                                       27

<210> SEQ ID NO 148
<211> LENGTH: 26
<212> TYPE: DNA
<213> ORGANISM: artificial
<220> FEATURE:
<223> OTHER INFORMATION: methylation independent oligonucleotide primer

<400> SEQUENCE: 148
tcggagttga gaggttttt cctttt                                         26

<210> SEQ ID NO 149
<211> LENGTH: 26
<212> TYPE: DNA
<213> ORGANISM: artificial
<220> FEATURE:
<223> OTHER INFORMATION: methylation independent oligonucleotide primer

<400> SEQUENCE: 149
caccatttcc aaactttct aaacga                                         26

<210> SEQ ID NO 150
<211> LENGTH: 22
<212> TYPE: DNA
<213> ORGANISM: artificial
<220> FEATURE:
<223> OTHER INFORMATION: methylation independent oligonucleotide primer

<400> SEQUENCE: 150
tcggttttgt tcgttttagg at                                            22

<210> SEQ ID NO 151
<211> LENGTH: 28
<212> TYPE: DNA
<213> ORGANISM: artificial
<220> FEATURE:

<223> OTHER INFORMATION: methylation independent oligonucleotide primer

<400> SEQUENCE: 151
accgactaaa ataacaaaaa aaaaattc                                           28

<210> SEQ ID NO 152
<211> LENGTH: 2074
<212> TYPE: DNA
<213> ORGANISM: Homo sapiens

<400> SEQUENCE: 152

| | | | | | |
|---|---|---|---|---|---|
| aacacaggga | ctaatgaaag | agaaaaaaaa | caaagcacga | aaggacagca | gaaatagctc | 60 |
| cataatctca | ctttccagga | ataacctcta | tggacatttt | gttgtgtgtc | tattgctttt | 120 |
| ctaatatata | catttttta a | tcaaatggaa | ttgcctcaaa | tatgctattt | aatagcttgc | 180 |
| ttcttttcat | actatttgaa | aattaagaaa | cgattataat | atgcttcatt | taaaaacttt | 240 |
| aagtttaggc | cgggcacagt | ggctcacgca | tgtaatccca | gtacttggag | ggaccgaggt | 300 |
| gggcggatca | caaggtcagg | agattgagac | catcctggcc | agcatggtga | aaccccgtct | 360 |
| ctactaaaaa | tacaaaactt | agctgggcat | gatggcacgt | gcctgtagtc | ccagctactt | 420 |
| gggaggctga | ggcaggagaa | tcgcttgaac | ccgggaggtg | gaggttgcag | tgagcggaga | 480 |
| ttgcaccact | gcactcgcct | ggtgacagag | caagactcta | tctcaaaaaa | caaacaaaga | 540 |
| aaacttgaag | tatagtatcc | ttttaaattt | taaatagata | atagaaactg | gtttcccccc | 600 |
| atttaaacca | gaatttaagt | ttaacttat  | atattcttga | cagtttggat | tttgtccttc | 660 |
| aacctcataa | aattgggaat | ttaagcatca | cctggttcga | tttaaatgca | atgtagaatt | 720 |
| tgcattaaaa | tactacatta | aagcctcaga | tttgtagtag | ctaacagcac | ttctatgtat | 780 |
| gtgtcaggga | ctgctctaaa | tacttcatat | atattaactc | ctctattctg | tacttctgtt | 840 |
| cccgttttat | acagcaggaa | attgaaacac | tgagaggtta | agtaactaaa | gttacagagc | 900 |
| tagagtgaca | ggagtaaagc | ttcaactcag | gcaacccaga | cttccagagt | tctgatctcc | 960 |
| actactaagc | tgctagcata | gcttttctgg | taactatttt | taattcaaat | ataattcgag | 1020 |
| tgatctatct | aacaagtcat | cactctgaca | actcagtgac | ttgtaatgta | aaattattca | 1080 |
| ttgtaattca | tttaatatta | ttgtttctct | gtgctgcaaa | aatcatagca | atcgagatgt | 1140 |
| aatttattac | tctccctccc | acctccggca | tcttgtgcta | atccttctgc | cctgcggacc | 1200 |
| tcccccgact | ctttactatg | cgtgtcaact | gccatcaact | tccttgcttg | ctggggactg | 1260 |
| gggccgcgag | ggcataccccc | cgaggggtac | ggggctaggg | ctaggcaggc | tgtgcggttg | 1320 |
| ggcggggccc | tgtgccccac | tgcggagtgc | gggtcgggaa | gcggagagag | aagcagctgt | 1380 |
| gtaatccgct | ggatgcggac | cagggcgctc | cccattcccg | tcgggagccc | gccgattggc | 1440 |
| tgggtgtggg | cgcacgtgac | cgacatgtgg | ctgtattggt | gcagcccgcc | agggtgtcac | 1500 |
| tggagacaga | atggaggtgc | tgccggactc | ggaaatgggg | taggtgctgg | agccaccatg | 1560 |
| gccaggcttg | ctgcgggggg | agggggggaag | gtggttttcc | ctcgcactgt | cttaaaccga | 1620 |
| tggcctttcc | ttggcacagg | gtccactgca | gcatgccaaa | cgaggaggca | ggggcgtcgt | 1680 |
| cccccgccc | cccactgcag | cactggagat | ggatttcctg | tacttcggat | ccagggtttt | 1740 |
| tgacagaaga | ggaagaaggg | ggaggggtag | aagtgttaag | gggagtctgc | tgagaaaagc | 1800 |
| tgtttttgaa | gccagaaggg | gttttttgttt | ttataatgcc | atttgacaga | gtggaataac | 1860 |
| agtatctaag | gaaacgggta | gaggacaaca | aagaatggag | catattcatg | gcgaggagca | 1920 |
| aaagctctac | cccattgaaa | ggcttctttt | cctcccctggc | gacaaggaca | catgcattgg | 1980 |

```
tggccaaaag agagaggaga caaaaccgct gcagatggct gatgtgaatc tagtggaaag   2040
agctactggg gatgagagaa agaggaggag gcag                              2074

<210> SEQ ID NO 153
<211> LENGTH: 1158
<212> TYPE: DNA
<213> ORGANISM: Homo sapiens

<400> SEQUENCE: 153
tcgccacgca gcctctgaag agaggagcat ctacatacaa agaggcttaa actgcccaga     60
acctccgaat gacgaagaat caccgccagt ctcaactcgt aagctgggag caaaacccc    120 aaagcttccc taccaaggga aaacctttgg cctcaaaggt ccttctgtcc agcatagccg    180
ggtccaataa ccctccatcc cgcgtccgcg cttacccaat acaagccggg ctacgtccga    240
gggtaacaac atgatcaaaa ccacagcagg aaccacaata aggaacaaga ctcaggttaa    300
agcaaacaca gcgacagctc ctgcgccgca tctcctggtt ccagtggcgg cactgaactc    360
gcggcaattt gtcccgcctc tttcgcttca cggcagccaa tcgcttccgc cagagaaaga    420
aaggcgccga aatgaaaccc gcctccgttc gccttcggaa ctgtcgtcac ttccgtcctc    480
agacttggag gggcggggat gaggagggcg gggaggacga cgagggcgaa gagggtgggt    540
gagagccccg gagcccgagc cgaagggcga gccgcaaacg ctaagtcgct ggccattggt    600
ggacatggcg caggcgcgtt tgctccgacg ggccgaatgt tttggggcag tgttttgagc    660
gcggagaccg cgtgatactg gatgcgcatg ggcataccgt gctctgcggc tgcttggcgt    720
tgcttcttcc tccagaagtg ggcgctgggc agtcacgcag ggtttgaacc ggaagcggga    780
gtaggtagct gcgtggctaa cggagaaaag aagccgtggc cgcggagga  ggcgagagga    840 gtcgggatct gcgctgcagc caccgccgcg gttgatacta ctttgacctt ccgagtgcag    900
tggtaggggc gcggaggcaa cgcagcggct tctgcgctgg gaaattcagt cgtgtgcgac    960
ccagtctgtc ctctccccag accgccaatc tcatgcaccc ctccagagtg gcccttgact   1020
cctccctctc ctcactccat cttttcctggc ctctctccgg gtgcttagcg gacttggcca   1080
ataacctcct ccttttaaac gccctgaatt gaaccctgcc tcctgcgcat cctctttttg   1140
tgtcacctta gggttcag                                                1158

<210> SEQ ID NO 154
<211> LENGTH: 2046
<212> TYPE: DNA
<213> ORGANISM: Homo sapiens

<400> SEQUENCE: 154
agattctgca atctcagatt tcagagttgg agtcgtcagg ggaagtggcg tcagcagctg     60
gcgtgatcca attcaataaa ccagaggtgg cttgggatag acaactgacc gggtgcagac    120
ccccgcccct caatctctgc atttcctgca cgctctgggc accctgggag gccccggctc    180 catccccat  tccagctctc cgcgaggagg ggtcgggttt cctgtggcgc cttccacgcg    240
cctcctccag gccagctccc cacccggccg tgggctccca agccagtgc  cgccaccgc     300 tccccggccg ccggaaacgc taagccctg ctggggcgag ggcacctcct tgcgggtgc     360 gtagccctgg gctcccggtg gggcgggct gggcgggagc ttccaggccg caggcacctc    420
tcgggaaagg aaacccaatc cctccttcgg cccacggaga acgaaagtgg agaagcagtg    480
ggaaggaagg aactgtgggt gccggttcga gaagcagcct tgggagtccg ggggaatagt    540
```

```
gtccccaggg gcagagggac atactccctc tcgccccgag cgccggccca gcctaggttg    600
cctgcatggg cctggagagc tgagggtcac cacctggcct cccagcctcc cggcccttgg    660
cctccaaagc ggggtagcct ggagcgcgcg cctgagaaga gcctggagca gggccggcca    720
ctgctgtgca gccgagccac gaaggtgcaa agcggggccc tgtcctgccc cggccgggtg    780
tggggagaca gaggacgcaa acctaagagg gcacccagag cgccgggaa cgcagcctgg     840 ggacctcgaa gcccctcgaa agcgctcctc tagaggtgac agcaccagat cctggcgaag    900
gaccaggccc cggggtcgga ggataggggg acaggtggcc ggggctccgc ggcggctggg    960
actccgcggt gctgtgggct ccggctcgct caccttctcc tgcgcgcggg tgagcttctt   1020
ctgcacgttg ctggcgatct ttcccgccgt caccccttta ctgcccatct ctgccatcgc   1080
ggcgcaggcc tcgcccggtg cagggccg ctctcgcgcg gggagatctt gcgccgcg     1140 ctcccagccc ccagccccgg ccgcgcgtcc agaccggctg ccgctccacg ccgcgcaccc   1200
gacagcggag ccaactgacg gaggcggagc gtgcgccgga cgggcgagcg agccagcgag   1260
ctagccagcg agcgacgcgg ggacagaggg agggagaggg gaggggccgg gcctcaggcc   1320
gcggtcggcg ccccccgccc gccccctccg gacaataagc tgccttttaa agggccactc   1380
cgggcgccgg caccgccagg tccgcgagga gggaggggcg cgcgcggcgc tggggctgcg   1440
gcgagcggga ctcccctgac gctccagctg caccgccccg gggcggggac taatccgccg   1500
gcctggcgtc ttggtcttcc ccgcaagcag taatctcctg caacccagga aaggagacta   1560
ggtggaggag aggagtgctt tcgaaatcaa agagaaagtg cggcgaaggg ggcgcggccc   1620
tgaacagagg agccgcggct gctgggagaa cgcgcccgga gccccctcct tttccagggg   1680
ctcacctccc gcccggtgcc cggtgcccgg tgcccgacgc tccgcctcct cccagccttc   1740
ggccctcggg ttttcgcccg gataccctag gcgcctccgg gacatctcca catctttgcc   1800
tacggcgcct agcccagtac caaccggtgc ttggtcttcc cgttcgctaa aaatttatta   1860
taataacaac aacctagcat tactgagtgc ttactgtgta ctaagtgact tgacaggcat   1920
tatttcattc ggtctccgtg gccctagagg taggtgctat tactgttcct actttacaac   1980
caacgcgccg ggatcgagga acgagatctc tgcctctgtc tcccaggtgc tccaccacca   2040
tacgcc                                                             2046

<210> SEQ ID NO 155
<211> LENGTH: 681
<212> TYPE: DNA
<213> ORGANISM: Homo sapiens

<400> SEQUENCE: 155
aggtctccaa tctatccact ggatttccgt gagaattgtg cccgctctgg tattggatgt     60
tcctctccat aagactacag tttctaagga acactgtggc gaagaccttt cattccgcaa    120
cgcatgctgg aaataattat ttccctccac ccccccaaca atccttatta cttatattta    180
ccgaaactgg agacctccat tagggcgaa agagtggggg attgggacct cttcttacga     240
ctgctttgga caataggtag cgattctgac cttcgtacag caattactgt gatgcaataa    300
gccgcaactg gaagagtaga ggctagaggg caggcacttt atggcaaact caggtagaat    360
tcttcctctt ccgtctcttt ccttttacgt catccggggg cagactgggt ggccaatcca    420
gagccccgag agacgcttgg ctcttttctgt ccctcccatc ctctgattgt accttgattt    480
cgtattctga gaggctgctg cttagcggta gccccttggt ttccgtggca acggaaaagc    540
gcgggaatta cagataaatt aaaactgcga ctgcgcggcg tgagctcgct gagacttcct    600
```

```
ggacgggga  caggctgtgg  ggtttctcag  ataactgggc  ccctgcgctc  aggaggcctt     660
caccctctgc  tctgggtaaa  g                                                 681

<210> SEQ ID NO 156
<211> LENGTH: 898
<212> TYPE: DNA
<213> ORGANISM: Homo sapiens

<400> SEQUENCE: 156
attctcctgc  ctcagcctcc  cgagtagttg  ggattacagg  catgcaccac  cacgcccagc     60
taatttttgt  atttttagta  gagacaaggt  ttcaccgtga  tggccaggct  ggtcttgaac    120
tccaggactc  aagtgatgct  cctgcctagg  cctctcaaag  tgttgggatt  acaggcgtga    180
gccactgcac  ccggcctgca  cgcgttcttt  gaaagcagtc  gagggggcgc  taggtgtggg    240
cagggacgag  ctggcgcggc  gtcgctgggt  gcaccgcgac  cacgggcaga  gccacgcggc    300
gggaggacta  caactcccgg  cacaccccgc  gccgccccgc  ctctactccc  agaaggccgc    360
ggggggtgga  ccgcctaaga  gggcgtgcgc  tcccgacatg  ccccgcggcg  cgccattaac    420
cgccagattt  gaatcgcggg  accgttggc  agaggtggcg  gcggcggcat  gggtgccccg    480
acgttgcccc  ctgcctggca  gcccctttctc  aaggaccacc  gcatctctac  attcaagaac    540
tggcccttct  tggagggctg  cgcctgcacc  cggagcggg  tgagactgcc  cggcctcctg    600
gggtccccca  cgcccgcctt  gccctgtccc  tagcgaggcc  actgtgactg  ggcctcgggg    660
gtacaagccg  ccctcccctc  ccgtcctgt  cccagcgag  gccactgtgg  ctgggccccct    720 tgggtccagg  ccggcctccc  ctccctgctt  tgtcccatc  gaggcctttg  tggctgggcc    780
tcggggttcc  gggctgccac  gtccactcac  gagctgtgct  gtcccttgca  gatggccgag    840
gctggcttca  tccactgccc  cactgagaac  gagccagact  tggcccagtg  tttcttct      898

<210> SEQ ID NO 157
<211> LENGTH: 1256
<212> TYPE: DNA
<213> ORGANISM: Homo sapiens

<400> SEQUENCE: 157
atacgttcat  atatatatat  atatatgtac  atttttaaag  gcagagatgt  gcgtctcgcc     60
atgttgccgc  gtctggtctc  gagctcccgg  gctcaagcga  tcttcccgcc  tcgacctccc    120
aaggctctgg  gagtacagac  gtgagccaca  gcggccggcc  cgtgtttaac  tcagataaaa    180
tctgggtaac  acactttcaa  cgcttcaacc  ccctcgggcg  caccgctctg  cgctcattgc    240
aactttgaaa  gcaggaagga  agaaatgcgc  aggctccagc  cgcgtccccg  caggccccac    300
tcccgtttcc  tagcaacgcc  gggtcacgtg  cgccgccgcc  cggattccgt  agcgtgagcc    360
tgccggagcc  ggcgcgtaca  tgcgagcgtg  tgcgcgcgtg  cgcaggcggg  gcgaccggcg    420
tccccggcgc  tcgccccgcc  ccgagatga  cgccgtgcgt  gcgcgcgccc  ggtccgcgcc    480
tccgccgctt  tttatagcgg  ccgcgggcgg  cggcggcagc  ggttggaggt  tgtaggaccg    540
gcgaggaata  ggaatcatgg  cggctgcgct  gttcgtgctg  ctgggattcg  cgctgctggg    600
cacccacgga  gcctccgggg  ctggtgagga  gcgggtaggg  ggcgggggtg  cggtcctgca    660
ggggccggga  atggaggccg  cggtgccgac  ccgaagccga  cgggagcctg  ggcctcggc    720 gcggggcggc  ctggggtgcg  aaaggccggc  cccgggggct  tcccgcgcca  gcatggagct    780
tgggggtgaa  gtcccagggt  ttgaggggg  actagaggtt  cctcccggcg  cggcctgccg    840
```

| | | | |
|---|---|---|---|
| ggctcccccg | ggcgctccgg | cctcgagccc ggcctctgtg tgtgggcgtg aagctccctg | 900 |
| cttggaggcg | ggagccaggg | ggtcctggcc aggccggtct tggtcagggg aggtgggcgt | 960 |
| cttgcttttc | ggtcacctgg | ggttgggggt gacctgcttc ctgggtgagg gcgtctgcga | 1020 |
| aggcggttgg | aggtggcccg | cccgccggtc ccatcggcca ggagaaggga gacccaaagc | 1080 |
| ctgggtgagc | gtccccttg | gcctggagcc aggggtcagg ggctggttgg tgcctgccca | 1140 |
| acccgtcctg | ctggggctgg | actccgcagg acctggggaa agcggcctgg gcgtggaatc | 1200 |
| tggagacggg | tccaccctgc | ctgcgagtgt tagggtcaga gaccctcccc tgagac | 1256 |

<210> SEQ ID NO 158
<211> LENGTH: 4256
<212> TYPE: DNA
<213> ORGANISM: Homo sapiens

<400> SEQUENCE: 158

| | | | |
|---|---|---|---|
| gaaaaagaca | ttcacgactc | tcaagtggag agaggataga aagtcaagtg gcggggggtcg | 60 |
| cgaccagtga | tcgggatttc | agtctgatct cagtacccag cggaacagga ccataaccta | 120 |
| aagaaatgag | cttttccgg | agcaaagagc ggccccgatt tcaaagtaga aaaaataaac | 180 |
| tgcttggggg | tggaagatgg | cgaggggcgg ggggcgggga gggaggcggg tcgcggcgct | 240 |
| ggctccgggg | tccgcggcac | ggcctcctct gccgcgctgc ccagggcccg gaccctgccc | 300 |
| ggcgctgcgc | ccaccgcgag | ggtgccagac ccgccgcgcc gccgccgcgc tctcccagcc | 360 |
| gcggcccct | ccccgccgc | ttcctcttgc tctcccagcc ccttccccca cgtgtggatg | 420 |
| acgtcaaaat | tccgcgaaaa | agccgcgtgg tggctccccg agcggaggcg cgattccgcc | 480 |
| gcccagcggc | cccctccggg | gggcgcctgg aggggagaa gggcggaggc ggccggttcc | 540 |
| ttctcctccc | gggaggcagg | accccccgac gccgaccgcc ggacgccccc cgccccaaag | 600 |
| cttattggaa | aattcacttt | tgtaaagcaa atgtatttcc agagctattt tcggccgcgt | 660 |
| gaggcgtgtc | ctaagctgaa | tcagacagga agagggggaa gttcgggtct tttaattttt | 720 |
| tttttttccg | aagggagggg | agtgagatgc taggtgggtg acagacggca ggcgctcgcc | 780 |
| ttcttaactc | acgcctgtcg | catctgccgc ctcagtaatc cagccccgtc caagccgaaa | 840 |
| ttcgccgaag | ggagtgcgga | tgcacaggcc tggcggactc tgccccctc cagaacgcag | 900 |
| cggcccagcg | ccccggcggg | cgcggctgcg accagagggt cccggaagcg agtgaacacc | 960 |
| tgcaatcgca | ctgcccgtcc | ccacccaccc tgctccccg tgctctccgc ttcccgacgt | 1020 |
| tttcctcttc | tccttgtccg | catttttcta ctttgcctgc actccctcct tcctcttgat | 1080 |
| gtgcctccta | tgtgtcccct | cggatttatg tgtcccctcg cattttgcca gtcgggtttt | 1140 |
| cggttttgat | tgaccgtcca | tccctccacg gagaaacaca aacacagctc cactctttgg | 1200 |
| gggagccgag | gggaaggcag | tggctcccat ttctgagcct gaactcagtc actacccgct | 1260 |
| ccccacctgg | cctaggcgcc | cctgcgcgga gaaggcggga ctcgaactcg cgctgctccc | 1320 |
| gggccttgag | ccgaccgcgg | aatcacctgg ctggaggca tcctccaggt aagcttggga | 1380 |
| gtatgtgtgc | ttagtgctgc | aggctcctgc agaaaagtgc ctataaacac ccaacaccct | 1440 |
| gctgcaccct | ccacctccag | gctttgtaca ctttccaacc gaaactccaa aacgctagcg | 1500 |
| tagggggtgg | ggagccggcc | ggaaaaagaa taaaagtcca ataaaactgg cgttcgctaa | 1560 |
| agtttatcac | cagtcctaca | tgggatatat atatatgtat ttttttttcc gtgaagggtg | 1620 |
| aaaaggagat | aaggaagaac | caacaatcta cccccctcccg ccgcccccca ccccgcgcc | 1680 |
| acggtgatca | gtttggactt | caaagccaga gcacaggctc ttgcgctttt tcttgaaacc | 1740 |

```
gaagtctaca ctgaaagaaa gtgtgcactt tgcctagaa ggcaacatgc gttttcccgc    1800
gtgctaggtg gagtgcattt taacaagaca ttagggtttt aacacatggc tggagtggcg    1860
accaaaaggg aaaactcagt ttccagtcca agcctcctag agacattcct gccaacctcc    1920
gcaccctctc acgccccacc ccacgtgtga gagtctgcaa aaccaccggg gattggattc    1980
gatggcgagc ttcacgctcg ggaacagtca gtaatcggaa ggggaagtgg acagggaac     2040 ttcaagaggc gagcctgcca cgcgggaagc gcccgaactt gcgggtctcc atgaatgcag    2100
agggcgccgg aagggggggg catccggccg cgaccctctc tgcccctccc attcgctgcc    2160
cccctccccg ctggaatttc tctgtaaagc aagacggagt aggggagggg ggagagggaa    2220
ggggcgagag ggccctcggc tcactcccga cgtgagga ctcgccaccc aggcattctc      2280
ctcggggtgg gctgggcccc gggacgacca cccgcttctt cctcgccccc gctgccccca    2340
cttcgggaga cccagagctc tggatgcctt tccccggaga agggggggtg tgcggagtcg    2400
gggtggaaga gaccttgctc gcagagctat atcaagtgat gtccagaggc tgggagcccc    2460
ggcggcctct gtcccttgcc tgtcgggtta gatttatact ttaaaaatac ctcccgccct    2520
ccctccttct ctcgcctctc cccgctgcaa cttttcttga tccgctcaaa ggtggcttag    2580
gtgaaattgg agtaattccc ttatgggggt cttaaaatgt aagtgaatgt ccttatccgg    2640
ggtgactcaa aagcttaagt cgggaagccc aacgtgacta aaaccaatag gtgattgttc    2700
ggggccgact gtgtgcgggt gtacacggta ttcggcccgg gtgtcatccg cggcgctgga    2760
ctgtttcatt ttgagtttgc aacttggggtt tttcagcgag cttttttttct tcctgaaagc    2820 taatggcttc cacagcaatt agacattttc ctcgcccgcc ccttccctcc cctttcttta    2880
catataggag atgggatact cattcccgct gctattgata aggtcggagg cggccgggcc    2940
tctccccagc tttcgcccgc cccagcgccc gctctccctc cgccctccct tggcttcctt    3000
ttgatgtagt ggggaacgcg tcctactaaa aaaaaaaaa aaaaaaaaaa aaaaagtaa     3060 tctgcccggt aacaatcagc gcgcagtagc aggagcccca gagctattgg ctatgcaaat    3120
agagggaggg gagacggcgc cccaaactct tcctcaccct tttaaagcga tatcccctcc    3180
tttccccccc accaccccctt ccgccccacc ctcgtttaaa gaggctggct ccggggcctg    3240
agttaatcgc ttgcacctct agtttattcg ctcccctcct ccgccttgca gggaacctag    3300
tgtacggctc acccagcccg cgccccaccc cgccttgctg gctctccgcg ccctgcccg     3360 ggcccctct ctcggtgagg gaggcactca gtcggcctcg gtgtgcccag agagctcgag     3420
ccacgccatg cccgctgcac gtgccagctt ggccagcaca tcagggcgct ggtctctccc    3480
cttcctcctg gagtgaaata caccaaaggg cgcggtgggg gtgggggggtg acgggaggaa    3540 ggaggtgaag aaacgccacc agatcgtatc tcctgtaaag acagccttga ctcaagcatg    3600
cgttagagca cgtgtcaggg ccgaccgtgc tggcggcgac ttcaccgcag tcggctccca    3660
gggagaaagc ctggcgagtg aggcgcgaaa ccggaggggt cggcgaggat gcgggcgaag    3720
gaccgagcgt ggaggcctca tgcctccggg gaaaggaagg ggtggtggtg tttgcgcagg    3780
gggagcgagg gggagccgga cctaatccct cactcgcccc ctcccctcc cgggccattt     3840 cctagaaagc tgcatcggtg tggccacgct cagcgcagac acctcgggcg gcttgtcagc    3900
agatgcaggg gcgaggaagc gggttttttcc tgcgtggccg ctggccgcgg gggaaccgct    3960
gggagccctg cccccggcct gcggcggccc tagacgctgc accgcgtcgc ccacggcgc     4020 ccgaagagcc cccagaaaca cgatggtttc tgctcgagga tcacattcta tccctccaga    4080
```

| | | |
|---|---|---|
| gaagcacccc ccttccttcc taatacccac ctctccctcc ctcttcttcc tctgcacaca | 4140 | |
| ctctgcaggg gggggcagaa gggacgttgt tctggtccct ttaatcgggg ctttcgaaac | 4200 | |
| agcttcgaag ttatcaggaa cacagacttc agggacatga cctttatctc tgggta | 4256 | |

<210> SEQ ID NO 159
<211> LENGTH: 1710
<212> TYPE: DNA
<213> ORGANISM: Homo sapiens

<400> SEQUENCE: 159

| | |
|---|---|
| tgaaagagtg agaccccatc tccaaaacga acaaacaaaa aatcccaaaa aacaaaagaa | 60 |
| ctcagccaag tgtaaaagcc ctttctgatc ccaggtctta gtgagccacc ggcggggctg | 120 |
| ggattcgaac ccagtggaat cagaaccgtg caggtcccat aacccaccta gaccctagca | 180 |
| actccaggct agagggtcac cgcgtctatg cgaggccggg tgggcgggcc gtcagctccg | 240 |
| ccctggggag gggtccgcgc tgctgattgg ctgtggccgg caggtgaacc ctcagccaat | 300 |
| cagcggtacg gggggcggtg cctccggggc tcacctggct gcagccacgc accccctctc | 360 |
| agtggcgtcg gaactgcaaa gcacctgtga gcttgcggaa gtcagttcag actccagccc | 420 |
| gctccagccc ggcccgaccc gaccgcaccc ggcgcctgcc ctcgctcggc gtccccggcc | 480 |
| agccatgggc ccttggagcc gcagcctctc ggcgctgctg ctgctgctgc aggtaccccg | 540 |
| gatcccctga cttgcgaggg acgcattcgg gccgcaagct ccgcgcccca gccctgcgcc | 600 |
| ccttcctctc ccgtcgtcac cgcttcccct cttccaagaa agttcgggtc ctgaggagcg | 660 |
| gagcggcctg gaagcctcgc gcgctccgga ccccccagtg atgggagtgg ggggtgggtg | 720 |
| gtgaggggcg agcgcggctt tcctgccccc tccagcgcag accgaggcgg gggcgtctgg | 780 |
| ccgcggagtc cgcggggtgg gctcgcgcgg gcggtggggg cgtgaagcgg ggtgtagggg | 840 |
| gtggggtgtg gagaaggggt gccctggtgc aagtcgaggg ggagccagga gtcgtgggga | 900 |
| cgatcttcga gggaaggaga ggggcatccg tagaaataaa ggcacctgcc atgccaagaa | 960 |
| aggtcgtaaa taggagtgag ggtcccgggg ataagaaagt gaggtcggag gaggtgggag | 1020 |
| cgcccctcgc tctgaggagt ggtgcattcc cggtctaagg aaagtggggt actggagaat | 1080 |
| aaagacatct ccaataaaat gagaaaggag actgaaaggg aacggtgggc taggtcttga | 1140 |
| gggggtgact cggcggcccc ctcccgggag ttcctggggg ctcggcggcc gtaggtttcg | 1200 |
| gggtggggga gggtgacgtc gctgcccgcc cgtcccgggg ctgcgggctg gggtcctccc | 1260 |
| ccaatcccga cgccgggagc gagggagggg cggcgctgtt ggtttcggtg agcaggaggg | 1320 |
| aaccctccga gtcacccggt tccatctacc tttcccccac cccaggtctc ctcttggctc | 1380 |
| tgccaggagc cggagccctg ccaccctggc tttgacgccg agagctacac gttcacggtg | 1440 |
| ccccggcgcc acctggagag aggccgcgtc ctgggcagag gtgagggcgc gctgccggtg | 1500 |
| tccctgggcg gagtagggag ggggttggaaa ggggccgaga aattgcactc ccacacccct | 1560 |
| gggttgcaat gggcaagctc cctccttggc tcaaacgaca ccccttggaa tttacgcaga | 1620 |
| tttggggatc caaacgtttta cgactgaaca ctgtggtgga ggggggtaacc ctgcctggtt | 1680 |
| gttgactatg ttataaagaa gaggaggttg | 1710 |

<210> SEQ ID NO 160
<211> LENGTH: 2209
<212> TYPE: DNA
<213> ORGANISM: Homo sapiens

<400> SEQUENCE: 160

```
aagctctgtt cgcctcagtt tcccacgatt gagggctgt gtgaaggag gtccaggttc    60
aatggtactg cgagaaccac atgtctaagt cgttgtaacc cgaatgggga agcctccacc   120
ggcggttatc tcctcctcct cctagcctgg gctagagacg aattatctgt ttacgaaatc   180
acaccaaaca aaacaagtgc cgaatgcgcc ccggactttt cgagggcctt tcctacctgg   240
tcttctagga agcggctgct gccctagacg ctggctcctc agtagcatca gcacgagggc   300
cacagcggcg ggcgccctg cgctgccca ctcccccgtg agccgcggga tgtgaaccac   360
gaaaaccctc actcgcggcg ggccgcacgc gcgccgaatc cggagggtca ccaagaacct   420
gcgcaccatg ttctcgccgc ctccaggcc gagctcggca gccgctgcgc cgcccttttgg   480
caccagaggt gagcagcgcc actcctgccc ccttaactgc agactgggac ccacgcaccg   540
cccctgccc atctccgccc cgcaggcgcg cacccgcctt ccctgagcgc gcccgccccc   600
caccttcacc cccaccccca cccaccccc actcccaccc ggacctccaa gatctcggaa   660
cggctctgag ccctgcgcac gcgggaaggg ctgccggagg cgcccgtagg gaggcgcgcg   720
cgcgggcggc tcagggcccg cgttcctctc cctcccgcct accgccactt tcccgccctg   780
tgtgcgcccc cacccccacc accatcttcc caccctcagc gcgggcgccc cgcggtgacg   840
gcccaggggc cggacgcctg gaacgcaact ccaggcagct cgcccctag ctacatccgt   900
cacctgacac ggccctacca ggaacagccg cgctcccgcg gattctggtg ctgctcgcgt   960
ccccgctccc ctattccct tatttattc ctggctcccc tcgtcgaaag tcttccattc  1020
ttcaaactag attatttaaa aatgaaaaag gaagaaagga aagcgaggtc atctcattgc  1080
tctatccgcc aatcaggagg ctgaatgtca gtttttgaact aaaagccgct ccgctcctct  1140
tctagatttg gaaaacaagc gaaattaaac taaaccgctg cacgcctctg acgcgacatc  1200
tggacacggc gcggcgctgg cgctgccgga gctgtcgacc cggcctggcg ccggactagg  1260
taggtggagt cgcaccccggg ggtcccagct gggtccgggc gcccattccc ctcccagctg  1320
cccgcgtcgc cgagggcgcc tggctgggac aagcaccgag tcctttgtgt ctagcccatt  1380
tttattttcg gttttaacct tcacgacagc cgcggagcat ctgagcgctt cttcctcttt  1440
cctcttcccc cgcgctcccc tcccctgctg gccgctcccc tcctgtcgcc gcgtcctcgc  1500
gtagaatggt tgtcttggcg accgttggcc gctgccgcct ccacgctctg ccccgcgccc  1560
agacaccccg actcccttg atcccgccgc ctgactcctc ggcgtacgtt ctctctccgg  1620
tctccccctc catgtcccct cctcccctt tcttccacat caccgatcct ttctggactc  1680
tctcccttcc tcctttccag ctgggagaca ggaaaagcgg tcctgtttgg gaacagtaaa  1740
agcagggcaa ggaaaggaag gagcggcaga aggaggggt gagtcgagga cacaggggca  1800
gccgagaat gcggaggagc cgggtcctga gcgcggtcta gcgaggctc ggctctcgtc  1860
caggaactcg gacgcgggct cgccggctct ccgcgcgcgg gaagtcgagc ccaggacgcc  1920
gccttcaggc cggcgcgctg acccggtgcc ccgaccggga gctgcgtc tgcctggatc  1980
cgtcctaaac ctcgcgggct ggacccgcgg cctgagtggg tgggtgtgtg ccagaggatt  2040
cgggactagg cccagctccg ggaacctgga aatgtggccc gcttctcagt ggcttcctgt  2100
tcatgcgctt gggcctagtg gcctagttga agaagtggaa ccacagcgtg agccgacagg  2160
gccttacaga tcagacgtca agcccccag accttacagg ggaggaaag             2209

<210> SEQ ID NO 161
<211> LENGTH: 943
<212> TYPE: DNA
```

<213> ORGANISM: Homo sapiens

<400> SEQUENCE: 161

| | | | | | |
|---|---|---|---|---|---|
| aggcagcgag | tggttaagtg | acttctccga | ggttacacag | ctaggaaatg | gtggcaacag | 60 |
| taagagccca | cgaagagctg | cggttggtag | ttcattctgg | acagccctcc | cgtgaaccgt | 120 |
| ccctgtactg | gcacttgttg | ctggggactg | tcgctgtcct | ctccctcccc | gggccaggtg | 180 |
| tgtcctggag | ggcagggaag | cgtcttggca | cgcgggtgcg | cgccgccccc | tcggcctcct | 240 |
| gggctccctg | aacctcgcag | gaccccggca | acttcgagcc | ccgccccagc | tccaggccgc | 300 |
| gggggcgcat | cgcgggcgtc | gggcggggcg | gcccagcggg | taaaagctgc | gcggccgcaa | 360 |
| gctcggcact | cacggctctg | agggctccga | cggcactgac | ggccatggcg | cgttcgaacc | 420 |
| tcccgctggc | gctgggcctg | gccctggtcg | cattctgcct | cctggcgctg | ccacgcgacg | 480 |
| cccgggcccg | gccgcaggag | cgcatggtcg | agaactccg | ggacctgtcg | cccgacacc | 540 |
| cgcaggtgca | gaaggcggcg | caggcggccg | tggccagcta | caacatgggc | agcaacagca | 600 |
| tctactactt | ccgagacacg | cacatcatca | aggcgcagag | ccaggtgcgg | cggcggggt | 660 |
| gctgggaggg | gacaccccggc | ccagatgggg | gaggccacag | gcgctgcccc | agcgtgcatg | 720 |
| aaggggggcct | aaaagcgcaa | tcgggatatt | ttcatgcaat | attttaaaaa | tcgaattaat | 780 |
| gctaaaactc | cacgatggac | aaccatctaa | atttcaagga | agacataat | taaaccctgt | 840 |
| attgcactac | ctgccttcct | ggcttgcctg | gtcctagtct | ctgccctgat | ggggtggatc | 900 |
| ggggaggagg | gaaggcaggt | ggggacagtg | ggcagctccc | tag | | 943 |

<210> SEQ ID NO 162
<211> LENGTH: 1703
<212> TYPE: DNA
<213> ORGANISM: Homo sapiens

<400> SEQUENCE: 162

| | | | | | |
|---|---|---|---|---|---|
| ttattatcta | tctgtcccac | cagaatgcag | gtttccggaa | ggcagggatt | taaaaaaatc | 60 |
| tgttttgttc | tatgtgattt | tcccatacca | agcaccgtgc | ccggcacaag | ctgggatccc | 120 |
| agtacacatc | tcgggacgga | agaaccgtgt | ttccctagaa | cccagtcaga | gggcagctta | 180 |
| gcaatgtgtc | acaggtgggg | cgcccgcgtt | ccgggcggac | gcactggctc | cccggccggc | 240 |
| gtgggtgtgg | ggcgagtggg | tgtgtgcggg | gtgtgcgcgg | tagagcgcgc | cagcgagccc | 300 |
| ggagcgcgga | gctgggagga | gcagcgagcg | ccgcgcagaa | cccgcagcgc | cggcctggca | 360 |
| gggcagctcg | gaggtgggtg | ggccgcgccg | ccagcccgct | tgcagggtcc | ccattggccg | 420 |
| cctgccggcc | gccctccgcc | caaaaggcgg | caaggagccg | agaggctgct | tcggagtgtg | 480 |
| aggaggacag | ccggaccgag | ccaacgccgg | ggactttgtt | ccctccgcgg | agggggactcg | 540 |
| gcaactcgca | gcggcagggt | ctggggccgg | cgcctggag | ggatctgcgc | ccccactca | 600 |
| ctccctagct | gtgttcccgc | cgccgccccg | gctagtctcc | ggcgctggcg | cctatggtcg | 660 |
| gcctccgaca | gcgctccgga | gggaccgggg | gagctcccag | gcgcccgggt | gagtagccag | 720 |
| gcgcggctcc | ccggtccccc | cgaccccgg | cgccagcttt | tgctttccca | gccagggcgc | 780 |
| ggtgggttt | gtccgggcag | tgcctcgagc | aactgggaag | gccaaggcgg | agggaaactt | 840 |
| ggcttcgggg | agaagtgcga | tcgcagccgg | gaggcttccc | cagccccgcg | ggccgggtga | 900 |
| gaacaggtgg | cgccggcccg | accaggcgct | ttgtgtcggg | gcgcgaggat | ctggagcgaa | 960 |
| ctgctgcgcc | tcgtgtgggcc | gctcccttcc | ctcccttgct | ccccccgggcg | gccgcacgcc | 1020 |
| gggtcggccg | ggtaacggag | agggagtcgc | caggaatgtg | gctctgggga | ctgcctcgct | 1080 |

```
cggggaaggg gagagggtgg ccacggtgtt aggagaggcg cgggagccga gaggtggcgc   1140
gggggtgcca ccgttgccgc aggctggaga gagattgctc ccagtgaggc gcgtaccgtc   1200
tgggcgaggg cttcattctt ccgcggcgtc cctggaggtg ggaaagctgg gtgggcatgt   1260
gtgcagagaa aggggaggcg ggaggccag tcacttccgg agccggttct gatcccaaca    1320
gaccgcccag cgtttgggga cgccgacctc ggggtgccgt ggtgcccggc cccacgcgcg   1380
cgcggggctg aggggtcggg ggcgtccctg gccgcccagc tttaacaaag ggtgctcctc   1440
tccaccccgc gaggaggggc agctccggag accggtctt cagcgagcgg ggtcttagcg    1500
ccggggaggt ctacttcctt ttggggttgc cattttacta ttattattgc ctttttttt    1560 tcttcaaaag gactggagac tgatgcatga gggggctacg gaggcgcagg agcggtggtg   1620
atggtctggg aagcggagct gaagtgccct gggctttggt gaggcgtgac agtttatcat   1680
gaccgtgttc aggcaggaaa acg                                           1703

<210> SEQ ID NO 163
<211> LENGTH: 1349
<212> TYPE: DNA
<213> ORGANISM: Homo sapiens

<400> SEQUENCE: 163
tccagcagcg acgacaagta aagtaaagtt cagggaagct gctctttggg atcgctccaa    60
atcgagttgt gcctggagtg atgtttaagc caatgtcagg gcaaggcaac agtccctggc   120
cgtcctccag cacctttgta atgcatatga gctcgggaga ccagtactta aagttggagg   180
cccgggagcc caggagctgg cggagggcgt tcgtcctggg actgcacttg ctcccgtcgg   240
gtcgcccggc ttcaccggac ccgcaggctc ccggggcagg gccggggcca gagctcgcgt   300
gtcggcggga catgcgctgc gtcgcctcta acctcgggct gtgctctttt tccaggtggc   360
ccgccggttt ctgagccttc tgccctgcgg ggacacggtc tgcaccctgc ccgcggccac   420
ggaccatgac catgaccctc cacaccaaag catctgggat ggccctactg catcagatcc   480
aagggaacga gctggagccc ctgaaccgtc cgcagctcaa gatccccctg gagcggcccc   540
tgggcgaggt gtacctggac agcagcaagc ccgccgtgta caactacccc gagggcgccg   600
cctacgagtt caacgccgcg gccgccgcca acgcgcaggt ctacggtcag accggcctcc   660
cctacggccc cgggtctgag gctgcggcgt tcggctccaa cggcctgggg ggtttccccc   720
cactcaacag cgtgtctccg agcccgctga tgctactgca cccgccgccg cagctgtcgc   780 cttttcctgca gccccacggc cagcaggtgc cctactacct ggagaacgag cccagcggct   840
acacggtgcg cgaggccggc ccgccggcat tctacaggta cccgcgcccg cgccgcccgt   900
cggggtggcc gccgcgcccg gcaggaggga gggaggagg gagggagaag ggagagccta    960
gggagctgcg ggagccgcgg gacgcgcgac ccgagggtgc gcgcagggag cccggggcgc   1020
gcggcccagc ccgggggttc tgcgtgcagc ccgcgctgcg ttcagagtca agttctctcg   1080
ccgggcagct gaaaaaaacg tactctccac ccacttaccg tccgtgcgag aggcagaccc   1140
gaaagcccgg gcttcctaac aaaacacacg ttggaaaacc agacaaagca gcagttattt   1200 gtggggggaaa acacctccag gcaaataaac acggggcgct tgagtcact tgggaaggtc    1260 tcgctcttgg catttaaagt tggggtgtt tggagttagc agagctcagc agagttttat   1320
ttatcctttt aatgtttttg tttaatgtg                                     1349

<210> SEQ ID NO 164
```

```
<211> LENGTH: 1135
<212> TYPE: DNA
<213> ORGANISM: Homo sapiens

<400> SEQUENCE: 164 gttgaccccca gtctgttagc agacccagat agacaggaga cagcgctggg tggcggctag      60
tcactaaagt caaaagcccg gctgggaggg cgcgacaaaa ggcagcaaag acttccgaat     120
tccccagaag ccagtggact agcacttggc tcccctctcc aggtgatttg tggatgccgg     180
gttccaactc ttcttggggc cgacgagaca aaggcggctg caacagcgcc accgctatca     240
ccttcaggaa gttgttctga ggcaagcgct cccacaggct gctgagaaac ctggcgggac     300
gctccgcttc ggccttcccc acctcctgca gacgctccag cagcagctcc gcctgggtct     360
tcatcagaga gtcctcctgg agatttgggt tctctctata gccattgaag cgcagcatgt     420
gcaccgcaga ccgccggcgg gcaaggcggg ccaggctctc ttggagtgtc tcctcatcgg     480
cgtcccggac gcccgggccg ggaaagagtt gctgcaccag gtggtaacga gctgcatccc     540
cgagggcccg gttctccagc aggcgcagag agagcaggac gtcacagtga ccgagggcct     600
ggaagttcgc taatcccgga actggacccc gcccaaagcc gccctcttgc ctccactggt     660
tgtgcagccg ccgctccaga gccgtgcgaa tggggccatg ccgaccaaag cgccgatgga     720
tgtggcgcag gtagcgcgcc cactgcaagg cccggcgcac ggtggcgggg tcccaggtgc     780
tgacgtaggt agtgcttgag accgccgaaa gctcggaaaa gcgatccagg tgctgcagaa     840
gggattccat gaggtgcgcg aaggccctac ttccgctttc accttggaga cggcgactct     900
ctgcgtactg attggaacat ccgcgaaatg atacgcctct ctgcaatgct attggtcgaa     960
atgcatgtca atctcccagc gtctttatcc gtgttccttg actctgggca acttaaaagc    1020
cctaatactt ttactttcgc cacacaaaga ggttcttctt agtggaggga gagcagatgt    1080
agggcatcct accgagaatt tccggaacca cgtgcgagat gatgccagtc atgaa         1135

<210> SEQ ID NO 165
<211> LENGTH: 1425
<212> TYPE: DNA
<213> ORGANISM: Homo sapiens

<400> SEQUENCE: 165
ccactgcact ccagcctggg ccacagcgtg agactacgtc ataaaataaa ataaaataac      60
acaaaataaa ataaaataaa ataaaataaa ataaaataaa ataaaataaa ataaaataaa     120
aaaataaaat aaaataaaat aaaataaagc aatttccttt cctctaagcg gcctccaccc     180
ctctcccctg ccctgtgaag cgggtgtgca agctccggga tcgcagcggt cttagggaat     240
ttccccccgc gatgtcccgg cgcgccagtt cgctgcgcac acttcgctgc ggtcctcttc     300
ctgctgtctg tttactccct aggccccgct ggggacctgg gaaagaggga aaggcttccc     360
cggccagctg cgcggcgact ccggggactc caggcgcccc ctctgcggcc gacgcccggg     420
gtgcagcggc cgccggggct ggggccggcg ggagtccgcg ggaccctcca gaagagcggc     480
cggcgccgtg actcagcact ggggcggagc ggggcgggac caccttata aggctcggag     540 gccgcgaggc cttcgctgga gtttcgccgc gcagtcttcc gccaccagtg agtacgcgcg     600
gcccgcgtcc ccggggatgg ggctcagagc tcccagcatg gggccaaccc gcagcatcag     660
gcccgggctc ccggcagggc tcctcgccca cctcgagacc cgggacgggg gcctagggga     720
cccaggacgt ccccagtgcc gttagcgcgt ttcaggggc ccggagcgcc tcggggaggg     780
atgggacccc gggggcgggg aggggggggca gactgcgctc accgcgcctt ggcatcctcc     840
```

```
cccgggctcc agcaaacttt tctttgttcg ctgcagtgcc gccctacacc gtggtctatt      900
tcccagttcg aggtaggagc atgtgtctgg cagggaaggg aggcaggggc tggggctgca      960
gcccacagcc cctcgcccac ccggagagat ccgaaccccc ttatccctcc gtcgtgtggc     1020
ttttaccccg ggcctccttc ctgttcccgc cctctcccgc catgcctgct cccgccccag     1080
gtgttgtgtg aaatcttcgg aggaacctgt ttccctgttc cctccctgca ctcctgaccc     1140
ctccccgggt tgctgcgagg cggagtcggc ccggtcccca catctcgtac ttctccctcc     1200
ccgcaggccg ctgcgcggcc ctgcgcatgc tgctggcaga tcagggccag agctggaagg     1260
aggaggtggt gaccgtggag acgtggcagg agggctcact caaagcctcc tgcgtaagtg     1320
accatgcccg ggcaagggga gggggtgctg ggccttaggg ggctgtgact aggatcgggg     1380
gacgcccaag ctcagtgccc ctccctgagc catgcctccc ccaac                    1425
```

<210> SEQ ID NO 166
<211> LENGTH: 9809
<212> TYPE: DNA
<213> ORGANISM: Homo sapiens

<400> SEQUENCE: 166

```
gttggggacc cttcttatcc tcctagctca gagggaaaga ttcaagagtt tactcttcgc       60
ccaatgccca cttcagctag gggttcctgg aagaacgggg ctgtggagta tctcagaaaa      120
ctttcctccc tctactgtct tcaggcccca ggagacaaac ctccttccaa gcctcctggt      180
cccagtggct tccctctcac cgaaatcgaa agaacccgag tcccagcccg accccttctc      240
tcgccgagcc ctggctggga taccttggcc gggaggacag gacggcctca ggctggccgc      300
cagacgcact ccgcaggacg cgcgcgctcg agcctcggtg gactcagccg ccggccccgg      360
gaggccgcct ccctgcgcag cacctcctgc cacccgcgcg ggcacgtggg atcttgactc      420
gccgcccccg cctccttctg ctccgcgtcc ccagcccgcg gctcggggcg cggcgtggcg      480
cggcgcgtgg gcgtgctgcg gggcgaccat ggctgtagac tgttacctcc agttcccaca      540
gtaacaatcg aaagccacgg ttgccctgga gacgcggggg cggggcgcgc ggacggcgcc      600
ggcgcggggc gggctgacgt cagggccgcg ggggggcggg cggggcggcg gggctgagg      660 agcgcgcgtg ggccaccgcc cctcgcagcc cctaggggacc cggacggggc ggcccgatgg      720
cggcgcctgc gttgatcagc accgcggaca gcggcggcgc aggcagcggg ccgggggcgg      780
ggccctgagg gacggggact gggggtcccc gggcgcggcg gcggcggccg gggccgcggt      840
cctggggcgg ggccaggcgt cggtggccgt gactggagac tgttactgag ggcggcccgg      900
gcagtaagca gtctagagcc aaggtgccgg cgcgctgtcc gggcggggtg cccccggtcgc     960 cccggctgcc ccggctgggg gctctgctgc tccgcctccc ctgcgtctcc cgccctgccc    1020
cgcccggcgc tcgcgaccag gcacgcggcc cctgacgtca gagggccgtg acgtcaaaga    1080
tgtcccagag ggggcacttc cggcggggc gtggggcgg ggcggacct gggaggcccc       1140 gcccccccgg tcctgagagg acagctccgc tcgcagaggc gggaagccgt gggcgccgcg    1200
ggacccgctg gacgggacct gccgggaagg ggcgcccgac gccatgcggg gcggggtcc     1260 caggagggcc ggggaagcgg gggtggcgt ccgtctctcg cctgcacccc cgctcagccg    1320
gcccgggcag cgaggctgag tcaccgcgcc gcagggaggg agaggagggg gcgcgtctcc    1380
tggggcgcca gcaccttcgc ctcactttcc tgggagaatg gcgcaggagc cccaagaaag    1440
ccgggggggg gtctccgagg tcggtcctcc actcgatgct cctccgaagt agctgcgtgt    1500
```

```
ccatcgggcg ccggcaggtg ctgcgcgggc tcgtgtcgtc tctggcccg gctccgcagc    1560 cgcgagggga ccccggtgcc ccccgtccgc cccatcccc accccggagg ggccgcccca    1620
cccgccgcct gcccgtcccc tcctcgtcct cccgtccgtg tccgcacatc tgtccctccg    1680
cggctggtcc gtcccgctta cctggcgggc cgcgtcgcca ctgcccgtc gcctcccgca    1740 gcctggccgg cgcggcggct tttataggcg cgcgtagtac tcgtgcggcg gctcattcat    1800
gcggccgcgc ctcctacaca ctgacgcgct gccgacgtca gcgggaatt taggaaatgg    1860 gaaaagggc tatttatagt ggcgaggcgg ggggtgggga ccgaggcgac cgggagggga    1920 ggaggggcg cggaagcggc ggcggggtag ggggagccgc gccctgccc agccgacaag    1980 gggttaactt tccggaaccg cgggcctggg gccggggagg cggcgcggag gggcgcggcg    2040 ggccttcga gcttattcac gctctccttc cggagcccg cggctcctgg ggtcttcac     2100 gtggcagccc cttccccctc ctcagttcct ggacctgacg tttctgccgt cacacccgc    2160 aaggccactg cggtgtcgcc accctctcgt cctgcagggt gggcaggaga ggaagctgga    2220
ctcccgtggg ggcctgggc gcagcgaggg ctgtggcgtc ggggccggg agaagaagag     2280 tagggagcc caaagtagcc caggagtctt tagcggagga acctgggcct gggagggaag    2340
gcccagcggg gattcaggta ccacccagga gctgagacc cgagggacgg cagagaagtt    2400
ggggaaggtg ggccaacctc cccagaaatg atgagcaacg ggatcctcta tgagggagct    2460
gggggaacgc gccagaggta ggggtgagag gaatgggcag cctcagcaag ggagagagga    2520
aaggctgtca gtgccacgct ccagagcctg gcatccagga cccaccttcg gaccatttgt    2580
ggcacgatgg acgctcccag agctcacgtt agggtaatag agagtgaagg agaccagcag    2640
cttggccaag aggggccccc agggatgag gaggacggtt tcctggagaa gttaatgttc    2700
ccggagacca gaattggcag ggagagccca tgacttgtgg ggcagttccc ctggtgggga    2760 gcgggaaat gcatggtcct ggcccagcct ggctccatcg agatggagga agggtctaaa    2820
tgagaggagt gtgttcagac gaggagctgg accaggatgg ggagggctgt gcaaggcatg    2880
gccggaagag cggggcaggg agagaaaggt cgaagagtga agtgcacagg agggcaaggc    2940
ggtcctcacc ctgcctgggc tggggcaggg ctgtgagacc ctcccttaca gaagcaatga    3000
gggcttgagg aggggttag gggcctgggc tggggcaggg ctgtgagacc ctcccttaca    3060
gaagcaatga gggcttgagg aggggttag gggcctgggc tggggcaggg ctgtgagacc    3120
ctcccttaca gaagcaatga gggcttgagg atggggttag gggcctgggc tggggcaggg    3180
ctgtgagacc ctcccttaca gaagcaatga gggcttgagg aggggttag gggcctgggc    3240 tggggcaggg ctgtgagacc ctcccttaca gaagcaatga gggcttgagg aggggttag    3300 gggcctgggc tggggcaggg ctgtgagacc ctcccttaca gaagcaatga gggcttgagg    3360 aggggttag gggcctgggc tggggcaggg ctgtgagacc ctcccttaca gaagcaatga    3420
gggcttgagg atggggttag gggcctgggc tggggcaggg ctgtgagacc ctcccttaca    3480
gaagcaatga gggcttgagg atggggttag gggcctgggc tggggcaggg ctgtgagacc    3540
ctcccttaca gaagcaatga gggcttgagg atggggttag gggcctgggc tggggcaggg    3600
ctgtgagacc ctcccttaca gaagcaatga gggcttgagg atggggttag gggcagtaag    3660
ttaacttggg gagcggatgt gggggaacgc tgaagaataa agactgtggg cacagcagac    3720 ccctgggca ggttagcaat gcacagactc cactgcacaa gatacatggg gcggaggggc    3780
tctttggaag tcggggtgg gggatctgac tctatcaaaa agagaaaaga taaagagat     3840 ggggtcagag aggccctgca tagtctggat ttggcctact agagctccag ttttcttgcc    3900
```

```
gctagcctttt gttccaggga ttctgttatt cacaaatgcc ttcctgctcg gtagaagaac    3960
tcctattcat ccgtcaaagc ccagctctag gagcacttat gaggagcctc tccacctccc    4020
ctcaacactc cgtaacttcc acctcaggcc gcagcacgtc cctcgggcga gatgtcgggg    4080
tccgccttcc ctagagaccg gcagctccgg aggcctccgt tttcctcttt gggacctcac    4140
tgcttctaaa gtgaggatgc tatggggaga catgggagag ggagtgggta agatggatcc    4200
agaacatggg gcggactcag gcagcggcgg gaatcaggcg gactcgtttg gaccgaagcc    4260
tccgccaggc accgaagccg tgaagtcgcc tgcgcagcaa agggagcctc cggggggcgc    4320
ccgagacctt ggtgtcgctc gggggccgct ggtagccgcg cccgctgccc ctcgcccggt    4380
gactcagccg gtacctctgg cggggccatg ggggccagag gacagcgcgg ggggcggcga    4440
gcgcggttgc taagctctcc aaggcctcgg agggacagga tctgggcgca cctcaccggt    4500
tgccatggta acgcagcgcc ccagcccctc gcgctccgcg gtggagggag gcgcagccaa    4560
tcggaagcgg cggagttctc ggggaccccc ccccccccg ctccacgccg tgtgtgggcg    4620
ggggtcagga ggtgcggggc ggaggcggag cgtgggccgc ggagatccgg cgttcgcagg    4680
aggcttggtg cgcggcgggg ctgcacgggg ccacttccgg agtagtactg cgagcagcgg    4740
cgcgacagtg cggggtcccc tttctcccag aagagacgtc acccacacaa acctgacctt    4800
cacgtggggc gcgggacctt gcggggtccc agccgcaggc gccctgttg tttccttcgg    4860
gcgggtgggt tggagaagaa gtccacgcgg gattcttcaa aacggcgtac aggggattc    4920
tagggcccca tggttacttc tttgaccccc ccggaggcgc tgtccagcca cttccagtcg    4980
ccctgatgac tcgtcgtggg ttcctttagg agacccgaaa gttcagggcg ggctgtgtgg    5040
gtaacacctc tgcccaggtt cccggagggc cctacgtggc tgcccctgga gtatcccaga    5100
gcgctagggc tgcgggaagg ggcgggtgtg cttctggaaa catgagcgcc tgttagtatc    5160
agtgcctgga tagggctggg gacaaatcag tttatgccgc gcacaccgaa tccatgcgcc    5220
tgagtgaggg tgggtgtgtt ggggagtgcg tccaagtgga cagtgccgta cagtaatgtc    5280
tacggggagt tccaggagag ctcggctact cctgcgcagg ataacctctc ccccaccacc    5340
cgagtcccgt gctcgcgggc aggactttttc cgaactgggg ctgtgtgcct agaaatacgt    5400
acatgggagc gctcagctca aagccccagg gtttctggga ctcgcgtgtc cggggtcggg    5460
gtcccaggtg ggtacaggtg ggagggcgaa cctgcgggta gggtgggccc ctccccgcgg    5520
gctcagcatc tgtgcgcctc cagctcaggt gcgcgggagg aaggcagcgg cctgccgcgc    5580
agagccctgc gcgcccgcga ggtggcgcca tagccgcagc agcgcccgcc ggcccgggcc    5640
gctccagata agagtgtgcg gaaagcgcgg cggggctgag acgcgaccag gacgcgggga    5700
ggacggacca gcaggacaga ccgaccgggg gcccggcggg cggagggcag cgcagccacg    5760
tcccccctgg atccgccgtc agccgggccc ggggctttcg acatgccccc caggtgggtc    5820
ctcgagccgg ggaccgggag ggacggggga cccgggacag cccggtcctc gtgcgtcggc    5880
cgcctcgggt gcatcttctg gcgcgggtgc cccatcgcgg ctggcggctg gcgttcaggg    5940
ctccgggtgt cgtcccttc ggactcagga ccaccgggcc gcggctccgc gccgggttca    6000
cggcggggtc agcggcccgg ggccggctct gcccgcacat gggctggaga ggcgagggga    6060
agggaaggga aggggagctg gcgggcgggg ctggcagggg cgctgccctg gcacagctcg    6120
gggcctggca gcgcgggtg gggcatcggc taagagctgc caccgccgcg gggaggggag    6180
cccggcccgc cgggaccgca ggtaacgggc gcgggggccc cgcggggccag gagggggaacg    6240
```

```
gggtcgggcg ggcgagcagc gggcagggga gctcagggct cggctccggg ctctgccgcc    6300
ggatttgggg gccgcgagga agagctgcga gccgagggcc tggggccggc gcactcctcc    6360
cgccctgtct gcagttggaa aacttttccc caagtttggg gcggcggagt tccgggggag    6420
aaggggccgg gggagccgcg gagggaggcg ccgggcccgc gcgtgtaggg cccaggccga    6480
ggccgggacg cgggtggggc gcaggcccgg gtcagggccg cagccggctg tgcgccgtgc    6540
ccgcccgggg cgctgccccc tccctcccct gggagctgcg tggctccccc ctcccccca    6600 cctgcttcct gcctcagcct cctgcccgga tataacgccc tccccgcgcc gggcccggcc    6660
ttcgcgctct gcccgccacg gcagccgctg cctccgctcc ccgcgcggcc gccgcccggg    6720
ccccgaccga gggttgacag ccccccggcca gggcggcgcc agggcgggca ccgcgctccc    6780
ctcctccgta tcacttcccc caactggggc aacttctccc gaggcgggag gcgctggttc    6840
ctcggctccc tttctcccta cttgggtaaa gttctccgcc ctgaatgact tttcctgaag    6900
cggacatttt acttaaatcg ggtaactgtc tccaaagggg tcactgcgcc tgaacagttt    6960
tcttctcgga agccccagca cccagccagg tgccctgggg cgtgcaggcc gccctggcct    7020
cccctccacc ggcggccgct cacctcctgc tccttctcct ggtccgggcg ggccggcctg    7080
ggctcccact ccagagggca gccggtcctt cgccggtgcc caggccgcag ggctgatgcc    7140
cccgctcagc tgagggaagg ggaagtggag gggagaagtg ccgggctggg gccaggcggc    7200
cagggcgccg cacggctctc acccggccgg tgtgtgtccc cgcaggagag tgtgctgggc    7260
agacgatgct ggacacgatg gaggcgcccg gccactccag gcagctgctg ctgcagctca    7320
acaaccagcg caccaagggc ttcttgtgcg acgtgatcat cgtggtgcag aacgccctct    7380
tccgcgcgca caagaacgtg ctggcggcca gcagcgccta cctcaagtcc ctggtggtgc    7440
atgacaacct gctcaacctg gaccatgaca tggtgagccc ggccgtgttc cgcctggtgc    7500
tggacttcat ctacaccggc cgcctggctg acggcgcaga ggcggctgcg gccgcggccg    7560
tggcccgggg ggctgagccg agcctgggcg ccgtgctggc cgccgccagc tacctgcaga    7620
tccccgacct cgtggcgctg tgcaagaaac gcctcaagcg ccacggcaag tactgccacc    7680
tgcggggcgg cggcggcggc ggcggcggct acgcgcccta ggtcggccg ggccggggcc    7740 tgcgggccgc cacgccggtc atccaggcct gctaccgtc cccagtcggg cctccgccgc    7800
cgcctgccgc ggagccgccc tcgggcccag aggccgcgt caacacgcac tgcgccgagc    7860
tgtacgcgtc gggacccggc ccggccgccg cactctgtgc ctcggagcgc cgctgctccc    7920
ctctttgtgg cctggacctg tccaagaaga gccgccggg ctccgcggcg ccagagcggc    7980
cgctggctga gcgcgagctg cccccgcgcc cggacagccc tcccagcgcc ggccccgccg    8040
cctacaagga gccgcctctc gccctgccgt cgctgccgcc gctgcccttc cagaagctgg    8100
aggaggccgc accgccttcc gacccatttc gcggcggcag cggcagcccg ggacccgagc    8160 ccccccggccg ccccgacggg cctagtctcc tctatcgctg gatgaagcac gagccgggcc    8220
tgggtagcta tggcgacgag ctgggccggg agcgcggctc cccagcgag cgctgcgaag    8280 agcgtggtgg ggacgcggcc gtctcgcccg ggggccccc gctcggcctg gcgccgccgc    8340
cgcgctaccc tggcagcctg gacgggcccg gcgcgggcgg cgacgcgac gactacaaga    8400 gcagcagcga ggagaccggt agcagcgagg accccagccc gcctggcggc cacctcgagg    8460
gctacccatg cccgcacctg gcctatggcg agcccgagag cttcggtgac aacctgtacg    8520
tgtgcattcc gtgcggcaag ggcttcccca gctctgagca gctgaacgcg cacgtggagg    8580
ctcacgtgga ggaggaggaa gcgctgtacg gcagggccga ggcggccgaa gtggccgctg    8640
```

| | |
|---|---:|
| gggccgccgg cctagggccc ccttttggag gcggcggga caaggtcgcc ggggctccgg | 8700 |
| gtggcctggg agagctgctg cggccctacc gctgcgcgtc gtgcgacaag agctacaagg | 8760 |
| acccggccac gctgcggcag cacgagaaga cgcactggct gacccggccc tacccatgca | 8820 |
| ccatctgcgg gaagaagttc acgcagcgtg ggaccatgac gcgccacatg cgcagccacc | 8880 |
| tgggcctcaa gcccttcgcg tgcgacgcgt gcggcatgcg gttcacgcgc cagtaccgcc | 8940 |
| tcacggagca catgcgcatc cactcgggcg agaagcccta cgagtgccag gtgtgcggcg | 9000 |
| gcaagttcgc acagcaacgc aacctcatca gccacatgaa gatgcacgcc gtgggggggcg | 9060 |
| cggccggcgc ggccggggcg ctggcgggct ggggggggct ccccggcgtc ccggccccg | 9120 |
| acggcaaggg caagctcgac ttccccgagg gcgtctttgc tgtggctcgc ctcacggccg | 9180 |
| agcagctgag cctgaagcag caggacaagg cggccgcggc cgagctgctg gcgcagacca | 9240 |
| cgcacttcct gcacgacccc aaggtggcgc tggagagcct ctacccgctg gccaagttca | 9300 |
| cggccgagct gggcctcagc cccgacaagg cggccgaggt gctgagccag ggcgctcacc | 9360 |
| tggcggccgg gcccgacggc cggaccatcg accgtttctc tcccacctag agcgcccctc | 9420 |
| gccagcccgc tctgtcgctg ctgcgcggcc ctggcccgca ccccagggag cggcgggggc | 9480 |
| ggcgcgcagg gcccactgtg cccgggacaa ccgcagcgtc gccacagtgg cggctccacc | 9540 |
| tctcggcggc ctcacctggc ctcactgctt cgtgccttag ctcggggtc ggggagaac | 9600 |
| cccgggacgg gggtgggatg gggtaaggga aatttatatt tttgatatca gctttgacca | 9660 |
| aaggagaccc caggcccctc ccgcctcttc ctgtggttcg tcggcccct ccccggctc | 9720 |
| cgcgctgctc ttagagggg aggggtgtca ctgtcggggc actcctagcc ctacctccgg | 9780 |
| cccttgcgac cacacccatt ctcactgtg | 9809 |

<210> SEQ ID NO 167
<211> LENGTH: 1963
<212> TYPE: DNA
<213> ORGANISM: Homo sapiens

<400> SEQUENCE: 167

| | |
|---|---:|
| cgagctgctc ttaaccacgt ttattgagag gggccggggg aaggggatgg acggtcctcc | 60 |
| ccgcggcggg gttttcagcc ctcgcgggtg ggcagcgtct tgtcctcagg tgtagatgct | 120 |
| ccagtctcgg ctcagccaaa cactgtcagg gcccctgga aagcagaagc cgagcttgag | 180 |
| tgcccccagc cctgccacca agaactcagg cggggggcgcg gcagcggccg gctctgtggg | 240 |
| gagcgggagc ggggcggttc cgctggcgtc tccggggac gcgcaccgc gcggggccat | 300 |
| ctccgccttc cccgcccctg cagctcggat gcgccccacc cagttcccac ccggagaccc | 360 |
| gggcttctcc cagggacagg gcttggaggg gcaggacggg aaacagccct gacgtagggc | 420 |
| cgggacacct ctggtgcagt tttgaggctg gccgggaagg gatgcccgcg caggaagggc | 480 |
| acccggggtg cccactttac cagcagggcc ttcaggcct tcacggcccc cacggcctgg | 540 |
| ggacccagct cagccacaca cttctgggag ccctctatga ggtggttcac ggggatgccc | 600 |
| aggctgctca gcaggagctt cagcggggttg agggtgccga ggggttggc cagggtcccg | 660 |
| gccccggcct ccgccgccga ctccagcgca gcgacaggc gggccacagg cttggccgag | 720 |
| cccactaaga aagcagcagc tgcaagcgaa cagggagggg tcaccgcctg cgcgccgggg | 780 |
| tccccagaag gcaggtccag gacgcgcccc gcgggagcc gccaggaac cgtcgcgccc | 840 |
| tgcccggctc cccgaccgcc cctccctcct gcgccgaggc ctgccaggtg cgagccccg | 900 |

```
ggacacaggc gggtctgggg aggcggcccc gccaggagac gctgcagggt caccggagtg    960
gcctgagggt ggcggaagga ccggtgaact ctgtgcaggg tccggacag gcccccaagg    1020 gaggggacac tcgcgctgcg ccttgcagga tgaggagccg gtctccagac ggggggcaga   1080
cgggtgtccc caggccaggg gcggcctcca tcccggcacg aggctggaga cagccctgag   1140
agggggaggc cgcgggctgc aggcgcgggg ccccggggtg gcggagccct ctgggcgccg   1200
ggcgaggctg gaaggacctg ggatccacga tcggcgcagg cagcggcggg ggcgcagcgg   1260
gcgccgaggc ctcaggcccc accgtgcgcg ccaggagccc ggggcgctca ccggagctgc   1320
aggacagggc cacgcagagc cccaggaggg cggcgagctt catggcgcgg gggctcgggg   1380
cgcgcgggga acctgcggct gcccgggcaa ggccacgagg cttcttatac ccggtcctcg   1440
cccctccagc gccggcctcg cccgcgctcc tgagaaagcc ctgcccgctc cgctcacggc   1500
cgtgccctgg ccaacttcct gctgcggccg gcgggccctg ggaagcccgt gccccttcc    1560 ctgcccgggc ctcgaggact tcctcttggc aggcgctggg gccctctgag agcaggcagg   1620
cccggccttt gtctccgcga ggcccacccc ggcccgcacc ttcgctttgc ggtctgaccc   1680
cacgcgcccc cctgcagggc tgggcccggg tgagggagc ttccctcgcg ccagggcagg    1740 ggcggggcg gcgcagttcc tggctccctg gtccctgcct ctgatcccag accgtggcaa    1800
cgtcgggcac tgggggtcct cgtgggcgcc ttctgcgcct ggggaggtgg aggcgccagg   1860
gacgatcagg cctcactccc ggccgcctcc ccggccgggc cacaggcagc cacagtgcaa   1920
acagaagtgg ggcgtttttc tgtcttcgaa actagcctcg acg                     1963

<210> SEQ ID NO 168
<211> LENGTH: 1900
<212> TYPE: DNA
<213> ORGANISM: Homo sapiens

<400> SEQUENCE: 168
aatgagattt actcaaaatt ggaaacttgg tgtttggttt ttcaggagaa caatcaacga     60
ctgtgatttg aagttcacca gggtattctg agagatctaa tcaaagatag agtgctggtt    120
tgaaattatt aaaaggtaac agtaaaaggg agagcaaaac cccagtccca acgcaaccca    180
taaatctact ttgtcttcct cgaaagaggg gcgcgggtgg gcgcgtctcc ccgcgagcat    240
ctcacctaag ggggaatccc tttcagcgca cggcgaagtt cccccctcggc tgtcccacct   300 ggcagtccct ctaggatttc ggccagtccc taattggctc cagcaatgtc cagccggagc    360
ttctttgggc ctccgagtgg gagaaaagtg agagcaggtg cttccccagc ggcgcgctcc    420
gctagggccc ggcaggatcc cgcccccaag tcggggaaag ttggtcggcg ccttttctcc    480
ccgacgaagc cgctccaggg ctgctctcag aggacgcgcg gcaggcaaag agaatgaacc    540
tgagcgtcca cgaaacgtcc tgcacggctc ccgggagctg ggagaaacag gtgcctttct    600
ccgacgtccg cgggcgacgc ctgccgcacc ttgcccgctg ccgcgcccct ccgggcacc    660 cctcgccctc ggcgccctg cccccgcccc cagtgccagg gcggaggcag tcccggctcg    720
caggtaatta ttgccagcgg agccgccgg ggagcggggg tgggcgcgcc ggcggtgggc     780
gggcgggcgc ggcggggcgc gggcataaag gggcgcggcg cggggcccg gagcctggct    840 cccgcgcagc atgcccgcca gcgccccgcc gcgccgcgcc cggccgccgc cgccgtcgct    900
gtcgctgctg ctggtgctgc tgggcctggg cggccgccgc ctgcgtgcgg agccgggcga    960
cggcgcgcag acctgggccc gtttctcgcg gcctcctgcc cccgaggccg cgggcctctt   1020
ccagggcacc ttccccgacg gcttcctctg ggccgtgggc agcgccgcct accagaccga   1080
```

```
gggcggctgg cagcagcacg gcaagggtgc gtccatctgg gatacgttca cccaccaccc      1140
cctggcaccc ccgggagact cccggaacgc cagtctgccg ttgggcgccc cgtcgccgct      1200
gcagcccgcc accggggacg tagccagcga cagctacaac aacgtcttcc gcgacacgga      1260
ggcgctgcgc gagctcgggg tcactcacta ccgcttctcc atctcgtggg cgcgagtgct      1320
ccccaatggc agcgcgggcg tccccaaccg cgaggggctg cgctactacc ggcgcctgct      1380
ggagcggctg cgggagctgg gcgtgcagcc cgtggtcacc ctgtaccact gggacctgcc      1440
ccagcgcctg caggacgcct acggcggctg ggccaaccgc gccctggccg accacttcag      1500
ggattacgcg gagctctgct ccgccactt cggcggtcag gtcaagtact ggatcaccat       1560
cgacaacccc tacgtggtgg cctggcacgg ctacgccacc gggcgcctgg ccccggcat       1620 ccggggcagc ccgcggctcg ggtacctggt ggcgcacaac ctcctcctgg tgagtgcgag      1680
gggccaggcg gagggccacg caggggagac agagggcctc cacaggggcc aggggaagt      1740 gtgggaactg agtctccccc agacgaggct tcacttggac acgtgtatgt ggtcaccggg     1800
ggaaactgag cagttctgac ttcccttgga aggcgtggaa ttaggagaga aatcccttag     1860
tgggcacacg agtgagtgcc ccttggagtc catctgtgga                           1900
```

<210> SEQ ID NO 169
<211> LENGTH: 1788
<212> TYPE: DNA
<213> ORGANISM: Homo sapiens

<400> SEQUENCE: 169

```
actggagact tgcatttcac aaacgggttt gctccaggcc gcactccatc cccgagggaa       60
agctccccag aagttctgga gttgggctga aggatgtgat ggcaagatgt gaatgatgtc      120
agaatcccca tctccagagt ccggctgggg agctaagcgc aggtgagctt acatcagaag      180
agaaagccaa accccccaca cgtcgctaaa ctagggcacg ggaatggcgt gttatgcaac      240
ggccgccgtt cgcgtggcca cgaaagcgct cctgcgcctc gggccgcgtc ccgccaagac      300
cgtgagcaaa ctcgcagagt tggcgcggca gccggccggg agacgccgag cagggcctgg      360
ccgcccgcag cccgggagga acggcgcccc cagggtccgg tggcctctga ggggctgact      420
ggcccgtgag ccggcggcgc ggccgcgggg aacggggtgg gaaccgcgcg gcagtgggtg      480
aggcggcgca gccaccgggg gctgaggggc ggcgcggcct cgactgcggc accgcgtgg      540 gtccgtcggc tcgcgggacg acggggcggc cggcggggc caacagggcg ggctctgaag      600
gactgattgg cccgtgggac gatgcgcgcg ccggaggat ggccccggat ccgtgggacc      660
gctgcgccgc cggaccgggg gtcccgaggc tgtcagggc gcccggccgg gcgtctagtg      720
aaaagccgat cccccggaga cagcggaagc agaggcgcgc ccggcgctac ggcctttcgg      780
gtctaggaca ccgcccccgg cccgcgccgc ccctgccccg ccgggatccc ggccgccccg      840
gtcgccgcac aacaaagcgg cgcagccccg ctgcccccgc ccgacgccgg cctccaactt      900
ccccggctcc tctggaaccg gctccgcggg ctccgtacgg cctggactac gagccgccgg      960
gcgggggcgg ctccgggcgg gcgcggaccg tgggggcagg gcgcagggct ccgtccggac     1020
aaacttcctc ggccgccccg ccgggcgccc ttccgagc ctcggcacca cagtaggtgc       1080
gcggagccgc agggctcgac cgcttcgcgg aaactctcgc caccctccga gctgccgccc     1140
cgaccccagc tccagccccc ctcacctcca ggggcgcggt ctaccctc ggggcgtcc        1200 tggccggcgg ctcccggggcc tctcgcgccg ggagaccggg cactggtggc tggagctgct    1260
```

-continued

```
gctggccccg cagggacggg ggagccccgg gcggcggcgg tggcgtggac ggcgactgct    1320
ccatcttccc ggggcgctca cgccgcggtt ccaaagcgca gacccaagtg ggacattcgc    1380
tacattgttg gcattccacg ggcgtcacgt gaccccgcct ccgcgtcac tctcggccgc     1440 ataccagtcc gggcggggcg cctgcggccc ctgctcctcc gcggccgctc cgcccagccc    1500
cgcccggccg tgcttcctgc ctccggcctc gaccgccacc tgcccacggc ctccctgctg    1560
gcctgcggta gctcgccagg gcctctcgga cctatttgac tggctgctat ctgccccaa    1620 acttgagtat ttgccctctc gactgcattt gtattaaaag ttggtaactg tcgttaaagc    1680
cactattctt aagtatctca taccagtctt ggtgaaagaa aaaaaaagt tagcaggcct     1740 gaaggagcca ccaagttacc aactagtggc tggacactaa aaataggg              1788
```

<210> SEQ ID NO 170
<211> LENGTH: 1528
<212> TYPE: DNA
<213> ORGANISM: Homo sapiens

<400> SEQUENCE: 170

```
gtccaaggca agagaatagg ctttaaagtc cctggctcgg ttaaaaagct ggttgcgtag      60
attcctgtca atgctcagga tcctctgcct tgtgatatct ggagataagt caacgccttg     120
caggacgctt acatgctcgg gcagtacctc tctcagcaac acctccatgc actggtatac     180 aaagtcccccc tcaccccagc cgcgacccct caaggccaag aggcggcaga gcccgaggcc     240
tgcacgagca gctctctctt caggagtgaa ggaggccacg ggcaagtcgc cctgacgcag     300
acgctccacc agggccgcgc gctcgccgtc cgccacatac cgctcgtagt attcgtgctc     360
agcctcgtag tggcgcctga cgtcgcgttc gcgggtagct acgatgaggc ggcgacagac     420
caggcacagg gccccatcgc cctccggagg ctccaccacc aaataacgct gggtccactc     480
gggccggaaa actagagcct cgtcgacttc catcttgctt cttttgggcg tcatccacat     540
tctgcgggag gccacaagag cagggccaac gttagaaagg ccgcaagggg agaggaggag    600
cctgagaagc gccaagcacc tcctccgctc tgcgccagat cacctcagca gaggcacaca    660
agcccggttc cggcatctct gctcctattg gctggatatt tcgtattccc cgagctccta    720
aaaacgaacc aataggaaga gcggacagcg atctctaacg cgcaagcgca tatccttcta    780
ggtagcgggc agtagccgct tcagggaggg acgaagagac ccagcaaccc acagagttga    840
gaaatttgac tggcattcaa gctgtccaat caatagctgc cgctgaaggg tggggctgga    900
tggcgtaagc tacagctgaa ggaagaacgt gagcacgagg cactgaggtg attggctgaa    960
ggcacttccg ttgagcatct agacgtttcc ttggctcttc tggcgccaaa atgtcgttcg   1020
tggcaggggt tattcggcgg ctggacgaga cagtggtgaa ccgcatcgcg gcggggaag   1080 ttatccagcg gccagctaat gctatcaaag agatgattga gaactggtac ggagggagtc   1140
gagccgggct cacttaaggg ctacgactta acgggccgcg tcactcaatg gcgcggacac   1200
gcctctttgc ccgggcagag gcatgtacag cgcatgccca caacggcgga ggccgccggg   1260
ttccctgacg tgccagtcag gccttctcct tttccgcaga ccgtgtgttt ctttaccgct   1320
ctcccccgag accttttaag ggttgtttgg agtgtaagtg gaggaatata cgtagtgttg   1380
tcttaatggt accgttaact aagtaaggaa gccacttaat ttaaaattat gtatgcagaa   1440
catgcgaagt taaagatgt ataaaagctt aagatgggga gaaaaacctt ttttcagagg   1500
gtactgtgtt actgttttct tgcttttc                                      1528
```

<210> SEQ ID NO 171
<211> LENGTH: 2802
<212> TYPE: DNA
<213> ORGANISM: Homo sapiens

<400> SEQUENCE: 171

| | | | | | |
|---|---|---|---|---|---|
| agctgggcca | gggccgggac | aaaggtttcc | cagggagggc | caactcttcc | gtgtctctgg | 60 |
| cgggttttcc | ttgttaaagg | ctcacaggtt | ggagcctgtt | cgcggctctt | ggcctggtag | 120 |
| ggattttatt | agctctgctc | tggcaactgc | aagccaggaa | cacaatgtcc | tgtgcagggg | 180 |
| attgcccatg | cagcccagct | cgtgagatcg | cgggatggcg | gggcagtgag | ccggtgccgc | 240 |
| tctgggagcc | tgagccaggg | cggcagtcct | gtcggcctcg | gagagggaac | tgtaatctcg | 300 |
| caaccaggcc | gccgcgaggc | cttctgcctt | tgcaaagctg | cgccccaccg | gcgccctccc | 360 |
| aggcggcgct | gccttccaca | ttctctcctg | gtctacttgg | cctgtacctc | cacaacatcc | 420 |
| tcccccatc | cctcccagac | tccgtgctgg | ctcctacccg | gactcgggct | tccgtaaggt | 480 |
| tggtccacac | agcgatttct | tcgcgtgtgg | acatgtccgg | gtagcggttc | ctctggaaag | 540 |
| tggcctccag | ctcctggagc | tgctggctgg | taaagtgagt | ccgctgccgc | ctttgccgct | 600 |
| tcttcttaga | cgggtcctcg | gcgcccacgt | cctcattctt | ccctgctgg | cttttatctt | 660 |
| tctctgaaaa | cgaaacacac | acactttccc | gtcagcatgc | ccacctgcaa | cgcggacgcc | 720 |
| aactggaccg | gcggcagaag | ccgtggaaga | gctgggctgc | ctggcgccgg | aggagggtgc | 780 |
| gcgcggcggc | tccgggccgc | gaggagcgct | gcgcctgtgg | ggtgtgcagg | cgcaagtgtg | 840 |
| ggtgtccgcg | ccccatttcc | tcccctcccc | cagcgccgca | cgttttattt | acatgtttat | 900 |
| ctcactgcag | cggcacattc | acttttatag | cctgtgcttt | caagtatatt | tatacacctc | 960 |
| tgcgcagaca | caccaaatct | cctgggacgc | gcacacgcgc | gtggtttaca | gacccccctc | 1020 |
| cccctcgcag | aaagctcaga | tttccatgcg | gtttgggaag | gctaggaaaa | gatgtgggga | 1080 |
| ttcggttggg | caccgaagtt | cgccggccct | ttcccaaaaa | aaaaaaaaaa | atgcctcttc | 1140 |
| gcgaagggca | tttctgagtg | gtttcaggca | atttcctaac | gagtggagct | cctcgggagc | 1200 |
| tgaaagccga | gaggaaaaca | gggacagagg | tcggcggcct | ctgaaggtcc | tcgaatcaag | 1260 |
| atgctgggat | ttttgtgacc | caggaaacag | aagggaggcc | agggtacgaa | tagagagggc | 1320 |
| ggcagaattg | ctcgcgccct | tagcgcccca | ggagccgggc | cggtcgaggg | agaactaaag | 1380 |
| ggatgcgggg | tagtcaaaat | tccggctccc | ggaagttctg | cggggagcca | ggcgaacgac | 1440 |
| cactcccacc | acgcctcccc | ccggagggc | tgacttcctt | ggggcgagag | ggagcgggtg | 1500 |
| gcgcagagca | gctgagcggg | aatgtctgca | gggcggcgcg | gcgccttacc | tgcggcctcc | 1560 |
| gggctggagg | tgtcggagat | ggtgtgcacc | tccagcctgt | gcttggagga | gtccagcgac | 1620 |
| cggggctgac | cgggagccag | aaccgaagcc | atggctaacg | gctggggatg | gtgacaggaa | 1680 |
| gatgaggaga | cggccgacag | cttggtcccc | gctgctcggt | gctccaagtg | aagcgggcct | 1740 |
| ttcatgcagt | tcatggacga | gggagcgcga | cgctctacta | gtccttggct | actgccccgc | 1800 |
| cgagcccccg | tagccgccgc | tgcccgctcc | gggtcgcgct | ctaggcgcgg | agtttccccg | 1860 |
| ctgcggggag | agccagggga | cgcaacccc | gccgagttct | caagccaagc | tgccccgtc | 1920 |
| tcctccggaa | ggctcaagcg | aaaaagtccg | gagacggaaa | gtcagcgggc | aaacgaagac | 1980 |
| atgggatgtg | ggcagaaggg | caccactcag | agcgtcttta | gggagcaggc | ttccaagctc | 2040 |
| caaagcgaaa | caagagtggg | caagaccccc | ttcttctct | ccctccctcc | cccaagaacc | 2100 |
| cctccaataa | ggaaagctaa | cgccgaccgc | gctctgcccg | ccccccccccc | acgcggcagc | 2160 |

```
cctgacagag aagtgtcaag agtgacaggg acaggtaggt gatattagat cccctgcggc   2220
ggcagcagcc gctgcagcca cgacgcggcc ctctgagcgc accctccgca acgcgcacac   2280
gcacacccct cgggcggtcg aacaggagcc gggccttgcc gcagctcagc tccaggcacc   2340
caggcgagcg acggaccaga tctgcggctc cgcgcttccc tgttggccta acatcttaaa   2400
accagaggcg ggcttcctgg tgccgagacg tcactccgcc gcggccctcc ccagccctct   2460
ccgcctccgc ctcctcccag acccttctcc gggtgcgact gacgtggctc cgcaccaatc   2520
aggacgcccc gagccgcggt ggagggactg tcctgcctgc acctatcagc agtgcgggc    2580
cgggctactg cctcgccgtg cgcactgggt ctacacaggc aagctcccgg gaattcagct   2640
cctgcccagc ccaaggcgat ccggctttta gtacgaaccc aaaggtgaag agatgaggct   2700
aggagtcgaa ggcttgggag aagagagtgg aatggtcaag aagagaaagg tacaaggatc   2760
aacaagacac ccactctttg tgtctcacta catccatttc ca                     2802
```

<210> SEQ ID NO 172
<211> LENGTH: 3752
<212> TYPE: DNA
<213> ORGANISM: Homo sapiens

<400> SEQUENCE: 172

```
aagaaaacgc cggcttgtgc gctcgctgcc tgcctctctg gctgtctgct tttgcagggc     60
tgctgggagt ttttaagctc tgtgagaatc ctgggagttg gtgatgtcag actagttggg    120
tcatttgaag gttagcagcc cgggtagggt tcaccgaaag ttcactcgca tatattaggc    180
aattcaatct ttcattctgt gtgacagaag tagtaggaag tgagctgttc agaggcagga    240
gggtctattc tttgccaaag ggggaccag aattccccca tgcgagctgt ttgaggactg    300
ggatgccgag aacgcgagcg atccgagcag ggtttgtctg gcaccgtcg gggtaggatc    360
cggaacgcat tcggaaggct ttttgcaagc atttacttgg aaggagaact tgggatcttt   420
ctgggaaccc cccgccccgg ctggattggc cgagcaagcc tggaaaatgg taaatgatca   480
tttggatcaa ttacaggctt ttagctggct tgtctgtcat aattcatgat tcggggctgg   540
gaaaaagacc aacagcctac gtgccaaaaa aggggcagag tttgatggag ttgggtggac   600
ttttctatgc catttgcctc cacacctaga ggataagcac ttttgcagac attcagtgca   660
agggagatca tgtttgactg tatggatgtt ctgtcagtga gtcctgggca atcctggat   720
ttctacactg cgagtccgtc ttcctgcatg ctccaggaga aagctctcaa agcatgcttc   780
agtggattga cccaaaccga atggcagcat cggcacactg ctcaatgtag gtttattttt   840
ttcccttctt ctaccaagaa aaaaaaaatt gtctctcttg catgcaataa agacgttgga   900
aataaactgc attggtagca agacaaagga tttaatgatt taatgctgaa ggggtgtgat   960
atgctggcat gcatattgat tcccttttgct gaaaatttcc tgttagatgt ttcttccca   1020
aataactaga ggataagcac ttttgcagac attcagtgca agggagatca tgtttgactg   1080
tatggatgtt ctgtcagtga gtcctgggca atcctggat ttctacactg cgagtccgtc  1140
ttcctgcatg ctccaggaga aagctctcaa agcatgcttc agtggattga cccaaaccga   1200
atggcagcat cggcacactg ctcaatgtag gtttattttt ttcccttctt ctaccaagaa   1260
aaaaaaaatt gtctctcttg catgcaataa agacgttgga aataaactgc attggtagca   1320
agacaaagga tttaatgatt taatgctgaa ggggtgtgat atgctggcat gcatattgat   1380
tcccttttgct gaaaatttcc tgttagatgt ttcttccca aataaccct cccgccccca    1440
tgctcctctc cttaccaacc ttatagtctc ttgaaaacag tttttaaaat atgcataaaa   1500
```

```
atgtgggggg tggggagtag agggtgacca caagacttta aaacattctt caagtagggc    1560
aatttgacac attttgcagt ttttactaaa atgtatgcag agtggaattt aactttgctg    1620
ttctttggat tagctactag ttgtataggt cccccacec cttgtgtatt ccaacagtcc     1680
aaagtaatta aaatatgaca ttttccttga aaggaattta gtttaattaa ggtggctgct    1740
gctcccgaag ttcataaacc accagttcaa gctgccgctt ccaatgtttt ccttgctaag    1800
gaaaggcaat atttcttagc attgaccctg ctgccacctt tccaagtcac tttgttggtc    1860
taagaagttg ctgtttaaga aaacgccggc ttgtgcgctc gctgcctgcc tctctggctg    1920
tctgcttttg cagggctgct gggagttttt aagctctgtg agaatcctgg gagttggtga    1980
tgtcagacta gttgggtcat ttgaaggtta gcagcccggg tagggttcac cgaaagttca    2040
ctcgcatata ttaggcaatt caatctttca ttctgtgtga cagaagtagt aggaagtgag    2100
ctgttcagag gcaggagggt ctattctttg ccaaaggggg gaccagaatt cccccatgcg    2160
agctgtttga ggactgggat gccgagaacg cgagcgatcc gagcagggtt tgtctgggca    2220 ccgtcgggt aggatccgga acgcattcgg aaggcttttt gcaagcattt acttggaagg     2280
agaacttggg atctttctgg gaaccccccg ccccggctgg attggccgag caagcctgga    2340
aaatggtaaa tgatcatttg gatcaattac aggctttag ctggcttgtc tgtcataatt     2400
catgattcgg ggctgggaaa aagaccaaca gcctacgtgc caaaaaaggg gcagagtttg    2460
atggagttgg gtggacttt ctatgccatt tgcctccaca cctagaggat aagcacttt      2520 gcagacattc agtgcaaggg agatcatgtt tgactgtatg gatgttctgt cagtgagtcc    2580
tgggcaaatc ctggatttct acactgcgag tccgtcttcc tgcatgctcc aggagaaagc    2640
tctcaaagca tgcttcagtg gattgaccca aaccgaatgg cagcatcggc acactgctca    2700
atgtaggttt attttttcc cttcttctac caagaaaaaa aaaattgtct ctcttgcatg     2760
caataaagac gttggaaata aactgcattg gtagcaagac aaaggattta atgatttaat    2820
gctgaagggg tgtgatatgc tggcatgcat attgattccc tttgctgaaa atttcctgtt    2880
agatgttttc ttcccaaata actagaggat aagcactttt gcagacattc agtgcaaggg    2940
agatcatgtt tgactgtatg gatgttctgt cagtgagtcc tgggcaaatc ctggatttct    3000
acactgcgag tccgtcttcc tgcatgctcc aggagaaagc tctcaaagca tgcttcagtg    3060
gattgaccca aaccgaatgg cagcatcggc acactgctca atgtaggttt attttttcc    3120 cttcttctac caagaaaaaa aaaattgtct ctcttgcatg caataaagac gttggaaata    3180
aactgcattg gtagcaagac aaaggattta atgatttaat gctgaagggg tgtgatatgc    3240
tggcatgcat attgattccc tttgctgaaa atttcctgtt agatgttttc ttcccaaata    3300 accctcccg cccccatgct cctctcctta ccaaccttat agtctcttga aaacagtttt     3360
taaaatatgc ataaaaatgt gggggtggg gagtagaggg tgaccacaag actttaaaac     3420
attcttcaag tagggcaatt tgacacattt tgcagttttt actaaaatgt atgcagagtg    3480
gaatttaact ttgctgttct ttggattagc tactagttgt ataggtcccc ccaccccttg    3540
tgtattccaa cagtccaaag taattaaaat atgacatttt ccttgaaagg aatttagttt    3600
aattaaggtg gctgctgctc ccgaagttca taaaccacca gttcagctg ccgcttccaa     3660 tgttttcctt gctaaggaaa ggcaatattt cttagcattg accctgctgc cacctttcca    3720
agtcactttg ttggtctaag aagttgctgt tt                                  3752
```

<210> SEQ ID NO 173

```
<211> LENGTH: 1137
<212> TYPE: DNA
<213> ORGANISM: Homo sapiens

<400> SEQUENCE: 173
gtggtaattt ccctcaccc taaaggttct ggaggggggtc atgagtgttt gagaagaggc      60
aagcctggga agatggactc cgaggacagt aggcacaaac cctttctcaa gaagggccaa    120
ggcattttaa agataagaaa cttaaaatca gcgtatttt acatataagc agccacctct     180
gctcatctgt ggcccagata cgagtggagt gcgacaaggg ataaaccatt ttcgcgcact    240
cttcagcgat ggggcgaaag taacggacct agtcctcggg agctgtcccc gccgaccccc    300
tctgccgcga cttgacccgc ggcgactgcg ctgccccttg gctgcccctt ccgctctcgt    360
aggcgcgcgg ggccactact cacgcgcgca ctgcaggcct ttgcgcacga cgccccagat    420
gaagtcgcca cagaggtcgc accacgtgtg cgtggcgggc cccgcgggct ggaagcggtg    480
gccacggcca ggaccagct gccgtgtggg gttgcacgcg gtgccccgcg cgatgcgcag    540
cgcgttggca cgctccagcc gggtgcggcc cttcccagcg cgcccagcgg gtgccagctc    600
ccgcagctca atgagctcag gctcccccga catggcccgg ttgggcccgt gcttcgctgg    660 cttttgggcgc tagcaagcgc gggccgggcg gggccacagg gcgggccccg acttcagcgc    720
ctcccccagg atccagactg ggcggcggga aggagctgag gagagccgcg caatggaaac    780
ctgggtgcag ggactgtggg gcccgaaggc ggggctgggc gcgctctcgc agagcccccc    840
ccgccttgcc cttccttccc tccttcgtcc cctcctcaca ccccaccccg gacggccaca    900
acgacgcgca ccgcaaagca ccacgcggag atacccgtgt ttctggaggc cagctttact    960
gtgctagagg aagaggggtcc ccacatccgg ccctggccct cctggtccgg tttgctgaag   1020
caacacactt ggcctaccca ctgggtgggg caggaagtct cgagccttca cttggggtga   1080
ggaggaggga gatcggtcag cagctttacc gcccgctctg ctctccactg cggagac      1137

<210> SEQ ID NO 174
<211> LENGTH: 1121
<212> TYPE: DNA
<213> ORGANISM: Homo sapiens

<400> SEQUENCE: 174
ccaagccgtg cctgccctgc cctgccctgc cctggttgcg ggagcacaga tgcaggctgt      60
gcaggagtgc ggtggggccg ggctgggtgt ggaggcctca cctggcttgg ctgccgactg    120
aggaggggcc tggatcccag ctggcgcggc tccagagcct ggaaggatat gggccaagtg    180 atcccttcc ctccccttcc cgccgtgggg ccggggtccc gttggtcggt aggccaagcg     240
tggggagcct cctttccggt agagcagctt tgtttagggg taggaggaac agaaagcgga    300
agagcccgcg gggtaagcgc tggtgtgggt ggaggggaaa gacggggtgg aggggaacgg    360
gggcggctca ccctggtgcg tggccgcctg cagctgcccg ccatctcctg caggcccat     420 gtcgcgcagc acgttagcgg tgagctcggc gccgtaggtc tccaggtaga agctgaccag    480
cttgtcggtg aggtccaagg cgtccatgga cagcagcgcg cccgcgggga tgcgcccgta    540
gccctcgcgc agcggcaccg acagcagctt cagcttgaac ttcttgagct cctcggcggt    600
caggttctcc agcgcatcca ggatggcgtc gcgcgcgcgc ccatggctc caggatcccc     660 ggccgctgcc gccgctcacc ccgctgcagc cgccgaccag gaggaagtcg gctccggggc    720
ggaacctgga ctccccgcct tcctcccact ctggtctccc gactcccgc cccggtccgt    780 tgccctccag caaaaggcgc ttccttacta cacccttggt ccctcccac ccaggcctct     840
```

| | | | |
|---|---|---|---|
| ggattggggc | cccaggccgt | cggggggacgc | caggatcgcg | ccctccagct | ggcctgcgag | 900 |
| gtgggacccg | ggaggggcc | gcagagggc | tcatgggtgg | cgcctgcttg | tctctgggct | 960 |
| tgcaccagcg | ggtacagacc | ggaaacctgg | gctggctctc | actgggttta | ttggagcacc | 1020 |
| taggcttaga | acctcggatt | tctagaaccc | cgaaacctcc | gcggttcccc | gaaccttagg | 1080 |
| atcctctccc | acatgtcgta | gaatcttgga | atcatgacag | c | | 1121 |

<210> SEQ ID NO 175
<211> LENGTH: 2343
<212> TYPE: DNA
<213> ORGANISM: Homo sapiens

<400> SEQUENCE: 175

| | | | | | | |
|---|---|---|---|---|---|---|
| tgagaaatta | agctgaacaa | cctggaagga | tttcagccca | agggcaagag | gaagtgggtg | 60 |
| ggtggaaagg | aggaggaggt | ggaatttgtt | ttaaaacatt | tgttttaagg | agaacaaaaa | 120 |
| ttgaaagccg | aaagaaaggg | tggcgctgac | aaaacggtcc | ttacccgtga | ccctgggtgt | 180 |
| ctctgtctcc | cctcctgtca | cgcacactca | cgcgcacaca | cacccctcac | cagggcgcat | 240 |
| ccccctggag | actgctctcc | ctagcggggt | cagaccggcc | ttccggggac | gctggggggcg | 300 |
| cgaggcaacg | gtgccaagtg | aggtgggaag | gctgagcgga | gagtgggaga | ggggaggaaa | 360 |
| tcgaggtgga | ctgggaaccg | cggcctggcc | ggcctgccgt | ctgccacctg | agaggcgaag | 420 |
| gggtgcagcg | gcgcggtcct | tacctaggtc | tccggccctg | ctgaggggggt | ggggggctcc | 480 |
| gcctgctagt | gggacgcgga | catggaccag | gccccctcca | tcctccagac | cgagaaggcg | 540 |
| tagctgagcc | gctcgtgagc | cacatagctg | cagcttgcca | tcttggagtc | cagctcgtcg | 600 |
| ctctggagga | cctggtagag | gaagtcgatg | tacctggccg | ccagcttgag | ggtctgaatc | 660 |
| ttgctcagct | tgtccgaggg | cagcgtgggg | atgatcttcc | gcagcgcggc | gaacgcctcg | 720 |
| ttcagcgact | gggtgcgctg | gcgctcccgc | acgttggcca | tgacccgctg | cgtctgcagc | 780 |
| tcctcgtaag | actgcggact | cccgccgccg | ctgctgctgc | cgccgccgcc | gcccgcgccg | 840 |
| ccgccgccgc | cacagcccgc | agacttcttg | ccgcgcttgc | cctgggccgg | gctgcccggc | 900 |
| tcgtcgccgc | ctccgacgcc | cccacccgcg | gctccgccgg | gccccgcgcc | gccgcccgcg | 960 |
| ctgcgcctgc | tgctgcgccg | cttgcgtccc | ccgcgcttgc | cgctcggcgg | ctgctgccgg | 1020 |
| tctggctctt | cctcgctgtt | gctcaggctg | tcgtcggccg | gcgagactgg | cgagctggac | 1080 |
| acgtcctgca | tcatctctcg | agcggcgacg | cgtggcctcg | cgggcccggg | gcagaggaga | 1140 |
| agagcggggc | gcctcagccc | gccagcttcc | ccgcgcgcg | gcgccggccc | gggcgatgcg | 1200 |
| gcccgcggag | gagagagcag | gaggacggac | gggagggacc | tccgcgggga | gggcgcgcgg | 1260 |
| gggaggcggg | gagggaggcg | ggaggggggag | gggacggtgt | ggatggcccc | gaggtccaaa | 1320 |
| aagaaagcgc | ccaacggctg | gacgcacacc | ccgccaggcc | tcctggaaac | ggtgccggtg | 1380 |
| ctgcagagcc | cgcgaggtgt | ctgggagttg | ggcgagagct | gcagacttgg | aggctcttat | 1440 |
| acctccgtgc | aggcggaaag | tttgggggca | gcagtgtcat | tggcctgacg | tgaggaggag | 1500 |
| ggacttttcg | aagtttata | ggaaagtttc | cgctttccag | tcccctccc | ccgtcccacc | 1560 |
| tcccttcctc | ggggtctaac | aattcgtcct | cccaaaccat | tcaaaaacga | cctgcccgg | 1620 |
| gcggccggcc | cctccacccg | cctcctagcc | gccctcccc | ttccctcccc | gtcgccttcc | 1680 |
| tccggcgggc | gcggggcgat | ttccttcccc | gccggagcgt | gcgggcagcg | ccccgaaccc | 1740 |
| ctagcgcagc | ccaggaagcg | gtcggaggag | actgtcctgg | ccgcggtggc | agccccatcc | 1800 |

| | |
|---|---|
| ggagtggctg tgacagcagc aatggcaaca gcttctacac agtgggtgat gtctcatctc | 1860 |
| gcccaagagc cctctaggtc cgtggggccg atttgggatt gctggggctg ggggggtggt | 1920 |
| gtggcgcggg gtggggggc atgccaagaa aagtgtcaac cgcggagccc acccaatggt | 1980 |
| caggtagacg aacccttgg agttccaaag gccaaaccgc ggcggccag cccggaggtc | 2040 |
| ctgggcgttt ctgaagacgt ggccgcgccg cgggggctga ggatttgcgt cccggcctgc | 2100 |
| tctctcgccc ttctgggccc tccttttcccc tctacaacga cccagtctga cgctccccaa | 2160 |
| catccaaagg actacgcctc ggaaggtgct cgaaagaggc agaagttcac tcttcggtgg | 2220 |
| aaggaaaccc agtccatggg aaaggcagca gagccagagg ggggcagcgc agcgcctttg | 2280 |
| ctgcggccct aacagctggc aatgccaacc aagggagag accctgtggc catttcatcc | 2340 |
| cca | 2343 |

<210> SEQ ID NO 176
<211> LENGTH: 1083
<212> TYPE: DNA
<213> ORGANISM: Homo sapiens

<400> SEQUENCE: 176

| | |
|---|---|
| ggcagtctta ggcaagttgg ggcccagcgg ggagaagttg cagaagaact gattagagga | 60 |
| ccccaggagg cttcagagct gggcgaggta gagagtctcc tgtgcgcctt ctctcctctc | 120 |
| tgcaattcgg ggactccttg cactgggggca ggccccccgc caggtgcatg ggaggaagca | 180 |
| cggagaattt acaagcctct cgattcctca gtccagacgc tgttgggtcc cctccgctgg | 240 |
| agatcgcgct tccccccaaat ctttgtgagc gttgcggaag cacgcggggt ccgggtcgct | 300 |
| gagcgctgca agacagggga gggagccggg cgggagaggg aggggcggcg ccggggcggg | 360 |
| ccctgatata gagcaggcgc cgcgggtcgc agcacagtgc ggagaccgca gccccggagc | 420 |
| ccgggccagg gtccacctgt ccccgcagcg ccggctcgcg ccctcctgcc gcagccaccg | 480 |
| gtgagtgccg cggtcctgag atccccgggc cggatgcgcg gcggcccag ctcccgagcg | 540 |
| tctgcctccc ccgccctggg ctgcccgggc tccctgggct ccccggcggc tgcacggagt | 600 |
| caaggcgccc cgtcccgggc gtccccgcg ggtgccgatc caggctgccc ggagtccgga | 660 |
| gcccagagag gagagagaca gctggggagc ctggtcaccg cgggcatctc ccctgcgctg | 720 |
| cagtcgcccg cctggcctgc cttcccgttc ctccgcctct tgccctgact tctccttcct | 780 |
| ttgcagagcc gccgtctagc gccccgacct cgccaccatg agagccctgc tggcgcgcct | 840 |
| gcttctctgc gtcctggtcg tgagcgactc caaagtgagt gcgctcttgc tttgactgat | 900 |
| gctgcccaag gacctctgat cagcaccagg ggagaggagg ggctgctcag ggagctgggg | 960 |
| tcctccggat tccatccaca gcagggccag actctccccca ggaaatggga cagggtggca | 1020 |
| gcggaggctt gagaaccacg ggggttggca ctggctggca agggaggaag aggccgccgg | 1080 |
| gac | 1083 |

<210> SEQ ID NO 177
<211> LENGTH: 2350
<212> TYPE: DNA
<213> ORGANISM: Homo sapiens

<400> SEQUENCE: 177

| | |
|---|---|
| ttctgtgtga tgttttgagg aattgccaca atttttttcct gcgcctgcac cagggacacg | 60 |
| tctcggagct ggcgaactgg acttgggggtg ggagggaaag gaagcattaa agatgccccc | 120 |
| agctttcacg gagatgagaa cggtgccccg ggagggcggg acgggatcag ggtcctgtga | 180 |

```
acgggttatc agtgtaaact cctctgagag atatcaggaa aagcaggaag aagcctctgg    240
gacccttcgg gaggtaactc ctcttcgcag cggggcgcgc tctcccagtc cctgcagccg    300
ccgccgccct ctcctgagct tcctcgagcg gacgccaggc aagggcgggg gtcgtagcgg    360
ggcggagcgg ggctttgtcc acggaccgcg cgaagaggcc tcagggcccg cgcgggcgc    420 cggaggggga cttgctcgca gggggaacgc gaaggttcct cagtctgcgg gacgcagagc    480
tccgtggggc gcgcgagccgg ggccggggaa gcgactctgc ctaggggac gtcgcgggcg    540 cggggcacag ggtcctgcgg ggctggaggg ctacaggctg cggcgcgcgc gagccggaag    600 gccgggatc gtgggttctg gggccgcagc ttcacgggtt cgtctccccc gcctccccgg    660
gggagcagga tgtcaggggg tcgccccgc ccgggagaca gggtgtcaag ggcccccgg    720 ggacggggct tcaggggcac ccggagccgc tcggccccag gcgggatgc ggggacaggg    780 ccccaaggta ccagggccac gaggggcgcg cgggtccctt ggggatgcgc gcgaggaggc    840
gccgtccctt cctagcaggg gtccctgggg acccgcggcc gcctcccgcg ccctctgtc    900 ccctcccgtg ttcggcctcg ggaagtcggg gcggcgggcg gcgcgggccg ggaggggggcg    960 cctcgggctc accccgcccc agggccgccg ggcggaaggc ggaggccgag accagacgcg   1020
gagccatggc cgaggtgttg cggacgctgg ccggtgagtg caggcctcgg ccccgggtgc   1080
ccgcgaggga gccgctaccg cagggaatgc ggggtgcacc cgacagccgg gccggggtgg   1140
gggcgctcag ggctgcgagg cttcgggccg gccgccgccc cagcctccga gaccctgcgt   1200
cctggggagc cggcgggcag gtgggcttgg ccgcgctgtg ggtgcctggg acccgcaggg   1260
aggatgggcg cggtggcgcg gcctggcggg gggctcgtct ccggggtccc cgggtcctgg   1320
tgagagcggg gtccctcgac gccgtggcgg tctccagcct ctcctcgccc ctccacgctc   1380
cccgccttcc atgagctgct attttcagca cctaccgccc gaccctggac taggacaagg   1440
ctctgggctg ccctgcccgc ccccagccc ttccctcggg cacggcggcc aggcgcccgg   1500
gttgaccggg aacagcctcc ataccccaaa cgcggaggcg cctcgggaag gcgaggtggg   1560
caagttcaat gccaagcgtg acgggggaac tgtgccccgg gccctcaggt gatataggag   1620
ttaagaagaa attattgagg caaccagatg cggtgactca ggcctgtaac cccagcactt   1680
tgggaggccg agggtggatc acctgtcctt aattttcttg gcgccagaag atgaattgag   1740
tatttaccca gacaacaacg tcgcttcaga gggagggatg cagaacgcag ggccacgggg   1800
cgcaggctgc aggccagtga accccaacgc caaaggccag ggagagccgg gtggggtacc   1860
cagagccagc acacagccct ttaatttaga ggagtgctgt gtacacattt ggggagagat   1920
gttttacttt gatttggaat caggtggcgg ataaggcata ctgaggcctg acttggtgag   1980
ggctcctgcc ccgaggtgc agccctggag gagcgggagg cagaggagtg gaaaattcat   2040
gaagaaaact gggtatggtg taggtcgagg ccctgccctc agtaatgctc accatttgtc   2100
agtgtttact gtgaggcagc actgtgttca atatcgctga gttctcagga aggaacggta   2160
aatacttccc gggtcattct ttcacccacg ggaaaacagg tttggagaga tctgggacag   2220
tgctctggtc ccaggcagga agggctgagt ggggcctggg actcaggtct gactgcaaac   2280
acctgcctcc tccctgtgct gccagcgcct tccgggttct tccctgtccc tcctttgtgg   2340
tctttgtttt                                                           2350
```

<210> SEQ ID NO 178
<211> LENGTH: 2250
<212> TYPE: DNA

<213> ORGANISM: Homo sapiens

<400> SEQUENCE: 178

```
cgctgaaatg ttttaaatat tttaagtaat aaatgttgat tcaaactcac ctaggaagat      60
taggaagggg aaaaaaagca cttggcattt aaatcttcag aagagaattt aatgacaggt     120
tcagcctgtt taatgacaag cccagcacca caccctctc ttatgatgtt tcattattac      180
tgcataaatt tcctttatta ctcatgataa ataaaaataa gatacctgac aaagtgggtt     240
taaataggta agagtgcaaa caaagattta ctgtacaaat atgatgaaac tgggatctca     300
gattcttaaa gtataatttt tttttgtctt atgtgtgcca ggttgccact ctcaatctcg     360
aactagtttt tttctctttt aagggttgta tccataatgc aaaaatggaa agaattaaaa     420
agcacacgca aaacatgatt ctcgggattt ttctctattt ttatggttga ctaattcaaa     480
cagaaagaca catccaagag aaaattgcta agtttgatac aagttatgaa acttgtgaag     540
cccaagtact gcctggggat gaatttaact tgtatgacag gtgcagagct gtcgctttca     600
gacatcttaa gaaacacgga gttattttga atgactttct ctcggtcaca agggagccac     660
caacgtctcc acagtgaaac caactggctg gctgaaggaa cagaaatcct ctgctccgcc     720
tactggggat taggagctga gggcagtggt gaacattccc aaaatattag ccttggcttt     780
actggacatc cagcgagcag tgcagccagc attcctggcg gctccctggc ccagtctctg     840
gcgcatgcgt cctagcatct ttgggcaggc ttccccgccc tcgtgacgcg tcggcccggg     900
cctggcctcc cggcgatcac agcggacagg gggcggagcc taaggggtg gggagacgcc      960
ggccccttgg cccagctgaa aacgaaattc tttgccggct ggctcccac tctgccagag     1020
cgaggcgggg cagtgaggac tccgcgacgc gtccgcaccc tgcggccaga gcggctttga     1080
gctcggctgc gtccgcgcta ggcgcttttt cccagaagca atccaggcgc gcccgctggt     1140
tcttgagcgc caggaaaagc ccggagctaa cgaccggccg ctcggccact gcacggggcc     1200
ccaagccgca gaaggacgac gggagggtaa tgaagctgag cccaggtctc ctaggaagga     1260
gagagtgcgc cggagcagcg tgggaaagaa gggaagagtg tcgttaagtt tacggccaac     1320
ggtggattat ccgggccgct gcgcgtctgg ggctgcgga atgcgcgagg agaacaaggg     1380
catgcccagt gggggcggca gcgatgaggg tctggccagc gccgcggcgc ggggactagt     1440
ggagaaggtg cgacagctcc tggaagccgg cgcggatccc aacggagtca accgtttcgg     1500
gaggcgcgcg atccaggtag ctggggcccc agggcctcgc cggcagggg cgcgcgaacg      1560
cggggcgcgg cctcggcgga tcgggctgg aacctagatc gccgatgtag atttgtacag     1620
gagtctccgt tggccggagg tgtgcattcc acgcgtaaaa caggctttta cccagcaaaa     1680
atcctaaaga gagacattga aaacccact gtttaagctt tttttagtgg ttttgttct      1740
gccatctcat gatcagagat gcaaggaata gactgaattg gggagaaaag gagaaaagga     1800
aagcttattt agggaagaag attatcttgt ctgtctgctt tcaacgataa agataagtaa     1860
agtataagtt acgcattcta gattggattt aaggaattct acaaaatcat agtacatgga     1920
aaaaatcaat gtaaacttct aagctactat atgaaatctg ttgtattgtt ttctcataga     1980
ggttaattga gaatgagacg ggattcctca accacagtac ttagttcctt ttatgttagc     2040
agtgtcttat gagtgatgca taagagaaaa aatatatagt tctataggtt tctcattctt     2100
taattatcat actcagtgcc cagattacaa aatattcct gcagcaactg ttaggtcctt      2160
tttgaatggc aaaggatctt cataaataat gcatctttat cttcattgtt aaatacact      2220
tattcaatgt ttaagtacga atcctgcttt                                      2250
```

<210> SEQ ID NO 179
<211> LENGTH: 2550
<212> TYPE: DNA
<213> ORGANISM: Homo sapiens

<400> SEQUENCE: 179

```
cctagatccc agaaatctgg gagcggctgg agcgagaaaa cagaggcaag tggcaggcaa      60
ttgccaagca ccagctccag catgtgttca gcccctcaga gcaggacctg cggctgcagg     120
cgcgaaggta aggcctgtgg aaatggcagg gagggtggag gggatgcagg aggcatggat     180
gtgggtgggg tgcccccacc ttccagggcc agtcagacct tcctgacttt cccccaggtg     240
ggctgagacc tacaggctgg atgtgctaga ggcagtggct ccagagcggc cccgctgtgc     300
ttactgcagt gcagaggctt ctaagcgctg ctcacgatgc cagaatgagt ggtattgctg     360
caggtgaggg tatcctagaa ccttggacct ctaagcccta ctcccacatc ccccacatgc     420
attgccatcc tcaataccca cctgcctgca gggagtgcca agtcaagcac tgggaaaagc     480
atggaaagac ttgtgtcctg gcagcccagg gtgacagagc caaatgaggg ctgcagttgc     540
tgagggccga ccacccatgc caagggaatc cacccagaat gcacccctga acctcaagat     600
cacggtccag cctctgccgg agcccagtc tccgcagtgg agagcagagc gggcggtaaa      660
gctgctgacc gatctccctc ctcctcaccc caagtgaagg ctcgagactt cctgccccac     720
ccagtgggta ggccaagtgt gttgcttcag caaaccggac caggagggcc agggccggat     780
gtggggaccc tcttcctcta gcacagtaaa gctggcctcc agaaacacgg gtatctccgc     840
gtggtgcttt gcggtcgccg tcgttgtggc cgtccggggt ggggtgtgag gaggggacga     900
aggagggaag gaagggcaag gcggggggg ctctgcgaga gcgcgcccag ccccgccttc      960
gggccccaca gtccctgcac ccaggtttcc attgcgcggc tctcctcagc tccttcccgc    1020
cgcccagtct ggatcctggg ggaggcgctg aagtcgggc ccgccctgtg gccccgcccg     1080
gcccgcgctt gctagcgccc aaagccagcg aagcacgggc ccaaccgggc catgtcgggg    1140
gagcctgagc tcattgagct gcgggagctg gcaccgctg ggcgcgctgg aagggccgc      1200
acccggctgg agcgtgccaa cgcgctgcgc atcgcgcggg gcaccgcgtg caaccccaca    1260
cggcagctgg tccctggccg tggccaccgc ttccagcccg cggggcccgc cacgcacacg    1320
tggtgcgacc tctgtggcga cttcatctgg ggcgtcgtgc gcaaaggcct gcagtgcgcg    1380
cgtgagtagt ggccccgcgc gcctacgaga gcggaagggg cagccaaggg gcagcgcagt    1440
cgccgcgggt caagtcgcgg cagaggggt cggcgggac agctcccgag gactaggtcc     1500
gttactttcg ccccatcgct gaagagtgcg cgaaaatggt ttatcccttg tcgcactcca    1560
ctcgtatctg ggccacagat gagcagaggt ggctgcttat atgtaaaaat acgctgattt    1620
taagtttctt atctttaaaa tgccttggcc cttcttgaga aagggtttgt gcctactgtc    1680
ctcggagtcc atcttcccag gcttgcctct tctcaaacac tcatgacccc ctccagaacc    1740
tttagggtga agggaaatta ccacctatgg gagggagcct ggaaaaattt agaacctttg    1800
gtgggccccc tgcaagcagg agttttgttg agtctttatt tagcaaacac ccttttctga    1860
cccagtgaat cagatgctaa aatatgcacg cagccacaca cccagcagtc cttctgcacc    1920
cctgggaatc gccagcaagc aaaggttgct ctcccctggg tagacaccag ctggaatcac    1980
caggggtgct tttacagtcc tcccgctag cctggatccc accgcagacc tgttgaatca     2040
actgctggga gtggacccta ggcatcagta aattttaaaa actccccaaa ttattgtaac    2100
```

```
atggagtctg ggttgagcat cactgctctg gcctatttag gaacttgtgg atggatagtg    2160
tcccaggtct gtgtgtgcat ggagaccctc tcatccggta caagaggaca tcacaaattc    2220
agctgggggg agcacaaagt tgtgacagaa tgcaaagaat gaacaagggg ccgagcgcgg    2280
tggctcatgc ctgtaatccc agcacttcgg aaggcgagg cgggtggatc acctgaggtc     2340
aggagttcaa gaccagcctg gccaacatgg tgaaacctca tgtctactaa aaaataaaaa    2400
aaaatgagcc aggcgtagtg gcgggtgcct gtaatcccag ctactcggga ggctgaggtg    2460
ggagaattgc ttgaacacag gaggcggagg ttgcagtgag ccgagatcgt gccactgccc    2520
tccagccttg gcgacagagt gagactctgt                                     2550

<210> SEQ ID NO 180
<211> LENGTH: 2550
<212> TYPE: DNA
<213> ORGANISM: Homo sapiens

<400> SEQUENCE: 180
catcatgagg tgctcagata catggttaag cattatttct gggcgtgtct gtaagggtgt      60
ttttggatga gattagcaat tgaacctta aaccaattcc tcacgtctcc cttctatttg      120
ttgtgtctct ggagaaccct catacagttg tatcaaagat acagaatcaa ctcgataaaa     180
gtgggctcac accggacact ttcatatgag ctagggtttg aagagtgagc agcattttga     240
caggcagaga aagaaggaaa gggtcttctg atcagaagga agactgtgag gaaggcaggg    300
aggggtgatg tggggaaggt gcaaacagtg ctagaagctt ctgaggcctc ctcgtggtgg    360
tgatgaatgc agagattaca gagttctctg cttcgggctc agcatgcacc ctccatagct    420
aggctggggg ctaacgttag taagaattta ctgatttact gagtacctac acgaagtttc    480
acattttcac aaagtagagt cactttaagt ttgtttacat gtgacctcca caaacacaca    540
caattacaaa atagtttagt taatcaaggg atgtataata aacaagaggt cggaggcccc    600
gggccgctcc cgcccacctc cgcggacgag cgcccccctc cgaccccatt ccctgcggtc    660
tgggcgttca ggcccttcgg tctgggcgat cccggagaac cacccacggg gctttaaaaa    720
tgttggtgcc caccacctcc ccggaacagg gcccgctcta cctcggtcgg ggagcgcggg    780
acctcagcgt tcccttaacg ccaccgtccg cgggtccgct ttgcgcaggc gcggcgcccc    840
cactcagtac ccgctccggg cgtggcatgg tgcgcaggcg cgatgtcccc cactgcagcc    900
ccgctcgact ccggcgtggt gcgcaggcgc ggtatccccc ctccccgcc agctcgaccc    960 cggtgtggtg cgcaggcgca gtctgcgcag ggactgcggg gactgcgcgg cggcaacagc    1020
agacatgtcg ggggtccggg gcctgtcgcg gctgctgagc gctcggcgcc tggcgctggc    1080
caaggcggtg agtccgtgcc gcggaccggg gcggggcagg cggggccga gcggcggta     1140 ggagcgggac ggtccccagc gggtccgagc ggagcgggcg ccgggtccct gcgccctctg    1200
tcccgggatc gggaagggc tgagagagcc ctgggccggt gcgaggggaa gccgcggggc    1260
ggactcgggg acccggggag ctcggtcctt agtagatagt ccgcgtccgg gtgaaggtca    1320
caaccccgcg ggcttgctgg gcgtcccctc cgccgccttg gtccgggcct ggggtcctgg    1380
gaccccgcgg gctgaggtag cccctcgcct cagtgcctgg caggtggact cggggaggag    1440
tcgtgtctgc ccaaggtcac ccgggcggat agcggccggt ggccgccctg gctgggctgg    1500
gcctctgccg ccctctgtgc gggttgtcct gaggagcagc ccgcagcccg tgggtgggc     1560 cggcggggcg ggtgagaccg cccgggtggg tgcgaggagt ggccgggctc ggcccggtgg    1620
gcgtccggtg ggaagcgtgg cgcgcccgag cttaggcttg cagttcgcct ttccagaaag    1680
```

```
cgcaaatctg tccatgtcca cttcgagacc ttgtaagtta agggcttcta ctttgggtcg    1740
tgtttggtgg tccttatgcc accaaaaatg tgccagtgtt taaaagcagc tgtgccagtt    1800
tttaaaactc aggcggagag ctcagcgcac tgaccgggcg aggacgccgg gacctgtgct    1860
tgcctgtgcg ctgagtgcct ctagggccgg gctcggctta gtccaggatg gtggtcaggg    1920
ttatacttcc ctgagccctt gctctctgag tgtctgaatg tgccctctac gattgcatct    1980
taagaatcgg ccttctaggg ttttatttaa tcaagctaaa ttggataggt ttagttgttt    2040
ggttctttta aatgaactta cccacccacc tccttaatta caagtaatt ttaaattgca     2100 gaataaaaat ctcaatagga accaaggcat tcagcaatat tgatttgaat tatgcctgta    2160
attgtgcaat tttctccttt ttgaaatact tattaaaaat ctcgttgagt taaatgtgag    2220
gattagtcat acagccatcc tgccaacatc agaaagcgtg taaaccgttc tagtgtgttg    2280
ctgtggttgg tactgactga gcagagaccc ctgccgcatc ttgggctttt aagagctgct    2340
aggagggcgt ccacaagcag gaaggaaagc ccatggtcag tggggctttt taggggaaat    2400
ggtagcttgt gattggagaa aagctagagc tagtgccttt gtcctcaacc cagatggtgc    2460
ccggtgttcc ttctgcagac taagaccctg ccagcggcgg aggcacctca gacgggatgg    2520
caagatagca aaattgaacc aaaatttagt                                     2550

<210> SEQ ID NO 181
<211> LENGTH: 2550
<212> TYPE: DNA
<213> ORGANISM: Homo sapiens

<400> SEQUENCE: 181
atctctacaa ataatttttt aaaaaaatta tccgggtggc cgggcgcggt ggctcatgcc      60
tgtaattcca gtactttggg aggccgaggt gggtggctca cgaggtcagg agttcaagac     120
cagcctggcc aagatggtga acccccatct ctactaaaaa cacaaaaaaa ttagccgggc     180
atgatggcgg acgcctataa tcccagctac tcggaggct gaggcaggga attgcttgaa      240
cccgggaggc ggaggttgca gtcagccgag atcgcgccac tgcactccag cctgggagac     300
agagcgatac tccatctcaa aaaaagaaa aaaaaaaaa ctacccgggt atggtggctc       360
acacgcctgt agtcccagct actctggagg tgggaggatc gcttgagcct gggaagtcga     420
ggctgcagtg agccaagact gcacaccggc ctggcaaca gagtgagacc ctgtctgaaa      480
aaaaaaaaaa aaattggccg gcgcagtgg ctcatgcctg taattccagc actttgggag      540
gccaaggtgg gcggatcacg aggtcaggag ttcaagacca gtctggccaa gatgatgaaa     600
ccccgtctct actaaaaata caaaaaatta gccgggtgtg atggtgtgcg cctgtaatcc     660
cagctactcg ggaggctgag gcaggagaat cgcgtgaacc cggaggcgg aggttgcagt      720 gagccaagat cgcgccattg cactccagcc cgggaaacag tgcgagactc catctcaaac     780
aaacaaacaa aaattccagg aataaagagg ttgaaatcgg gcagggacc cggataggat      840 ggctccgccc catctaagtc ttagccccac cccctgaaag tcgccctgcc tctcagactc     900 ctccccttc tgagaaggtc acggggaag ccaaatgggc atgcgccgct actgcgctat       960
tgcgcacgct cgctgtgctt gccccgcctt ccctccgccc acccgggaaa ccggaagccg    1020
cctcccactt ggttgctcgt acgcggctag tgggtcctca gtggatgtag ctgggcgcc     1080 gcgatgttcg acgggacacc ggcggagagc gacctcgggg ttaaggggtg gggctgacgt    1140
caggagccaa gatggcggcg gtggtcgccc tctccttgag gcgccggttg ccggccacaa    1200
```

```
cccttggcgg agcctgcctg caggtgagtc ctggagcctc agagagggaa aagtcaggaa    1260
agccacagag actgcctgga gctgatgggg ctgcggagag actgaggaag catagggcaa    1320
ggcctcaggg agatggagga cctcctcccc ctggtgcagt gctttggttt ggcttcgagc    1380
atccctgtca agttatcttt ctgcgcctcg cagcagcttg tgagttaggg cacgggcaat    1440 ttttttacagc taagggtgcg ggggggggggg acgttcagaa aggggacttg aattgctcaa    1500
ggtcacatgg caagcgaatg actgctggaa ccagaatttg aatccagaca ttggagttcc    1560
aagccctttt tctgccacca aactatcgcc tctgtagaaa agggagacct gcggggtgtg    1620
aaggatggga attgggaagc gaggtaattc ctcaagggtg cgaggttgag gaccgggatg    1680
ggtgaggaaa ggacatgtga attgttgggg acagggcagg ggaagggaga gatggaggga    1740
aatgcaccca gccccctacc tcgaaggatc ccggaggtgg gtggtggggg ttgcaggaaa    1800
gactgggttc cttaaagcag tgtcaccaca gtttcactag tatcctctca gtgtttctga    1860
ctctaaaggt catataataa tacggacctc atagagttga catggaatga caggtagagg    1920
gcttggcgct gttcttgttt attactatgc cgtgtgcagt aacagatttt cccacgcccc    1980
ttgtatggcc aagaaacaac acatttctga cctgccttct aagtgggaac atttagaagg    2040
ggaagggaaa ttgcttttgt atacataagg gactaaggat ttgcaaatcc tttctaagtc    2100
tgttcctctt ctgggattct caacaacccc tttaaggtgg gcaagcaaga atccttaccc    2160 tccttttttgg agctttgaaa acttgaggcc cccagaaaga aaattttggg cttgctcaaa    2220
atatcacatt cccaagaagc agacctgagg cagttttta acatggtacc agaaaaactc    2280
cttagcatag atcttgggac atggttggtg tccaagaaat tttagttcct cttcctctct    2340
tgcacttaaa tgaggacatc tttcatctta agtgcctgct atggctgcat aacacagtac    2400
atattgccca tgttccaatc ctggttctat ccagcatgct gtgtgtgaac ttggatccac    2460
tctgtctgca tcagcctttc tgaaaagggg agatagagga agaagacagc ctaccagagc    2520
ctcaagctga catcctctca gtattaaatt                                      2550
```

<210> SEQ ID NO 182
<211> LENGTH: 2550
<212> TYPE: DNA
<213> ORGANISM: Homo sapiens

<400> SEQUENCE: 182

```
attcatctga tgcagaaata agtgaatttg tgctatttaa atcctgaagt gcagggatgc      60
taaatataca taagatctga atattaatat aattgagtat ttttttttgta gaaataggag     120 ttgctctagc ctgtcccttt tactcctctc caccctactc cccacaagag tcaagaactt     180
ttgtgctctg ttcccttcct ttatcatttg ctcttcttct ttcttcagtc ttgagtgctc     240
ggcagttgat tcctgtgctt gggttcccta aaactgtata tatatatata cacatatata     300
aatcaaagcg tgttcttccc ctcactccgg gttcttctag ctgtgggtgt cacccacata     360
gcgctgaaac aacgaacaag ggagcattgt cctcggctag tgggcgcctg gtccatgtgg     420
cagctcaaac ccaggaattg tggggtctaa tcgaggtggt tagatgaggc tcctcgtttt     480
cgggaatggg ggtccgcaag gtcttctcga ggccctcta cacactcccc aacttaggtc     540
acaatttatg tatctgtctg gttaaagctt cgtattagaa agggagggaa cccaaagtat     600
cttttctctt cggggtctca accggccaac caccacgttt ttaggccgac ctggaggca     660 gggggaacga acagactgc gaagtcctta aggaagaatc taaacaagtc cgccgtttgc     720
tgtttgggag tgcgatacaa aatgaatatg tacgcaggtg gaacgtagac tgcagatttt     780
```

```
gagccagcgg cgtttctgcc gaaatcctgg caaattccgg tagaagtcgg ctgcaggagg      840
cggaggagga gactaaaaaa ccagaaaaca accagcaaac cagctaggca gagctgagcg      900
gagaagctcc agagccttt aaagagactc tcgtcacatg acaccccaa ccccgacccc       960 cagccggcgc gcctccgccc tcgggtggcg gggccgcctg gcgtcacttc cgtccagacc     1020
ggaacccaag atggctgcgc tgttgctgag gtgacttcag tgggactggg agttggtgcc     1080
tgcggccctc cggagatctg aactggcccc tcacgttttg ctgataactg tttatcctgt     1140
gcctgggcag ggaaaggacc catgggtgtg gaggccaagc gctcgggat cctagagacc      1200 ccttttcccg tcccccccag ccgctccggt gcgctccgta gggcttcggg gtcactgact     1260
tcgtatcgag gggccctcgg ctctcgcccc ttctgttttc cccacctcct ctagtacttc     1320
taacgcaaat tgctctcggg cctgcaccca gagccgagct ctgagaaaat aacttcaagg     1380
tcagccaccc atgggtccta cgatttcgag agcgtattta gacatttagc ttcggagaga     1440
gagatcttcg tgtattttgc ctttgcttcg aatgccttca gacactagct gctcccaccg     1500
tgagtgggcg ctgtctgggt tcccagcggg ctgctggcaa aggtggatc cctactgggg     1560 tggcgattag cattagcacc cagggcggac ctctgctgcc ccagagcaac ccggggaatt     1620 cattttagt taatcatttt acttgggagg gagagtgagt gtcccagttt ttctctaaaa      1680
tgtgaattag ttgtccagag aaatacccta gatttcttt cattctgaac tttccgctgt      1740
ctaggtctca ttctctgctc agcctctcta gtcacagcga ctagcgcctt tagacacgcc     1800
tggtacaaat cccagcatag ttttgtgcca gccttatttt tggaaattgt ttgttatgga     1860
aagttagctt caatgctgtt gagatttcaa tccctgattt ccccaaatgt gttctcattt     1920
ctctttccac ttcagtcacc cagttttaaaa atagagggac tttgttagt ttttctgtga     1980 caaaatgatt cctcttggag ttgaaatcag ggttatctta atccttcatt ttctccctgt     2040
ttttcatctc catatgtatc ttctgtctaa ggtatgccaa ggcttgtctt gccagtgctg     2100
tcttctttat tccagatggt ttgaccataa ttgaatgctt ttgaattctc tgatatattt     2160
tggtatcgat gttaggggct tttggtaaaa ttaacattta gtttgaagtg atcatattgg     2220
ttccaaacag ttcattttag gagttttgga attagtgttt aaaagctgag gatcattata     2280
gtcattaagt gtatccatac agtatcattt tgagttgtgc agcgctgtcc actgaaggga     2340
tgggtcgccc ctccacacct gtgggtgttt ctcgttaggt ggaacgagag acttggaaaa     2400
gaaagagaca cagacaaagt atagagaaag aaaaaagggg gcccagggaa ccggcgttca     2460
gcatacagag gatccccgcc ggcctctgag ttcccttagt atttattgat cattattggg     2520
tgtttctcgg agaggggat gtggcagggt                                       2550
```

<210> SEQ ID NO 183
<211> LENGTH: 2550
<212> TYPE: DNA
<213> ORGANISM: Homo sapiens

<400> SEQUENCE: 183

```
ctagccaggg ttcttgctgg tcatccgagc accctcttcc tcccacccaa aaggaaaaaa       60 ccatttacc aagagcttac tatttgtgag gctgggtact aagaaatcag ttctctctaa       120
ggtcctcaag gatagctgtc atcacctccc atttaagagg cgtgattatg tagtccaagg      180
tcatgtagcc agcaagaagt caggccgcgt tagaaccatg tccgaagggc tccaaaccct      240
tgttctacat ccatagtcta cagcgactac ttcagagtcc accttcctcc gataatgttc      300
```

```
tagtcgtttt caaatacatt gtcgcatatg atcctcacaa tccagtgagg cagtggggtg    360
acggcgacac caaaacccac agtggatgag tatcttttct acgggcacgt ggcctgcaag    420
gagcagaggg aggatgagaa cccagatctt tcgaatgcca gcccagtcat gtcgccggct    480
aactagtctc ccgtacccct tgcgtcgccc aatcttccct gttttacacc tttctttc     540 tccacgctac gcttatatac ctggcacctg agcactaccg gtcaccaggg acaggagagc    600
cataactttg tctttcgtga ggggaatggg atgcagccgg gatcgagcac cagtgagccg    660
ccagtgtaca gacctccgag cgtgcccagg accaccaagg aaggtgaaac ttcctttccc    720
ttcaccctcc ccgtcccgc  acctgtgcag taaactgcgc cttctgctgc tcggcggcca    780
ccaggcgctg caactccgct tcatcggctt cgcccagctc cgccattgtt cgcctcaggc    840
tcgccacctt ccgacagctg tgtttgcgca tgcgcgacgg gtgtgcaccg cctctcgact    900
tccggttcac ccagcatttc ctcttccctg ttttctttcg tcgtcgtggg tgggaattgt    960
cgcctaagtg gttccgggtt ggtggatgac cttgagccct caggaacgag atggcggttc    1020
tctggaggct gagtgccgtt tgcggtgccc taggaggccg aggtgagggg tcttcccacc    1080
ctgaggtgct tagcgtagcc tccagccagg aaggggatg  gaagtgagga ctcatctgcc    1140
gggtgggaga tctcttgagg agaagaaaat accgaaatca cagcaatgac cactgtagtc    1200
taggggtcca gatgtttacc cgaaggtata tttcacttgc tgtgagctga cgagttgagg    1260
gaataatcag aaagagagct ccctctggaa gtcgcagtcc tgatgaggct aatccacata    1320
gcagttctgt tttctccccg ttcactgtcc ctagaatgct ccccactcgc tcccaccctg    1380
agtcgggaaa gagggttagg agcttgccca tttcttctgg agttggtgtg tttggatgtg    1440
ggagtggagg ggggatcagt tcgaaaatca tttaacctgg gcatttgtgt tacctcaggt    1500
actgtagtaa tgctaggata caaatgtgaa gaaaacgtag ttcccgccct caacgagctt    1560
tcattctgat gaggaaaaca ctgtcatagt agtccgggca agatgaggtc ctgaactagg    1620
aaagtagcac aaagaaaaga agattgtctc aagaactgtt aaagagatac gccaatagga    1680
tttggcgatt gaatttaggg gaaaagtctc tcatgatttc cagattactg agttaggtta    1740
aagaatgcct gaggtgtcat taaataaagt agggaacatg cagatgttcc ctggtcttaa    1800
cttcacagta accccagtga aatagatgct atcttcattt tacaaataag atgttatccc    1860
ctatttattg ttaagtagct tacctatggt catttagaaa gtttgtcagt cctgttaaag    1920
gagaggttct tatgatcatc ctaatgactc tttcctcagc tctgttgctt cgaactccag    1980
tggtcagacc tgctcatatc tcagcatttc ttcaggaccg acctatccca gaatggtgtg    2040
gagtgcagca catacacttg tcaccgagcc accattgtat gttctctcca tcgctgctgc    2100
tttctgggct ctagccatct ttaccttcac taatggtcat gcctttagca ggacttccta    2160
cctgtagggg ggactcttgt gtccaacttt gtcaaatgaa gacctagttt acacctttgg    2220
gcagacagtg ccattatggt tgaatgatgc catttataat catagaagac cttctagcct    2280
aagtctttac aaatttttt  cttttgtttt cttttttttt gagacagagt ctcgctctgt    2340
tatgcaggct ggagtgcagt ggtgcgatct cggctcactg caacctccac cttctgagtt    2400
caagcaattc tcctgcccct gcctcccgac tagctgggat tacaggcgcc caccaccatg    2460
cccagctaag ttttgtactt ttagtagaga cgggtttcac cgtgttggcc gggctggtct    2520
caaactcctg acctcctcaa actcctgacc                                    2550
```

<210> SEQ ID NO 184
<211> LENGTH: 3001

<212> TYPE: DNA
<213> ORGANISM: Homo sapiens

<400> SEQUENCE: 184

```
actcagactg caacctttac ttcgcccct aattcctgac tcagaatccc cacctagagg      60
cagaacttcg acttcaattc ctgactccca taccccactg agacctctaa ccccaatccc     120
aatctcttaa ctcagagccc cccattcaga acctctaccc aaagacagac tccagaccct    180
gactccagtc gccaactcgg acctcccttg gatctcaact cagagccatg atgcagactc    240
cagaccggga ttcaggtccc caactcagac tcccgatcct ctgtccctaa tgaggcccta    300
cctaaaacca ccatgcggac tccagacccg gactgactgg gaccccaact actcagatcc    360
caactcaggc aaactcccag ccaggatgtg gaccctagac ccgaattctg atcccaacta    420
ggatacctaa ctcagaacca caacgggat tcccacctcc gatcctaatt cgggccctga    480
ctcagaacca ctaagtggat ttccgactcc ggtcccaatt cgggctttga ctcaaaacca    540
caacatggat tcccaacttc catcccaata gcgcggactc agaaccacga tgcggattcc    600
agactccaat cccaattcag cccactctga accaccatga gaactataga cccggaatcc    660
gatccttggg acgcggccag gaactcggac ctcgaccctg ccacgctgt ccataaggtg    720
cagatgggag cgcactgccc aggccaggct gcactgctga cgcctgtgat ctgggacggc    780
cgcggggcac acagctcacc tcagcaacgc cagtgatcac ccgtcccgcg ccgtccgccc    840
aggtccgtgc tgaccgtgtt caaaccctcc cagagagatg ggagggccg cgctgaggag    900
agtctgggag aaccgcactg aggagccgcc gggagagtgc cgcgctgagg agccccgggg    960
gagagtgccg cgctgaggag ccccaggag agtgccgcgc tgaggaggcc caggaggac    1020
cgcgcggagg agaaccatgc tgaggagccc ccgggagaa cagaaccgcg gcgagaggcc   1080
cccggagaga accgcgccga agaacccccg gggacaaccg cgccgaagaa ccccggga    1140
gaaccgcgcc gaaaagcccc gggtgccccg aggagaacgg cgccgaggag tccccgggga   1200
gaactgcgcc gaggagcccc cagaagagcg ccgcgctgag gagccccgag gagaaccgcg   1260
ccgaggggcg cgccgggag aaccacgatg actgacgcac cgaggaggac cgcgctgagg   1320
ggcgcaccgg gagaatcgtg ctgaggagcc ccggggagga ccacgctgag aggcaccccg   1380
gcagaatcgc gctgaggggc gccctggcag gatcttgctg aggagctccc tggaggtccg   1440
tgctgaggcg acgcggcgac cgttctgcct ggagactgcg gcagcgctcc gactgccccc   1500
gccgctgccg acgtggcgac cgccccccac ctgctgattg ggcggcagca ggggaaggct   1560
tgcggcgggc tgctgcacgg attggctggg tgcggaaagt gatgtgccgt gtcctgtcat   1620
tggccgaaag agtctcgttt tgatgccacc cgggctcaga ttggcccagc gggtccagcg   1680
ccgcatgagg cactggctgg gtgtgaggtg gcgcgagccg ccgccctccc tgcccccacc   1740
cgtcgtccct gagcaccacc ggggccggg gccagcgcca gcctcagcgt tggcatcgcc   1800
ggggtgagct ggagacacgg gccagttctc tgcgtgatgt gttcaccacc ccggggtgac   1860
cgcgtgagga cagcggccgc accccgacac tgctgtgggc cctcggtgtg gaggcctgtg    1920
ggcgtccagg ccacgcccga gaccagcccc tccgccggcg ccgctgcagc gaccctcgaa   1980
cccgggcaag gtctccaccg ccgtggcacc gggtgcggga ggcgttttcc ccctcccag    2040
cgggtccatg caggggatcg ggatgttctg aagcccccac tgctgtgcct ggaacacccg   2100
tgtctgccgc tcacccctga ggacttggga cctcaggggg tgagtggcag gggtggccgg   2160
gacatgccag gccacccacc tggcaaaggg cagcgccgag ggcgcccgc gcctgccagc   2220
```

```
gcccggccgg gcccgccctg cccacctccc atcccccatc cgggcgtgac acttgaccgc    2280
gtctgccggc ccctcccctt gtccgtccc tccgcgccgc tggcgcgcgc cttctgaatg    2340
ccaagcattg ccataaactc cggggacaaa agcctgggtc acaaaagccc cctctagaag    2400
ttcacaccct gaggcttccc tggcaaggct ggggggccgtt tggcccttcc atgtggactg    2460
caaaaacagt gttggaatgc aggactctgg gtatgttctc gaaagttgtt acaaccccaa    2520
cccaggggttg acctcaaaca caggaggaag ggggaggctg gagccagcca agcgagccag    2580
ccgtcccccc accaaggcac gcaaggaggc cattcatctt cactgcctct gccgaaaata    2640
tacgtctacg ggagagccag gaatctctct ccaagggtga ccgggttggg ggttttgttg    2700
ttcttcagcc cagaagagaa agagaaaatg gtgtcatttt ttcaggcagc aagtgattcc    2760
tttcaggcct tcagcaacga cgcccagatg agtccactcc ctgcctcctg ctcagcccac    2820
aggcaatctg ggcacaagtg acacatcccc tgggcgcctg tcccttcgca ctggcccagg    2880
gagttcatgt gtctgatcag agggcgcagt ccaccctcac tatctagctg ggaagttttt    2940
gtcatctgcc tgtccgagag gcagctgtgc aaccagtgcc atcactcaga gccagtgctc    3000
a                                                                   3001
```

<210> SEQ ID NO 185
<211> LENGTH: 26
<212> TYPE: DNA
<213> ORGANISM: artificial
<220> FEATURE:
<223> OTHER INFORMATION: methylation independent oligonucleotide primer

<400> SEQUENCE: 185
gcggagagag aagtagttgt gtaatt                                        26

<210> SEQ ID NO 186
<211> LENGTH: 21
<212> TYPE: DNA
<213> ORGANISM: artificial
<220> FEATURE:
<223> OTHER INFORMATION: methylation independent oligonucleotide primer

<400> SEQUENCE: 186
tacgcccaca cccaaccaat c                                             21

<210> SEQ ID NO 187
<211> LENGTH: 22
<212> TYPE: DNA
<213> ORGANISM: artificial
<220> FEATURE:
<223> OTHER INFORMATION: methylation independent oligonucleotide primer

<400> SEQUENCE: 187
cgaagagggt gggtgagagt tt                                            22

<210> SEQ ID NO 188
<211> LENGTH: 24
<212> TYPE: DNA
<213> ORGANISM: artificial
<220> FEATURE:
<223> OTHER INFORMATION: methylation independent oligonucleotide primer

<400> SEQUENCE: 188
acgccatatc caccaataac caac                                          24

<210> SEQ ID NO 189
<211> LENGTH: 28

```
<212> TYPE: DNA
<213> ORGANISM: artificial
<220> FEATURE:
<223> OTHER INFORMATION: methylation independent oligonucleotide primer

<400> SEQUENCE: 189
ggacgtaaat ttaagagggt atttagag                                    28

<210> SEQ ID NO 190
<211> LENGTH: 27
<212> TYPE: DNA
<213> ORGANISM: artificial
<220> FEATURE:
<223> OTHER INFORMATION: methylation independent oligonucleotide primer

<400> SEQUENCE: 190
cttcgccaaa atctaatact atcacct                                     27

<210> SEQ ID NO 191
<211> LENGTH: 27
<212> TYPE: DNA
<213> ORGANISM: artificial
<220> FEATURE:
<223> OTHER INFORMATION: methylation independent oligonucleotide primer

<400> SEQUENCE: 191
ggaaaagcgc gggaattata gataaat                                     27

<210> SEQ ID NO 192
<211> LENGTH: 24
<212> TYPE: DNA
<213> ORGANISM: artificial
<220> FEATURE:
<223> OTHER INFORMATION: methylation independent oligonucleotide primer

<400> SEQUENCE: 192
atcccccgtc caaaaaatct caac                                        24

<210> SEQ ID NO 193
<211> LENGTH: 19
<212> TYPE: DNA
<213> ORGANISM: artificial
<220> FEATURE:
<223> OTHER INFORMATION: methylation independent oligonucleotide primer

<400> SEQUENCE: 193
cgccgccacc tctaccaac                                              19

<210> SEQ ID NO 194
<211> LENGTH: 21
<212> TYPE: DNA
<213> ORGANISM: artificial
<220> FEATURE:
<223> OTHER INFORMATION: methylation independent oligonucleotide primer

<400> SEQUENCE: 194
ggggtggatc gtttaagagg g                                           21

<210> SEQ ID NO 195
<211> LENGTH: 20
<212> TYPE: DNA
<213> ORGANISM: artificial
<220> FEATURE:
<223> OTHER INFORMATION: methylation independent oligonucleotide primer

<400> SEQUENCE: 195
```

```
cgccgaaacc ccaaactccc                                              20

<210> SEQ ID NO 196
<211> LENGTH: 22
<212> TYPE: DNA
<213> ORGANISM: artificial
<220> FEATURE:
<223> OTHER INFORMATION: methylation independent oligonucleotide primer

<400> SEQUENCE: 196
ggttttgtag gggtcgggaa tg                                           22

<210> SEQ ID NO 197
<211> LENGTH: 26
<212> TYPE: DNA
<213> ORGANISM: artificial
<220> FEATURE:
<223> OTHER INFORMATION: methylation independent oligonucleotide primer

<400> SEQUENCE: 197
gaagtggata ggggaattttt aagagg                                      26

<210> SEQ ID NO 198
<211> LENGTH: 25
<212> TYPE: DNA
<213> ORGANISM: artificial
<220> FEATURE:
<223> OTHER INFORMATION: methylation independent oligonucleotide primer

<400> SEQUENCE: 198
cgacgccctc tacattcata aaaac                                        25

<210> SEQ ID NO 199
<211> LENGTH: 26
<212> TYPE: DNA
<213> ORGANISM: artificial
<220> FEATURE:
<223> OTHER INFORMATION: methylation independent oligonucleotide primer

<400> SEQUENCE: 199
gttgtggtcg gtaggtgaat ttttag                                       26

<210> SEQ ID NO 200
<211> LENGTH: 26
<212> TYPE: DNA
<213> ORGANISM: artificial
<220> FEATURE:
<223> OTHER INFORMATION: methylation independent oligonucleotide primer

<400> SEQUENCE: 200
tacgtaacta caaccaaata aacccc                                       26

<210> SEQ ID NO 201
<211> LENGTH: 28
<212> TYPE: DNA
<213> ORGANISM: artificial
<220> FEATURE:
<223> OTHER INFORMATION: methylation independent oligonucleotide primer

<400> SEQUENCE: 201
tcgaattcgg agggttatta agaatttg                                     28

<210> SEQ ID NO 202
<211> LENGTH: 25
<212> TYPE: DNA
<213> ORGANISM: artificial
```

<220> FEATURE:
<223> OTHER INFORMATION: methylation independent oligonucleotide primer

<400> SEQUENCE: 202
acgctactca cctctaatac caaaa                                            25

<210> SEQ ID NO 203
<211> LENGTH: 27
<212> TYPE: DNA
<213> ORGANISM: artificial
<220> FEATURE:
<223> OTHER INFORMATION: methylation independent oligonucleotide primer

<400> SEQUENCE: 203
gttcggtatt tacggttttg agggttt                                          27

<210> SEQ ID NO 204
<211> LENGTH: 27
<212> TYPE: DNA
<213> ORGANISM: artificial
<220> FEATURE:
<223> OTHER INFORMATION: methylation independent oligonucleotide primer

<400> SEQUENCE: 204
caaaatacga ccaaaaccaa acccaac                                          27

<210> SEQ ID NO 205
<211> LENGTH: 19
<212> TYPE: DNA
<213> ORGANISM: artificial
<220> FEATURE:
<223> OTHER INFORMATION: methylation independent oligonucleotide primer

<400> SEQUENCE: 205
gcgcggagtt gggaggagt                                                   19

<210> SEQ ID NO 206
<211> LENGTH: 22
<212> TYPE: DNA
<213> ORGANISM: artificial
<220> FEATURE:
<223> OTHER INFORMATION: methylation independent oligonucleotide primer

<400> SEQUENCE: 206
ctccgaacta ccctaccaaa cc                                               22

<210> SEQ ID NO 207
<211> LENGTH: 27
<212> TYPE: DNA
<213> ORGANISM: artificial
<220> FEATURE:
<223> OTHER INFORMATION: methylation independent oligonucleotide primer

<400> SEQUENCE: 207
gcgttcgttt tgggattgta tttgttt                                          27

<210> SEQ ID NO 208
<211> LENGTH: 20
<212> TYPE: DNA
<213> ORGANISM: artificial
<220> FEATURE:
<223> OTHER INFORMATION: methylation independent oligonucleotide primer

<400> SEQUENCE: 208
tctaaccccg accctacccc                                                  20

```
<210> SEQ ID NO 209
<211> LENGTH: 25
<212> TYPE: DNA
<213> ORGANISM: artificial
<220> FEATURE:
<223> OTHER INFORMATION: methylation independent oligonucleotide primer

<400> SEQUENCE: 209
gcgggttagg tttttttgga gtgtt                                           25

<210> SEQ ID NO 210
<211> LENGTH: 27
<212> TYPE: DNA
<213> ORGANISM: artificial
<220> FEATURE:
<223> OTHER INFORMATION: methylation independent oligonucleotide primer

<400> SEQUENCE: 210
aatacaactc gttaccacct aatacaa                                         27

<210> SEQ ID NO 211
<211> LENGTH: 22
<212> TYPE: DNA
<213> ORGANISM: artificial
<220> FEATURE:
<223> OTHER INFORMATION: methylation independent oligonucleotide primer

<400> SEQUENCE: 211
gagaagtacg agatgtgggg at                                              22

<210> SEQ ID NO 212
<211> LENGTH: 20
<212> TYPE: DNA
<213> ORGANISM: artificial
<220> FEATURE:
<223> OTHER INFORMATION: methylation independent oligonucleotide primer

<400> SEQUENCE: 212
tacactccta acccctcccc                                                 20

<210> SEQ ID NO 213
<211> LENGTH: 23
<212> TYPE: DNA
<213> ORGANISM: artificial
<220> FEATURE:
<223> OTHER INFORMATION: methylation independent oligonucleotide primer

<400> SEQUENCE: 213
ggcggttcgg gtagtaagta gtt                                             23

<210> SEQ ID NO 214
<211> LENGTH: 24
<212> TYPE: DNA
<213> ORGANISM: artificial
<220> FEATURE:
<223> OTHER INFORMATION: methylation independent oligonucleotide primer

<400> SEQUENCE: 214
aacgaaacaa caaaaccccc aacc                                            24

<210> SEQ ID NO 215
<211> LENGTH: 23
<212> TYPE: DNA
<213> ORGANISM: artificial
<220> FEATURE:
<223> OTHER INFORMATION: methylation independent oligonucleotide primer
```

<400> SEQUENCE: 215
cgaggttgga aggatttggg att                                          23

<210> SEQ ID NO 216
<211> LENGTH: 23
<212> TYPE: DNA
<213> ORGANISM: artificial
<220> FEATURE:
<223> OTHER INFORMATION: methylation independent oligonucleotide primer

<400> SEQUENCE: 216
cgcacgataa aacctaaaac ctc                                          23

<210> SEQ ID NO 217
<211> LENGTH: 26
<212> TYPE: DNA
<213> ORGANISM: artificial
<220> FEATURE:
<223> OTHER INFORMATION: methylation independent oligonucleotide primer

<400> SEQUENCE: 217
gcggtaggta aagagaatga atttga                                       26

<210> SEQ ID NO 218
<211> LENGTH: 26
<212> TYPE: DNA
<213> ORGANISM: artificial
<220> FEATURE:
<223> OTHER INFORMATION: methylation independent oligonucleotide primer

<400> SEQUENCE: 218
cgtcgaaaaa aaacacctat ttctcc                                       26

<210> SEQ ID NO 219
<211> LENGTH: 22
<212> TYPE: DNA
<213> ORGANISM: artificial
<220> FEATURE:
<223> OTHER INFORMATION: methylation independent oligonucleotide primer

<400> SEQUENCE: 219
gagacgtcga gtagggtttg gt                                           22

<210> SEQ ID NO 220
<211> LENGTH: 26
<212> TYPE: DNA
<213> ORGANISM: artificial
<220> FEATURE:
<223> OTHER INFORMATION: methylation independent oligonucleotide primer

<400> SEQUENCE: 220
tcacgaacca atcaacccct caaaaa                                       26

<210> SEQ ID NO 221
<211> LENGTH: 26
<212> TYPE: DNA
<213> ORGANISM: artificial
<220> FEATURE:
<223> OTHER INFORMATION: methylation independent oligonucleotide primer

<400> SEQUENCE: 221
gtcgagtcgg gtttatttaa gggtta                                       26

<210> SEQ ID NO 222

```
<211> LENGTH: 25
<212> TYPE: DNA
<213> ORGANISM: artificial
<220> FEATURE:
<223> OTHER INFORMATION: methylation independent oligonucleotide primer

<400> SEQUENCE: 222
acatacgcta tacataccte taccc                                         25

<210> SEQ ID NO 223
<211> LENGTH: 24
<212> TYPE: DNA
<213> ORGANISM: artificial
<220> FEATURE:
<223> OTHER INFORMATION: methylation independent oligonucleotide primer

<400> SEQUENCE: 223
aagtcgtgga agagttgggt tgtt                                          24

<210> SEQ ID NO 224
<211> LENGTH: 23
<212> TYPE: DNA
<213> ORGANISM: artificial
<220> FEATURE:
<223> OTHER INFORMATION: methylation independent oligonucleotide primer

<400> SEQUENCE: 224
cttacgccta cacaccccac aaa                                           23

<210> SEQ ID NO 225
<211> LENGTH: 24
<212> TYPE: DNA
<213> ORGANISM: artificial
<220> FEATURE:
<223> OTHER INFORMATION: methylation independent oligonucleotide primer

<400> SEQUENCE: 225
cgagttgttt gaggattggg atgt                                          24

<210> SEQ ID NO 226
<211> LENGTH: 22
<212> TYPE: DNA
<213> ORGANISM: artificial
<220> FEATURE:
<223> OTHER INFORMATION: methylation independent oligonucleotide primer

<400> SEQUENCE: 226
aatacgttcc gaatcctacc cc                                            22

<210> SEQ ID NO 227
<211> LENGTH: 26
<212> TYPE: DNA
<213> ORGANISM: artificial
<220> FEATURE:
<223> OTHER INFORMATION: methylation independent oligonucleotide primer

<400> SEQUENCE: 227
gttttagatg aagtcgttat agaggt                                        26

<210> SEQ ID NO 228
<211> LENGTH: 24
<212> TYPE: DNA
<213> ORGANISM: artificial
<220> FEATURE:
<223> OTHER INFORMATION: methylation independent oligonucleotide primer

<400> SEQUENCE: 228
```
ccccacacga caactaatcc ctaa                                          24

<210> SEQ ID NO 229
<211> LENGTH: 27
<212> TYPE: DNA
<213> ORGANISM: artificial
<220> FEATURE:
<223> OTHER INFORMATION: methylation independent oligonucleotide primer

<400> SEQUENCE: 229
gcgcgcgttt tatggtttta ggatttt                                       27

<210> SEQ ID NO 230
<211> LENGTH: 23
<212> TYPE: DNA
<213> ORGANISM: artificial
<220> FEATURE:
<223> OTHER INFORMATION: methylation independent oligonucleotide primer

<400> SEQUENCE: 230
ccgaaaccga cttcctccta atc                                           23

<210> SEQ ID NO 231
<211> LENGTH: 24
<212> TYPE: DNA
<213> ORGANISM: artificial
<220> FEATURE:
<223> OTHER INFORMATION: methylation independent oligonucleotide primer

<400> SEQUENCE: 231
gagggtagcg tggggatgat tttt                                          24

<210> SEQ ID NO 232
<211> LENGTH: 27
<212> TYPE: DNA
<213> ORGANISM: artificial
<220> FEATURE:
<223> OTHER INFORMATION: methylation independent oligonucleotide primer

<400> SEQUENCE: 232
ctacaaacgc aacgaatcat aaccaac                                       27

<210> SEQ ID NO 233
<211> LENGTH: 24
<212> TYPE: DNA
<213> ORGANISM: artificial
<220> FEATURE:
<223> OTHER INFORMATION: methylation independent oligonucleotide primer

<400> SEQUENCE: 233
gggcgggttt tgatatagag tagg                                          24

<210> SEQ ID NO 234
<211> LENGTH: 26
<212> TYPE: DNA
<213> ORGANISM: artificial
<220> FEATURE:
<223> OTHER INFORMATION: methylation independent oligonucleotide primer

<400> SEQUENCE: 234
ctacgaaaac aaataaaccc taaccc                                        26

<210> SEQ ID NO 235
<211> LENGTH: 24
<212> TYPE: DNA

<213> ORGANISM: artificial
<220> FEATURE:
<223> OTHER INFORMATION: methylation independent oligonucleotide primer

<400> SEQUENCE: 235
ttcgggttta tttcgtttta gggt                                          24

<210> SEQ ID NO 236
<211> LENGTH: 22
<212> TYPE: DNA
<213> ORGANISM: artificial
<220> FEATURE:
<223> OTHER INFORMATION: methylation independent oligonucleotide primer

<400> SEQUENCE: 236
gcaacacctc gaccataact cc                                            22

<210> SEQ ID NO 237
<211> LENGTH: 31
<212> TYPE: DNA
<213> ORGANISM: artificial
<220> FEATURE:
<223> OTHER INFORMATION: methylation independent oligonucleotide primer

<400> SEQUENCE: 237
gttaggcgtt tttttttaga agtaatttag g                                  31

<210> SEQ ID NO 238
<211> LENGTH: 27
<212> TYPE: DNA
<213> ORGANISM: artificial
<220> FEATURE:
<223> OTHER INFORMATION: methylation independent oligonucleotide primer

<400> SEQUENCE: 238
tacgacttaa aaccccgtac aataacc                                       27

<210> SEQ ID NO 239
<211> LENGTH: 31
<212> TYPE: DNA
<213> ORGANISM: artificial
<220> FEATURE:
<223> OTHER INFORMATION: methylation independent oligonucleotide primer

<400> SEQUENCE: 239
tcgggtttta tagtttttgt atttaggttt t                                  31

<210> SEQ ID NO 240
<211> LENGTH: 22
<212> TYPE: DNA
<213> ORGANISM: artificial
<220> FEATURE:
<223> OTHER INFORMATION: methylation independent oligonucleotide primer

<400> SEQUENCE: 240
cctcccccaa aatccaaact aa                                            22

<210> SEQ ID NO 241
<211> LENGTH: 24
<212> TYPE: DNA
<213> ORGANISM: artificial
<220> FEATURE:
<223> OTHER INFORMATION: methylation independent oligonucleotide primer

<400> SEQUENCE: 241
cggggtttta aaaatgttgg tgtt                                          24

<210> SEQ ID NO 242
<211> LENGTH: 27
<212> TYPE: DNA
<213> ORGANISM: artificial
<220> FEATURE:
<223> OTHER INFORMATION: methylation independent oligonucleotide primer

<400> SEQUENCE: 242 cgaaccccccg acatatctac tattacc                27

<210> SEQ ID NO 243
<211> LENGTH: 22
<212> TYPE: DNA
<213> ORGANISM: artificial
<220> FEATURE:
<223> OTHER INFORMATION: methylation independent oligonucleotide primer

<400> SEQUENCE: 243
cgggggaagt aaatgggta tg                22

<210> SEQ ID NO 244
<211> LENGTH: 22
<212> TYPE: DNA
<213> ORGANISM: artificial
<220> FEATURE:
<223> OTHER INFORMATION: methylation independent oligonucleotide primer

<400> SEQUENCE: 244
cgcccaacct acatccacta aa                22

<210> SEQ ID NO 245
<211> LENGTH: 34
<212> TYPE: DNA
<213> ORGANISM: artificial
<220> FEATURE:
<223> OTHER INFORMATION: methylation independent oligonucleotide primer

<400> SEQUENCE: 245
tcgttatatg atatttttaa tttcgatttt tagt                34

<210> SEQ ID NO 246
<211> LENGTH: 30
<212> TYPE: DNA
<213> ORGANISM: artificial
<220> FEATURE:
<223> OTHER INFORMATION: methylation independent oligonucleotide primer

<400> SEQUENCE: 246
atcttaaatt ccgatctaaa cgaaaataac                30

<210> SEQ ID NO 247
<211> LENGTH: 22
<212> TYPE: DNA
<213> ORGANISM: artificial
<220> FEATURE:
<223> OTHER INFORMATION: methylation independent oligonucleotide primer

<400> SEQUENCE: 247
cgggttggtg gatgattttg ag                22

<210> SEQ ID NO 248
<211> LENGTH: 24
<212> TYPE: DNA
<213> ORGANISM: artificial
<220> FEATURE:

```
<223> OTHER INFORMATION: methylation independent oligonucleotide primer

<400> SEQUENCE: 248
cctcacctcg acctcctaaa acac                                              24

<210> SEQ ID NO 249
<211> LENGTH: 23
<212> TYPE: DNA
<213> ORGANISM: artificial
<220> FEATURE:
<223> OTHER INFORMATION: methylation independent oligonucleotide primer

<400> SEQUENCE: 249
ccacgacgat aaaaaccttta ccc                                              23

<210> SEQ ID NO 250
<211> LENGTH: 29
<212> TYPE: DNA
<213> ORGANISM: artificial
<220> FEATURE:
<223> OTHER INFORMATION: methylation independent oligonucleotide primer

<400> SEQUENCE: 250
gtttaggtta cgttcgagat tagtttttt                                         29

<210> SEQ ID NO 251
<211> LENGTH: 94
<212> TYPE: DNA
<213> ORGANISM: Homo sapiens

<400> SEQUENCE: 251
cgtttgcgac ttggtgagtg tctgggtcgc ctcgctcccg gaagagtgcg gagctctccc       60
tcgggacggt ggcagcctcg agtggtcctg cagg                                   94

<210> SEQ ID NO 252
<211> LENGTH: 94
<212> TYPE: DNA
<213> ORGANISM: Homo sapiens

<400> SEQUENCE: 252
cgtttgcgat ttggtgagtg tttgggtcgt ttcgttttcg gaagagtgcg gagttttttt       60
tcgggacggt ggtagtttcg agtggttttg tagg                                   94

<210> SEQ ID NO 253
<211> LENGTH: 94
<212> TYPE: DNA
<213> ORGANISM: Homo sapiens

<400> SEQUENCE: 253
cgtttgtgat ttggtgagtg tttgggttgt tttgtttttg gaagagtgtg gagttttttt       60
ttgggatggt ggtagttttg agtggttttg tagg                                   94

<210> SEQ ID NO 254
<211> LENGTH: 98
<212> TYPE: DNA
<213> ORGANISM: homo sapiens

<400> SEQUENCE: 254
gggttcggag gggtgtagat agagtcgggc ggcagttttc gagagtagtt attcggattc       60
ggcgtttttt ttgtgtatttg gttaggtgtt tggtcgtt                              98
```

```
<210> SEQ ID NO 255
<211> LENGTH: 180
<212> TYPE: DNA
<213> ORGANISM: homo sapiens

<400> SEQUENCE: 255
ggcggggccc tgtgccccac tgcggagtgc gggtcgggaa gcggagagag aagcagctgt      60
gtaatccgct ggatgcggac cagggcgctc cccattcccg tcgggagccc gccgattggc     120
tgggtgtggg cgcacgtgac cgacatgtgg ctgtattggt gcagcccgcc agggtgtcac     180

<210> SEQ ID NO 256
<211> LENGTH: 180
<212> TYPE: DNA
<213> ORGANISM: homo sapiens

<400> SEQUENCE: 256
ggcggggttt tgtgttttat tgcggagtgc gggtcgggaa gcggagagag aagtagttgt      60
gtaattcgtt ggatgcggat tagggcgttt tttattttcg tcgggagttc gtcgattggt     120
tgggtgtggg cgtacgtgat cgatatgtgg ttgtattggt gtagttcgtt agggtgttat     180

<210> SEQ ID NO 257
<211> LENGTH: 180
<212> TYPE: DNA
<213> ORGANISM: homo sapiens

<400> SEQUENCE: 257
agacttggag gggcggggat gaggagggcg gggaggacga cgagggcgaa gagggtgggt      60
gagagccccg gagcccgagc cgaagggcga gccgcaaacg ctaagtcgct ggccattggt     120
ggacatggcg caggcgcgtt tgctccgacg ggccgaatgt tttggggcag tgttttgagc     180

<210> SEQ ID NO 258
<211> LENGTH: 180
<212> TYPE: DNA
<213> ORGANISM: homo sapiens

<400> SEQUENCE: 258
agatttggag gggcggggat gaggagggcg gggaggacga cgagggcgaa gagggtgggt      60
gagagtttcg gagttcgagt cgaagggcga gtcgtaaacg ttaagtcgtt ggttattggt     120
ggatatggcg taggcgcgtt tgtttcgacg ggtcgaatgt tttggggtag tgttttgagc     180

<210> SEQ ID NO 259
<211> LENGTH: 120
<212> TYPE: DNA
<213> ORGANISM: homo sapiens

<400> SEQUENCE: 259
tggggagaca gaggacgcaa acctaagagg gcacccagag cgccggggaa cgcagcctgg      60
ggacctcgaa gcccctcgaa agcgctcctc tagaggtgac agcaccagat cctggcgaag     120

<210> SEQ ID NO 260
<211> LENGTH: 120
<212> TYPE: DNA
<213> ORGANISM: homo sapiens

<400> SEQUENCE: 260
tggggagata gaggacgtaa atttaagagg gtatttagag cgtcggggaa cgtagtttgg      60
ggatttcgaa gttttttcgaa agcgttttttt tagaggtgat agtattagat tttggcgaag    120
```

<210> SEQ ID NO 261
<211> LENGTH: 180
<212> TYPE: DNA
<213> ORGANISM: homo sapiens

<400> SEQUENCE: 261
cgtattctga gaggctgctg cttagcggta gccccttggt ttccgtggca acggaaaagc    60
gcgggaatta cagataaatt aaaactgcga ctgcgcggcg tgagctcgct gagacttcct   120
ggacggggga caggctgtgg ggtttctcag ataactgggc ccctgcgctc aggaggcctt   180

<210> SEQ ID NO 262
<211> LENGTH: 180
<212> TYPE: DNA
<213> ORGANISM: homo sapiens

<400> SEQUENCE: 262
cgtattttga gaggttgttg tttagcggta gttttttggt tttcgtggta acggaaaagc    60
gcgggaatta tagataaatt aaaattgcga ttgcgcggcg tgagttcgtt gagattttt    120 ggacggggga taggttgtgg ggttttttag ataattgggt ttttgcgttt aggaggtttt   180

<210> SEQ ID NO 263
<211> LENGTH: 120
<212> TYPE: DNA
<213> ORGANISM: homo sapiens

<400> SEQUENCE: 263 gggggggtgga ccgcctaaga gggcgtgcgc tcccgacatg ccccgcggcg cgccattaac    60
cgccagattt gaatcgcggg acccgttggc agaggtggcg gcggcggcat gggtgccccg   120

<210> SEQ ID NO 264
<211> LENGTH: 120
<212> TYPE: DNA
<213> ORGANISM: homo sapiens

<400> SEQUENCE: 264 gggggggtgga tcgtttaaga gggcgtgcgt tttcgatatg tttcgcggcg cgttattaat    60
cgttagattt gaatcgcggg attcgttggt agaggtggcg gcggcggtat gggtgtttcg   120

<210> SEQ ID NO 265
<211> LENGTH: 180
<212> TYPE: DNA
<213> ORGANISM: homo sapiens

<400> SEQUENCE: 265
cacccacgga gcctccgggg ctggtgagga gcgggtaggg ggcggggtg cggtcctgca     60 ggggccggga atggaggccg cggtgccgac ccgaagccga cgggagcctg ggcctcggc    120 gcggggcggc ctggggtgcg aaaggccggc cccgggggct tcccgcgcca gcatggagct   180

<210> SEQ ID NO 266
<211> LENGTH: 180
<212> TYPE: DNA
<213> ORGANISM: homo sapiens

<400> SEQUENCE: 266
tatttacgga gttttcgggg ttggtgagga gcgggtaggg ggcggggtg cggttttgta     60 ggggtcggga atggaggtcg cggtgtcgat tcgaagtcga cggagtttg gggtttcggc    120 gcggggcggt ttggggtgcg aaaggtcggt ttcgggggtt tttcgcgtta gtatggagtt   180

<210> SEQ ID NO 267
<211> LENGTH: 180
<212> TYPE: DNA
<213> ORGANISM: homo sapiens

<400> SEQUENCE: 267
gatggcgagc ttcacgctcg ggaacagtca gtaatcggaa ggggaagtgg acagggaac    60 ttcaagaggc gagcctgcca cgcgggaagc gcccgaactt gcgggtctcc atgaatgcag   120
agggcgccgg aagggggggg catccggccg cgaccctctc tgcccctccc attcgctgcc   180

<210> SEQ ID NO 268
<211> LENGTH: 180
<212> TYPE: DNA
<213> ORGANISM: homo sapiens

<400> SEQUENCE: 268
gatggcgagt tttacgttcg ggaatagtta gtaatcggaa ggggaagtgg ataggggaat    60
tttaagaggc gagtttgtta cgcgggaagc gttcgaattt gcgggttttt atgaatgtag   120
agggcgtcgg aagggggggg tattcggtcg cgattttttt tgtttttttt attcgttgtt   180

<210> SEQ ID NO 269
<211> LENGTH: 120
<212> TYPE: DNA
<213> ORGANISM: homo sapiens

<400> SEQUENCE: 269
ccctggggag gggtccgcgc tgctgattgg ctgtggccgg caggtgaacc ctcagccaat    60
cagcggtacg gggggcggtg cctccggggc tcacctggct gcagccacgc acccctctc   120

<210> SEQ ID NO 270
<211> LENGTH: 120
<212> TYPE: DNA
<213> ORGANISM: homo sapiens

<400> SEQUENCE: 270
ttttggggag gggttcgcgt tgttgattgg ttgtggtcgg taggtgaatt tttagttaat    60
tagcggtacg gggggcggtg tttttcgggt ttatttggtt gtagttacgt attttttttt   120

<210> SEQ ID NO 271
<211> LENGTH: 180
<212> TYPE: DNA
<213> ORGANISM: homo sapiens

<400> SEQUENCE: 271
gaaaaccctc actcgcggcg ggccgcacgc gcgccgaatc cggagggtca ccaagaacct    60
gcgcaccatg ttctcgccgc ctccagggcc gagctcggca gccgctgcgc cgccctttgg   120
caccagaggt gagcagcgcc actcctgccc ccttaactgc agactgggac ccacgcaccg   180

<210> SEQ ID NO 272
<211> LENGTH: 180
<212> TYPE: DNA
<213> ORGANISM: homo sapiens

<400> SEQUENCE: 272
gaaaattttt attcgcggcg ggtcgtacgc gcgtcgaatt cggagggtta ttaagaattt    60
gcgtattatg ttttcgtcgt ttttagggtc gagttcggta gtcgttgcgt cgttttttgg   120
tattagaggt gagtagcgtt attttgttt ttttaattgt agattgggat ttacgtatcg    180

<210> SEQ ID NO 273
<211> LENGTH: 120
<212> TYPE: DNA
<213> ORGANISM: homo sapiens

<400> SEQUENCE: 273
gctcggcact cacggctctg agggctccga cggcactgac ggccatggcg cgttcgaacc    60
tcccgctggc gctgggcctg gccctggtcg cattctgcct cctggcgctg ccacgcgacg    120

<210> SEQ ID NO 274
<211> LENGTH: 120
<212> TYPE: DNA
<213> ORGANISM: homo sapiens

<400> SEQUENCE: 274
gttcggtatt tacggttttg agggtttcga cggtattgac ggttatggcg cgttcgaatt    60
tttcgttggc gttgggtttg gttttggtcg tattttgttt tttggcgttg ttacgcgacg    120

<210> SEQ ID NO 275
<211> LENGTH: 120
<212> TYPE: DNA
<213> ORGANISM: homo sapiens

<400> SEQUENCE: 275
ggagcgcgga gctgggagga gcagcgagcg ccgcgcagaa cccgcagcgc cggcctggca    60
gggcagctcg gaggtgggtg gccgcgccg ccagcccgct tgcagggtcc ccattggccg    120

<210> SEQ ID NO 276
<211> LENGTH: 120
<212> TYPE: DNA
<213> ORGANISM: homo sapiens

<400> SEQUENCE: 276
ggagcgcgga gttgggagga gtagcgagcg tcgcgtagaa ttcgtagcgt cggtttggta    60
gggtagttcg gaggtgggtg ggtcgcgtcg ttagttcgtt tgtagggttt ttattggtcg    120

<210> SEQ ID NO 277
<211> LENGTH: 120
<212> TYPE: DNA
<213> ORGANISM: homo sapiens

<400> SEQUENCE: 277
cccgggagcc caggagctgg cggagggcgt tcgtcctggg actgcacttg ctcccgtcgg    60
gtcgcccggc ttcaccggac ccgcaggctc ccggggcagg gccggggcca gagctcgcgt    120

<210> SEQ ID NO 278
<211> LENGTH: 120
<212> TYPE: DNA
<213> ORGANISM: homo sapiens

<400> SEQUENCE: 278
ttcgggagtt taggagttgg cggagggcgt tcgttttggg attgtatttg ttttcgtcgg    60
gtcgttcggt tttatcggat tcgtaggttt tcggggtagg gtcggggtta gagttcgcgt    120

<210> SEQ ID NO 279
<211> LENGTH: 120
<212> TYPE: DNA
<213> ORGANISM: homo sapiens

<400> SEQUENCE: 279

```
gcaccgcaga ccgccggcgg gcaaggcggg ccaggctctc ttggagtgtc tcctcatcgg      60
cgtcccggac gcccgggccg ggaaagagtt gctgcaccag gtggtaacga gctgcatccc     120
```

<210> SEQ ID NO 280
<211> LENGTH: 120
<212> TYPE: DNA
<213> ORGANISM: homo sapiens

<400> SEQUENCE: 280

```
gtatcgtaga tcgtcggcgg gtaaggcggg ttaggttttt ttggagtgtt tttttatcgg      60
cgtttcggac gttcgggtcg ggaaagagtt gttgtattag gtggtaacga gttgtatttt     120
```

<210> SEQ ID NO 281
<211> LENGTH: 120
<212> TYPE: DNA
<213> ORGANISM: homo sapiens

<400> SEQUENCE: 281

```
cctgatctgc cagcagcatg cgcagggccg cgcagcggcc tgcggggagg gagaagtacg      60
agatgtgggg accgggccga ctccgcctcg cagcaacccg gggaggggtc aggagtgcag     120
```

<210> SEQ ID NO 282
<211> LENGTH: 120
<212> TYPE: DNA
<213> ORGANISM: homo sapiens

<400> SEQUENCE: 282

```
tttgatttgt tagtagtatg cgtagggtcg cgtagcggtt tgcggggagg gagaagtacg      60
agatgtgggg atcgggtcga tttcgtttcg tagtaattcg gggaggggtt aggagtgtag     120
```

<210> SEQ ID NO 283
<211> LENGTH: 180
<212> TYPE: DNA
<213> ORGANISM: homo sapiens

<400> SEQUENCE: 283

```
cctggggcgg ggccaggcgt cggtggccgt gactggagac tgttactgag ggcggcccgg      60
gcagtaagca gtctagagcc aaggtgccgg cgcgctgtcc gggcggggtg ccccggtcgc     120
cccggctgcc ccggctgggg gctctgctgc tccgcctccc ctgcgtctcc cgccctgccc     180
```

<210> SEQ ID NO 284
<211> LENGTH: 180
<212> TYPE: DNA
<213> ORGANISM: homo sapiens

<400> SEQUENCE: 284

```
tttggggcgg ggttaggcgt cggtggtcgt gattggagat tgttattgag ggcggttcgg      60
gtagtaagta gtttagagtt aaggtgtcgg cgcgttgttc gggcggggtg tttcggtcgt     120
ttcggttgtt tcggttgggg gttttgttgt ttcgtttttt ttgcgttttt cgttttgttt     180
```

<210> SEQ ID NO 285
<211> LENGTH: 120
<212> TYPE: DNA
<213> ORGANISM: homo sapiens

<400> SEQUENCE: 285

```
ggcgaggctg aaggacctg ggatccacga tcggcgcagg cagcggcggg ggcgcagcgg       60
gcgccgaggc ctcaggcccc accgtgcgcg ccaggagccc ggggcgctca ccggagctgc     120
```

<210> SEQ ID NO 286
<211> LENGTH: 120
<212> TYPE: DNA
<213> ORGANISM: homo sapiens

<400> SEQUENCE: 286

```
ggcgaggttg aaggatttg ggatttacga tcggcgtagg tagcggcggg ggcgtagcgg       60
gcgtcgaggt tttaggtttt atcgtgcgcg ttaggagttc ggggcgttta tcggagttgt     120
```

<210> SEQ ID NO 287
<211> LENGTH: 180
<212> TYPE: DNA
<213> ORGANISM: homo sapiens

<400> SEQUENCE: 287

```
ccgacgaagc cgctccaggg ctgctctcag aggacgcgcg gcaggcaaag agaatgaacc       60
tgagcgtcca cgaaacgtcc tgcacggctc ccgggagctg ggagaaacag gtgcctttct     120
ccgacgtccg cgggcgacgc ctgccgcacc ttgcccgctg ccgcgcccct cccgggcacc     180
```

<210> SEQ ID NO 288
<211> LENGTH: 180
<212> TYPE: DNA
<213> ORGANISM: homo sapiens

<400> SEQUENCE: 288

```
tcgacgaagt cgttttaggg ttgttttag aggacgcgcg gtaggtaaag agaatgaatt       60
tgagcgttta cgaaacgttt tgtacggttt tcgggagttg ggagaaatag gtgttttttt     120
tcgacgttcg cgggcgacgt ttgtcgtatt ttgttcgttg tcgcgttttt ttcgggtatt     180
```

<210> SEQ ID NO 289
<211> LENGTH: 180
<212> TYPE: DNA
<213> ORGANISM: homo sapiens

<400> SEQUENCE: 289

```
cgtgagcaaa ctcgcagagt tggcgcggca gccggccggg agacgccgag cagggcctgg       60
ccgcccgcag cccgggagga acggcgcccc cagggtccgg tggcctctga ggggctgact     120
ggcccgtgag ccggcggcgc ggccgcgggg aacggggtgg gaaccgcgcg gcagtgggtg     180
```

<210> SEQ ID NO 290
<211> LENGTH: 180
<212> TYPE: DNA
<213> ORGANISM: homo sapiens

<400> SEQUENCE: 290

```
cgtgagtaaa ttcgtagagt tggcgcggta gtcggtcggg agacgtcgag tagggtttgg       60
tcgttcgtag ttcgggagga acggcgtttt tagggttcgg tggttttga ggggttgatt     120 ggttcgtgag tcggcggcgc ggtcgcgggg aacggggtgg gaatcgcgcg gtagtgggtg     180
```

<210> SEQ ID NO 291
<211> LENGTH: 180
<212> TYPE: DNA
<213> ORGANISM: homo sapiens

<400> SEQUENCE: 291

```
ttatccagcg gccagctaat gctatcaaag agatgattga gaactggtac ggagggagtc    60
gagccgggct cacttaaggg ctacgactta acgggccgcg tcactcaatg gcgcggacac   120
gcctctttgc ccgggcagag gcatgtacag cgcatgccca caacggcgga ggccgccggg   180
```

<210> SEQ ID NO 292
<211> LENGTH: 180
<212> TYPE: DNA
<213> ORGANISM: homo sapiens

<400> SEQUENCE: 292

```
ttatttagcg gttagttaat gttattaaag agatgattga gaattggtac ggagggagtc    60
gagtcgggtt tatttaaggg ttacgattta acgggtcgcg ttatttaatg gcgcggatac   120
gtttttttgt tcgggtagag gtatgtatag cgtatgttta taacggcgga ggtcgtcggg   180
```

<210> SEQ ID NO 293
<211> LENGTH: 120
<212> TYPE: DNA
<213> ORGANISM: homo sapiens

<400> SEQUENCE: 293

```
aactggaccg gcggcagaag ccgtggaaga gctgggctgc ctggcgccgg aggagggtgc    60
gcgcggcggc tccgggccgc gaggagcgct gcgcctgtgg ggtgtgcagg cgcaagtgtg   120
```

<210> SEQ ID NO 294
<211> LENGTH: 120
<212> TYPE: DNA
<213> ORGANISM: homo sapiens

<400> SEQUENCE: 294

```
aattggatcg gcggtagaag tcgtggaaga gttgggttgt ttggcgtcgg aggagggtgc    60
gcgcggcggt ttcgggtcgc gaggagcgtt gcgtttgtgg ggtgtgtagg cgtaagtgtg   120
```

<210> SEQ ID NO 295
<211> LENGTH: 180
<212> TYPE: DNA
<213> ORGANISM: homo sapiens

<400> SEQUENCE: 295

```
gggtctattc tttgccaaag gggggaccag aattccccca tgcgagctgt ttgaggactg    60
ggatgccgag aacgcgagcg atccgagcag ggtttgtctg ggcaccgtcg gggtaggatc   120
cggaacgcat tcggaaggct ttttgcaagc atttacttgg aaggagaact tgggatcttt   180
```

<210> SEQ ID NO 296
<211> LENGTH: 180
<212> TYPE: DNA
<213> ORGANISM: homo sapiens

<400> SEQUENCE: 296

```
gggtttattt tttgttaaag gggggattag aattttttta tgcgagttgt ttgaggattg    60
ggatgtcgag aacgcgagcg attcgagtag ggtttgtttg ggtatcgtcg gggtaggatt   120
cggaacgtat tcggaaggtt ttttgtaagt atttatttgg aaggagaatt tgggattttt   180
```

<210> SEQ ID NO 297
<211> LENGTH: 180
<212> TYPE: DNA
<213> ORGANISM: homo sapiens

<400> SEQUENCE: 297
aggcgcgcgg ggccactact cacgcgcgca ctgcaggcct ttgcgcacga cgccccagat       60
gaagtcgcca cagaggtcgc accacgtgtg cgtggcgggc cccgcgggct ggaagcggtg      120
gccacggcca gggaccagct gccgtgtggg gttgcacgcg gtgccccgcg cgatgcgcag      180

<210> SEQ ID NO 298
<211> LENGTH: 180
<212> TYPE: DNA
<213> ORGANISM: homo sapiens

<400> SEQUENCE: 298
aggcgcgcgg ggttattatt tacgcgcgta ttgtaggttt ttgcgtacga cgttttagat       60
gaagtcgtta tagaggtcgt attacgtgtg cgtggcgggt ttcgcgggtt ggaagcggtg      120
gttacggtta gggattagtt gtcgtgtggg gttgtacgcg gtgtttcgcg cgatgcgtag      180

<210> SEQ ID NO 299
<211> LENGTH: 120
<212> TYPE: DNA
<213> ORGANISM: homo sapiens

<400> SEQUENCE: 299
caggttctcc agcgcatcca ggatggcgtc gcgcgcgcgc cccatggctc caggatcccc       60
ggccgctgcc gccgctcacc ccgctgcagc cgccgaccag gaggaagtcg gctccggggc      120

<210> SEQ ID NO 300
<211> LENGTH: 120
<212> TYPE: DNA
<213> ORGANISM: homo sapiens

<400> SEQUENCE: 300
taggtttttt agcgtattta ggatggcgtc gcgcgcgcgt tttatggttt taggattttc       60
ggtcgttgtc gtcgtttatt tcgttgtagt cgtcgattag gaggaagtcg gtttcggggc      120

<210> SEQ ID NO 301
<211> LENGTH: 120
<212> TYPE: DNA
<213> ORGANISM: homo sapiens

<400> SEQUENCE: 301
ttgctcagct tgtccgaggg cagcgtgggg atgatcttcc gcagcgcggc gaacgcctcg       60
ttcagcgact gggtgcgctg gcgctcccgc acgttggcca tgacccgctg cgtctgcagc      120

<210> SEQ ID NO 302
<211> LENGTH: 120
<212> TYPE: DNA
<213> ORGANISM: homo sapiens

<400> SEQUENCE: 302
ttgtttagtt tgttcgaggg tagcgtgggg atgattttc gtagcgcggc gaacgtttcg       60
tttagcgatt gggtgcgttg gcgttttcgt acgttggtta tgattcgttg cgtttgtagt      120

<210> SEQ ID NO 303
<211> LENGTH: 180
<212> TYPE: DNA
<213> ORGANISM: homo sapiens

<400> SEQUENCE: 303
gagcgctgca agacagggga gggagccggg cgggagaggg aggggcggcg ccggggcggg       60

```
cccctgatata gagcaggcgc cgcgggtcgc agcacagtgc ggagaccgca gccccggagc    120
ccggggcagg gtccacctgt ccccgcagcg ccggctcgcg ccctcctgcc gcagccaccg    180

<210> SEQ ID NO 304
<211> LENGTH: 180
<212> TYPE: DNA
<213> ORGANISM: homo sapiens

<400> SEQUENCE: 304
gagcgttgta agatagggga gggagtcggg cgggagaggg aggggcggcg tcggggcggg     60
ttttgatata gagtaggcgt cgcgggtcgt agtatagtgc ggagatcgta gtttcggagt    120
tcgggttagg gtttatttgt tttcgtagcg tcggttcgcg ttttttttgtc gtagttatcg    180

<210> SEQ ID NO 305
<211> LENGTH: 175
<212> TYPE: DNA
<213> ORGANISM: homo sapiens

<400> SEQUENCE: 305
tcggggcggc gggcggcgcg ggccgggagg gggcgcctcg ggctcacccc gccccagggc     60
cgccgggcgg aaggcggagg ccgagaccag acgcggagcc atggccgagg tgttgcggac    120
gctggccggt gagtgcaggc ctcggccccg ggtgcccgcg agggagccgc taccg         175

<210> SEQ ID NO 306
<211> LENGTH: 175
<212> TYPE: DNA
<213> ORGANISM: homo sapiens

<400> SEQUENCE: 306
tcggggcggc gggcggcgcg ggtcgggagg gggcgtttcg ggtttatttc gttttagggt     60
cgtcgggcgg aaggtggagg tcgagattag acgcggagtt atggtcgagg tgttgcggac    120
gttggtcggt gagtgtaggt ttcggttttcg ggtgttcgcg agggagtcgt tatcg         175

<210> SEQ ID NO 307
<211> LENGTH: 180
<212> TYPE: DNA
<213> ORGANISM: homo sapiens

<400> SEQUENCE: 307
tgcggccaga gcggctttga gctcggctgc gtccgcgcta ggcgcttttt cccagaagca     60
atccaggcgc gcccgctggt tcttgagcgc caggaaaagc ccggagctaa cgaccggccg    120
ctcggccact gcacggggcc ccaagccgca gaaggacgac gggagggtaa tgaagctgag    180

<210> SEQ ID NO 308
<211> LENGTH: 180
<212> TYPE: DNA
<213> ORGANISM: homo sapiens

<400> SEQUENCE: 308
tgcggttaga gcggttttga gttcggttgc gttcgcgtta ggcgtttttt tttagaagta     60
atttaggcgc gttcgttggt ttttgagcgt taggaaaagt tcgagttaa cgatcggtcg    120 ttcggttatt gtacggggtt ttaagtcgta gaaggacgac gggagggtaa tgaagttgag    180

<210> SEQ ID NO 309
<211> LENGTH: 87
<212> TYPE: DNA
```

<213> ORGANISM: homo sapiens

<400> SEQUENCE: 309

```
tcgggcccca cagtccctgc acccaggttt ccattgcgcg gctctcctca gctccttccc    60
gccgcccagt ctggatcctg ggggagg                                        87
```

<210> SEQ ID NO 310
<211> LENGTH: 87
<212> TYPE: DNA
<213> ORGANISM: homo sapiens

<400> SEQUENCE: 310

```
tcgggtttta tagtttttgt atttaggttt ttattgcgcg gttttttta gttttttttc    60
gtcgtttagt ttggattttg ggggagg                                        87
```

<210> SEQ ID NO 311
<211> LENGTH: 332
<212> TYPE: DNA
<213> ORGANISM: homo sapiens

<400> SEQUENCE: 311

```
cggggcttta aaatgttgg tgcccaccac ctccccggaa cagggcccgc tctacctcgg     60
tcggggagcg cggacctca gcgttccctt aacgccaccg tccgcgggtc cgctttgcgc   120
aggcgcggcg cccccactca gtacccgctc cgggcgtggc atggtgcgca ggcgcgatgt   180
cccccactgc agccccgctc gactccggcg tggtgcgcag gcgcggtatc cccctcccc    240
cgccagctcg accccggtgt ggtgcgcagg cgcagtctgc gcaggactg gcgggactgc   300
gcggcggcaa cagcagacat gtcgggggtc cg                                 332
```

<210> SEQ ID NO 312
<211> LENGTH: 332
<212> TYPE: DNA
<213> ORGANISM: homo sapiens

<400> SEQUENCE: 312

```
cggggtttta aaatgttgg tgtttattat tttttcggaa tagggttcgt tttatttcgg    60
tcggggagcg cggattttta gcgttttttt aacgttatcg ttcgcgggtt cgttttgcgt   120
aggcgcggcg tttttattta gtattcgttt cgggcgtggt atggtgcgta ggcgcgatgt   180
tttttattgt agtttcgttc gatttcggcg tggtgcgtag gcgcggtatt ttttttttt    240
cgttagttcg atttcggtgt ggtgcgtagg cgtagtttgc gtagggattg gcgggattgc   300
gcggcggtaa tagtagatat gtcgggggtt cg                                 332
```

<210> SEQ ID NO 313
<211> LENGTH: 157
<212> TYPE: DNA
<213> ORGANISM: homo sapiens

<400> SEQUENCE: 313

```
cgggggaagc caaatgggca tgcgccgcta ctgcgctatt gcgcacgctc gctgtgcttg    60
ccccgccttc cctccgccca cccgggaaac cggaagccgc ctcccacttg gttgctcgta   120
cgcggctagt gggtcctcag tggatgtagg ctgggcg                            157
```

<210> SEQ ID NO 314
<211> LENGTH: 157
<212> TYPE: DNA
<213> ORGANISM: homo sapiens

<400> SEQUENCE: 314
cgggggaagt taaatgggta tgcgtcgtta ttgcgttatt gcgtacgttc gttgtgtttg    60
tttcgttttt ttttcgttta ttcgggaaat cggaagtcgt tttttatttg gttgttcgta   120
cgcggttagt gggttttttag tggatgtagg ttgggcg                           157

<210> SEQ ID NO 315
<211> LENGTH: 102
<212> TYPE: DNA
<213> ORGANISM: homo sapiens

<400> SEQUENCE: 315
tcgtcacatg acaccccccaa ccccgacccc cagccggcgc gcctccgccc tcgggtggcg    60
gggccgcctg gcgtcacttc cgtccagacc ggaacccaag at                      102

<210> SEQ ID NO 316
<211> LENGTH: 102
<212> TYPE: DNA
<213> ORGANISM: homo sapiens

<400> SEQUENCE: 316
tcgttatatg atattttaa tttcgatttt tagtcggcgc gttttcgttt tcgggtggcg    60 ggtcgtttg gcgttatttt cgtttagatc ggaatttaag at                      102

<210> SEQ ID NO 317
<211> LENGTH: 94
<212> TYPE: DNA
<213> ORGANISM: homo sapiens

<400> SEQUENCE: 317
cgggttggtg gatgaccttg agccctcagg aacgagatgg cggttctctg gaggctgagt    60
gccgtttgcg gtgccctagg aggccgaggt gagg                               94

<210> SEQ ID NO 318
<211> LENGTH: 94
<212> TYPE: DNA
<213> ORGANISM: homo sapiens

<400> SEQUENCE: 318
cgggttggtg gatgattttg agttttttagg aacgagatgg cggttttttg gaggttgagt    60
gtcgtttgcg gtgttttagg aggtcgaggt gagg                               94

<210> SEQ ID NO 319
<211> LENGTH: 180
<212> TYPE: DNA
<213> ORGANISM: homo sapiens

<400> SEQUENCE: 319
cgcgtgagga cagcggccgc acccgacac tgctgtgggc cctcggtgtg gaggcctgtg    60
ggcgtccagg ccacgcccga gaccagcccc tccgccggcg ccgctgcagc gaccctcgaa   120
cccgggcaag gtctccaccg ccgtggcacc gggtgcggga ggcgttttcc cccctcccag   180

<210> SEQ ID NO 320
<211> LENGTH: 180
<212> TYPE: DNA
<213> ORGANISM: homo sapiens

<400> SEQUENCE: 320

```
-continued cgcgtgagga tagcggtcgt atttcgatat tgttgtgggt tttcggtgtg gaggtttgtg      60
ggcgtttagg ttacgttcga gattagtttt ttcgtcggcg tcgttgtagc gattttcgaa     120
ttcgggtaag gtttttatcg tcgtggtatc gggtgcggga ggcgtttttt ttttttttag    180
```

METHOD FOR DETECTING METHYLATION STATUS BY USING METHYLATION-INDEPENDENT PRIMERS

All patent and non-patent references cited in the application, or in the present application, are also hereby incorporated by reference in their entirety.

FIELD OF INVENTION

The present invention relates to a method of detecting methylated CpG-containing nucleic acids by nucleic acid amplification and melting curve analysis of amplification products.

BACKGROUND OF INVENTION

The modification of DNA in eukaryotes by methylation has regulatory effects on gene regulation.

Cancer treatments, in general, have a higher rate of success if the cancer is diagnosed early and treatment is started earlier in the disease process. The relationship between improved prognosis and stage of disease at diagnosis hold across all forms of cancer for the most part. Therefore, there is an important need to develop early assays of general tumorigenesis through marker assays that measure general tumorigenesis without regard to the tissue source or cell type that is the source of a primary tumor. Moreover, there is a need to address distinct genetic alteration patterns that can serve as a platform associated with general tumorigenesis for early detection and prognostic monitoring of many forms of cancer.
Importance of DNA Methylation Methylation of DNA is a mechanism for changing the sequence of DNA without altering its coding function. DNA methylation is a heritable, reversible and epigenetic change. DNA methylation harbours the potential to alter gene expression which in turn affects developmental and genetic processes. The methylation reaction involves flipping a target cytosine out of an intact double helix thereby allowing the transfer of a methyl group from S-adenosylmethionine in a cleft of the enzyme DNA (cytosine-5)-methyltransferase (Klimasauskas et al., Cell 76:357-369, 1994) to form 5-methylcytosine (5-mCyt). This enzymatic conversion is the only epigenetic modification of DNA known to exist in vertebrates and is essential for normal embryonic development (Bird, Cell 70:5-8, 1992; Laird and Jaenisch, Human Mol. Genet. 3:1487-1495, 1994; and Bestor and Jaenisch, Cell 69:915-926, 1992).

CpG-rich sequences are known as CpG islands (1). CpG islands are distributed across the human genome and often span the promoter region as well as the first exon of protein coding genes. Methylation of individual promoter region CpG islands usually turns off or reduce the rate of transcription by recruiting histone deacetylases, which supports the formation of inactive chromatin (2). CpG islands are typically between 0.2 to about 1 kb in length and are located upstream of many housekeeping and tissue-specific genes, but may also extend into gene coding regions. Therefore, it is the methylation of cytosine residues within CpG islands in somatic tissues, which is believed to affect gene function by altering transcription (Cedar, Cell 53:3-4, 1988).

Abnormal methylation of CpG islands associated with tumor suppressor genes may also cause decreased gene expression. Increased methylation of such regions may lead to progressive reduction of normal gene expression giving abnormal cells a growth advantage (i.e., a malignancy).

Methylation promoter regions, particularly in tumour suppressor genes, and genes involved in apoptosis and DNA repair, is one of the hallmarks of cancer (2). Changes in the methylation status of these genes are an early event in cancer and continue throughout the different stages of the cancer. Specifically, distinct tumour types often have characteristic patterns of methylation, which can be used as markers for early detection and/or monitoring the progression of carcinogenesis (3, 4). For therapeutic purposes, the methylation of certain genes, particularly DNA repair genes, can cause sensitivity to specific chemotherapeutics and methylation of those genes can thereby act as a predictive marker if those chemotherapeutic agents are used (5).

A number of current methodologies for methylation studies already exist (9). Sequencing of bisulphite-treated DNA is the gold standard for methylation studies as it reveals directly the status of each CpG dinucleotide. The technique is, however, both time consuming and cost inefficient, and therefore not immediately applicable for large scale analysis such as screening programmes.

Another technique is the methylation specific PCR (MSP) (21). U.S. Pat. No. 5,786,146 discloses a method of methylation specific PCR (MSP) for identifying DNA methylation patterns in a CpG containing nucleic acid. The method uses agents to modify unmethylated cytosine in the nucleic acid. CpG specific oligonucleotide primers are used to distinguish between modified methylated and unmethylated nucleic acid. The identification of the methylated nucleic acid is based on the presence or absence of amplification product resulting from the amplification and distinguishing modified methylated and non-methylated nucleic acids. However, methylation-specific PCR (MSP) is prone to false positive results and may result in overestimation of the number of methylated samples. Furthermore, MSP mainly offers a qualitative result of the methylation status of the target nucleic acid. The results are not easily quantified.

An alternative methodology for determination of methylation status is methylation-sensitive melting curve analysis (MS-MCA) or high resolution melting curve analysis (HRMS-MCA), which is rapid and relatively inexpensive (27). MS-MCA is a reliable technique, and the results do not need to be verified by other techniques, such as is required for example for positive MSP results. The MS-MCA technique is based on the fact that the melting temperature of methylated and unmethylated alleles are different after modification of unmethylated cytosine and amplification, which converts methylated C:G base pairs to A:T base pairs with a lower melting temperature. The standard protocol for determination of methylation status MS-MCA stipulates that the oligonucleotide primers used to amplify the target nucleic acid are devoid of CpG dinucleotides to ensure that the primers does not discriminate between methylated an unmethylated target alleles. This constraint limits the primer binding sites to regions of the template without CpG dinucleotides, which can be very difficult or impossible to find within a CpG cluster in the region of interest. Furthermore, the unmethylated and methylated alleles are not equally efficient amplified. There is a significant bias towards the unmethylated allele in the PCR amplification (23).

Currently, no methylation detection method has been established for reliable, fast and cost-effective locus specific methylation testing that is readily applicable for both research and diagnostic settings. The research-based methods have various limitations and pitfalls and contradictory results can be obtained using different protocols, therefore none of them have found ready applicability in diagnostics (9).

A new more reliable method for promoter methylation analyses in clinical samples is needed.

The present invention offers a method for the determination of methylation status of a CpG-containing nucleic acid by nucleic acid amplification employing a novel design of primers, methylation-independent oligonucleotide primers, that allows for the use of only one set of primers to detect both alleles of a CpG-containing nucleic acid after it has been subjected to C to T conversion by conventional techniques.

SUMMARY OF INVENTION

The present invention relates to methods and compositions for detection of methylated CpG-containing nucleic acids by nucleic acid amplification and subsequent analysis of amplification products.

In one aspect, the present invention relates to a method for detecting methylation status of a CpG-containing nucleic acid in a sample comprising the steps of a) modifying said CpG-containing nucleic acid using an agent which modifies at least one unmethylated cytosine in said methylated CpG-containing nucleic acid, and b) amplifying said CpG-containing nucleic acid by means of at least one methylation-independent oligonucleotide primer.

Another aspect of the present invention relates to a kit for the detection of methylation status of a CpG-containing nucleic acid in a sample, said kit comprising at least one methylation-independent oligonucleotide primer, which comprises at least one CpG dinucleotide.

In a third aspect, the present invention relates to a use of at least one methylation-independent oligonucleotide primer for detecting methylation status of a CpG-containing nucleic acid.

In all aspects of the present invention, embodiments of the methylation-independent oligonucleotide primer comprise primers which comprise at least one CpG dinucleotide, preferably in the 5' end.

DESCRIPTION OF DRAWINGS

The patent or application file contains at least one drawing executed in color. Copies of this patent or patent application publication with color drawings will be provided by the Office upon request and payment of the necessary fee.

The melting peaks were obtained by plotting the negative derivative of fluorescence (−dF/dT) over temperature versus temperature (T). (A) The melting profiles for the PCR product performed with primers designed according to Reference 6. The melting profiles after amplification with the redesigned primers according to the present invention containing one CpG dinucleotide each at Ta (B) 62° C. and (C) 69° C.

FIG. 2. The promoter sequence of PPP3CC (NM_005605) spanning 22,355,033-22,355,131 bp on chromosome 8p21.3. F1, R1 and F2, R2 are the primer sets used in the methylation sensitive melting curve analysis (MS-MCA) experiments. From Genome Browser, May 2004, UCSC.

Figure 3:
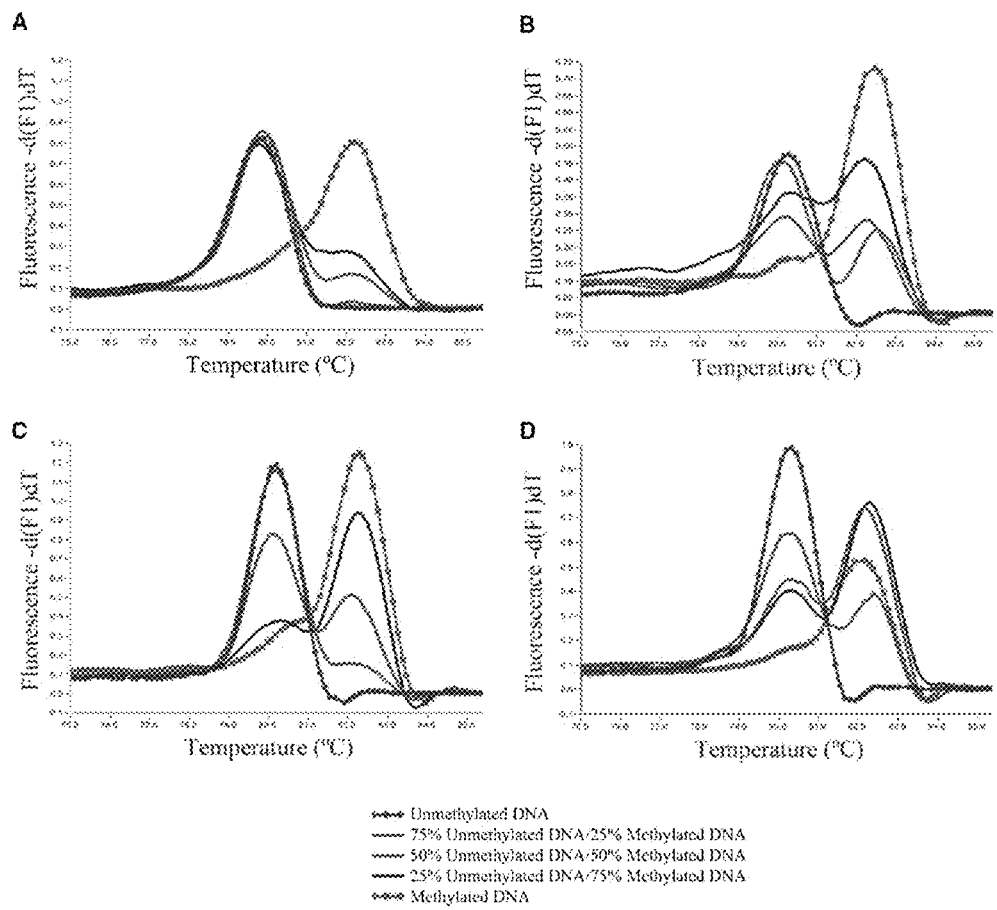

FIG. 3. Annealing temperature (Ta) dependent amplification of methylated and unmethylated variants of the sequence. Melting profiles of the PCR products amplified from the promoters of two putative tumor suppressor genes. Panels A and B sequence one amplified at Ta 61° or 68° C., respectively, and panels C and D sequence two amplified at Ta 60° and 64° C., respectively.

Figure 4:
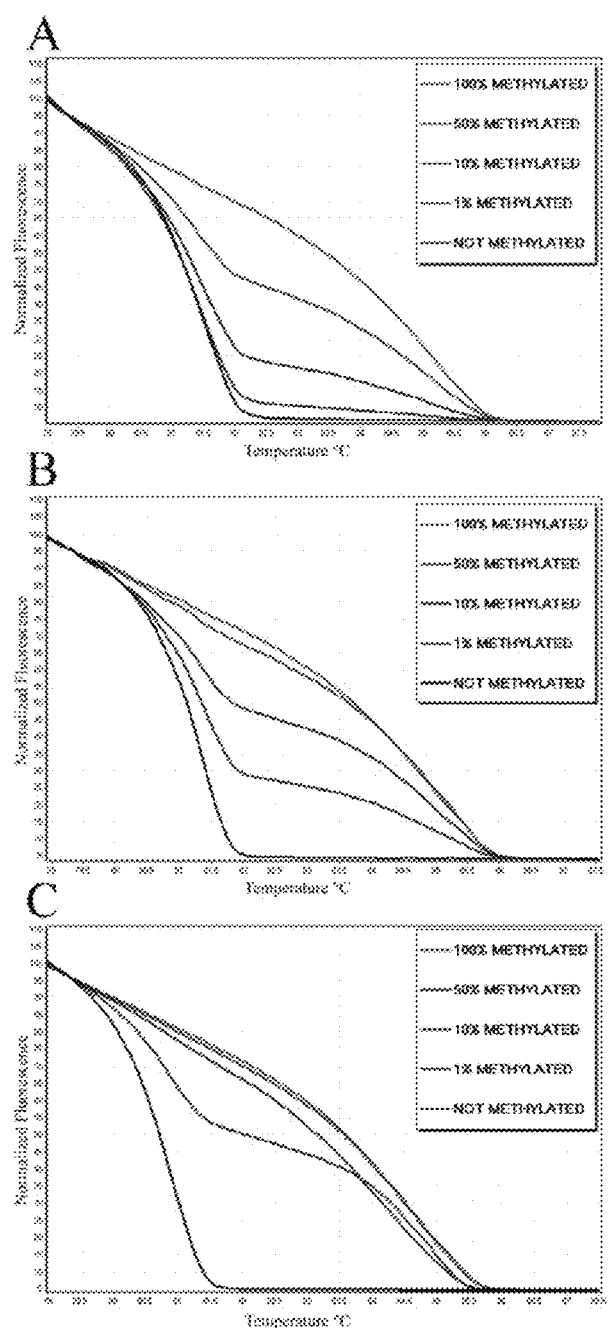

FIG. 4. The effect of annealing temperature on the sensitivity of the MS-HRM assay. The MGMT MS-HRM1 assay was run at the following annealing temperatures. (A) 60° C., (B) 62° C. and (C) 63° C.

Figure 5:
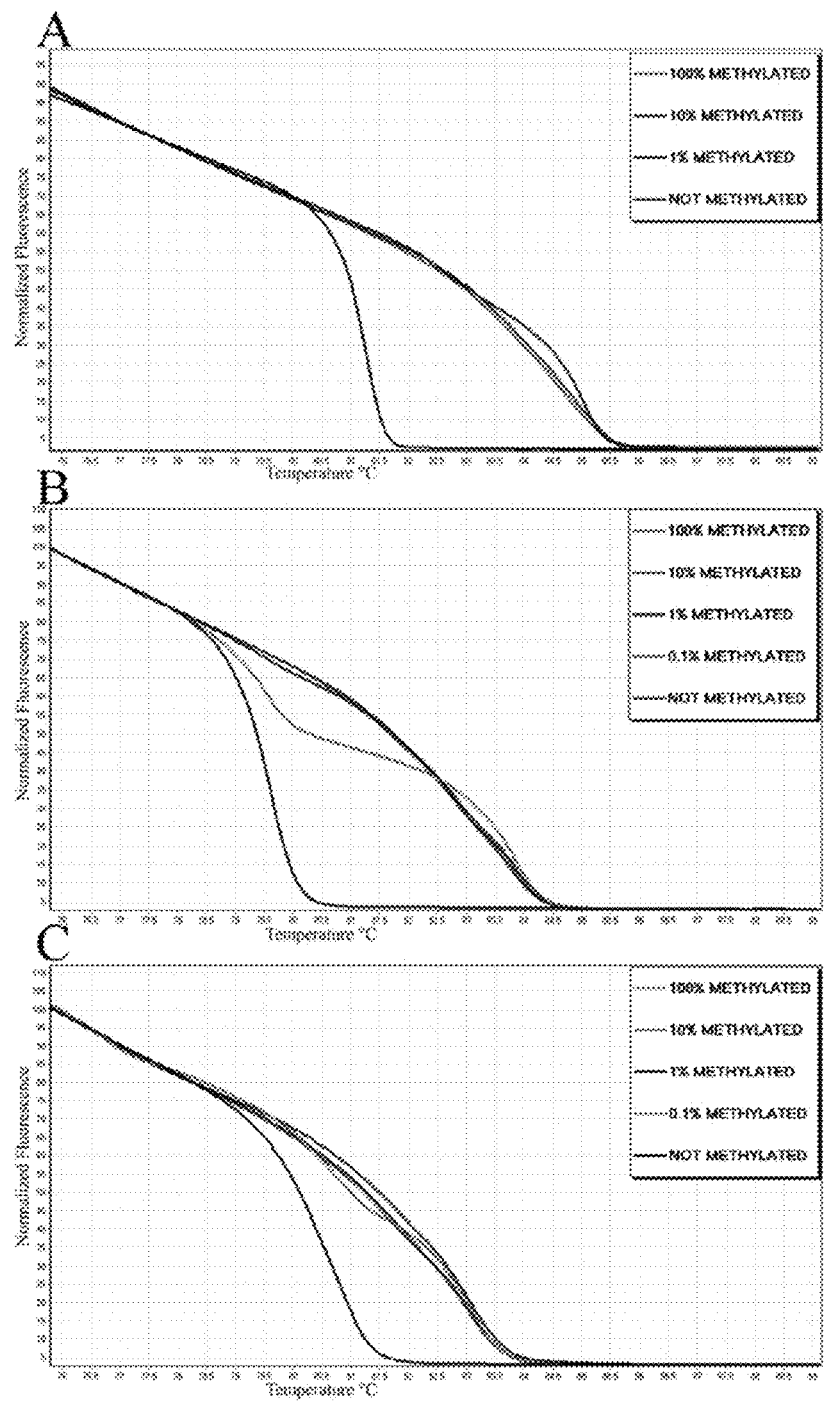

FIG. 5. The sensitivity of different MS-HRM assays for MGMT methylation. (A) MGMT MS-HRM1, (B) MGMT MS-HRM2 and (C) MGMT MS-HRM3. All the assays were run at the annealing temperature of 64° C. which enables the highest sensitivity of methylation detection. The results from the 0.1% methylation dilution for MGMT MS-HRM1 were not reproducible between replicates and this dilution was excluded from the figure.

FIG. 6. Validation of the MGMT MS-HRM1 assay by the MGMT MethylLight assay. The samples are the series of dilution standards and three of the cell lines (MDA MB 468, SW480 and HS578T). Panel A shows the MGMT MS-HRM1 assay and panel B shows the MethylLight assay. The MS-HRM assay was run at an annealing temperature of 61° C.

Figure 7:
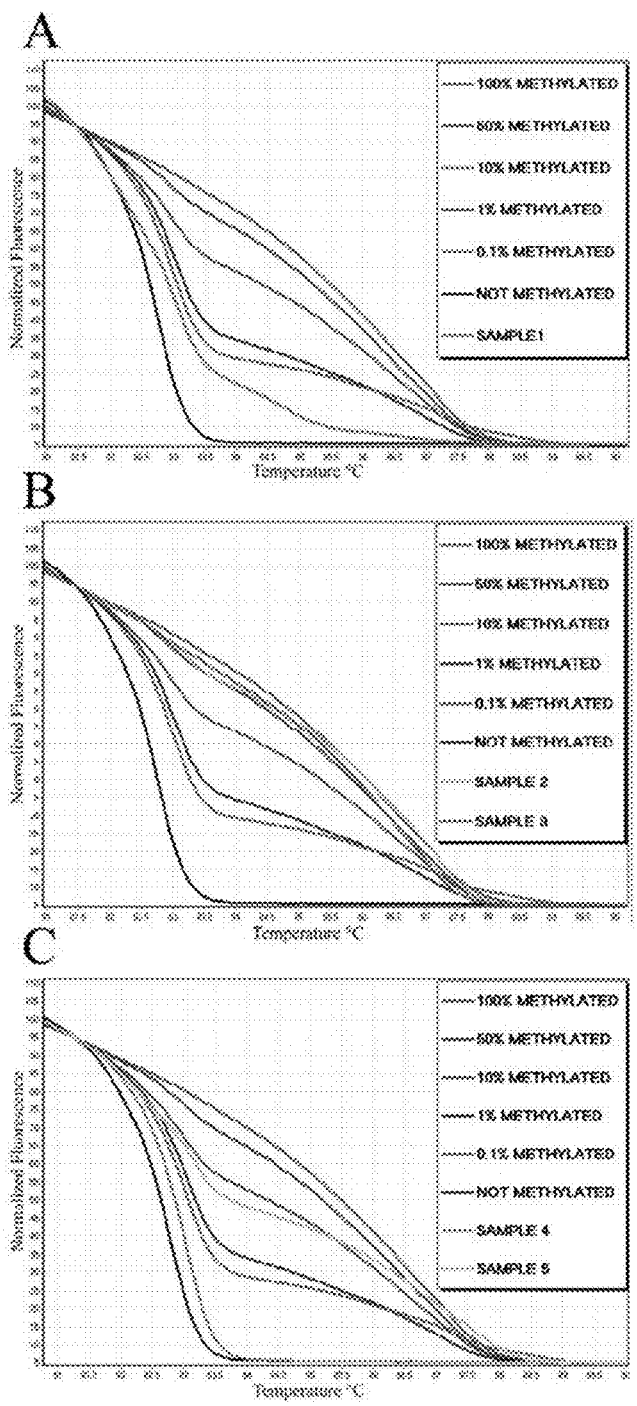

FIG. 7. The MS-HRM assay for BNIP3 methylation. Results of the BNIP3-MS-HRM assay for five clinical samples compared to the dilution standards. Samples 1-5 show different methylation levels. The samples have been distributed over three panels to help distinguish the individual samples.

FIG. 8-40. Different embodiments of the present invention. Different primer sets are disclosed for detection of methylation status in respect of specific genes. The preferred annealing temperature in respect of each primer set is indicated in each figure. The performance of the MS-HRM assay tested on the mixes on methylated template (percentage indicated in the legend and replicates in the same colour) in unmethylated template background. The examined gene name is indicated below in the legend of each figure.

FIG. 8. APC
FIG. 9. ATM
FIG. 10. BIN1
FIG. 11. BRCA1
FIG. 12. BIRC5
FIG. 13. BSG
FIG. 14. CCND2
FIG. 15. CDH1
FIG. 16. CDKN2A/p16
FIG. 17. CST6
FIG. 18. DAPK1
FIG. 19. ESR1
FIG. 20. FANCF
FIG. 21. GSTP1
FIG. 22. HIC1
FIG. 23. HIN1
FIG. 24. KL
FIG. 25. LAT52
FIG. 26. MLH1
FIG. 27. PITX2
FIG. 28. RAR beta2
FIG. 29. RASSF1A
FIG. 30. TMS1
FIG. 31. TWIST
FIG. 32. UPA
FIG. 33. ABO
FIG. 34. p15/CDKN2B
FIG. 35. RASSF1A
FIG. 36. SDHA
FIG. 37. SDHB
FIG. 38. SDHC
FIG. 39. SDHD
FIG. 40. Assay for LIT1 involved in imprinting disorders.

The performance of the MS-HRM assay tested on the mixes on methylated template in unmethylated template background. Normal tissue—dotted line, Fully methylated control—solid line FIG. 41. The example of primer design for MS-HRM assay targeting the promoter of the MGMT gene (chr10:131, 155, 538-131, 155,631 by UCSC Genome Browser, March 2006). The primers were designed to include a limited number of CpGs that allowed the control of PCR bias during PCR amplification. Bold print—primer binding sites, underlined—CpGs.

Figure 42:
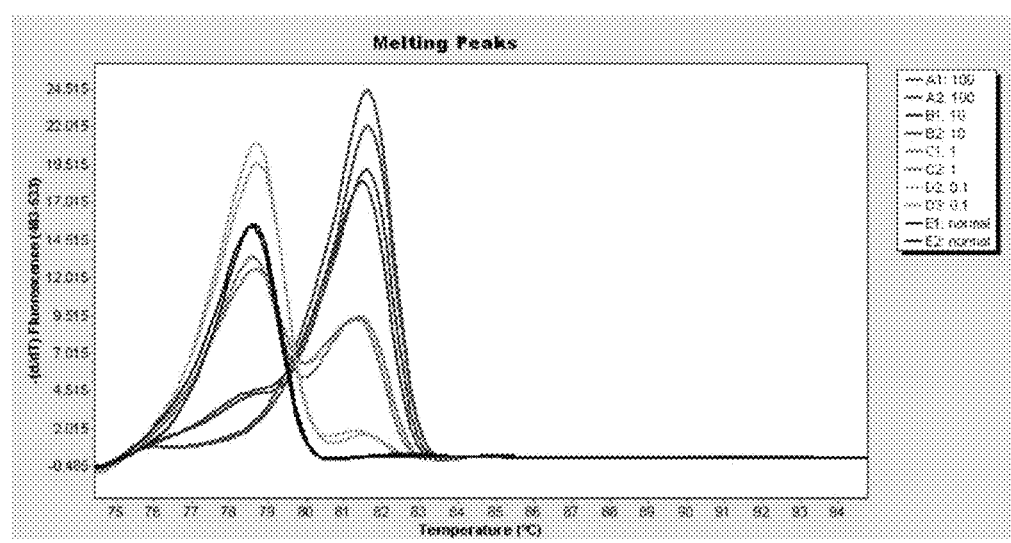

FIG. 42. Melting peak analyses (first derivative of the melting curves) of the MGMT gene. Details of the MS-HRM assay are given in (6) and Note 7. The melting curves were derived from samples with known methylated to unmethylated template ratios (ranging from 100% to 0.1%) of fully methylated template diluted in unmethylated template. The experiments were performed on the LC480.

FIG. 43. a. An example of "Gene Scan" analyses (see 3.8.1.) of melting curves of the MGMT MSHRM assay (see Note 7), in which melting curves derived from mixtures of methylated and unmethylated template were normalized for input fluorescence. The use of normalization allows similarly shaped curves to be grouped together. b. An example of the estimation of the methylation levels of an unknown sample (red) on the basis of the similarity of its normalized melting profile to normalized melting profiles of standards of known methylated to unmethylated template ratios. The unknown sample shows methylation level at around 10% as its normalized melting profile is similar to the melting profile of the standard with 10% methylated template.

Figure 44:
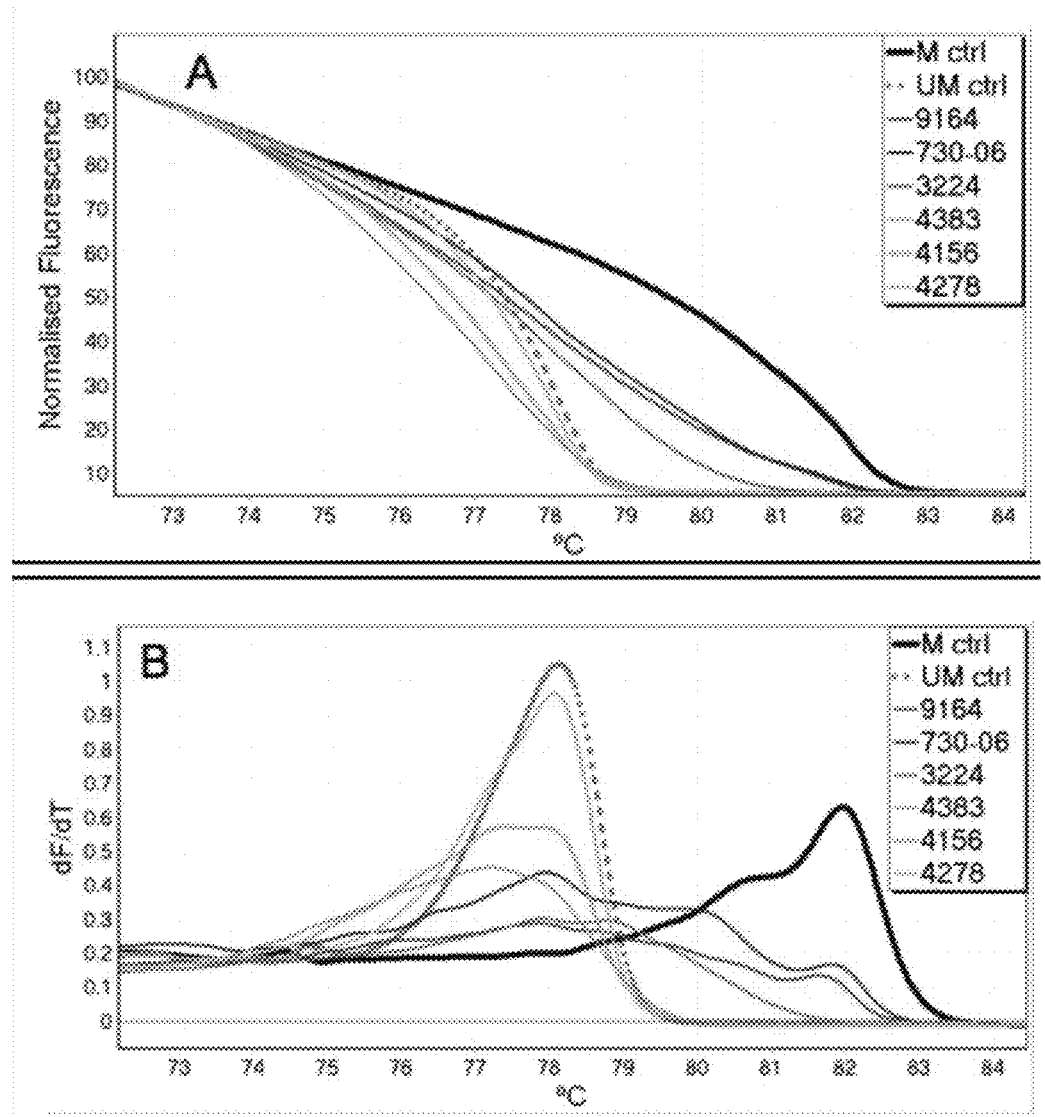

FIG. 44. AML samples analysed using conventional MS-HRM. MS-HRM can distinguish homogeneous from heterogeneous DNA methylation as each have characteristic melting profiles. The fully methylated DNA control is indicated by a solid black line (M ctrl), and the WGA control by a broken grey line (UM ctrl). The six AML samples are indicated by unbroken coloured lines. A. shows the normalised melting curves, and B. shows the negative first derivative (or Tm) curves. Apart from 4276, the AML samples do not fit into the range set by the controls. They begin melting before the controls, with three continuing to melt into the region normally indicative of methylation. All five show broad melting ranges, in direct contrast to the controls.

Figure 45:
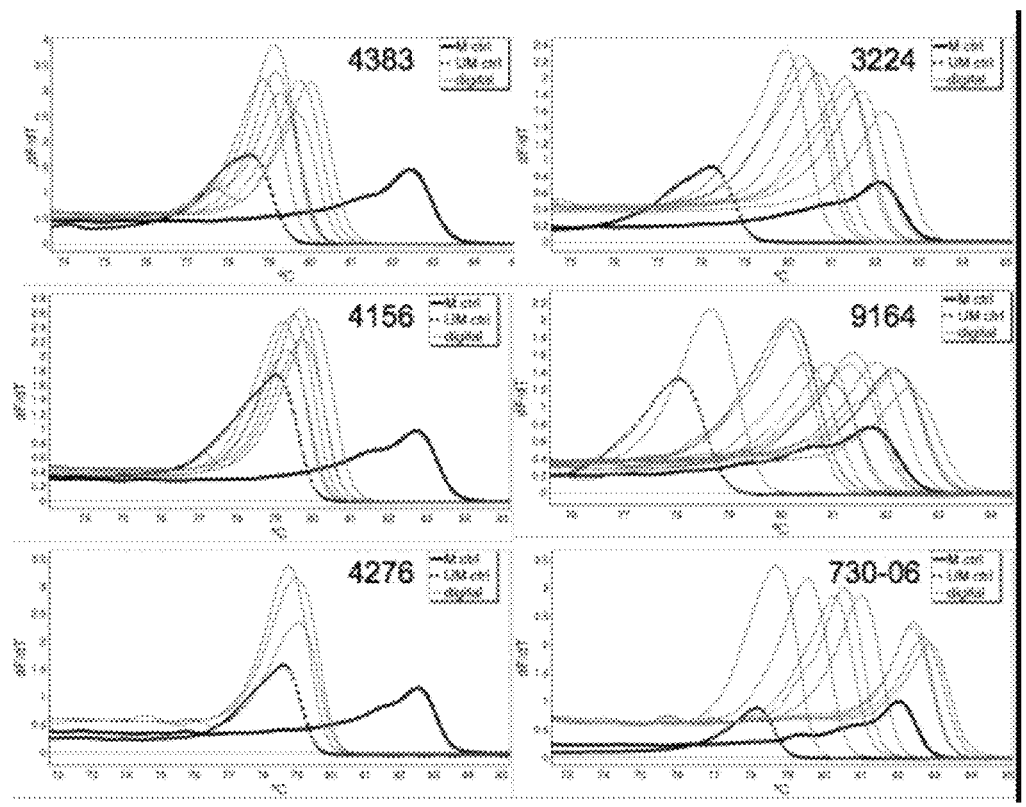

FIG. 45. MS-HRM and dMS-HRM profiles for AML samples. Negative first derivative (or Tm) curves are shown. The MS-HRM curves for the controls are shown. The fully methylated DNA control is indicated by a solid black line (M ctrl), and the WGA control by a broken grey line (UM ctrl). Digital MS-HRM peaks seen in each AML sample are shown in grey. Only one representative of each variant peak is shown for clarity.

Figure 46:
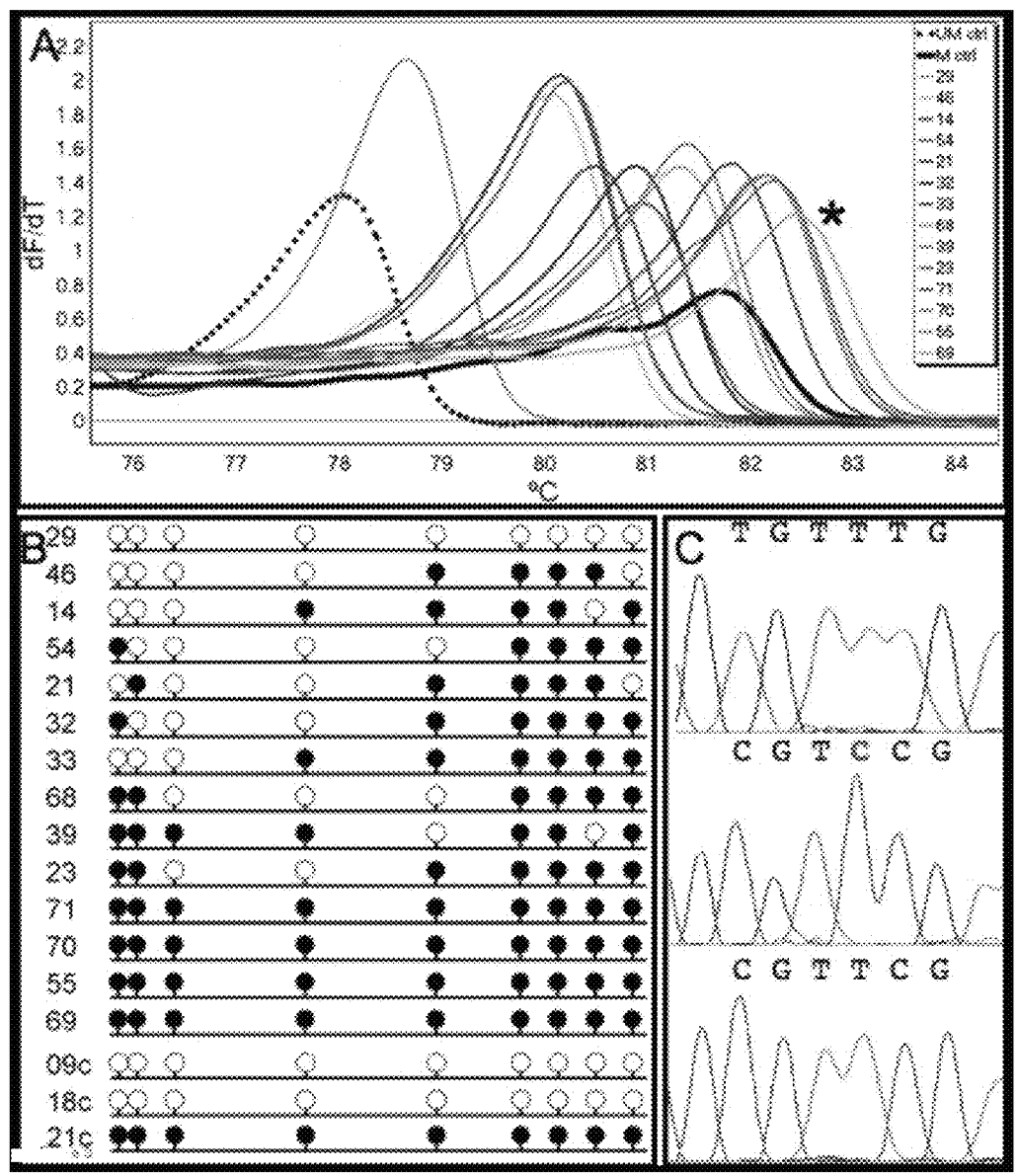

FIG. 46. Sequencing of dMS-HRM products. A: Digital MS-HRM of sample 9164 exhibits alleles appearing to contain differing levels of methylation. The cyan peak indicated with an asterisk (*) falls beyond the upper limit of the expected region of results, and was found to contain a non-CpG cytosine that failed to be converted. B: Methylation pattern obtained by direct sequencing of the dMS-HRM products from A, shown as lollipops, where unmethylated CpG sites are filled, and unmethylated sites are open. Open and filled circles represent unmethylated and methylated CpG sites, respectively. Those denoted with a 'c' are control samples C: One dMSHRM product (number 69, indicated by an asterisk (*) in A) shows one incompletely converted cytosine (highlighted in red), shown in comparison to unmethylated control (above) and fully methylated control (below).

DETAILED DESCRIPTION OF THE INVENTION

The present invention provides methods, oligonucleotide primers and kits for the identification of DNA methylation patterns in a biological sample comprising CpG containing nucleic acids. Determination of methylation status of promoter regions of a number of genes is applicable for diagnosis of various diseases including hyperproliferative disorder such as cancer, imprinting disorders, environmental and age related methylation changes based disorders.

Definitions

Amplification according to the present invention is the process wherein a plurality of exact copies of one or more starting molecule (template) is synthesised, without employing knowledge of the exact composition of the starting molecule. Hence a template may be amplified even though the exact composition of said template is unknown. In one preferred embodiment of the present invention, amplification of a template comprises the process wherein a template is copied by a nucleic acid polymerase or polymerase homologue, for example a DNA polymerase or an RNA polymerase. For example, templates may be amplified using reverse transcription, the polymerase chain reaction (PCR), ligase chain reaction (LCR), in vivo amplification of cloned DNA, and similar procedures capable of generating a complementing nucleic acid sequence.

A double stranded polynucleotide contains two strands that are complementary in sequence and capable of hybridizing to one another. In general, a gene is defined in terms of its coding strand, but in the context of the present invention, an oligonucleotide primer, which hybridize to a gene as defined by the sequence of its coding strand, also comprise oligonucleotide primers, which hybridize to the complement thereof.

A nucleotide is herein defined as a monomer of RNA or DNA. A nucleotide is a ribose or a deoxyribose ring attached to both a base and a phosphate group. Both mono-, di-, and tri-phosphate nucleosides are referred to as nucleotides.

The term 'nucleotides' as used herein refers to both natural nucleotides and non-natural nucleotides capable of being incorporated—in a template-directed manner—into an oligonucleotide, preferably by means of an enzyme comprising DNA or RNA dependent DNA or RNA polymerase activity, including variants and functional equivalents of natural or recombinant DNA or RNA polymerases. Corresponding binding partners in the form of coding elements and complementing elements comprising a nucleotide part are capable of interacting with each other by means of hydrogen bonds. The interaction is generally termed "base-pairing". Nucleotides may differ from natural nucleotides by having a different phosphate moiety, sugar moiety and/or base moiety. Nucleotides may accordingly be bound to their respective neighbour(s) in a template or a complementing template by a natural bond in the form of a phosphodiester bond, or in the form of a non-natural bond, such as e.g. a peptide bond as in the case of PNA (peptide nucleic acids). Nucleotides according to the invention includes ribonucleotides comprising a nucleobase selected from the group consisting of adenine (A), uracil (U), guanine (G), and cytosine (C), and deoxyribonucleotide comprising a nucleobase selected from the group consisting of adenine (A), thymine (T), guanine (G), and cytosine (C). Nucleobases are capable of associating specifically with one or more other nucleobases via hydrogen bonds. Thus it is an important feature of a nucleobase that it can only form stable hydrogen bonds with one or a few other nucleobases, but that it can not form stable hydrogen bonds with most other nucleobases usually including itself. The specific interaction of one nucleobase with another nucleobase is generally termed "base-pairing". The base pairing results in a specific hybridisation between predetermined and complementary nucleotides. Complementary nucleotides according to the present invention are nucleotides that comprise nucleobases that are capable of base-pairing. Of the naturally occurring nucleobases adenine (A) pairs with thymine (T) or uracil (U); and guanine (G) pairs with cytosine (C). Accordingly, e.g. a nucleotide comprising A is complementary to a nucleotide comprising either T or U, and a nucleotide comprising G is complementary to a nucleotide comprising C.

The term 'oligonucleotide' is used herein interchangebly with polynucleotide. The term oligonucleotide comprises oligonucleotides of both natural and/or non-natural nucleotides, including any combination thereof. The natural and/or non-natural nucleotides may be linked by natural phosphodiester bonds or by non-natural bonds. Preferred oligonucleotides comprises only natural nucleotides linked by phosphodiester bonds. Oligonucleotide is used interchangeably with polynucleotide. The oligomer or polymer sequences of the present invention are formed from the chemical or enzymatic addition of monomer subunits. The term "oligonucleotide" as used herein includes linear oligomers of natural or modified monomers or linkages, including deoxyribonucleotides, ribonucleotides, anomeric forms thereof, peptide nucleic acid monomers (PNAs), locked nucleotide acid monomers (LNA), and the like, capable of specifically binding to a single stranded polynucleotide tag by way of a regular pattern of monomer-to-monomer interactions, such as Watson-Crick type of base pairing, base stacking, Hoogsteen or reverse Hoogsteen types of base pairing, or the like. Usually monomers are linked by phosphodiester bonds or analogs thereof to form oligonucleotides ranging in size from a few monomeric units, e.g. 3-4, to several tens of monomeric units, e.g. 40-60. Whenever an oligonucleotide is represented by a sequence of letters, such as "ATGCCTG," it will be understood that the nucleotides are in 5'→3' order from left to right and the "A" denotes deoxyadenosine, "C" denotes deoxycytidine, "G" denotes deoxyguanosine, and "T" denotes thymidine, unless otherwise noted. Usually oligonucleotides of the invention comprise the four natural nucleotides; however, they may also comprise methylated or non-natural nucleotide analogs. Suitable oligonucleotides may be prepared by the phosphoramidite method described by Beaucage and Carruthers (Tetrahedron Lett., 22, 1859-1862, 1981), or by the triester method according to Matteucci, et al. (J. Am. Chem. Soc., 103, 3185, 1981), both incorporated herein by reference, or by other chemical methods using either a commercial automated oligonucleotide synthesizer or VLSIPS.TM. technology. When oligonucleotides are referred to as "double-stranded," it is understood by those of skill in the art that a pair of oligonucleotides exist in a hydrogen-bonded, helical configuration typically associated with, for example, DNA. In addition to the 100% complementary form of double-stranded oligonucleotides, the term "double-stranded" as used herein is also meant to refer to those forms which include such structural features as bulges and loops. For example as described in U.S. Pat. No. 5,770,722 for a unimolecular double-stranded DNA. It is clear to those skilled in the art when oligonucleotides having natural or non-natural nucleotides may be employed, e.g. where processing by enzymes is called for, usually oligonucleotides consisting of natural nucleotides are required. When nucleotides are conjugated together in a string using synthetic procedures, they are always referred to as oligonucleotides.

A plurality of individual nucleotides linked together in a single molecule may form a polynucleotide. Polynucleotide covers any derivatized nucleotides such as DNA, RNA, PNA, LNA etc. Any oligonucleotide is also a polynucleotide, but every polynucleotide is not an oligonucleotide.

The term "dinucleotide" as used herein refers to two sequential nucleotides. The dinucleotide may be comprised in an oligonucleotide or a polynucleotide. In particular, the dinucleotide CpG, which denotes a cytosine linked to a guanine by a phosphodiester bond, may be comprised in an oligonucleotide according to the present invention. A CpG dinucleotide is also herein referred to as a CpG site.

Methylation status: the term "methylation status" as used herein, refers to the presence or absence of methylation. In particular, the present invention relates to detection of methylated cytosine (5-methylcytosine). A nucleic acid sequence may comprise one or more methylation sites. The nucleic acid sequence may be methylated on all methylation sites (i.e. 100% methylated), or unmethylated on all methylation sites (i.e. 0% methylated). However, the nucleic acid sequence may also be methylated on a subset of its methylation sites, such as on at least 50%, such as on at least 60%, such as on at least 70%, for example on at least 80%, such as on at least 90%, such as on at least 95%, for example on at least 99%, such as least 99.9% of its methylation sites. The term "methylation status" as used herein reflects any relative or absolute amount of methylation of a nucleic acid sequence.

Thus, methylation may be heterogeneous and the present invention is suitable to detect sequence heterogeneity. This is because heteroduplexes created from sequence heterogeneity broaden the shape of the melting curves. The CpG position relative to the position within the amplicon can also affect shape. Both melting temperature as well as curve shape can be used in combination for epigenetic studies.

The term "PCR bias" as used herein refers to conditions, wherein PCR more efficiently amplifies a specific nucleic acid allele. In the present invention, PCR bias often relates to the fact that unmethylated nucleic acid template is more efficiently amplified than methylated nucleic acid template.

Samples

According to the present invention the nucleic acid to be analysed with respect to its methylation status as described in the present invention is obtained from a sample of any source. Thus, detection of methylated CpG may be performed on samples selected from the group consisting of breast tissue, ovarian tissue, uterine tissue, colon tissue, prostate tissue, lung tissue, renal tissue, thymus tissue, testis tissue, hematopoietic tissue, bone marrow, urogenital tissue, expiration air, stem cells, including cancer stem cell, and body fluids, such as sputum, urine, blood and sweat.

In preferred embodiments the sample is selected from the group consisting of breast tissue, ovarian tissue, uterine tissue, colon tissue, prostate tissue, lung tissue, renal tissue, thymus tissue, testis tissue, hematopoietic tissue, bone marrow, urogenital tissue, expiration air, stem cells, including cancer stem cell, and body fluids, such as sputum, urine, blood and sweat.

In another embodiment the sample is selected from the group consisting of breast tissue, ovarian tissue, uterine tissue, colon tissue, prostate tissue, lung tissue, urogenital tissue, stem cells, including cancer stem cell, and body fluids, such as sputum, urine, blood and sweat.

In even another embodiment the sample is selected from the group consisting of breast tissue, ovarian tissue, uterine tissue, colon tissue, prostate tissue and lung tissue. In yet another embodiment the sample is selected from the group consisting of stem cells and cancer stem cells.

In an even other embodiment the sample is selected from the group consisting of body fluids, sputum, urine, blood and sweat.

In an even further embodiment the sample is selected from the group consisting of ovarian tissue, uterine tissue, colon tissue, and urogenital tissue In an especially preferred embodiment the sample is breast tissue. In another especially preferred embodiment the sample is bladder tissue. In another especially preferred embodiment the sample is colon tissue. In another especially preferred embodiment the sample is blood tissue. In another especially preferred embodiment the sample is lung tissue. In another especially preferred embodiment the sample is skin tissue. In another especially preferred embodiment the sample is prostate tissue. In another especially preferred embodiment the sample is ovarian tissue.

The nucleic acid to be analysed for the presence of methylated CpG may be extracted from the samples by a variety of techniques such as that described by Maniatis, et al (Molecular Cloning: A Laboratory Manual, Cold Spring Harbor, N.Y., pp 280, 281, 1982). However, the sample may be used directly.

Any nucleic acid, in purified or nonpurified form, can be utilized as the starting nucleic acid or acids, provided it contains, or is suspected of containing, the specific nucleic acid sequence containing the target site (e.g., CpG).

Therefore, for example, DNA or RNA, including messenger RNA, microRNA, siRNA, shRNA, rRNA, snoRNA, tRNA and SNRNA, wherein DNA or RNA may be single stranded or double stranded may be used as target material. Where RNA is to be used as a template, enzymes, and/or conditions optimal for reverse transcribing the template to DNA would be utilized as known to a person skilled in the art. A DNA-RNA hybrid which contains one strand of each may also be utilized. A mixture of nucleic acids may also be employed, or the nucleic acids produced in a previous amplification reaction herein, using the same or different primers may be so utilized.

The specific nucleic acid sequence which is to be amplified may be a part of a larger molecule or is present initially as a discrete molecule. The nucleic acid sequence to be amplified need not to be present in a pure form, it may for example be a fraction of a complex mixture of other DNA molecules, and/ or RNA. In one example, the nucleic acid sequence is a fraction of a genomic nucleic acid preparation.

The amount of the nucleic acid used as target sequence according to the method of the present invention is in the range of micrograms to nanograms. It is appreciated by the person skilled in the art that in practical terms no upper limit for the amount of nucleic acid to be analysed exists. The problem that the skilled person encounters is that the amount of sample to be analysed is limited. Therefore, it is beneficial that the method of the present invention can be performed on a small amount of sample and thus a limited amount of nucleic acid in said sample. The amount of the nucleic acid to be analysed is thus at least 0.01 ng, such as 0.1 ng, such as 0.5 ng, for example 1 ng, such as at least 10 ng, for example at least 25 ng, such as at least 50 ng, for example at least 75 ng, such as at least 100 ng, for example at least 125 ng, such as at least 150 ng, for example at least 200 ng, such as at least 225 ng, for example at least 250 ng, such as at least 275 ng, for example at least 300 ng, 400 ng, for example at least 500 ng, such as at least 600 ng, for example at least 700 ng, such as at least 800, ng, for example at least 900 ng or such as at least 1000 ng.

In one preferred embodiment the amount of nucleic acid as the starting material for the method of the present invention is 50 ng, alternatively 100 ng or 200 ng.

The sample may be from any mammal including a human. For example the sample may be from mouse, hamster, rat, rabbit, cow, dog, pig, cat, sheep, goat, monkey, ape or humans. In a preferred embodiment the sample is from a human.

Modification of DNA

The method of the present invention for detecting methylation status of CpG-containing nucleic acids in a sample comprises a step of modifying the CpG-containing nucleic acids using an agent which modifies unmethylated cytosine in the CpG-containing nucleic acid. As used herein the term "modifies" refers to the conversion of an unmethylated cytosine to another nucleotide which will distinguish an unmethylated cytosine from a methylated cytosine. In one preferred embodiment, an agent modifies unmethylated cytosine to uracil. Such an agent may be any agent conferring said conversion, wherein unmethylated cytosine is modified, but not methylated cytosine. In one preferred embodiment the agent for modifying unmethylated cytosine is sodium bisulfite. Sodium bisulfite ($NaHSO_3$) reacts readily with the 5,6-double bond of cytosine, but only poorly with methylated cytosine. The cytosine reacts with the bisulfite ion, forming a reaction intermediate in the form of a sulfonated cytosine which is prone to deamination, eventually resulting in a sulfonated uracil. Uracil can subsequently be formed under alkaline conditions which removes the sulfonate group.

During a nucleic acid amplification process uracil will by the Taq polymerase be recognised as a thymidine. The product upon PCR amplification of a Sodium bisulfite modified nucleic acid contains cytosine at the position where a methylated cytosine (5-methylcytosine) occurred in the starting template DNA of the sample. Moreover, the product upon PCR amplification of a Sodium bisulfite modified nucleic acid contains thymidine at the position where an unmethylated cytosine (5-methylcytosine) occurred in the starting template DNA of the sample. Thus, an unmethylated cytosine in converted into a thymidine residue upon amplification of a bisulfite modified nucleic acid.

In a preferred embodiment of the present invention, the CpG-containing nucleic acid are modified using an agent which modifies methylated cytosine in the CpG-containing nucleic acid. In a specific embodiment, such an agent is bisulfite.

Methylation-independent Primer

The term "methylation-independent primer" refers to the oligonucleotide primers of the present invention. A methylation-independent primer is capable of hybridizing to both methylated and unmethylated nucleic acid alleles and modified as well as unmodified alleles. The oligonucleotide primers of the present invention are capable of being employed in amplification reactions, wherein the primers are used in amplification of template DNA originating from either a methylated or an unmethylated strand. The preferred methylation-independent primers of the present invention comprise a CpG dinucleotide, as described below. Accordingly, in a methylated and bisulfite modified nucleic acid target sequence, the primer sequence will anneal to the nucleic acid template with a perfect match, wherein all of the nucleotides in a consecutive region of the primer forms base pairs with a complementary region in the nucleic acid target. However, in an unmethylated nucleic acid target after bisulfite modification, the methylation-independent primers of the present invention will anneal to the nucleic acid template with an imperfect match, wherein the primer sequence comprise a mis-match (i.e. the primer and template does not form base pairs) at the position of the unmethylated Cytosine at a CpG site in the nucleic acid template. Nonetheless, as the primers of the present invention are methylation-independent, the primers will hybridize to both unmethylated and methylated nucleic-acid sequences after bisulfite modification, and the primers will form a perfect match with the target sequence of a methylated nucleic acid target and an imperfect match, where the primers and target nucleic acid sequence does not form base pairing at the positions of unmethylated Cytosine (which is converted by bisulfite to Uracil) at CpG sites.

The methylation-independent primers of the present invention will, due to the mis-match after bisulfite modification at positions of unmethylated cytosine of a CpG-site in the nucleic acid target sequence, hybridize less efficiently to an unmethylated nucleic acid sequence. However, by reducing the stringency of hybridization, the methylation-independent primers of the present invention are able to anneal to the nucleic acid target, also when the nucleic acid target comprise unmethylated CpG-sites, which have been modified by for example bisulfite treatment. In one example, the stringency is reduced by reducing the annealing temperature as described elsewhere herein.

The design of oligonucleotide primers suitable for nucleic acid amplification techniques, such as PCR, is known to people skilled within the art. The design of such primers involves analysis of the primer's melting temperatures and ability to form duplexes, hairpins or other secondary structures. Both the sequence and the length of the oligonucleotide primers are relevant in this context. The oligonucleotide primers according to the present invention comprise between 10 and 200 consecutive nucleotides, such as at least 60, at least 65, at least 70, at least 75, at least 80, at least 85, at least 90, at least 95, at least 100, at least 110, at least 120, at least 130, at least 140, at least 150, at least 160, at least 180 or at least 200 nucleotides. In a specific embodiment, the oligonucleotide primers comprise between 15 and 60 consecutive nucleotides, such as 15, 16, 17, 18, 19, 20, preferably 21, 22, 23, 24, 25, 26, 27, 28, 29, 30, such as 31, 32, 33, 34, 35, 36, 37, 38, 39, 40, alternatively at least 41, at least 42, at least 44, at least 46, at least 48, at least 50, at least 52, at least 54, at least 56, at least 58, or at least 60 consecutive nucleotides.

The present invention relates to a method for determining the methylation status of a CpG-containing nucleic acid, said method comprising amplification of the CpG-containing nucleic acid by use of a methylation independent oligonucleotide primer of the present invention. In one embodiment, the oligonucleotide primers of the present invention are able to hybridize to a nucleic acid sequence comprising CpG islands. In a preferred embodiment, at least one of the oligonucleotide primers according to the present invention comprises at least one CpG dinucleotide. In another embodiment of the present invention, the oligonucleotide primers comprise 2, alternatively 3, 4, 5, 6, 7, 8, 9 or 10 CpG dinucleotides. In even further embodiments, the oligonucleotide primers of the present invention comprise at least 10 CpG dinucleotides. In one preferred embodiment the at least one methylation-independent oligonucleotide primer comprises one CpG dinucleotide at the 5'-end of the primer.

The CpG dinucleotide may be located anywhere within the oligonucleotide primer sequence. However, in a preferred embodiment of the present invention, the at least one CpG dinucleotide is located in the 5'-end of the oligonucleotide primer. In another preferred embodiment, the at least one CpG dinucleotide constitute the first two nucleotides of the 5'-end. In an even further preferred embodiments of the present invention, the at least one CpG dinucleotide is located within the first 3, 4, 5, 6, 7, 8, 9, or 10 nucleotides of the 5'-terminus. In alternative embodiments, the at least one CpG dinucleotide is located within the first 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or 120 nucleotides of the 5'-terminus.

The primers of the present invention comprises at least one CpG site, whereby annealing with a higher efficiency to a methylated than to an unmethylated template upon modification of unmethylated cytosine is achieved. The primers of the present invention comprise at least one CpG site. However, the primers comprise also for example two CpG sites.

The at least one CpG site is positioned in the 5' end of the primer. For example within the first 10 nucleotides in the 5' end of the primer, within the first 9 nucleotides in the 5' end of the primer, within the first 8 nucleotides in the 5' end of the primer, within the first 7 nucleotides in the 5' end of the primer, within the first 6 nucleotides in the 5' end of the primer, within the first 5 nucleotides in the 5' end of the primer, within the first 4 nucleotides in the 5' end of the primer or within the first 3 nucleotides in the 5' end of the primer. In a preferred embodiment the CpG site is introduced immediately after the first nucleotide of the 5' end of the primer.

Specific hybridization typically is accomplished by a primer having at least 10, for example at least 12, such as at least 14, for example at least 16, such as at least 18, for example at least 20, such as at least 22, for example at least 24, such as at least 26, for example at least 28, or such as at least 30 contiguous nucleotides, which are complementary to the target template. Often the primer will be close to 100% identical to the target template. However, the primer may also be 98% identical to the target template or for example at least 97%, such as at least 96%, for example at least 95%, such as at least 94%, for example at least 93%, such as at least 92%, for example at least 91%, such as at least 90%, for example at least 89%, such as at least 88%, for example at least 87%, such as at least 86%, for example at least 85%, such as at least 84%, for example at least 83%, such as at least 82%, for example at least 81%, such as at least 80%, for example at least 79%, such as at least 78%, for example at least 77%, such as at least 76%, for example at least 75%, such as at least 74%, for example at least 73%, such as at least 72%, for example at least 71%, such as at least 70%, for example at least 68%, such as at least 66%, for example at least 64%, such as at least 62% or for example at least 60% identical to the target template. If there is a sufficient region of complementary nucleotides, e.g., at least 10, such as at least 12, for example at least 15, such as at least 18, or for example at least 20, for example at least 30, such as at least 40, for example at least 50, such as at least 60, for example at least 70 nucleotides, then the primer may also contain additional nucleotide residues that do not interfere with hybridization but may be useful for other manipulations. Examples of such other residues may be sites for restriction endonuclease cleavage, for ligand binding or for factor binding or linkers.

The methylation-independent oligonucleotide primer of the present invention is designed to hybridize to CpG-containing nucleic acids in a sample. Importantly, the CpG-containing nucleic acids in that sample are treated with an agent which modifies unmethylated cytosine in said CpG-containing nucleic acid. Thereby, any unmethylated Cytosine of CpG dinucleotides comprised in the CpG-containing nucleic acid are converted to Uracil as explained elsewhere herein. Consequently, in primers comprising a CpG dinucleotide, designed to hybridize with the complementary CpG dinucleotide of the CpG-containing nucleic acid of the sample, the CpG dinucleotide will only hybridize to the methylated CpG dinucleotide fraction of the CpG-containing nucleic acid. In the unmethylated fraction of CpG dinucleotides comprised in the CpG-containing nucleic acid of the sample, Cytosine are modified to uracil which does not hybridize with the CpG dinucleotide of the CpG-containing oligonucleotide primer.

The methylation-independent oligonucleotide primers according to the present invention are designed to comprise sufficient nucleotides for specific hybridization to the target CpG-containing nucleic acid sequence regardless of its original methylation status. In some embodiments the oligonucleotide primers also comprise one or more CpG dinucleotides, as specified elsewhere herein. These CpG dinucleotides only hybridize with the originally methylated alleles of the CpG-containing nucleic acids. Nevertheless, the oligonucleotide primers can still be functionally used for amplification of both originally methylated and unmethylated nucleic acids. The CpG dinucleotides are typically comprised in the 5'-terminus of the oligonucleotide primers, as described elsewhere herein. A primer-template mismatch within the 5'-terminus of the primer usually allow the primers to hybridize with the target CpG-containing nucleic acid, and still function as primers in an amplification reaction.

The presence of one or more mismatches between the primer and template affects the optimal annealing temperature of said oligonucleotide primer for use in amplification reactions. The more hybridizing nucleotides comprised on the oligonucleotide primers, the higher is the optimal annealing temperature. Consequently, amplification of methylated alleles of CpG-containing nucleic acids by CpG-containing oligonucleotide primers according to the present invention is favoured by increased annealing temperature. Conversely, amplification of unmethylated alleles is favoured by decreased annealing temperature. In the present invention, the PCR bias towards amplification of unmethylated alleles of a nucleic acid template is reversed by amplification of said nucleic acid template at a relatively higher annealing temperature, which favours oligonucleotide primer binding and priming of the methylated allele. By modulation of the primer annealing temperature, the priming of either the unmethylated modified allele or the methylated allele of the nucleic acid can be favoured. By increasing the annealing temperature below the theoretical optimum, the amplification of the methylated allele is favoured, while a decrease of the annealing temperature will tend to favour amplification of the unmethylated allele.

Other factors than annealing temperature also affect hybridisation to a CpG-containing target sequence of a methylation-independent primer according to the present invention. At highly stringent conditions, hybridization between perfect matching primer and target sequences are favoured, such as hybridization between a methylation-independent primer according to the present invention and a methylated target sequence upon cytosine modification. Less stringent conditions will tend to favour oligonucleotide primer binding, priming and amplification of the unmethylated allele. Modulation of temperature is one way of adjusting the stringency of hybridization, but the stringency of hybridization may also be modulated by adjusting buffer composition, and/or salt concentrations in the hybridization mixture, which is known to those of skill within the art. The present invention comprises any such method of modulating hybridization stringency to balance the PCR bias towards amplification of unmethylated template. However, modulation of temperature is preferred.

In one embodiment, the methylation-independent oligonucleotide primer of the present invention is selected from the group consisting of SEQ ID NO.: 46 to 151. In another embodiment, the oligonucleotide primer of the present invention is selected from the group consisting of SEQ ID NO.: 185 to 250.

In a preferred embodiment the oligonucleotide primer of the present invention is selected from the group consisting of SEQ ID NO.: 132 to 139. In another preferred embodiment the oligonucleotide primers of the present invention are SEQ ID NO.: 138 and 139.

In another preferred embodiment the oligonucleotide primers of the present invention are selected from the group consisting of SEQ ID NO.: 142 and 143.

In another preferred embodiment the oligonucleotide primers of the present invention are selected from the group consisting of SEQ ID NO.: 144 to 151.

In another preferred embodiment the oligonucleotide primers of the present invention are SEQ ID NO.: 128 and 129. In another preferred embodiment the oligonucleotide primers of the present invention are SEQ ID NO.: 130 and 131. In another preferred embodiment the oligonucleotide primers of the present invention are SEQ ID NO.: 132 and 133. In another preferred embodiment the oligonucleotide primers of the present invention are SEQ ID NO.: 134 and 135. In another preferred embodiment the oligonucleotide primers of the present invention are SEQ ID NO.: 136 and 137. In another preferred embodiment the oligonucleotide primers of the present invention are SEQ ID NO.: 138 and 139. In another preferred embodiment the oligonucleotide primers of the present invention are SEQ ID NO.: 140 and 141. In another preferred embodiment the oligonucleotide primers of the present invention are SEQ ID NO.: 142 and 143. In another preferred embodiment the oligonucleotide primers of the present invention are SEQ ID NO.: 144 and 145. In another preferred embodiment the oligonucleotide primers of the present invention are SEQ ID NO.: 146 and 147. In another preferred embodiment the oligonucleotide primers of the present invention are SEQ ID NO.: 148 and 149. In another preferred embodiment the oligonucleotide primers of the present invention are SEQ ID NO.: 150 and 151.

In yet another preferred embodiment the oligonucleotide primer of the present invention is selected from the group consisting of SEQ ID NO.: 46 to 53. In another preferred embodiment the oligonucleotide primer of the present invention is selected from the group consisting of SEQ ID NO.: 54 to 61. In another preferred embodiment the oligonucleotide primer of the present invention is selected from the group consisting of SEQ ID NO.: 62 to 71. In another preferred embodiment the oligonucleotide primers of the present invention are selected from the group consisting of SEQ ID NO.: 72 to 79. In another preferred embodiment the oligonucleotide primer of the present invention is selected from the group consisting of SEQ ID NO.: 80 to 85. In another preferred embodiment the oligonucleotide primer of the present invention is selected from the group consisting of SEQ ID NO.: 86 to 97. In another preferred embodiment the oligonucleotide primer of the present invention is selected from the group consisting of SEQ ID NO.: 98 to 107. In another preferred embodiment the oligonucleotide primer of the present invention is selected from the group consisting of SEQ ID NO.: 108 to 115. In another preferred embodiment the oligonucleotide primer of the present invention is selected from the group consisting of SEQ ID NO.: 116 to 127. In another preferred embodiment the oligonucleotide primer of the present invention is selected from the group consisting of SEQ ID NO.: 128 to 151.

In one embodiment, the methylation-independent oligonucleotide primer of the present invention is selected from the group consisting of SEQ ID NO.: 185 to 200. In another embodiment, the oligonucleotide primer of the present invention is selected from the group consisting of SEQ ID NO.: 201 to 210. In a further embodiment, the oligonucleotide primer of the present invention is selected from the group consisting of SEQ ID NO.: 211 to 220. In another embodiment, the oligonucleotide primer of the present invention is selected from the group consisting of SEQ ID NO.: 221 to 230. In yet another embodiment, the oligonucleotide primer of the present invention is selected from the group consisting of SEQ ID NO.: 231 to 240. In yet another embodiment, the oligonucleotide primer of the present invention is selected from the group consisting of SEQ ID NO.: 241 to 250.

In one embodiment, present invention relates oligonucleotide primers which specifically hybridize to regions within 1 kb of the transcription start sites of genes. In particular, the present invention relates to oligonucleotide primers, which specifically hybridize to regions within 1 kb of the transcription start sites of genes, which comprise at least one CpG dinucleotide. In a specific embodiment of the present invention the oligonucleotide primers hybridize to a target polynucleotide sequence of a gene selected from the group consisting of PPP3CC, BNIP3, MGMT, SNRPN, GSTP1, RARB2, RASSF1A, TIMP3, APC, beta-Actin, PTGS2, 14-3-3 sigma, TNFRSF10B tumor necrosis factor receptor superfamily (member 10b), RUNX3 runt-related transcription factor 3, CGI-38 brain specific protein, SMPD2 sphingomyelin phosphodiesterase 2 (neutral membrane; neutral sphingomyelinase), MYBL2 v-myb myeloblastosis viral oncogene homolog (avian)-like 2, BARD1 BRCA1 associated RING domain 1,NDP Norrie disease (pseudoglioma), TM4SF11 transmembrane 4 superfamily member 11 (plasmolipin) DEKDEK oncogene (DNA binding), ASK activator of S phase kinase, HEC highly expressed in cancer, rich in leucine heptad repeats, ACTN1 actinin (alpha 1), FANCG Fanconi anemia (complementation group G), and HDGF hepatoma-derived growth factor (high-mobility group protein 1-like), or the complement thereof.

In another embodiment of the present invention the methylation-independent oligonucleotide primer hybridize to a target polynucleotide sequence of a gene selected from the group consisting of PPP3CC, BNIP3, MGMT, SNRPN, GSTP1, RARB2, RASSF1A, TIMP3, APC, beta-Actin, PTGS2 and 14-3-3 sigma, or the complement thereof.

In a further embodiment of the present invention, the methylation-independent oligonucleotide primer hybridize to a target polynucleotide sequence of a gene selected from the group consisting of TNFRSF10B tumor necrosis factor receptor superfamily (member 10b), RUNX3 runt-related transcription factor 3, TM4SF11 transmembrane 4 superfamily member 11 (plasmolipin), ACTN1 actinin (alpha 1), and FANCG Fanconi anemia (complementation group G), or the complement thereof.

In a preferred embodiment of the present invention the oligonucleotide primers hybridize to a target polynucleotide sequence of a gene selected from the group consisting of CHD1, COX2, PRSS3, PYCARD, BIN1, BRCA1, LATS2, PITX2, BCL2, EYA4, GSK3B, MLH1, TIMP-3, MSH6, MTHFR, PTEN, SFN, CD109, ERS1, PCDH10, DAPK1, FHIT, P16ink4a, PRSS3, RASSF1, TMS1, CAGE-1, GPR150, ITGA8, PRDX2, SYK, ALX3, HOXD11, PTPRO, WWOX, ABHD9, CAV9, GPR78, GSTP1, HIC1, PTGS2, CSMD1, C10orf59, MGMT, BNIP3, PPP3CC CSMD1, MAP3k7, C10orf59 and GRIFK2, or the complement thereof.

In another preferred embodiment of the present invention the oligonucleotide primers hybridize to a target polynucleotide sequence of a gene selected from the group consisting of BNIP3, APC, ATM, BIN1, BRCA1, BIRC5, BSG, CCND2, CDH1, CDKN2A/p16, CST6, DAPK1, ESR1, FANCF, GSTP1, HIC1, HIN1, KL, LAT52, MLH1, PITX2, RAR beta2, RASSF1A, TMS1, TWIST, UPA, ABO, CDKN2B/p15, RASSF1A, SDHA, SDHB, SDHC, SDHD and LIT1, or the complement thereof.

In a preferred embodiment of the present invention the at least one oligonucleotide primer hybridizes to a target polynucleotide sequence selected from the group consisting of SEQ ID NO.: 1-45 and 152-184, or the complement thereof.

In another embodiment of the present invention the methylation-independent oligonucleotide primers hybridize to a target polynucleotide sequence of a gene selected from the group consisting of CHD1, COX2, PRSS3 and PYCARD, as defined in SEQ ID NO.: 1-4, or the complement thereof.

In another embodiment of the present invention the oligonucleotide primers hybridize to a target polynucleotide sequence of a gene selected from the group consisting of BIN1, BRCA1, LATS2 and PITX2, as defined in SEQ ID NO.: 5-8, or the complement thereof.

In another embodiment of the present invention the oligonucleotide primers hybridize to a target polynucleotide sequence of a gene selected from the group consisting of BCL2, EYA4, GSK3B, MLH1 and TIMP-3, as defined in SEQ ID NO.: 9-13, or the complement thereof.

In another embodiment of the present invention the oligonucleotide primers hybridize to a target polynucleotide sequence of a gene selected from the group consisting of MSH6, MTHFR, PTEN and SFN, as defined in SEQ ID NO.: 14-17, or the complement thereof.

In another embodiment of the present invention the oligonucleotide primers hybridize to a target polynucleotide sequence of a gene selected from the group consisting of CD109, ERS1 and PCDH10, as defined in SEQ ID NO.: 18-20, or the complement thereof.

In another embodiment of the present invention the oligonucleotide primers hybridize to a target polynucleotide sequence of a gene selected from the group consisting of DAPK1, FHIT, P16ink4a, PRSS3, RASSF1 and TMS1, as defined in SEQ ID NO.: 21-26, or the complement thereof.

In another embodiment of the present invention the oligonucleotide primers hybridize to a target polynucleotide sequence of a gene selected from the group consisting of CAGE-1, GPR150, ITGA8, PRDX2 and SYK, as defined in SEQ ID NO.: 27-31, or the complement thereof.

In another embodiment of the present invention the oligonucleotide primers hybridize to a target polynucleotide sequence of a gene selected from the group consisting of ALX3, HOXD11, PTPRO and WWOX, as defined in SEQ ID NO.: 32-35, or the complement thereof.

In another embodiment of the present invention the oligonucleotide primers hybridize to a target polynucleotide sequence of a gene selected from the group consisting of ABHD9, CAV9, GPR78, GSTP1, HIC1 and PTGS2, as defined in SEQ ID NO.: 36-41, or the complement thereof.

In another embodiment of the present invention the oligonucleotide primers hybridize to a target polynucleotide sequence of a gene selected from the group consisting of CSMD1 (SEQ ID NO.: 42), C10orf59 (SEQ ID NO.: 43), MGMT, BNIP3, PPP3CC CSMD1, MAP3k7, C10orf59 and GRIFK2, or the complement thereof.

In a specific embodiment of the present invention the oligonucleotide primer hybridize to a target polynucleotide sequence of a gene selected from the group consisting of APC, ATM, BIN1, BRCA1, BIRC5, BSG, CCND2, CDH1, CDKN2A/p16, CST6, DAPK1, ESR1, FANCF, GSTP1, HIC1, HIN1, KL, LAT52, MLH1, PITX2, RAR beta2, RASSF1A, TMS1, TWIST, UPA, ABO, CDKN2B/p15, RASSF1A, SDHA, SDHB, SDHC, SDHD and LIT1, as defined in SEQ ID NO.: 152-184, or the complement thereof.

In a preferred embodiment, the methods and kits of the present invention comprise oligonucleotide primers that hybridize to PPP3CC, as defined in SEQ ID NO.: 45 or 45

In another preferred embodiment, the methods and kits of the present invention comprise oligonucleotide primers that hybridize to the BNIP3 gene.

In yet another preferred embodiment, the methods and kits of the present invention comprise oligonucleotide primers that hybridize to the MGMT gene. The methylation status of the MGMT gene is predictive of various cancers (6-8). The MGMT protein removes methyl/alkyl adducts from the O6-position of guanine and thereby acts to protect the cell from undergoing transition mutations. The tumour-specific methylation of the MGMT promoter and subsequent elimination of MGMT protein activity will render tumour cells susceptible to alkylating agents used in cancer chemotherapy.

Consistently, patients whose tumour was methylated at the MGMT promoter displayed significantly higher survival rates than patients with tumours that did not show methylation of MGMT when treated with alkylating agents (6-8).

However in another embodiment, the oligonucleotide primers of the present invention hybridize to regions within exons of genes.

Amplifying Step

The method of the present invention comprises an amplifying step, wherein the CpG-containing nucleic acid is amplified by means of at least one methylation-independent oligonucleotide primer. In a preferred embodiment the amplifying step is achieved by means of two methylation-independent oligonucleotide primers. The at least one methylation-independent primer preferably comprise at least one CpG dinucleotide as described elsewhere herein.

The amplifying step is a polymerisation reaction wherein an agent for polymerisation is involved, effecting an oligonucleotide primer extension. The agent for polymerization may be any compound or system which will function to accomplish the synthesis of primer extension products, including enzymes. Enzymes that are suitable for this purpose include, for example, E. coli DNA polymerase I, Klenow fragment of E. coli DNA polymerase I, T4 DNA polymerase, other available DNA polymerases, polymerase muteins, reverse transcriptase, and other enzymes, including heat-stable enzymes (i.e., those enzymes which perform primer extension after being subjected to temperatures sufficiently elevated to cause denaturation also known as Taq polymerases). Suitable enzymes will facilitate combination of the nucleotides in the proper manner to form the primer extension products which are complementary to each locus nucleic acid strand. Generally, the synthesis will be initiated at the 3' end of each primer and proceed in the 5' direction along the template strand, until synthesis terminates, producing molecules of different lengths. There may be agents for polymerization, however, which initiate synthesis at the 5' end and proceed in the other direction, using the same process as described above.

A preferred method for amplifying the CpG-containing nucleic acid by means of at least one methylation-independent oligonucleotide primer is by the polymerase chain reaction (PCR), as described herein and as is commonly used by those skilled in the art.

It is appreciated that PCR amplification requires a set of oligonucleotide primers, one forward primer and one reverse primer. According to the present invention, the forward primer is a methylation independent primer. The reverse primer is in another embodiment a methylation independent primer. However, both reverse and forward primer may be methylation independent oligonucleotide primers according to the definitions herein.

The amplification product may be of any length, however in one preferred embodiment, the amplification product comprise between 15 and 1000 nucleotides, such as between 15 and 500 nucleotides, such as between 50 and 120 nucleotides, preferably between 80 and 100 nucleotides.

The PCR reaction is characterised by three steps a) melting a CpG-containing nucleic acid template, b) annealing at least one methylation-independent oligonucleotide primer to said CpG-containing nucleic acid template, and c) elongating said at least one methylation-independent oligonucleotide primer.

Melting

The melting of a CpG-containing nucleic acid template may also be referred to as strand separation. Melting is necessary where the target nucleic acid (a CpG-containing nucleic acid) contains two complementary strands bound together by hydrogen bonds. This strand separation can be accomplished using various suitable denaturing conditions, including physical, chemical, or enzymatic means. One physical method of separating nucleic acid strands involves heating the nucleic acid until it is denatured. The denaturation by heating is the preferred procedure for melting in the present invention. Typical heat denaturation involves temperatures ranging from about 85 degrees Celsius to 102 degrees Celsius for times ranging from about 1 to 10 minutes.

The melting temperature is typically between 90 and 98 degrees Celsius, such as at least 91, for example at least 92, such as at least 94, preferably at least 95, at least 96, such as at least 97, for example at least 98 degrees Celsius. The PCR reaction mixture is incubated at the melting temperature for at least 5 seconds, alternatively at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, or at least 100 seconds.

Annealing

Separated strands are used as a template for the synthesis of additional nucleic acid strands. It is understood that the separated strands may result from the separation of complementary strands in an originally double stranded nucleic acid. However, separated strands originally single stranded are also used as templates according to the present invention. The synthesis of additional nucleic acid strands is performed under conditions that allow the hybridisation of oligonucleotide primers to templates. Such a step is herein referred to as annealing. The oligonucleotide primers form hydrogen bonds with the template.

The annealing temperature is between 40 and 75 degrees Celsius, such as at least 40, at least 45, for example at least 50, at least 52, at least 54, at least 56, at least 57, at least 58, at least 59 preferably at least 60, at least 61, at least 62, at least 63, at least 64, at least 65, at least 66, at least 67, for example at least 68, at least 69, at least 70, at least 72, at least 73, at least 75 degrees Celsius. The PCR reaction mixture is incubated at the annealing temperature for 1 to 100 seconds, such as at least 1, at least 2, at least 3, at least 4, preferably at least 5, at least 6, at least 7, at least 8, at least 9, at least 10, alternatively at least 11, at least 13, at least 15, at least 20, at least 25, at least 30, at least 35, at least 40, at least 45, at least 50, at least 55, at least 60, at least 65, at least 70, at least 75, at least 80, at least 85, at least 90, at least 95, or at least 100 seconds.

In a specific embodiment of the present invention, the annealing temperature is between at least 15 degrees Celsius above the optimal annealing temperature, such as at least 1, at least 2, at least 3, at least 4, at least 5, at least 6, at least 7, at least 8, at least 9, at least 10, at least 11, at least 12, at least 13, at least 14, at least 15 degrees Celsius above the optimal annealing temperature.

The optimal annealing temperature can be calculated by standard algorithms, as known to people skilled within the art. In one embodiment, the optimal primer annealing temperature (Tm) is calculated as: Tm=4(G+C)+2(A+T), wherein G, C, A, T designates the number of the respective nucleotides. In another embodiment, the optimal primer annealing temperature (Tm) is calculated as: Tm=64.9° C.+41° C.×(number of G's and C's in the primer−16.4)/N, where N is the length of the primer. However, the annealing temperature should be empirically determined in respect of each specific primer. The modulation of the annealing temperature is used to adjust hybridization stringency as described elsewhere herein. Thus, the optimal annealing temperature should be set at a level, wherein the PCR bias towards amplification of unmethylated nucleic acid template is balanced by the less efficient annealing of methylation-independent oligonucleotide primer according to the present invention to unmethylated nucleic acid target sequence. Preferred annealing temperature in respect of a number of methylation-independent oligonucleotide primer according to the present invention are specified elsewhere herein.

Elongation

The oligonucleotide primers annealed to the template is elongated to form an amplification product. The elongating temperature depends on optimum temperature for the polymerase, and is usually between 30 and 80 degrees Celsius. Typically, the elongating temperature is between 60 and 80 degrees Celsius, such as at least 60, at least 65, at least 68, at least 69, at least 70, preferably at least 71, at least 72, at least 73, at least 74, alternatively at least 75, at least 76, at least 77, at least 78, at least 79, at least 80 degrees Celsius. The PRC reaction mixture is incubated at the elongating temperature for 1 to 100 seconds, such as at least 1, at least 2, at least 3, at least 4, preferably at least 5, at least 6, at least 7, at least 8, at least 9, at least 10, alternatively at least 11, at least 13, at least 15, at least 20, at least 25, at least 30, at least 35, at least 40, at least 45, at least 50, at least 55, at least 60, at least 65, at least 70, at least 75, at least 80, at least 85, at least 90, at least 95, or at least 100 seconds.

Elongation occurs in a buffered aqueous solution, preferably at a pH of 7-9.

The two oligonucleotide primers are added to the reaction mixture in a molar excess of primer: template especially when the template is genomic DNA which will ensure an improved efficiency. Deoxyribonucleoside triphosphates dATP, dCTP, dGTP, and dTTP are added to the reaction mixture, either separately or together with the primers.

An appropriate agent for effecting the primer extension reaction, referred to and described elsewhere herein as an agent for polymerization is added to the reaction mixture. It is appreciated by a person skilled in the art that for PCR the agent for polymerisation preferable is a heat-stable polymerase enzyme, such as Taq polymerase.

Cycling

The PCR method comprises incubating the nucleic acid at a cycle of different specific temperatures in order to control the steps of amplification. The amplification buffer and polymerase required for PCR are well known to people of skill within the art.

The PCR reaction mixture is incubated sequentially at the melting temperature, the annealing temperature and the elongating temperature, respectively, for a number of cycles. The PCR reaction may run between 10 and 70 cycles. Typically, the PCR reaction run between 25 and 55 cycles, such as at least 25, at least 30, at least 35, at least 40, preferably at least 45, at least 50 or at least 55 cycles.

PCR can be performed on a PCR machine, which is also known as a thermal cycler. Specifically, the thermal cycler may be coupled to a fluorometer, thus allowing the monitoring of the nucleic acid amplification in real time by use of intercalating fluorescent dyes, or other fluorescent probes. Applicable dyes according to the present invention include any DNA-intercalating dye.

Suitable dyes include ethidium bromide, EvaGreen, LC Green, Syto9, SYBR Green, SensiMix HRM™ kit dye.

Real-time PCR allows for easy performance of quantitative PCR (qPCR), which is usually aided by algorithms comprised in the software, which is usually supplied with the PCR machines.

The fluorometer can furthermore be equipped with software that will allow interpretation of the results. Such software for data analyses may also be supplied with the kit of the present invention.

Another variant of the PCR technique, multiplex PCR, enables the simultaneous amplification of many targets of interest in one reaction by using more than one pair of primers.

PCR according to the present invention comprise all known variants of the PCR technique known to people of skill within the art. Thus, the PCR technology comprise real-time PCR, qPCR, multiplex PCR.

Analysis of Amplified CpG-containing Nucleic Acids

According to the present invention the nucleic acid (target) sample is subjected to an agent that converts an unmethylated cytosine to another nucleotide which will distinguish the unmethylated from the methylated cytosine. In a preferred embodiment the agent modifies unmethylated cytosine to uracil. The modifying agent can be sodium bisulphite. During the amplification process uracil will be converted to thymidine.

Thus, after conversion of unmethylated cytosines to uracils in the nucleic acid (target) sample, the subsequent PCR amplification converts uracils to thymine. As a consequence of the sodium bisulfite and PCR-mediated specific conversion of unmethylated cytosines to thymines, G:C base pairs are converted to A:T base pairs at positions, where the cytosine was methylated.

The difference in nucleic acid sequence at previously methylated or unmethylated cytosines allows for the analysis of methylation status in a sample.

By this method, analysis of the amplified nucleic acid after treatment with a modifying agent such as sodium bisulphite and subsequent PCR amplification can reveal the methylation status of the target nucleic acid sequence. Thus, in one embodiment, the method for detection of methylation status of a CpG-containing nucleic acid according to the present invention further comprises a step of analyzing the amplified CpG-containing nucleic acids.

Specifically, the subsequent analysis of the amplified CpG-containing nucleic acid is selected from the group consisting of melting curve analysis, high resolution melting analysis, nucleic acid sequencing, primer extension, denaturing gradient gel electrophoresis, southern blotting, restriction enzyme digestion, methylation-sensitive single-strand conformation analysis (MS-SSCA) and denaturing high performance liquid chromatography (DHPLC).

In a preferred embodiment of the present invention, the analysis of the amplified CpG-containing nucleic acid is melting curve analysis. In another preferred embodiment of the present invention, the analysis of the amplified CpG-containing nucleic acid is high resolution melting analysis (HRM), as disclosed in the co-pending application entitled "analysis of methylation status by high resolution melting analysis", hereby incorporated by reference.

Melting Curve Analysis

Melting curve analysis or high resolution melting analysis exploits the fact that methylated and unmethylated alleles are predicted to differ in thermal stability because of the difference in GC contents after bisulphite treatment and PCR-mediated conversion of methylated C:G base pairs to A:T base pairs. The melting temperature of an amplification product according to the present invention is determined by the composition of methylated and unmethylated alleles in the nucleic acid sample. If the nucleic acid is completely unmethylated, all cytosines are converted to thymines, and the resulting PCR product will have a relatively low melting temperature compared to a methylated nucleic acid. If on the other hand, the nucleic acids comprised in the sample contain methylated cytosines at all CpG dinucleotides, the melting temperature of the PCR product will be relatively higher. If the nucleic acid sample comprises a mixture of methylated and unmethylated alleles, bisulphite treatment followed by amplification will result in two distinct amplification products. The unmethylated alleles will display a low melting temperature and the methylated alleles a high melting temperature. If only a subset of the CpG dinucleotides of the target sequence contain a methylated cytosine, the amplification product represents a pool of molecules with different melting temperatures, which leads to an overall intermediate melting temperature.

Melting curve analysis is performed by incubating the nucleic acid amplification product at a range of increasing temperatures. The temperature is increased from a starting temperature of at least 50 degrees Celsius, alternatively at least 55, at least 60, at least 62, at least 64, preferably at least 65, at least 66, at least 67, at least 68, at least 69, at least 70, at least 71, at least 72, at least 73, at least 74, at least 75, for example at least 76, at least 78, at least 80, at least 82, at least 84 degrees Celsius. The temperature is then increased to a final temperature of at least 70, at least 72, at least 74, at least 76, at least 78, at least 80, at least 82, at least 84, at least 86, preferably at least 88, at least 89, at least 90, at least 91, at least 92, at least 93, at least 94, at least 95, at least 96, at least 97, at least 98, at least 99, at least 100 degrees Celsius. In one embodiment, the temperature transitions from the starting temperature to the final temperature are a linear function of time. In a specific embodiment of the present invention, the linear transitions are at least 0.05 degrees Celsius per second, alternatively at least 0.01, at least 0.02, at least 0.03, at least 0.04, at least 0.06, at least 0.07, at least 0.08, at least 0.09, at least 0.1, at least 0.2, at least 0.3, at least 0.4, at least 0.5, at least 0.6, at least 0.7, at least 0.8, at least 0.9, at least 1.0, at least 1.1, at least 1.2, at least 1.3, at least 1.4, at least 1.5, at least 1.6, at least 1.7, at least 1.8, at least 1.9, at least 2, at least 3, at least 4, at least 5, at least 6, at least 7, at least 8, at least 9, at least 10 degrees Celsius per second. In a preferred embodiment, the melting curve analysis is performed by incubating the nucleic acid amplification product at increasing temperatures, from 70 to 95 degrees Celsius, wherein the temperature increases by 0.05 degrees per second.

The melting of the nucleic acid can be measured by a number of methods, which are known to people within skill of the art. One method involves use of agents, which fluoresce when bound to a nucleic acid in its double stranded conformation. Such agents include fluorescent probes or dyes, such as ethidium bromide, EvaGreen, LC Green, Syto9, SYBR Green, SensiMix HRM™ kit dye. Thus, in one embodiment, the melting curve analysis is performed by measurement of fluorescence. The melting of the nucleic acid amplification product according to the present invention can then be monitored as a decrease in the level of fluorescence from the sample. After measurement of the fluorescence the melting curves can be generated by plotting fluorescence as a function of temperature.

For direct comparison of melting curves from samples that have different starting fluorescence levels, the melting curves for data collected in HRM can be normalized, as described in the examples of the present invention. Such normalization methods are known to people of skill in the art. One preferred means of normalization include calculation of the 'line of best fit' in between two normalization regions before and after the major fluorescence decrease representing the melting of the amplification product.

The 'line of best fit' is a statistical measure, designating a line plotted on a scatter plot of data (using a least-squares method) which is closest to most points of the plot. Calculation of the line of best fit is performed differentially on Light-Cycler and LightScanner, as illustrated in the examples of the present invention.

A platform with a combined thermal cycler and a fluorescence detector is ideal to perform intube melting analyses. Thus, in one embodiment, the melting curve analysis is performed on a thermal cycler coupled to a fluorometer, such as the Ligthcycler, LC480 (Roche) or the Rotorgene 6000 (Corbett Research). Thereby, the measurement of fluorescence, corresponding to the melting of the double stranded nucleic acid template, can be monitored in real time. In a specific embodiment, the melting curve analysis is performed immediately after amplification. This allows an in-tube methylation assay, wherein the amplification and melting curve analysis is performed sequentially without transferring the sample from the tube. This procedure reduces the risk of contamination of the sample as a result from handling during the methylation assay.

Melting curve analysis allows the determination of the relative amount of methylated CpG-containing nucleic acid in a sample. By comparison of the melting curve of an unknown sample with the melting curve of at least one standard sample comprising said CpG-containing nucleic acid, the relative amount of methylated CpG-containing nucleic acid can be estimated. Thus, the present invention relates to a method, wherein the relative amount of methylated CpG-containing nucleic acid is estimated by comparison the melting curve of at least one standard sample comprising said CpG-containing nucleic acid. In one embodiment of the present invention, said standard sample comprise any combination of methylated and unmethylated CpG-containing nucleic acid. In a specific embodiment, said standard sample comprise 100% methylated CpG-containing nucleic acid. In another specific embodiment, said standard sample comprise 100% unmethylated CpG-containing nucleic acid. In yet another specific embodiment, said standard sample comprise 50% methylated nucleic acid and 50% unmethylated CpG-containing nucleic acid. In even another specific embodiment, said standard sample comprise 0.1% 0.5%, 1%, 2%, 3%, 5%, 10%, 15%, 20%, 25%, 30%, 35%, 40%, 45%, 50%, 55%, 60%, 65%, 70%, 75%, 80%, 85%, 90%, 95%, or 100% methylated CpG-containing nucleic acid.

In one embodiment of the present invention, wherein the relative amount of methylated CpG-containing nucleic acid in the nucleic acid sample is between 40-60%. In another embodiment, the relative amount of methylated CpG-containing nucleic acid in the nucleic acid sample is below 50%. In yet another embodiment, the relative amount of methylated CpG-containing nucleic acid in the nucleic acid sample is below 10%, below 1% or below 0.1%. Thus, the term "presence of methylation" as used herein refers to a relative amount of methylated CpG-containing nucleic acid in the nucleic acid sample of at least 0.1%, such as at least 1%, for example at least 10%, such as at least 20%, for example at least 30%, such as at least 50%, for example at least 70%, such as at least 90%, or for example at least 99%.

If the melting temperature (as measured by the melting curve) of an unknown sample is higher than the melting temperature of a standard sample, then the relative amount of methylated CpG-containing nucleic acid in said unknown sample is also higher than the relative amount of methylated CpG-containing nucleic acid in the standard sample.

Conversely, if the melting curve of an unknown sample is lower, i.e. the melting temperature is lower, than the melting temperature of a standard sample, then the relative amount of methylated CpG-containing nucleic acid in said unknown sample is also lower than the relative amount of methylated CpG-containing nucleic acid in the standard sample. The amount of standard samples included in the melting curve analysis, thus determines the precision of the determination of methylation status. The more standard samples, the more precise can the relative amount of nucleic acids be determined.

Thus, in one embodiment of the present invention a higher melting temperature of the amplified nucleic acid sample than of the standard sample is indicative of a higher relative amount of methylated nucleic acid of that sample than of the standard sample.

Conversely, a lower melting temperature of the amplified nucleic acid sample than of the standard is indicative of a lower relative amount of methylated nucleic acid of that sample than of the standard sample.

Peak Melting Temperature.

The term "peak melting temperature" as used herein, refers to the temperature at which the largest discrete melting step occurs. The nature of nucleic acid melting is explained elsewhere herein. The top of the peak corresponds to the major drop in fluorescence on melting curve The peak melting temperature corresponds to the highest level of the negative derivative of fluorescence (−dF/dT) over temperature versus temperature (T). (−dF/dT) versus temperature (T) is graphically illustrated in FIG. 1 and FIG. 3 for different nucleic acid targets. A nucleic acid sample subjected to melting curve analysis may display more than one peak melting temperature. In a preferred embodiment of the present invention, the melting curve analysis display at least 1, 2 or 3 peak melting temperatures.

Nucleic Acid Sequencing

In another embodiment of the present invention, the method for analysis of the amplified nucleic acid is sequencing of the nucleic acid. By nucleic acid sequencing the order of nucleotides (base sequences) in the nucleic acid is determined. Sequencing is usually performed by extending a primer, which anneals to the nucleic acid sequence of interest. The primer is extended by a polymerase in the presence of deoxynucleonucleotides.

In the dideoxy sequencing method 2,3-Dideoxyribose—a deoxyribose sugar lacking the 3 hydroxyl group is incorporated into the extended polynucleotide chain. When 2,3-Dideoxyribose is incorporated into a polynucleotide chain, it blocks further chain elongation. This method is also known as the Sanger method or chain termination method. The primer is extended in the presence of the normal dNTPs (A, T, G, C) and a small amount of 2,3-DideoxyriboseNTPs (ddNTP). The reactions are either performed in four separate reactions, one for each of the ddNTPs (ddATP, ddTTP, ddCTP, ddGTP), or in a joint reaction, wherein ddATP, ddTTP, ddCTP and ddGTP are coupled to different fluorescent dyes. The primers are then extended to variable lengths, each transcript being terminated upon incorporation of a ddNTP. The sequence of the nucleic acid of interest can then by read after denaturing polyacrylamide gel electrophoresis. Such sequencing techniques are known to people skilled within the art. Additionally, a number of different commercial kits are available for sequencing of nucleic acids.

Primer Extension

In yet another embodiment of the present invention, the method for analysis of the amplified nucleic acid is primer extension. The primer extension method uses primers designed to hybridize with a target. The primers may end one base upstream of the position of the putative single nucleotide polymorphism, in this method, the C of a CpG dinucleotide. In the single nucleotide primer extension technique a single chain-ending nucleotide, such as a ddNTP, is added. The only one of the four nucleotides that will extend the primer is the one that is complementary. The identity of the added nucleotide is determined in a variety of ways known to people of general skill within the art. For example, the chain-ending nucleotide may be radioactively labelled or coupled to a fluorescent dye, which can subsequently be identified.

Restriction Enzyme Digestion

In a further embodiment, the method according to the present invention for analysis of the amplified nucleic acid is restriction enzyme digestion. Restriction enzymes can be divided into exonucleases and endonucleases. In a specific embodiment, the analysis of the amplified nucleic acid is restriction endonuclease digestion.

The method of the present invention results in the specific conversion of unmethylated cytosines to thymines, i.e. G:C base pairs are converted to A:T base pairs at positions, where a cytosine was methylated. This means that the nucleic acid sequence is changed, which may lead to disruption of a restriction endonuclease site or the change of a site specific for one restriction endonuclease to another restriction endonuclease.

In a preferred embodiment of the present invention, the modified and amplified nucleic acid is analyzed for disruption of a site specific for the endonuclease AciI, BstUI, HhaI, HinP1I, HpaII, HpyCH4IV, MspI, TaqαI, Fnu4HI, Hpy188I, HpyCH4III, NciI, ScrFI, BssKI, Hpy99I, Nt.CviPII. StyD4I, AatII, AccI, AcI, AfeI, AflIII, AgeI, AvaI, BanI, BmgBI, BsaAI, BsaHI, BsaJI, BsaWI, BsiEI, BsiWI, BsoBI, BspDI, BspEI, Barbie, Bari, Bessie, Byssi, Bestir, Begin, Scab 8I, Clay, Eerie, Eagan, Sip, Haiti, Hindi, Hpy188III, Kais, Mule, Slab 1I, NaeI, NarI, NgoMIV, NlaIV, Brui, Pear 7I, PmlI, PvuI, SacII, SalI, SfoI, SmaI, SmlI, SnaBI, TliI, TspMI, XhoI, XmaI, ZraI, RsrII, AscI, AsiSI, FseI, NotI, PspXI, SgrAI, AlwNI, DraIII, PflFI, Tth111I, AleI, BsaBI, MslI, PshAI, XmnI, AhdI, BglI, BslI, BstAPI, EcoNI, MwoI, PflMI, BsmBI, FauI, BstXI, DrdI, SfiI, XcmI, HgaI, EciI, BceAI, BtgZI, MmeI, NmeAIII, BsaXI, BcgI, CspCI, BaeI, AccII, AspLEI, Bsh1236I, BsiSI, BstFNI, BstHHI, CfoI, HapII, Hin6I, HspAI or MaeII. The digested nucleic acid sample is subsequently analysed by for example gel electrophoresis.

Denaturing Gradient Gel Electrophoresis

In another embodiment of the present invention, the method for analysis of the amplified nucleic acid is denaturing gradient gel electrophoresis (DGGE). In this technique, the modified and amplified nucleic acid is loaded on a denaturing gel. This techniques allows the resolution of nucleic acids with different melting temperatures, which is based on the conversion of C:G base pairs to A:T base pairs, explained elsewhere herein. For DGGE analysis the nucleic acid is subjected to denaturing polyacrylamide gel electrophoresis, wherein the gel contain an increasing gradient of denaturants, such as for example a combination of urea and formamide. The increasing denaturant concentration corresponds to increased temperature, and therefore, a gradient of denaturants mimics a temperature gradient within the gel. The concentrations of denaturants alone, however, are not sufficient to induce DNA melting. Therefore, the gel is immersed in a electrophoresis buffer kept at 54-60 degrees Celsius. When a nucleic acid molecule reaches a level of denaturant that matches the melting temperature of the lowest melting domain, a partially melted intermediate will be formed that moves very slowly. Small shifts in the melting temperature of the low melting domain induced by differences in G:C content will cause the domain to unwind at different concentrations of denaturant. Accordingly, the modified and amplified nucleic acid of the present invention will bi retarded at different positions in the gel, providing the basis for physical separation between species with different G:C contents.

Southern Blotting

In another embodiment of the present invention, the method for analysis of the amplified nucleic acid is Southern blotting. In this procedure, the nucleic acid to be analysed are separated by gel electrophoresis and transferred to a nitrocellulose filter, whereto it is immobilized. After immobilization, the transferred nucleic acids can be identified by hybridization with specific probes comprising a complementary nucleic acid. After hybridization and removal of excess unbound probe, the amount of hybridized indicate whether the sequence of interest was represented in the nucleic acids immobilized on the nitrocellulose membrane. The probes are usually radioactively labelled for subsequent detection by radiography. The details of the southern blotting technique are well known to people of skill within the art.

Temperature increments or increasing concentration of denaturants result in a series of melting steps of the double-stranded DNA molecule. Each melting step represents the melting of a discrete segment also known as a melting domain. Several melting domains may be present in a double stranded DNA molecule. The interaction of a C on one DNA strand with a G on the other DNA strand of the double-stranded molecule, referred to as a G:C base pair, involves three hydrogen bonds. The interaction of an A on one strand DNA strand with a T on the other DNA strand of the double-stranded molecule, referred to as an A:T base pair, involves two hydrogen bonds. Therefore, the melting temperature of a melting domain increases with an increase in G:C content.]

Methylation-Sensitive, Single-Strand Conformation Analysis (MS-SSCA)

MS-SSCA is a method of screening for methylation changes. MS-SSCA uses single-strand conformation analysis for the screening of an amplified region of bisulfite-modified nucleic acid. The amplified products are denatured and electrophoresed on a nondenaturing polyacrylamide gel, whereby the sequence differences between unmethylated and methylated sequences lead to the formation of different secondary structures (conformers) with different mobilities. Once the normal mobility pattern is established, any variation would indicate some degree of methylation.

Denaturing High Performance Liquid Chromatography (DHPLC)

DHPLC is yet another technique for methylation screening of bisulfite-modified PCR products. As for other techniques mentioned herein, DHPLC identifies single nucleotide polymorphisms, which are arise after bisulfite treatment of unmethylated alleles of the CpG containing nucleic acid. The optimum temperature for DHPLC can be predicted by the sequence of the fully methylated product. Subsequently, the temperature is verified to obtain tight peaks. The retention time of the peak reflects methylation status, because the more unmethylated the target is, the less GC rich the PCR product is and the lower the retention time is.

Disorders

The method of the present invention can by applied for the diagnosis of disorders, of which the presence or absence of CpG methylation is indicative of the disorder. In the case of protooncogenes, the absence of CpG methylation is usually indicative of an increased risk of developing cancer. Also, demethylation of transposable elements, such as retrotransposons may be indicative of an increased risk of developing cancer. Conversely, for tumour suppressor genes, the presence of CpG methylation is usually indicative of an increased risk of developing cancer.

In one embodiment, the methods and kits of the present invention can be used for the detection of methylation status of CpG-containing nucleic acids in a sample, wherein the presence or absence of methylated CpG-containing nucleic acid is indicative of a disorder selected from the group consisting of Alzheimer's disease, atherosclerosis, breast cancer, bladder cancer, ovarian cancer, melanoma, prostate cancer, lung cancer, renal cancer, colon cancer, gastric cancer, cervical cancer, leukaemia, low grade astrocytoma, anaplastic astrocytoma, glioblastoma, haematopoietic disorders, medulloblastoma, leukemia, metabolic disorders, endometrial cancer, neuroblastoma, diffuse large B-cell lymphoma, developmental disorders, Prader-Willi syndrome, Angelman syndrome and imprinting disorders.

In a preferred embodiment, the methods and kits of the present invention can be used for the detection of methylation status of CpG-containing nucleic acids in a sample, wherein the presence of methylated CpG-containing nucleic acid is indicative of a disorder selected from the group consisting of breast cancer, bladder cancer, ovarian cancer, melanoma, prostate cancer, lung cancer, colon cancer, endometrial cancer and leukaemia.

In another preferred embodiment, the methods and kits of the present invention can be used for the detection of methylation status of CpG-containing nucleic acids in a sample, wherein the presence of methylated CpG-containing nucleic acid is indicative of breast cancer.

In yet another preferred embodiment, the methods and kits of the present invention can be used for the detection of methylation status of CpG-containing nucleic acids in a sample, wherein the presence of methylated CpG-containing nucleic acid is indicative of bladder cancer.

In another preferred embodiment, the methods and kits of the present invention can be used for the detection of methylation status of CpG-containing nucleic acids in a sample, wherein the presence of methylated CpG-containing nucleic acid is indicative of ovarian cancer.

In another preferred embodiment, the methods and kits of the present invention can be used for the detection of methylation status of CpG-containing nucleic acids in a sample, wherein the presence of methylated CpG-containing nucleic acid is indicative of melanoma.

In another preferred embodiment, the methods and kits of the present invention can be used for the detection of methylation status of CpG-containing nucleic acids in a sample, wherein the presence of methylated CpG-containing nucleic acid is indicative of prostate cancer.

In another preferred embodiment, the methods and kits of the present invention can be used for the detection of methylation status of CpG-containing nucleic acids in a sample, wherein the presence of methylated CpG-containing nucleic acid is indicative of lung cancer.

In another preferred embodiment, the methods and kits of the present invention can be used for the detection of methylation status of CpG-containing nucleic acids in a sample, wherein the presence of methylated CpG-containing nucleic acid is indicative of colon cancer.

In another preferred embodiment, the methods and kits of the present invention can be used for the detection of methylation status of CpG-containing nucleic acids in a sample, wherein the presence of methylated CpG-containing nucleic acid is indicative of endometrial cancer.

In another preferred embodiment, the methods and kits of the present invention can be used for the detection of methylation status of CpG-containing nucleic acids in a sample, wherein the presence of methylated CpG-containing nucleic acid is indicative of leukaemia.

In another preferred embodiment, the methods and kits of the present invention can be used for the detection of methylation status of CpG-containing nucleic acids in a sample, wherein the presence of methylated CpG-containing nucleic acid is indicative of colon cancer.

In one embodiment, the methods and kits of the present invention can be used for the detection of methylation status of CpG-containing nucleic acids in a sample, wherein the presence of methylated CpG-containing nucleic acid is indicative of a disorder selected from the group consisting of gastric cancer and cervical cancer.

In one embodiment, the methods and kits of the present invention can be used for the detection of methylation status of CpG-containing nucleic acids in a sample, wherein the presence of methylated CpG-containing nucleic acid is indicative of imprinting disorders.

In one embodiment, the methods and kits of the present invention can be used for the detection of methylation status of CpG-containing nucleic acids in a sample, wherein the absence of methylated CpG-containing nucleic acid is indicative of imprinting disorders.

In a specific embodiment the methods and kits of the present invention comprise the primers according to SEQ ID NO.: 46 and 47 for the detection of methylation status of CHD1 as defined in SEQ ID NO.: 1, wherein the primer annealing temperature during amplification is 59 degrees Celsius, and the presence of methylation is indicative of Bladder cancer.

In another specific embodiment the methods and kits of the present invention comprise the primers according to SEQ ID NO.: 60 and 61 for the detection of methylation status of PITX2 as defined in SEQ ID NO.: 8, wherein the primer annealing temperature during amplification is 60 degrees Celsius, and the presence of methylation is indicative of Breast cancer.

In another specific embodiment the methods and kits of the present invention comprise the primers according to SEQ ID NO.: 68 and 69 for the detection of methylation status of MLH1 as defined in SEQ ID NO.: 12, wherein the primer annealing temperature during amplification is 62 degrees Celsius, and the presence of methylation is indicative of Colon cancer.

In another specific embodiment the methods and kits of the present invention comprise the primers according to SEQ ID NO.: 72 and 73 for the detection of methylation status of MSH6 as defined in SEQ ID NO.: 14, wherein the primer annealing temperature during amplification is 59 degrees Celsius, and the presence of methylation is indicative of Endometrial cancer.

In another specific embodiment the methods and kits of the present invention comprise the primers according to SEQ ID NO.: 80 and 81 for the detection of methylation status of CD109 as defined in SEQ ID NO.: 18, wherein the primer annealing temperature during amplification is 60 degrees Celsius, and the presence of methylation is indicative of Leukemia.

In another specific embodiment the methods and kits of the present invention comprise the primers according to SEQ ID NO.: 92 and 93 for the detection of methylation status of PRSS3 as defined in SEQ ID NO.: 24, wherein the primer annealing temperature during amplification is 59 degrees Celsius, and the presence of methylation is indicative of Lung cancer.

In another specific embodiment the methods and kits of the present invention comprise the primers according to SEQ ID NO.: 104 and 105 for the detection of methylation status of PRDX2 as defined in SEQ ID NO.: 30, wherein the primer annealing temperature during amplification is 61 degrees Celsius, and the presence of methylation is indicative of Melanoma.

In another specific embodiment the methods and kits of the present invention comprise the primers according to SEQ ID NO.: 114 and 115 for the detection of methylation status of WWOX as defined in SEQ ID NO.: 35, wherein the primer annealing temperature during amplification is 62 degrees Celsius, and the presence of methylation is indicative of Ovarian cancer.

In another specific embodiment the methods and kits of the present invention comprise the primers according to SEQ ID NO.: 116 and 117 for the detection of methylation status of ABHD9 as defined in SEQ ID NO.: 36, wherein the primer annealing temperature during amplification is 60 degrees Celsius, and the presence of methylation is indicative of Prostate cancer.

Kit

One aspect of the present invention relates to Another aspect of the present invention relates to a kit for the detection of methylation status of a CpG-containing nucleic acid in a sample, said kit comprising at least one methylation-independent oligonucleotide primer, which comprises at least one CpG dinucleotide. A kit will typically comprise both a forward and a reverse primer to be used in the amplifying step of the present invention. The forward primer, the reverse primer or both may be a methylation-independent oligonucleotide primer as described herein.

In one embodiment the kit further comprises at least one reference sample comprising control CpG-containing nucleic acid. Such a control CpG-containing nucleic acid is at least 97% identical to the target CpG-containing nucleic acid which is the object for detecting the methylation status. The target CpG-containing sequence may be any sequence prone to methylation or demethylation, for example tumor suppressor genes, oncogenes, retrotransposons as described elsewhere herein. For example, the at least one reference sample comprises 100% methylated CpG-containing nucleic acid, and/or 100% unmethylated CpG-containing nucleic acid. In a preferred embodiment the kit comprises at least two reference samples, wherein one of said reference samples comprises 100% methylated CpG-containing nucleic acid and a second reference sample comprises 100% unmethylated CpG-containing nucleic acid. The methylated and unmethylated CpG-containing nucleic acids may be mixed, by a person employing the kit, in ratios that are suitable for the detection of methylation in a particular sample.

It is understood that control samples in different ratios of methylated to unmethylated CpG-containing nucleic acids may be comprised in the kit. For example the kit may comprise, at least one reference sample comprising 50% methylated and 50% non-methylated nucleic acid.

The kit may also comprise additional reagents used in the amplifying step of the detection method as disclosed herein. Thus, the kit may further comprise deoxyribonucleoside triphosphates, DNA polymerase enzyme and/or nucleic acid amplification buffer. In another embodiment the kit further comprises an agent that modifies unmethylated cytosine nucleotides. Such an agent may for example be bisulfite.

The kit may in preferred embodiments further comprise instructions for the performance of the detection method of the kit and for the interpretation of the results. The kit involves the method of detecting the methylation status of a CpG-containing nucleic acid, wherein said CpG-containing nucleic acids is modified using an agent which modifies at least one unmethylated cytosine in said methylated CpG-containing nucleic acid and amplifying said CpG-containing nucleic acid by means of at least one methylation-independent oligonucleotide primer. The instructions for performing the method of the kit comprises for example information of particular annealing temperatures to be used for the at least one methylation-independent primers, as well as for example information on cycling parameters. The kit may further comprise instructions for the interpretation of the results obtained by the method. For example how to interpret the amplified products subsequently analysed by melting curve analysis or methods as described elsewhere herein. Information of the interpretation of melting curve analysis is described elsewhere herein.

The kit may in preferred embodiments further comprise software comprising an algorithm for calculation of primer annealing temperature and interpretation of results.

Preferred embodiments for the CpG-containing nucleic acid for which the methylation status is determined are CpG-containing nucleic acids having a sequence, which is at least 97% identical to the sequence selected from the group consisting of SEQ ID NO.: 1-45 and SEQ ID NO: 152-184.

The at least one methylation-independent oligonucleotide primer of the kit is selected from the group consisting of SEQ ID NO.: 46-151 and SEQ ID NO: 185-250.

It is appreciated that the kit may be used for the diagnosis of a disorder as specified elsewhere herein. The specific embodiments are described elsewhere herein.

Use

In one aspect, the present invention relates to the use of a methylation-independent oligonucleotide primer for detecting methylation status of a CpG-containing nucleic acid. Embodiments of that use comprise any methylation-independent oligonucleotide primer as described elsewhere herein. In a preferred embodiment, the primer comprises at least one CpG dinucleotide, such as at least two CpG dinucleotide. The CpG dinucleotide is preferably located in the 5' end region of the primer. In one example, the methylation-independent oligonucleotide primer for the use according to the present invention is any such primer, however in a preferred embodiment, the primer is selected from the group consisting of SEQ ID NOs: 46-150 and SEQ ID NOs: 185-250. In another embodiment, the primer is as described elsewhere herein Moreover, the use according to the present invention comprises detecting methylation status of any CpG-containing nucleic acid. In a preferred embodiment, the CpG-containing nucleic acid is selected from the group consisting of SEQ ID NOs: 1-45 and SEQ ID NOs: 151-184. In another embodiment, the CpG-containing nucleic acid is as defined elsewhere herein.

EXAMPLES

Example 1

Modification of CpG Containing Nucleic Acid in Sample

For bisulfite conversion the following reagents were used: 3 M sodium bisulfite, 10 mM hydroquinone, 3 M NaOH and 0.3 M NaOH.

200 ng of sample DNA is mixed with water up to final volume 18 µL. The DNA is denatured by adding 2 µL 3 M NaOH and incubating for 10 min at 37° C. followed by 5 min at 95° C. and directly placing the mixture on ice.

208 µL freshly prepared 3 M sodium bisulfite is added (final concentration 2.6 M) and 12 µL hydroquinone solution (final concentration 0.5 mM). The mixture is mixed with pipet, and incubated for 16 h (overnight) at 55° C.

The bisulfite reaction is diluted with water up to volume of 350-400 µL and the resulting solution transferred to an assembled Microcon YM-100 centrifugal filter unit.

The solution is subjected to centrifugation at 2800 rpm using a Model 5417R centrifuge (Eppendorf, Westbury, N.Y., USA) for 10 min. The filtrate is discarded, and 250 µL water is added to upper chamber, and centrifuged for 12 min at 2800 rpm. This filtration step is repeated. Again the filtrate is discarded and 300 µL 0.3 M NaOH is added to the upper chamber, incubated at 37° C. for 15 min, and centrifuged for 6 min at 2800 rpm. The resulting filtrate is discarded and 250 µL water is added to the upper chamber, and centrifuged at 2800 rpm for 15 min.

The sample is eluted by adding 50 µL Tris-EDTA (TE) buffer, mixed by use of a pipet, and allowed to stand for 15 min. The device is inverted and the TE solution of the bisulfite-converted DNA is transferred to a clean tube. The bilsulfite-converted DNA is kept overnight at −20° C. before use for analyses.

Amplification of Modified CpG Containing Nucleic Acids

Figure 1:
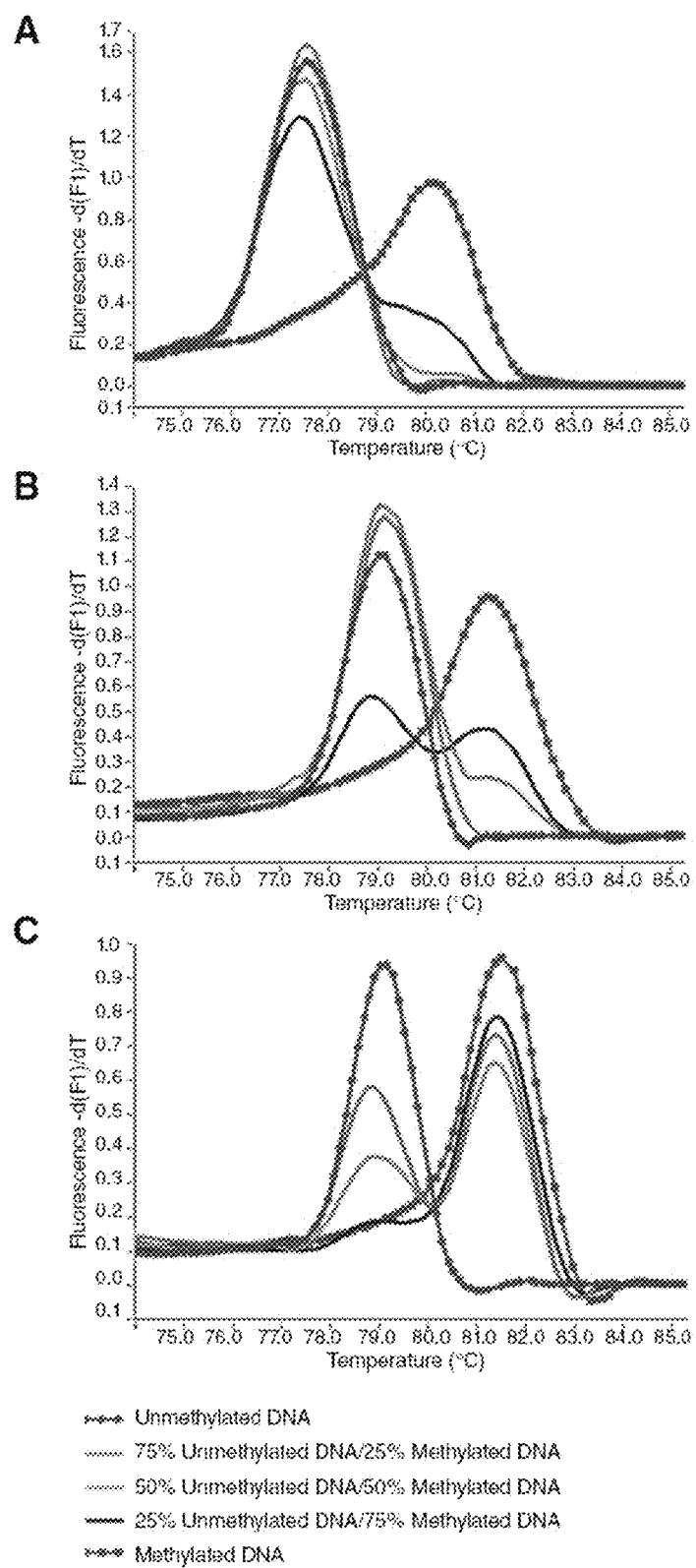
FIG. 1. In-tube DNA methylation-sensitive melting curve analyses (MS-MCAs) performed on five different template mixes consisting of varying ratios of fully methylated and unmethylated DNA.

The PCR amplifications were performed using the LightCycler® System (Roche Applied Science, Indianapolis, Ind., USA). The reaction mixture consisted of 10 pmol of each primer, 3 mM MgCl2, 1× LightCycler FastStart DNA Master SYBR® Green I (Roche Applied Science), and 1 µL bisulfite-treated DNA stock in a final volume 10 µL. The PCR amplification was initiated by heating to 95° C. for 10 min, followed by 45 cycles comprising 95° C. for 10 s, Ta (depending on primer set) for 10 s, and 72° C. for 10 s. Melting analyses were performed immediately after amplification, and the fluorescence of LightCycler FastStart DNA Master SYBR Green I was measured during linear temperature transition from 70°-95° C. at 0.05° C./s. The melting peaks were obtained by plotting the negative derivative of fluorescence (−dF/dT) over temperature versus temperature (T). FIG. 1 (A) The melting profiles for the PCR product performed with primers designed according to Reference 6. The melting profiles after amplification with the redesigned primers containing one CpG dinucleotide each at Ta (B) 62° C. and (C) 69° C.

The PCR bias toward the unmethylated allele due to the difference in CG content after bisulfite treatment was tested using different ratios of methylated and unmethylated DNA [CpGenome™ Universal Methylated DNA (Chemicon, Temecula, Calif., USA) and peripheral blood DNA as methylated and unmethylated control, respectively]. The majority of assays showed a positive methylation specific signal only in samples containing >50% methylated template. Representative results are shown in FIG. 1A, in which the target is a portion of the putative tumor suppressor gene PPP3CC.

Two changes were introduced in an attempt to address these limitations. First, the primers were redesigned to contain a limited number of CpG sites, thereby to anneal with a higher efficiency to the methylated than to the unmethylated template. FIG. 2 shows the original and redesigned primers for methylation screening experiments of PPP3CC. The new primer sets efficiently amplified both methylated and unmethylated alleles (FIG. 1B). Moreover, depending on the primer annealing temperature (Ta) during PCR, we were able to control the bias of the PCR amplification. At a relatively low Ta, both the methylated and unmethylated templates were amplified with comparable efficiency (FIG. 1B), whereas elevating the Ta resulted in a significantly more efficient amplification of the methylated template (FIG. 1C). In summary, by adjusting the Ta of the PCR amplification we were able to improve the sensitivity of our assay.

Example 2

Validation of our approach was performed using four assays previously designed according to Reference 26. The assays were developed to screen for methylation of putative tumor suppressor genes in prostate cancer samples, and two of them showed methylation in <15% of samples in our panel. The redesigned primers according to the present invention were tested using templates containing defined mixtures of methylated and unmethylated DNA in experiments analogous to those shown in FIG. 1. In all cases, the assays followed the pattern shown here for PPP3CC gene (i.e., depending on Ta, the same primer set was able to amplify the methylated allele of the gene of interest with higher efficiency; see FIG. 3). In panels A and B of FIG. 3 the promoter region of the CSMD1 gene (SEQ ID NO.:42) is amplified at annealing temperatures 61° or 68° C., respectively, by use of the primers identified by SEQ ID NO.: 144 and 145. In panels C and D a CpG rich region of the MAP3k7 gene is amplified at annealing temperatures Ta 60° and 64° C., respectively by use of the primers identified by SEQ ID NO.: 146 and 147.

For the two assays that previously had been used to detect methylation in clinical samples, the modified procedure allowed detection of 40%-50% more methylated samples from the same sample panel (unpublished data). The observed differences in methylation detection levels most likely result from increased sensitivity of the redesigned assays.

Analyses of primer sequences used during these experiments showed that more than two CpG sites in the sequence of a single primer resulted in no amplification of unmethylated template (data not shown) and that the primer CpG sites should be kept as close as possible to the 5' end of the primer sequence.

The primer design approach of the present invention—allowing CpG nucleotides into the primer sequences—significantly increases the flexibility in selection of amplification targets suitable for analyses, which is crucial for the experiment as the sequences subjected to MS-MCAs ideally should contain only one melting domain to ensure unambiguous results in the post-PCR melting analysis (29). Furthermore, the use of one primer set that is able to amplify both the methylated and unmethylated templates overcomes the problem of heterogeneous methylation of the primer binding sites, as primers always amplify the sequence of interest, no matter the methylation status of CpG sites included in primer binding sites.

This modified MS-MCA methodology serves as an alternative to other qualitative techniques currently used in methylation studies. By allowing users to control for the bias of PCR amplification, this method has potential in semiquantitative applications. The use of intercalating dyes reduces the costs of the experiments, as there is no need for the use of expensive probes. The method is characterized by high sensitivity; in our experiments we used a DNA bisulfite treatment protocol requiring only 200 ng genomic DNA, as described herein. This feature is especially relevant for diagnostics and cancer research experiments, which are frequently limited by a low quantity of tumor DNA.

Example 3

Methylation-sensitive High Resolution Melting (MS-HRM): a New Approach for Sensitive and High-throughput Assessment of Methylation This example illustrates that high resolution melting analysis (HRM) is a sensitive and specific method for the detection of methylation. Methylated DNA and unmethylated DNA acquire different sequences after bisulfite treatment resulting in PCR products with markedly different melting profiles. We used PCR to amplify both methylated and unmethylated sequences and assessed HRM for the determination of the methylation status of the MGMT promoter region. Reconstruction experiments showed that MGMT methylation could be detected at levels as low as 0.1%. Moreover, MS-HRM allows for estimation of the methylation level by comparing the melting profiles of unknown PCR products to the melting profiles of PCR products derived from standards with a known unmethylated to methylated template ratio. Here, MS-HRM is used for the analysis of eight cell lines of known methylation status and a panel of colorectal cancer specimens. The simplicity and high reproducibility of the MS-HRM protocol makes MS-HRM the method of choice for methylation assessment in many diagnostic and research applications.

DNA Samples and Controls

Colorectal cancer samples were provided by the Peter MacCallum Cancer Centre Tissue Bank. DNA was extracted from those samples by using the DNeasy Tissue Extraction Kit (Qiagen, Hilden, Germany) following the manufacturer's protocol. DNA from cell lines was purified by using the salting out method (11). As a positive/methylated control in our experiments, we used CpGenome™ Universal Methylated DNA (Chemicon, Millipore, Billerica, Mass.). DNA from peripheral blood mononuclear cells was used as a negative/unmethylated reference. To create the range of methylated and unmethylated allele dilutions, the above two controls were mixed in 0.1, 1, 10 and 50% methylated to unmethylated template ratios. Each of our experimental runs included the range of methylated/unmethylated standards.

Bisulphite Modification

We used the MethylEasy™ Kit (Human Genetic Signatures, Sydney, Australia) for bisulphite modification of the DNA. The starting amount of DNA for all the bisulphite modifications was 1 mg and all the modification reactions were performed according to the manufacturer's protocol with the exclusion of the second 70% ethanol wash.

High Resolution Melting Analysis (HRM)

PCR amplification and high resolution melting analysis were carried out sequentially on a Rotor-Gene™ 6000 (Corbett Research, Mortlake, Australia). PCR was carried out in a 20 ml total volume containing: 1× Buffer, 4mM Mgb2,200 mM of each of the four dNTPs, 250 nM of each primer, 5 mM Syto9 dye (Invitrogen, Carlsbad, Calif.), 1U HotStarTaq polymerase (Qiagen) and 1 ml of bisulphite modified template (theoretical concentration 20 ng/ml). The amplification consisted of 15 min at 95° C., followed by 50 cycles of 5 s 95° C., 5 s at the primer annealing temperature (Ta) and 10 s at 72° C. High resolution melting analyses were performed at the temperature ramping and florescence acquisition setting recommended by the manufacturer i.e. temperature ramping from 70-95° C., rising by 0.1° C. /2 s. All the reactions were performed in triplicate. The melting curves were normalized by calculation of the 'line of best fit' in between two normalization regions before and after the major fluorescence decrease representing the melting of the PCR product using the software provided with the Rotor-Gene™ 6000. This algorithm allows the direct comparison of the samples that have different starting fluorescence levels.

MGMT MethylLight Assay

The MGMT MethylLight assay used for validation of our experiments was as previously reported (12). The reaction consisted of: 1× Buffer, 4 mM Mgb2, 200 mM of each of the four dNTPs, 500 nM of each primer, 200 nM of probe, 1 U HotStarTaq polymerase and 1 ml of bisulphite modified template (theoretical concentration 20 ng/ml). The real-time amplifications were carried over and analysed on a Rotor-Gene™ 3000 machine (Corbett Research). After 15 min at 95° C., 50 cycles of 95° C. for 15 s and 60° C. for 30 s were performed. The assay was optimized on the same range of methylated/unmethylated template mixes as in MS-HRM analyses. All the PCR amplifications were performed in triplicate. MGMTMS-HRM and BNIP3 MS-HRM assays The primer sets for all MS-HRM assays were designed according to the principles recently set out to compensate for PCR bias (13). The primers were designed to amplify both methylated and unmethylated template. The primers used and the amplified sequences are disclosed in the co-pending application entitled "Method for detecting methylation status by using methylation-independent primers", hereby incorporated by reference.

The Sensitivity of the MS-HRM Assay

The sensitivity of the MGMT MS-HRM assay was tested by using dilutions of fully methylated control DNA into peripheral blood DNA. The inclusion of CpGs in the primer sequence gave us the possibility to direct the PCR bias towards the methylated templates by manipulating the annealing temperature of PCR amplification and, therefore, making our assays more sensitive for methylation detection. All assays showed annealing temperature dependent sensitivity (FIG. 4). The first assay that we designed (MGMT MS-HRM1) targeted a 175-bp long fragment of the MGMT promoter.

This assay did not give reproducible methylation signals at the 0.1% methylation measurement point. We addressed this by redesigning the primers to amplify shorter fragments of the template. Two new assays MGMT MS-HRM2 and MGMT MS-HRM3 amplified fragments of 109 and 94 bp, respectively. Both MGMT MS-HRM2 and MGMT MS-HRM3, when run at the annealing temperature that significantly favoured amplification of methylated template, were able to reproducibly detect methylation in the samples containing 0.1% methylated template shown in FIGS. 5B and C.

Profiling of Methylation Content of the Samples by MS-HRM

The consistency of normalized melting profiles derived from samples with different ratios of methylated and unmethylated template was tested. The normalized melting profiles of the PCR product amplified from the same mix of methylated and unmethylated template were consistent between replicates and between different runs (data not shown). Furthermore, the shapes of normalized melting profiles were amplification independent as samples with different starting amount of template displayed very similar profiles. The consistency of HRM profiles allows the design of MS-HRM for estimation of the methylation content of unknown samples on the basis of similarities of normalized HRM profiles. Nevertheless, when designing MS-HRM the length and the number of differences between methylated and unmethylated PCR products need to be taken into account. A short product will give high sensitivity but limited resolution between different levels of methylation because of the smaller differences in melting profiles between methylated and unmethylated products (FIG. 5 and unpublished data). On the other hand, a longer product will give readily distinguishable HRM profiles for PCR products derived from samples with different ratios of methylated and unmethylated template which will allow for the estimation of the methylated proportion of an unknown sample on the basis of similarities of HRM profiles of standards and unknown (FIGS. 4, 6A and 7). However, the annealing temperature at which the PCR amplification is in equilibrium between methylated and unmethylated product has to be empirically determined prior to analyses.

Validation of MS-HRM Results Against the MethylLight Assay

We validated the performance of the MGMT MS-HRM1 assay against a previously described MethylLight assay for the MGMT promoter region (12). In our hands, the performance of the MGMT MS-HRM1 assay for the detection of MGMT promoter region methylation was equivalent to the MethylLight assay as both of the assays gave reproducible results until the 0.1% methylation dilution (data not shown). However, the sensitivity of the MGMT MS-HRM2 and MS-HRM3 assays were superior to that observed for the MethylLight MGMT assay (12). MGMT MS-HRM2 as well as MGMT MS-HRM3 gave fully reproducible methylation signals from the standard sample containing 0.1% methylated template in the background of unmethylated DNA (data not shown).

Application of the MGMT MS-HRM Assay to Cell Lines

We also tested DNA from eight cell lines (MDA-MB-468, HS578T, SW480, MDA-MB-435, MDA-MB-231, PC3, T47D and SW48) for which the methylation status of the MGMT promoter had been previously reported (14) by using the MGMT MS-HRM1, MGMT MS-HRM3 and MethylLight assays. Four of the eight cell lines studied (SW480, MDA-MB-435, MDA-MB-231 and SW48) showed complete (100%) methylation (FIG. 6).

HS578T displayed a less characteristic melting profile which we interpreted as being due to heterogeneous methylation. Whereas there was no evidence for heteroduplex formation between PCR products arising from unmethylated and fully methylated templates, heteroduplexes could form if the individual PCR products differed at only a few bases. Therefore, the curve was differently shaped as a consequence of complex melting pattern of multiple heteroduplexes (FIG. 6). The results from MGMT MS-HRM were consistent with MethylLight data for the cell lines (FIG. 6B).

Application of the MGMT MS-HRM Assay to Clinical Specimens

The diagnostic applicability of MS-HRM assay was tested on a panel of 19 colorectal cancer samples. The MGMT MS-HRM3 assay was used in those experiments and we also validated the MS-HRM results against the MethylLight assay (12). MS-HRM assays detected MGMT methylation in 8 of the 19 samples (42%). However, two of the above samples showed a very low methylation level (less than the 0.1% standard).

Methylation of one of the above samples was only detectable by the MGMT-MS-HRM3 assay. We repeated all the runs to test the reproducibility of our results in between two different experiments and obtained identical results.

Verification of Accuracy of MS-HRM Approach: BNIP3 MS-HRM Assay

To verify that the MS-HRM approach is widely applicable in methylation studies, an MS-HRM assay was developed for the promoter region of BNIP3. The BNIP3 specific oligonucleotide primers are disclosed in the co-pending application entitled "Method for detecting methylation status by using methylation-independent primers", hereby incorporated by reference. BNIP3 has been reported to undergo aberrant methylation in various cancer types (15-17). As with the MGMT MS-HRM assay, we used the range of methylated/unmethylated mixes at different PCR annealing temperatures to determine the best conditions. In this model system, the BNIP3 MS-HRM assay was able to unambiguously detect methylation at the 0.1% level (FIG. 7). During evaluation of this assay, we performed the BNIP3 MS-HRM assay for the eight cell lines used in the MGMT methylation study. Three of the cell lines SW480, MDA-MB-435 and SW48 were methylated at the BNIP3 promoter (data not shown). The assay was also used to test for methylation of the panel of 19 colorectal cancer samples. Methylation of the BNIP3 promoter sequence was detected in 12 out of 19 (63%) of colorectal cancer samples. The methylation levels of 8 of these samples (42%) were less than 10% with 3 of them displaying 0.1% or less methylation (FIG. 7). All the results were reproducible between replicates (data not shown).

Discussion

There are many methods for the analysis of methylation at individual loci, each with their characteristic strengths and weaknesses (9). However, only a few protocols have gained widespread use. Genomic sequencing can be considered the gold standard (18,19). It provides the most detailed information but its sensitivity is relatively low (about 20%) and it is generally unsuitable for screening because it is expensive to run, particularly when individual clones are analysed. Pyrosequencing, which has been recently introduced, is more sensitive (about 5%) but is dependent on the availability of the proprietary instrumentation (20). The most widely used method is methylation-specific PCR (MSP) that uses primers specific for methylated, bisulphite-modified DNA (21). Unmethylated sequences are not normally amplified unless primers specific for unmethylated bisulphite modified DNA are designed. Despite its widespread use, MSP has a number of important limitations (9,22). As with other techniques that rely on PCR primer 30 mismatching to give specificity, false positives can arise if primers are badly designed or used at too low a temperature. MSP is very sensitive but is not quantitative. This can lead to the classification of a tumour as being methylated for a gene when a small minority of cells only is positive, or more seriously, if the bisulphite conversion of the DNA is incomplete. Consistent with these reservations, in the recent trial of temozolomide in glioblastoma, it was reported that testing for MGMT methylation using MSP gave 'highly variable and centre-dependent' results (8). The majority of applications in methylation studies utilize methylation-independent PCR (MIP) where the primers are designed to amplify the bisulphite-modified sequence regardless of its methylation status. However, the standard algorithms for the design of MIP primers and the protocols used do not always lead to the proportional amplification of methylated and unmethylated sequences (13,20,23). As it is often difficult to avoid CpG dinucleotides in primers designed to amplify CpG islands, some authors have suggested that the Cs in CpG sequences in primers get replaced by a mismatched base (19). Other authors have suggested that since the purpose of these assays is to detect methylation, some bias towards methylated sequences is acceptable and that a limited number of CpGs can be included in the primers, particularly if they are placed away from the 30 end (24). More recently, it has been shown that some CpGs are necessary in the primer sequence, otherwise PCR bias can lead to a significant underestimate of the degree of methylation (13). We have accordingly adopted the strategy of using primers containing limited numbers of CpGs and manipulating the annealing temperature to control the bias of PCR amplification in the design of MS-HRM assays. At lower annealing temperatures, the primers bind both methylated and unmethylated templates and PCR bias will favour the amplification of unmethylated sequences. At higher annealing temperatures, primer binding will favour methylated sequences, and thus at the optimal annealing temperature, amplification is effectively independent of methylation status. Therefore, MS-HRM can be used to estimate the proportion of methylation of a sample when run with standards. This is especially important when assessing clinical cancer samples for predictive markers such as MGMT where discrimination between tumour specimens that are methylated in all cells of the tumour from those that only show methylation in a small subset of their cells may have prognostic value. In the ideal situation, an estimate of the proportion of tumour cells in the sample will be given by pathological examination of the tissue and this can be compared with the estimated proportion of DNA that is methylated. Furthermore, if the tumour samples are of high purity, they can be used to determine whether the tumour is homozygously or heterozygously methylated. The technique would also be applicable to the diagnosis of imprinting disorders that are characterized by the abnormal methylation of imprinted genes. High resolution melting relies on the use of high sensitivity florescence detection instrumentation, fully saturating intercalating dyes and software allowing the analysis of the melting profiles of PCR products. We developed HRM for discrimination between methylated and unmethylated sequences after bisulphite modification of the target DNA. Sodium bisulphite converts unmethylated cytosines to uracil and leaves methylated cytosines intact. Therefore, the PCR product derived from a methylated template will have a higher melting temperature than that from an unmethylated template and those differences can be resolved by melting analysis. We have shown that HRM is applicable for the very sensitive detection of methylation in an unmethylated background. With MS-HRM, we were able to unambiguously detect the methylated fraction of DNA in samples containing as little as 0.1-1.0% of methylated DNA, the same range as seen for the MethylLight assay (25). MS-HRM is an in-tube method meaning that the analysis takes place without the PCR product leaving the tube that it was amplified in. This is of importance for diagnostic laboratories not only because of the rapidity that it affords, but also the elimination of PCR product contamination which has proven to be a major problem both in research and the diagnostic settings. An in-tube strategy based on the analysis of derivative peaks of melting curves of PCR products to assess methylation has already been reported (26,27). This has not become widely used presumably because of the difficulty of the suggested guidelines for assay design and the technical limitations of reagents, instrumentation and data analysis software which have now been overcome since the development of HRM methodology. MethylLight, the other in-tube method, is used by a greater number of laboratories. It is a quantitative adaptation of MSP that uses TaqMan probes. Whereas MethylLight assays methylation of CpG sites covered by the primers and probe, MS-HRM scans all of the CpGs flanked by the primers-binding to the target sequence, regardless of the methylation status of CpGs in the primer binding side. Thus, the results of MS-HRM are not compromised by heterogeneous methylation of a particular CpG dinucleotide or incomplete conversion of some of CpGs within the template, as the latter will fall below the limits of resolution.

Heterogeneous methylation can readily be distinguished from homogeneous methylation by the shape of the curves as seen for HS678T. Moreover, the use of probes in MethylLight complicates the design and increases the costs of experiments.

Also quantitative MethylLight requires normalization against a reference assay which needs to be run for each sample (24). By contrast, MS-HRM does not require a reference assay for normalization. All of the above make MethylLight experiments relatively complex and expensive. In summary, MS-HRM is a new approach that can be readily applied to the methylation analysis of MGMT. It can also be readily extended to other loci as we have shown for the BNIP3 locus. The sensitivity of MSHRM allows for detection of even a very small fraction of methylated material which is of importance as tumour samples may contain a low proportion of methylated sequences due to the presence of significant amounts of normal tissue or heterogeneity of the tumour. Furthermore, the high reproducibility and cost effectiveness of HRM makes this method suitable for both research and diagnostic applications.

References

1. Gardiner-Garden, M. and Frommer, M. (1987) CpG islands in vertebrate genomes. J. Mol. Biol., 196, 261-282.
2. Jones, P. A. and Baylin, S. B. (2002) The fundamental role of epigenetic events in cancer. Nat. Rev. Genet., 3, 415-428.
3. Esteller, M., Corn, P. G., Baylin, S. B. and Herman, J. G. (2001) A gene hypermethylation profile of human cancer. Cancer Res., 61, 3225-3229.
4. Adorjan, P., Distler, J., Lipscher, E., Model, F., Muller, J., Pelet, C., Braun, A., Florl, A. R., Gutig, D. et al. (2002) Tumour class prediction and discovery by microarray-based DNA methylation analysis. Nucleic Acids Res., 30, e21.
5. Teodoridis, J. M., Strathdee, G. and Brown, R. (2004) Epigenetic silencing mediated by CpG island methylation: potential as a therapeutic target and as a biomarker. Drug Resist. Updat., 7, 267-278.
6. Esteller, M., Garcia-Foncillas, J., Andion, E., Goodman, S. N., Hidalgo, O. F., Vanaclocha, V., Baylin, S. B. and Herman, J. G. (2000) Inactivation of the DNA-repair gene MGMT and the clinical response of gliomas to alkylating agents. N. Engl. J. Med., 343, 1350-1354.
7. Esteller, M., Gaidano, G., Goodman, S. N., Zagonel, V., Capello, D., Botto, B., Rossi, D., Gloghini, A., Vitolo, U. et al. (2002) Hypermethylation of the DNA repair gene O(6)-methylguanine DNA methyltransferase and survival of patients with diffuse large B-cell lymphoma. J. Natl. Cancer Inst., 94, 26-32.
8. Hegi, M. E., Diserens, A. C., Gorlia, T., Hamou, M. F., de Tribolet, N., Weller, M., Kros, J. M., Hainfellner, J. A., Mason, W. et al. (2005) MGMT gene silencing and benefit from temozolomide in glioblastoma. N. Engl. J. Med., 352, 997-1003.
9. Dobrovic, A. (2005) Methods for Analysis of DNA Methylation. In Coleman, W. B., Tsongalis, G. J. (eds.), Molecular diagnostics for the clinical laboratorian. Humana Press, Totowa, N. J., pp. 149-160.
10. Wittwer, C. T., Reed, G. H., Gundry, C. N., Vandersteen, J. G. and Pryor, R. J. (2003) High-resolution genotyping by amplicon melting analysis using LCGreen. Clin. Chem., 49, 853-860.
11. Miller, S. A., Dykes, D. D. and Polesky, H. F. (1988) A simple salting out procedure for extracting DNA from human nucleated cells. Nucleic Acids Res., 16, 1215.
12. Virmani, A. K., Tsou, J. A., Siegmund, K. D., Shen, L. Y., Long, T. I., Laird, P. W., Gazdar, A. F. and Laird-Offringa, I. A. (2002) Hierarchical clustering of lung cancer cell lines using DNA methylation markers. Cancer Epidemiol. Biomarkers Prev., 11, 291-297.
13. Wojdacz, T. K. and Hansen, L. L. (2006) Reversal of PCR bias for improved sensitivity of the DNA methylation melting curve assay. Biotechniques, 41, 274276, 278.
14. Paz, M. F., Fraga, M. F., Avila, S., Guo, M., Pollan, M., Herman, J. G. and Esteller, M. (2003) A systematic profile of DNA methylation in human cancer cell lines. Cancer Res., 63, 1114-1121.
15. Okami, J., Simeone, D. M. and Logsdon, C. D. (2004) Silencing of the hypoxia-inducible cell death protein BNIP3 in pancreatic cancer. Cancer Res., 64, 5338-5346.
16. Murai, M., Toyota, M., Satoh, A., Suzuki, H., Akino, K., Mita, H., Sasaki, Y., Ishida, T., Shen, L. et al. (2005) Aberrant DNA methylation associated with silencing BNIP3 gene expression in haematopoietic tumours. Br. J. Cancer, 92, 1165-1172.
17. Murai, M., Toyota, M., Suzuki, H., Satoh, A., Sasaki, Y., Akino, K., Ueno, M., Takahashi, F., Kusano, M. et al. (2005) Aberrant methylation and silencing of the BNIP3 gene in colorectal and gastric cancer. Clin. Cancer Res., 11, 1021-1027.
18. Frommer, M., Mcdonald, L. E., Millar, D. S., Collis, C. M., Watt, F., Grigg, G. W., Molloy, P. L. and Paul, C. L. (1992) A genomic sequencing protocol that yields a positive display of 5-methylcytosine residues in individual DNA strands. Proc. Natl. Acad. Sci. U.S.A., 89, 1827-1831.
19. Clark, S. J., Harrison, J., Paul, C. L. and Frommer, M. (1994) High sensitivity mapping of methylated cytosines. Nucleic Acids Res., 22, 2990-2997.
20. Colella, S., Shen, L., Baggerly, K. A., Issa, J. P. and Krahe, R. (2003) Sensitive and quantitative universal Pyrosequencing methylation analysis of CpG sites. Biotechniques, 35, 146-150.
21. Herman, J. G., Graff, J. R., Myohanen, S., Nelkin, B. D. and Baylin, S. B. (1996) Methylation-specific PCR: a novel PCR assay for methylation status of CpG islands. Proc. Natl. Acad. Sci. U.S.A., 93, 9821-9826.
22. Cottrell, S. E. and Laird, P. W. (2003) Sensitive detection of DNA methylation. Ann. NY. Acad. Sci., 983, 120-130.
23. Warnecke, P. M., Stirzaker, C., Melki, J. R., Millar, D. S., Paul, C. L. and Clark, S. J. (1997) Detection and measurement of PCR bias in quantitative methylation analysis of bisulphite-treated DNA. Nucleic Acids Res., 25, 4422-4426.
24. Dobrovic, A., Bianco, T., Tan, L. W., Sanders, T. and Hussey, D. (2002) Screening for and analysis of methylation differences using methylation-sensitive single-strand conformation analysis. Methods, 27, 134-138.
25. Trinh, B. N., Long, T. I., Nickel, A. E., Shibata, D. and Laird, P. W. (2002) DNA methyltransferase deficiency modifies cancer susceptibility in mice lacking DNA mismatch repair. Mol. Cell. Biol., 22, 2906-2917.
26. Guldberg, P., Worm, J. and Gronbaek, K. (2002) Profiling DNA methylation by melting analysis. Methods, 27, 121-127.

27. Worm, J., Aggerholm, A. and Guldberg, P. (2001) In-tube DNA methylation profiling by fluorescence melting curve analysis. Clin. Chem., 47, 1183-1189.
28. Aggerholm, A., P. Guldberg, M. Hokland, and P. Hokland. 1999. Extensive intra- and interindividual heterogeneity of p15INK4B methylation in acute myeloid leukemia. Cancer Res. 59:436-441.
26. Guldberg, P., J. Worm, and K. Gronbaek. 2002. Profiling DNA methylation by melting analysis. Methods 27:121-127.
29. Gotoh, O. 1983. Prediction of melting profiles and local helix stability for sequenced DNA. Adv. Biophys. 16:1-52.
30. Boyd, V. L. and G. Zon. 2004. Bisulfite conversion of genomic DNA for methylation analysis: protocol simplification with higher recovery applicable to limited samples and increased throughput. Anal. Biochem. 326:278-280.

Example 4

Melting Curve Assays for DNA Methylation Analysis

The ability of sodium bisulfite to modify cytosines in a methylation-dependent manner allows the conservation of DNA methylation information during PCR amplification. PCR products amplified from bisulfite modified DNA have significantly different base compositions according to whether they originate from methylated or unmethylated variants of the target template. Different base compositions give rise to different thermal properties of the PCR products. Hence, melting analysis of amplification products in methylation studies allows the determination of whether the PCR products originate from methylated or unmethylated templates. Here, we briefly review recent advances in methodologies based on melting analyses of PCR products derived from bisulfite modified templates and provide a methodology for methylation-sensitive high resolution melting.

1. Introduction

The introduction of bisulfite modification of genomic DNA enabled the general use of PCR amplification in methylation studies (1). Sodium bisulfite deaminates unmethylated cytosines to uracils leaving 5-methylcytosines intact. As a consequence, methylated cytosines are amplified during the subsequent polymerase chain reaction (PCR) as cytosines whereas unmethylated cytosines are amplified as thymines. Hence, the base composition of the PCR product depends on the 5-methylcytosine content of the template. The two complementary strands of DNA are held together by hydrogen bonds and stacking interactions. Dissociation of double-stranded DNA is known as DNA melting or denaturation and can be induced either by increased temperature or denaturing chemicals. The dissociation of the triple hydrogen bond between C and G requires more energy than the dissociation of the double hydrogen bond between T and A, therefore GC rich sequences melt at relatively higher temperatures compared to AT rich sequences. The melting of a DNA amplicon often consists of a series of progressive dissociations of shorter domains within the sequence, which due to their local GC content have different melting temperatures.

The sequence dependent melting of an amplicon across a denaturing gradient is described as a 'melting profile'. The melting profile of an amplicon can be determined by subjecting it to a gradually increasing temperature in the presence of an intercalating fluorescent dye, which emit fluorescence when bound (intercalated) to double-stranded DNA. At temperatures below the initiation of the melting process, the intercalating dye saturates the PCR product resulting in high levels of fluorescence. As the temperature rises, the fluorescence levels are stable until the point at which the double-stranded amplicon begins to separate into single strands, and a marked drop in fluorescence is observed as the dye is released from the double-stranded DNA. Thus, by monitoring the fluorescence during the increase of the temperature, it is possible to determine the melting profile of a PCR amplicon. The melting profiles of PCR products originating from methylated and unmethylated variants of the same template are significantly different due to their different GC content. Therefore the methylation status of an unknown sample can be determined by comparing the melting profile of the PCR product with the melting profiles of PCR products obtained from the amplification of methylated and unmethylated control templates. The first application of melting curve analysis to the profiling of DNA methylation was reported in 2001 (2). This methodology was not generally adopted as SYBR Green I, the principal fluorescent dye used at that time, could not be used at concentrations that fully saturated the PCR products, thereby blunting the resolution of the methodology. Current advances in fluorescence detection technology, new algorithms for data calculation, and the use of novel dyes have allowed the development of high resolution melting analysis (HRM) (3). We applied HRM to methylation analysis in the methodology that we called Methylation-Sensitive High Resolution Melting (MS-HRM). Together with a novel approach to primer design (see section 3.1), which allows the control of PCR bias and hence highly sensitive detection of low-level methylation, MS-HRM is proving to be a powerful new methodology for methylation analysis.

2. Materials 2.1. Bisulfite Modification of Genomic DNA

As an alternative to the procedure described in this chapter, some users may prefer to use one of the kits currently available from commercial suppliers.

1. 3 M sodium bisulfite (Sigma S9000): Dissolve 0.57 g of sodium bisulfite dilute in 1 mL of water (this step may take several minutes as sodium bisulfite does not easily dissolve).
2. 10 mM hydroquinone (Merck 8.22.333.0250): Prepare a 40 mM solution of hydroquinone: by dissolving 0.132 g of hydroquinone in 30 mL of water, and dilute it to 10 mM solution (10 mL of 40 mM hydroquinone solution plus 40 mL of water). Note that hydroquinone should be handled with care.
3. 3 M NaOH and 0.1 M NaOH: The 0.1 M NaOH should be made from the 3 M NaOH stock on the day of the procedure. Discard the 3 M NaOH stock when it becomes cloudy.
4. Microcon YM-100 centrifugal filter unit (Millipore).
5. Eppendorf microcentrifuge 5417R
6. TE buffer (10 mM Tris, 1 mM EDTA, pH 8)

2.2. Instrumentation

A platform with a combined thermal cycler and a fluorescence detector is ideal to perform intube melting analyses. PCR amplification of bisulfite modified template could be performed prior to melting analyses on any thermocycler but real-time monitoring of PCR amplification constitutes an important quality control step in the experiments allowing the elimination of samples where amplification failed with no need to run gel electrophoresis. The first experiments using melting profiles to differentiate methylated and unmethylated PCR product were performed on the LightCycler (Roche) (2).

Recently, a new generation of instruments capable of high resolution melting (HRM) analyses has been developed with superior data capture abilities and improved software. In our laboratory, we have used two HRM systems: the Roche LC480 and the Corbett RG600 as their real time PCR capacity allows the monitoring of the amplification which is invaluable for quality control.

2.3. DNA saturating dyes The very first intercalating dye reported to be suitable for melting based analyses of methylation was SYBR Green I (2). However, SYBR Green I at the concentration allowing saturation of PCR product was toxic to all polymerases we have tested (unpublished data). PCR amplifications in the presence of SYBR Green I were not robust and the very low yield of PCR products for post PCR melting analyses compromised our experiments. The new generation of saturating dyes includes the LC Green family (Idaho Technology Inc., Salt Lake City, Utah), Syto®9 (Invitrogen, Carlsbad, Calif.), ResoLight (Roche) and Eva Green (Biotium Inc., Hayward, Calif.). These dyes fully saturate the PCR product at concentrations that do not inhibit PCR amplification and allow for both real time monitoring of PCR amplification and subsequent in-tube melting analyses. These dyes can be used with most of the commercially available polymerases as an additive to the PCR reaction mix. The rapid development of High Resolution Melting has resulted in the introduction of two high resolution melting master mixes: LightCycler□ 480 High Resolution Melting Master (Roche) and SensiMixHRM□ (Quantace Ltd., London, UK). We routinely use 5 µM Syto®9 and or 1×LC Green (as recommended by the supplier).

3. Methods 3.1 Sodium Bisulfite Treatment of Genomic DNA

Bisulfite conversion of genomic DNA consists of 3 steps: sulfonation of cytosines, hydrolytic deamination of the cytosine sulfonates to uracil sulfonates, and alkaline desulfonation of the uracil sulfonates. Many parameters have to be taken in to account during the performance of the above steps and therefore many protocols have been published with different conditions for each step of conversion. In our experience, the most important parameters of the conversion are initial (sufficient) denaturation of the DNA template, incubation time with sodium bisulfite mixture (we have observed few problems with incomplete conversion when overnight incubation was used) the method used to recover bisulfite modified DNA that gives the highest yield possible. A protocol utilizing a column based recovery procedure (4) showed the highest recovery rates in our hands. Our modified version of that protocol was published in (5) and is described below. This operation should preferably be carried out in a safety cabinet or fume hood.

1. Mix 0.1-1 f g of genomic DNA with water to a final volume of 16 µL.
2. Add 1.1 µL of 3M NaOH to denature the DNA, and incubate at 37° C. for at least 15 min. Then place directly on ice and proceed promptly with the remainder of the protocol.
3. Add 173 µL of freshly prepared 3 M sodium bisulfite and 10 µL of the hydroquinone solution, mix with the pipette and incubate in the dark for 16 hours (overnight) at 50° C.
4. Dilute the bisulfite reaction with water to a total volume of 350-400 µL.
5. Transfer this solution to an assembled Microcon YM-100 centrifugal filter unit (Millipore).
6. Centrifuge at 2800 700 g for 10 min (Eppendorf microcentrifuge 5417R)
7. Discard the filtrate and add 300 µL of water to the upper chamber and centrifuge for 10 min at 700 g.
8. Repeat step 7.
9. Discard the filtrate, add 350 µL of 0.1 M NaOH to the upper chamber and centrifuge for 6 min at 700 g.
10. Discard the filtrate, add 350 µL of water to the upper chamber, and centrifuge at 700 g for 8 min.
11. Elute the sample by adding 50 µL of TE buffer; use the pipette for mixing of TE with the sample on the column membrane and let stand for 15 min.
12. Invert the device, and collect the bisulfite converted DNA in a clean tube 3.2. Primer Design for PCR Amplification The primers for amplification of bisulfite modified DNA for MS-HRM studies have to amplify the sequence of interest regardless of its methylation status (MIP—methylation independent primers) (6). It is important to note that when using one primer set for the amplification of two templates with different GC content, the PCR will be biased towards the template with lower GC content (FIG. 41) (5,7). The most commonly followed rules in primer design advise not to include any CG nucleotides into the primer sequence and, if this is not possible, to mismatch the C from CG with T (8). In our experience, following the above rules led to amplifications which showed strong bias towards the unmethylated sequence (5). We proposed new guidelines for MIP primer design where inclusion of a limited number of CGs towards the 5' end of the sequence allowed us to manipulate PCR bias (5,6, FIG. 41). When primers containing a limited number of CpGs are used, their relative binding affinity for methylated and unmethylated templates is annealing temperature dependent. Hence by manipulating the annealing temperature of the PCR amplification with MIP primers, one can shift the PCR bias from the unmethylated to the methylated sequence and make the assay highly sensitive for methylation detection. If there is no methylated template available, the primers with limited CpGs will amplify unmethylated sequence even at high annealing temperature. That allows not only the determination of the methylation status of the sample but at the same time to the confirmation of the unmethylated status of the template. Apart from this point, good practice for primer design such as matching primer melting temperatures, selection against unconverted sequences (inclusion of a T derived from a non-CpG at or near the 3' end of the primer) and prediction of primer dimer formation should be followed for the design of MIP primers. The melting temperature of MIP primers should be around 65° C. (e.g. using Oligonucleotide properties calculator for calculation of the melting temperature of the primers) allowing an annealing temperature of 60° C., which is an empirical value at which our primer design gives good results in our hands. Each primer set should be extensively tested on the mixes of methylated and unmethylated controls for the performance and the extent of PCR bias (see Note 2).

3.3. Predicting the Melting Behavior of the Sequence of Interest

Long sequences can have very complex melting profiles due to the fact that they consist of multiple small melting domains. Ideally, the melting profile of the sequence of interest should consist of a single melting domain that gives only one drop in the fluorescence and makes melting results easy to interpret. Amplicons of 100 bp or less often comprise only one major melting domain and therefore the recommended size of the PCR amplicon for melting analyses is around this size. A rough estimate of the melting profile of the sequence of interest can be made on freely available tools like POLAND, or the MELT94 algorithm. The complex melting of a PCR product containing more than one melting domain may complicate melting analyses as drops in fluorescence observed for short melting domains within the sequence can mask the fluorescence changes specific for the methylated/unmethylated alleles.

3.4. Predicting the Melting Temperature of Methylated/Unmethylated PCR Amplicons The tools described in 3.3. can also be used to estimate the melting temperature of methylated and unmethylated variants of the template. Sequences originating from methylated allele where the C within CpG dinucleotides has not been changed will have a higher melting temperature in comparison to the sequence originating from unmethylated allele where all the C were changed into Ts. The difference in melting temperature of unmethylated and methylated templates depends on the number and density of CpGs in the amplicon. It is important to make sure that the difference in melting temperature between methylated and unmethylated version of the sequence is large enough to unambiguously distinguish both alleles during melting. When low-resolution fluorescence detection systems are used the melting temperature differences between methylated and unmethylated PCR product has to be significant. With HRM systems, very small differences in melting temperature can be unambiguously resolved as the specification of the systems allow for highly sensitive fluorescence acquisition and precise control of temperature ramp rates (see Note 3).

3.5. PCR Amplification

PCR reagents from different suppliers differ in their ability to amplify bisulfite modified DNA (unpublished data). The differences tend to be polymerase dependent and good quality polymerases are necessary for successful PCR amplification of bisulfite-modified template. Hot Start protocols give superior results to regular amplification techniques when bisulfite modified DNA is used as a template (see Note 4), (unpublished data). 0.5-1 U polymerase with standard dNTP concentration (200 µM each) is sufficient in most of applications. The role of $Mg_{+2}$ concentration and input template amount will be discussed separately 3.5.1. $Mg_{+2}$ concentration The amplification of bisulfite modified DNA is rarely as robust as amplification of genomic DNA presumably due to the extensive degradation of DNA during incubation with bisulfite. As a consequence, the use of high concentrations of $Mg_{+2}$ to enhance PCR amplification is essential in many cases. The $Mg_{+2}$ concentration in polymerase buffers is generally insufficient to give a high yield of PCR product from bisulfite modified DNA. In our hands, most amplifications for melting analyses required a $Mg_{+2}$ concentration of 2.5-3.5 mM. In general, the concentration of $Mg_{+2}$ in amplifications of bisulfite-modified template has to be empirically adjusted for each assay and is dependent on the bisulfite modification protocol, the PCR reagents used and input of bisulfite-modified template. 3.5.2. Bisulfite template input for PCR amplification The main problem in methylation studies is the degradation of DNA during bisulfite modification. As high as 90% degradation of the template has been reported (9). Our practice shows that the greater the quantity of DNA that is subjected to bisulfite modification, the less the extent of degradation and more template available for PCR amplifications. In cancer research especially, the amount of available sample DNA is generally a limiting factor in methylation studies (see Note 5). The use of carrier DNA (e.g. herring or salmon sperm DNA) can partly solve the problem allowing for higher recovery rates when small amounts of genomic DNA are subjected to bisulfite modification. The sensitivity of the melting assay is directly correlated to the input DNA for bisulfite modification. With MS-HRM, we were able to reproducibly detect 1-0.1% methylated sequence in unmethylated background when 1 f g genomic DNA was used for bisulfite modification. Post modification DNA recovery rates also depend on the system used to purify DNA. In our experience, procedures using purification columns are superior to precipitation protocols, especially when an inexperienced person performed the bisulfite modification. 3.5.3. PCR amplification parameters The PCR amplification of bisulfite modified DNA may require up to 50-60 cycles of amplification to obtain a sufficient yield of PCR product for melting analyses. The number of cycles depends on the assay and real time monitoring of the amplification allows for the adjustment of the cycles number. The PCR should be stopped where possible just before amplification reaches the plateau phase. When amplification is carried on too long, the byproducts of PCR may disturb the melting profile of the sequence of interest (see Note 6). For an example, see Note 7.

3.6. Re-annealing of PCR product and the design of temperature gradient for melting analyses Before subjecting PCR products to temperature gradients, the PCR product should be reannealed. The protocol for re-annealing of the PCR product should consist of a denaturation step at 95° C. for one minute and fast cool down and hold for one minute (to allow reannealing of all the DNA strands) at the temperature from which acquisition of the fluorescence for melting procedure starts. The range of temperatures for temperature gradient has to be investigated empirically and it depends on the melting temperatures of unmethylated and methylated PCR product The gradient has to fully cover the melting temperatures of methylated and unmethylated PCR product (see Notes 3, 6 and 7).

3.7. Acquisition of the fluorescence The precise and accurate acquisition of fluorescence, and small temperature transition rates are the foundations of high resolution melting analysis. On the first generation of LightCyclers, the temperature ramp rates could be as low as 0.05° C./s. This allowed in combination with continuous fluorescence acquisition the attainment of detailed melting curves. Fluorescence acquisition systems in the new generation of the instruments have even higher specifications allowing collection of higher quality data. We have tested two of the HRM instruments available on the market, the LC480 (Roche) and the Rotor-Gene 6000 (Corbett). The settings for data collection in melting experiments giving us satisfactory results for the LC480 system were 50 fluorescence acquisition points per ° C. The corresponding temperature ramp rate for 50 acquisitions per degree was calculated automatically by the instrument by taking into account the time needed at each degree for sufficient acquisition of fluorescence. For the RG-6000 the HRM default settings were used consisting of the continuous acquisition of the fluorescence with a temperature ramp rate of 0.1° C. and a 2 s hold on each step. The parameters of the melting gradient can be adjusted individually for each melting assay on both the LC480 and the RG-6000 (see Note 7).

3.8. Analysis of the Results 3.8.1. Derivative peak Melting curves are generated by continuous acquisition of fluorescence from the samples subjected to the linear temperature gradient. For basic analyses, the melting curves can be converted to peaks by plotting the negative derivative of fluorescence over the temperature (−dF/dT) versus temperature (FIG. 42). The top of the peak represents the highest drop of fluorescence during melting and can be interpreted as the melting temperature of the PCR product (Tm). In methylation studies, two peaks, one for unmethylated (lower Tm) and one for methylated (higher Tm), are obtained from the control samples. Comparing the peaks of an unknown sample with controls scores the methylation status of the unknown sample (see Note 1). Heterogeneously methylated templates give a broader peak due to the formation of heteroduplexes (see Note 8).

3.8.2. Direct visualization of melting The high resolution data collected on HRM instruments allowed the development of new algorithms for melting curve analyses. After PCR amplification, even replicates of the same sample can differ in the amount of PCR product amplified and therefore display different fluorescence levels. The differences between samples are especially pronounced when HRM detection is used which does not allow for direct comparison of the curves as the HRM curves have to be normalized for starting and ending levels of fluorescence to make them comparable (FIG. 43a). The new algorithms supplied with HRM instruments allow for normalization of the starting levels of fluorescence. After normalization, similarly shaped curves, which before were visually not readily comparable, group together. If unknown samples are run with standards of known methylated to unmethylated template ratios, the level of methylation in screened samples can be estimated by comparison of their melting curves to the melting curves of standards (FIG. 43b, see Notes 2 and 6).

4. Notes

1. Bisulfite modified DNA should be used up as soon as possible after modification. For longer storage: aliquot the stock DNA into small amounts that are thawed for each run. Repetitive freezing and thawing of the bisulfite DNA hastens its degradation.
2. Standards for MS-HRM analyses/primers optimization can be obtained by mixing of bisulfite modified methylated and unmethylated controls. The equal amount of DNA has to be used for bisulfite modification of controls. Unmethylated control can be DNA from any tissue where the locus of interest is not methylated. The methylation status of the locus of interest in control DNA has to be investigated prior to analyses as some loci have different methylation status in different tissues. We routinely use CpGenome™ Universal Methylated DNA (Millipore Co.) for the methylated-control. SssI treated DNA is an alternative to CpGenome™ Universal Methylated DNA, but complete methylation of the genomic DNA by SssI enzyme can be difficult to achieve.
3. The numerical calculations of the melting temperatures of the methylated and unmethylated PCR products are a good estimate, nevertheless the range of the temperatures for melting experiments has to be adjusted/corrected after the first run of the experiments.
4. A 3 step PCR amplification protocol including an extension step was superior to a two step protocol. When a two step set up is used, some polymerases may generate by products and/or incompletely elongated amplicons that interfered with melting analyses.
5. MS-HRM analysis can also be performed on formalin fixed tissues. As many of these will be extensively degraded, the success rate will be increased here by using relatively small (less than 100 base pairs) amplicons.
6. In MS-HRM, the sensitivity of detection of lower levels of methylation depends on the extent of PCR bias during PCR amplification. As the PCR bias can be adjusted by annealing temperature, the range of the standards has to be designed to each experiment individually and depending on the goals of the user.
7. The MS-HRM protocol used in the methylation screening experiments of MGMT gene performed on the LC 480. Primers: F-CGTTTGCGATTTGGTGAGTGTT (SEQ ID NO: 136) and R-ACCCCGCCCTACCCTATAAATTC (SEQ ID NO: 139). PCR cycling and HRM analysis conditions were as follows: initial activation 10 min at 95° C. and 50 cycles of 5 s 95° C., 5 s at 63° C. and 5 s at 72° C. Subsequently the product was denatured for 1 min at 95° C., re annealed by fast cooling and held for 1 minute at 75° C. The HRM analyses were performed in the temperature interval 70-95° C. With 50 acquisitions per ° C. and the default fluorescence temperature gradient parameters selected by the instrument see paragraph 3.7 and FIG. 42 and FIG. 43 for an example of the analysis of the results.
8. Heterogeneously methylated templates can be observed in many amplifications. On derivative curves, these are characterized by a broader melting peak typically starting before the unmethylated peak and extending into the methylated peak area. This is due to the formation of heteroduplexes, between heterogeneously methylated templates. An important advantage of MS-HRM is that, unlike many other methods, it allows the detection of heterogeneous methylation.

6. References

1 Wang, R. Y., Gehrke, C. W., and Ehrlich, M. (1980) Comparison of bisulfite modification of 5-methyldeoxycytidine and deoxycytidine residues *Nucleic Acids Res.* 8, 4777-4790.
2 Worm, J., Aggerholm, A., and Guldberg, P. (2001) In-tube DNA methylation profiling by fluorescence melting curve analysis *Clin. Chem.* 47, 1183-1189.
3 Wittwer, C. T., Reed, G. H., Gundry, C. N., Vandersteen, J. G., and Pryor, R. J. (2003) High-resolution genotyping by amplicon melting analysis using LCGreen *Clin. Chem.* 49, 853-860.
4 Boyd, V. L., and Zon, G. (2004) Bisulfite conversion of genomic DNA for methylation analysis: protocol simplification with higher recovery applicable to limited samples and increased throughput *Anal. Biochem.* 326, 278-280.
5 Wojdacz, T. K., and Hansen, L. L. (2006) Reversal of PCR bias for improved sensitivity of the DNA methylation melting curve assay *Biotechniques* 41, 274-278.
6 Wojdacz, T. K., and Dobrovic, A. (2007) Methylation-sensitive high resolution melting (MS-HRM): a new approach for sensitive and high-throughput assessment of methylation *Nucleic Acids Res.* 35, e41.
7 Warnecke, P. M., Stirzaker, C., Melki, J. R., Millar, D. S., Paul, C. L., and Clark, S. J. (1997) Detection and measurement of PCR bias in quantitative methylation analysis of bisulphite-treated DNA *Nucleic Acids Res.* 25, 4422-4426.
8 Clark, S. J., Harrison, J., Paul, C. L., and Frommer, M. (1994) High sensitivity mapping of methylated cytosines *Nucleic Acids Res.* 22, 2990-2997.
9 Warnecke, P. M., Stirzaker, C., Song, J., Grunau, C., Melki, J. R., and Clark, S. J. (2002) Identification and resolution of artifacts in bisulfite sequencing *Methods* 27, 101-107.

Example 5

Methylation Sensitive High Resolution Melting (MS-HRM)

PCR products derived from sodium bisulfite modified templates have methylation dependent base compositions. Hence, they show different melting profiles when subjected to thermal denaturation. The Methylation Sensitive High Resolution Melting (MS-HRM) protocol is based on the comparison of the melting profiles of PCR products from unknown samples with profiles specific for PCR products derived from methylated and unmethylated references. The protocol consists of the PCR amplification of bisulfite modified DNA templates with primers designed to proportionally amplify both methylated and unmethylated templates at the same time and subsequent high resolution analysis of the PCR product. The MS-HRM protocol allows investigation of the methylation status of the locus of interest in less than 3 hours. Here we provide the methodology for highly sensitive, labor and cost efficient single locus methylation studies based on DNA high resolution melting technology.

Design of Primers Allowing Correction for PCR Bias (BOX1)

The proportional amplification of bisulfite modified methylated and unmethylated templates can be compromised by PCR bias due to the fact that they have different base compositions. PCR bias is described as the preferential amplification of one DNA template. The PCR bias in methylation studies has long been recognized and is principally directed towards the unmethylated (GC-poor) strand 16. The relative disproportionate amplification of the unmethylated strand may result in misinterpretation of the final results and the underestimation of methylation levels. The extent of PCR bias is sequence specific and can be compensated by optimizing the annealing temperature of PCR amplification 18. The widely adopted primer design guidelines for post amplification methylation analyses protocols advise not to include any CpG nucleotides into the primer sequence and if not possible to do so, to use a mismatched C from CpG dinucleotide with T to avoid the preferential binding of the primer to methylated template 11. We have shown that in some most cases, inclusion of limited number of CpGs into the primer sequence is necessary to compensate for PCR bias 15,17. Our primer design system is thus based upon the inclusion of a limited number of CpG dinucleotides into the primer sequence enabling the conditionally selective binding of the primer to the methylated sequence and therefore enables compensation of PCR bias that would otherwise normally favor the amplification of the unmethylated template. Furthermore, reversal of PCR bias to favor methylated sequences increases the sensitivity of the melting assays allowing detecting methylation levels as low as 1-0.1%, which is the level of sensitivity similar to MSP. Our primer design guidelines are outlined below (for examples see Table 1).

1. Primers should usually contain one or two CpGs dinucleotides each.
2. The CpGs should be placed as close as possible to the 5' end of the primer
3. The melting temperature of the primers should be matched, preferably within one degree.
4. The 3' end of the primer should contain one or more Ts specific to non-CpG Cs, to ensure amplification of only bisulfite converted template.
5. The primers should meet standard parameters for primer design e.g. secondary structure, primer dimer formation.
6. The preferred length of the amplified sequence should be around 100 bp to reduce the complexity of the melting profile.

Materials
Reagents
  Bisulfite modification kit
  EpiTect Bisulfite Kit, Qiagen cat. no. 59104
  Human Genetic Signatures, MethylEasy™ cat. no. ME001
  Zymo, EZ DNA Methylation Kit™ cat. no. D5001
  ABI, methylSSEQr™ cat. no. 4374710
  DNA intercalating dye
  LCGreen I and LCGreen plus (Idaho Technology Inc., cat. no. BCHM-ASY-0003 and BCHM-ASY-0005 respectively)
  Syto®9 (Invitrogen, cat. no. S-34854)
  LightCycler®480 ResoLight Dye (Roche, cat. no. 04909640001)
  Eva Green (Biotium Inc., cat. no. 00013)
  Taq polymerase
  Master mixes with PCR reagents and intercalating dye
  LightCycler☐ 480 High Resolution Melting Master (Roche cat. no. 04909631001)
  SensiMixHRM☐ (Quantace Ltd., cat. no. QT805-02)
  $Mg^{+2}$
  Methylated reference
  Unmethylated reference
  Dilution series of methylated in unmethylated controls
  DNA primers
Equipment
  High Resolution Melting fluorimeter ideally coupled with a real time PCR cycler
  LightCycler® 480 System (Roche cat. no. 04545885001)
  Rotor-Gene™ 6000 (Corbett Research cat. no. 6600)
  LightScanner and HR-1 instrument (Idaho Technologies cat. no. LSCN-ASY-0011 and HR01-ASY-0001 respectively).
Reagents Bisulfite modification of genomic DNA can be performed as described 8. Nevertheless, currently commercially available kits for bisulfite modification ensure highly efficient template conversion, reduction of the time needed for conversion and high bisulfite modified template recovery rates. CAUTION Bisulfite modified template is susceptible to rapid degradation. The bisulfite-modified sample should be used up soon after bisulfite modification or if required for a longer period of time, the DNA should be stored at −80° C. Freezing and thawing of the template should also be avoided.

DNA saturating dyes can be used as PCR additives as they do not interfere with the polymerase performance in saturating concentrations. High resolution PCR Master mixes containing all PCR reagents and saturating dye can be used for increased convenience of the setup. Extensive evaluation of HRM dyes has been described 21. $Mg^{+2}$ the concentration of $Mg^{+2}$ supplied in the PCR buffers is normally not sufficient to ensure efficient amplification of bisulfite modified template. An increase concentration of $Mg^{+2}$ to 2.5-3.0 mM significantly enhances the amplification. CAUTION increased $Mg^{+2}$ concentration enhances non-specific amplification and therefore has to be optimized for each primer set.

Methylated reference fully methylated reference for melting experiments can be obtained by subjecting genomic DNA to SSS1 enzyme treatment (NEB, Ipswich, Mass., cat. no. M0226L). Nevertheless complete methylation of DNA is hard to achieve without repeated rounds of incubation. Fully methylated genomic DNA can be also purchased from commercial suppliers (e.g. Millipore, CpGenome™ Universal Methylated DNA cat. no. S7821).

Unmethylated reference DNA from the tissue in which the sequence of interest does not show methylation can be used as a source of unmethylated reference. CAUTION Many genes show low level methylation in certain tissues. The methylation status of the DNA chosen as the unmethylated control has to be investigated prior to analyses. Unmethylated genomic DNA can be also purchased from commercial suppliers. Dilution series of methylated in unmethylated controls The dilution series of methylated template in unmethylated background has to be obtained to estimate the PCR bias extent and methylation levels in screened samples.

Equipment

A real time PCR thermocycler coupled with a High Resolution Melting capable fluorimeter is the ideal platform for MS-HRM experiments. To date, 4 HRM systems are available: the LightCycler480 (Roche), the RotorGene6000 (Corbett Research), the LightScanner® System and the HR-1 instrument (Idaho Technologies). The LightScanner® and HR-1 instruments contain only a HRM module.

Procedure
1. DNA template extraction via any "good practice" method. CAUTION Column based systems are preferred for the extraction of the DNA for HRM analyses as the impurities from the extraction procedure can interfere with melting analyses.
2. Sodium bisulfite modification of the DNA 11. When a commercially available kit is chosen follow the supplier's protocol. TROUBLESHOOTING (3).
3. Amplification of bisulfite modified DNA
   Bisulfite converted template (3-10 ng) 2 µl
   Primers 250 nM of each forward and reverse 0.5 µl
   $Mg_{+2}$ (3 mM final concentration) 2.4 µl
   LightCycler☐ 480 High Resolution Melting Master 10 µl
   H2O 5.1 µl
   Cycling
   10 min 95° C. (depends on the type of polymerase used and HotStart protocols are advised here)
   50 cycles of:
   5 s 95° C.
   5 s primer specific annealing temperature
   5 s 72° C.
   CAUTION The amplification of sufficient amount of PCR product from bisulfite modified template normally requires more cycles than a standard PCR amplification. Initial experiments should be run with 50 cycles and the number of the cycles should subsequently be adjusted. TROUBLESHOOTING (1,2)
4. Re-annealing of the PCR products
   1 min at 95° C. (to denature all amplified PCR product)
   cool down to 70° C.
   1 min at 70° C. (to allow all PCR product to hybridize)
5. HRM scans: The default settings of fluorescence acquisition and the temperature ramp rates suggested by the equipment supplier should be used during the initial experiments. A temperature gradient from 70° C. to 95° C. in advised. The ranges of the temperatures can subsequently be adjusted for each assay to cover the melting of temperatures of the methylated and unmethylated products TROUBLESHOOTING (3,4,5)
6. Investigation of equal amplification of the methylated and unmethylated template for primers without CpGs. To test CpG free primers for the extent of PCR bias the reaction mix from STEP 3 should be run with the 50:50 methylated and unmethylated template mix. An equal amount of the PCR product has to be seen for originating from each template to rule out the presence of preferential amplification of unmethylated sequence (see ANTICIPATED RESULTS section) TROUBLESHOOTING (6)
7. Optimization of the annealing temperature of PCR amplification for primers containing CpGs. To test the annealing temperature at which the primers are able to compensate for PCR bias, run the PCR mix on the range of the temperatures and the mixes of the methylated in unmethylated template. The analysis of the HRM scans will show at which annealing temperature the preferential amplification is eliminated. We advise to run the initial PCR amplification at the annealing temperature at 5° C. below the melting temperature of the primers.

TIMING
Bisulfite modification 5-16 h depending on the protocol used
PCR amplification 3 h
HRM analyses 30 min
Data analysis 30 min Troubleshooting
1a. Problem: Low efficiency PCR amplification
1b. Solution: Test the primers on control methylated/unmethylated control template, optimize the PCR chemistry and parameters, repeat PCR with new reagents, test bisulfite conversion protocol for losses of the template during purification step, when no HRM master mixes used decrease dye concentration.
2a. Problem: primer dimers in PCR product
2b. Solution: decrease the primer and/or the Mg+2 concentration, increase the annealing temperature of PCR amplification.
3a. Problem: non-reproducible results
3b. Solution: repeat bisulfite modification of the sample (the problem may arise from incomplete bisulfite conversion of the template), decrease the DNA input for bisulfite modification.
redesign the primers to contain 5' CpGs BOX1
4a. Problem: No unambiguous peaks are obtained in HRM analyses
4b. Solution: redesign primers to include more CpGs into the amplified sequence, and to include only one melting domain.
5a Problem: presence of non-specific peaks on the HRM scans
5b. Solution: redesign the primers, optimize the PCR chemistry, increase the annealing temperature of PCR amplification.
6a. Problem: amplification using primers without CpGs shows PCR bias towards unmethylated sequence.
6b. Solution: Optimize annealing temperature and $Mg_{+2}$ concentration of the PCR amplification.

Anticipated Results
Derivative Peaks
The melting curves data can be transformed into peaks by plotting the negative derivative of fluorescence over temperature. After this transformation, the top of the peak represents the sharpest drop in the florescence from the melting curve slope and therefore indicates the melting temperature of the amplicon. For each of the unmethylated and methylated reference samples, an unambiguous peak should be obtained. The unknown sample can be scored on the bases of the similarities to one of the two reference profiles. The samples containing PCR product derived from both methylated and unmethylated templates will display two peaks similar to the methylated and unmethylated references.

Normalized melting curves and estimation of methylation levels
The replicates of a sample after amplification display different amounts of PCR product. The algorithms developed for analyses of HRM data (the software packages are supplied with the machines) allow the normalization of the raw data and therefore direct comparison of the melting curves. If the unknown samples are run along with the standards representing different mixes of methylated and unmethylated templates the methylation levels of an unknown sample can be estimate by comparing it to the controls 15.

Heterogeneously Methylated Samples
A number of loci in the human genome do not undergo full methylation but altered methylation of single CpGs, which is known as heterogeneous methylation. Therefore the sequences that are heterogeneously methylated give rise to a mixture of PCR products with Ts at some CpG sites and Cs at others. The PCR products with minor differences in the sequence can cross-hybridize and form heteroduplexes. Heteroduplexes are less stable then homoduplexes in denaturing conditions and therefore display different melting temperature from the fully methylated and unmethylated references. The HRM melting profiles of the PCR products derived from the samples with heterogenously methylated templates show a characteristic complex melting pattern, which allows for their ready identification, especially when first derivative curves are analysed. The heterogeneous pattern of methylation can be investigated in detail by sequencing based methodologies.

Example 6

Rapid Analysis of Heterogeneously Methylated DNA Using Digital Methylation Sensitive High Resolution Melting (dMS-HRM)

List of abbreviations used
AML Acute Myeloid Leukaemia
dMS-HRM digital Methylation Sensitive High Resolution Melting
dPCR digital Polymerase Chain Reaction
FFPE Formalin-Fixed Paraffin-Embedded
MDS Myelodysplastic Syndrome
MS-HRM Methylation Sensitive High Resolution Melting
PCR Polymerase Chain Reaction
WGA Whole Genome Amplification Material and Methods DNA Samples Acute myeloid leukemia (AML) samples were obtained from patients referred to the Department of Hematology, Aarhus University Hospital. DNA was redissolved in TE Buffer (1×) with a final concentration of 5 ng/μL. Genomic DNA was extracted from peripheral blood of healthy controls using the QIAamp DNA Blood Mini Kit (Qiagen, Hilden, Germany) according to the manufacturer's instructions. The investigation was approved by the Peter MacCallum Cancer Centre Ethics of Human Research Committee (Approval number 02/26).

Whole-Genome Amplification (WGA)

Whole genome amplification was performed as described previously [14].

Bisulfite Modification

Two hundred ng of genomic DNA of the AML samples was subjected to bisulfite modification by using the EpiTect Bisulfite Kit (Qiagen) according to the manufacturer's instructions. DNA was eluted once in 20 μL of buffer EB. For the control DNA, Universal Methylated DNA (Chemicon, Millipore, Billerica, USA), and WGA, 500 ng of genomic DNA and WGA product, respectively, was modified and eluted twice, the second elution being in 30 μL of buffer EB.

Methylation Sensitive High Resolution Melting

PCR cycling and (d)MS-HRM analysis were performed on the Rotor-Gene 6000 (Corbett Research, Sydney, Australia). Each sample was analysed in duplicate for MS-HRM, and sixty times for dMS-HRM. Primers were designed according to the principles outlined in Wojdacz and Hansen [15] and subsequently in Wojdacz and Dobrovic [13]. The primers used to amplify bisulfite-treated DNA were CDKN2B-F, 5'-GTTAGGCGTTTTTTTTTAGAAGTAATTTAGG-3' (SEQ ID NO:237) and CDKN2B-R, 5'-TACGACT-TAAAACCCCGTACAATAACC-3' (SEQ ID NO:238) and do not amplify unmodified genomic DNA (data not shown). The amplified region corresponds to [GenBank: AL449423] nucleotides 99845 to 99958, and encompasses nine CpG dinucleotides. PCR was performed in a 100 μL PCR tube (Corbett Research) with a final volume of 20 μL, containing 200 nmol/L of each primer, 200 μmol/L of each dNTP, 0.5 U of HotStarTaq DNA polymerase (Qiagen) in the supplied PCR-buffer containing 2.5 mmol/L MgCl12, 5 μmol/L SYTO9 (Invitrogen, Carlsbad, USA), and different dilutions of bisulfite-treated DNA as template (see Results). The initial denaturation (95° C., 15 minutes) was followed by 50 cycles for MS-HRM (60 cycles for dMS-HRM) of 10 seconds at 95° C., 30 seconds at 59° C., 30 seconds at 72° C.; one cycle of 1 minute at 95° C., 72° C. for 1.5 minutes and a HRM step from 65° C. to 90° C. rising at 0.2° C. per second, and holding for 1 second after each stepwise increment.

Direct Sequencing dMS-HRM products were cleaned up with the PCR-M clean up kit (Viogene, Taipei, Taiwan), according to the manufacturer's instructions, further processed with ExoSapIT (GE Healthcare, Little Chalfont, England), followed by the sequencing reaction using Big Dye Terminator v3.1 chemistry (Applied Biosystems, Foster City, Calif.) according to the manufacture's instructions. Sequencing was performed in both directions using the PCR primers given above as sequencing primers. The initial denaturation (95° C., 1 minute) was followed by 30 cycles of 10 seconds at 95° C., 30 seconds at 59° C. and 3 minutes at 72° C. The sequencing products were purified by ethanol precipitation and separated on a 3100 Genetic Analyser (Applied Biosystems). The sequencing data obtained were analysed independently by two scientists (IC and TM) in a blinded manner. The methylation pattern of single dMS-HRM products were visualized using the BiQ Analyzer software (Max-Planck-Institut für Informatik, Saarbrücken, Germany) [16].

Results and Discussion

MS-HRM of AML Samples

FIG. 1 shows the melting profiles of the CDKN2B promoter region in acute myeloid leukemia (AML) samples analysed using MS-HRM. The amplicons derived from fully methylated DNA and the fully unmethylated WGA product defines the range of methylation. Due to the homogeneity of the DNA methylation pattern within these control samples, their melting profiles reflect the melting behaviour of homoduplexes only.

Heterogeneously methylated DNA samples result in multiple products after PCR. Not only will there be many different homoduplexes, but heteroduplexes will also form between similarly methylated sequences, giving rise to complex melting curves that often will not lie within the range defined by fully methylated and unmethylated DNA due to the earlier melting of heteroduplexes relative to homoduplexes. Dependent on the amount of DNA methylation (and the amount of normal cells present in the tumour sample), the resulting melting curve is flattened and exhibits a complex melting pattern. Detection of DNA methylation at the CDKN2B promoter has relied upon the sensitivity of the method used. However, this may have lead to an overestimation of methylation, as normal background levels of methylation can confound interpretation of results [9]. Whilst this can be resolved using bisulfite sequencing of individual clones [7,8], a cost- and time effective method, which separates individuals based on biological relevance and clinical significance is necessary. Cameron et al. state that about 40% of the CpG sites within the CDKN2B CpG island need to be methylated to achieve complete silencing of the gene, regardless of the CpG methylation pattern [7]. Methylation Sensitive High Resolution Melting (MS-HRM) [13] shows great sensitivity when the samples contains a mixture of fully methylated and fully unmethylated templates as it has been empirically observed that the sequence differences between these are too great for heteroduplexes to form.

However, its sensitivity is considerably diminished for heterogeneously methylated samples due to the PCR products forming heteroduplexes, resulting in an overall melting profile that cannot be correlated against fully methylated, unmethylated or normal controls. It is possible that samples from normal healthy individuals can give rise to profiles suggestive of heteroduplex formation, as underlying low-level methylation may be present in some cases.

Applying digital PCR (dPCR) to MS-HRM isolates single-copy templates, removing the possibility of heteroduplex formation and therefore allowing its resultant profile to lie within the fully methylated and whole genome amplified product (WGA, fully unmethylated) standards.

To use a PCR-based technique, potential PCR bias needs to be eliminated or at least minimised. Given that the DNA methylation pattern in the entire interrogated sequence and not just the primer binding sites influence bias [17], eliminating a PCR bias in a heterogeneous population of alleles becomes nearly impossible. Isolating single templates is desirable [18]. However cloning from a heterogeneous pool may introduce a cloning bias [11, 19].

Digital PCR addresses all of the problems above. HRM after dPCR is able to quantify the portion of methylation at each allele, and the number of alleles present at each level of methylation [20]. Proceeding onto sequencing of dMS-HRM products opens up the possibility to map the position of methylated CpG sites in the discrete amplicon, but this would rarely be necessary for prognostic information [5, 7, 21].

The dMS-HRM Approach

The basis of this approach is the PCR amplification of single molecules, which is readily attained by limiting dilution [22, 23]. The Poisson distribution can then be used to determine the expected distribution of templates. For example, if the sample is diluted such that one amplifiable template is found on average in the volume of template used per reaction, 36.8% of reactions will have no templates, 36.8% will have one template, and 26.4% will have more than one template. Amplification will occur, when one or more template molecules are present in the PCR reaction.

From a practical point of view, for a given sample the DNA concentration is determined and appropriately diluted. Dependent on the starting concentration, a reasonable dilution (in our cases in the order of 1:1000 to 1:2000) series should be applied. Another important point is the quality of the DNA. In general we observed that high-quality DNA (e.g. extracted from snapfrozen samples or cell lines) had to be more diluted than low-quality DNA (e.g. extracted from formalin-fixed paraffin-embedded (FFPE) samples), as would be expected.

The dilution which seems to perform best is empirically chosen and used for the final experimental setup. Amplifications from single molecules can be readily identified when the melting curves are analysed. They show a smooth and sharp single signal (FIG. 2), whereas melting curves from two or more molecules often result in signals showing two peaks or more complex patterns, resembling those seen before diluting.

dMS-HRM of AML Samples

FIG. 2 shows the digital melting profiles of the AML samples 4383, 4156, 4276, 3224, and 730-06. Sample 4276 does not show any methylated alleles. Sample 4156 shows mainly profiles which correspond either to fully unmethylated products or have only few CpG positions methylated. Sample 3224, 730-06 and 9164 covers a broad range of various heterogeneously methylated alleles.

Sequencing of the dMS-HRM products of sample 9164 confirms the broad range of various methylated alleles with different CpG sites being affected (FIG. 3A). There appears to be an even distribution between the melting peaks and the number of CpGs positions methylated, which vary only in the CpG positions being methylated.

In dMS-HRM, a slight increase in the melting temperature of the products relative to the controls can be seen (FIG. 3A). Sequencing of digital 'clones' obtained from the controls showed that the sequences were comparable to those from sample 9164 (FIG. 3B). dMS-HRM analysis of control DNA was replicated with the template DNA being diluted into an equivalent amount of background DNA used for MS-HRM (fish sperm and not bisulfite-treated, genomic control DNA), and the same result was obtained (data not shown). The shift may be due to a relative increase in the effective magnesium concentration around each amplicon [24, 25].

Incomplete conversion was encountered on one occasion in replicate 69 (FIG. 3), and confirmed by direct sequencing (FIG. 3C). This was detected using dMS-HRM, as the peak was slightly right-shifted beyond the fully methylated signal (FIG. 3A). Previous reports show that conversion of cytosine to uracil is 97.0 to 99.7% complete, whilst still leaving 5-methylcytosines intact [26, 27]. Such a low non-conversion rate is not expected to be a major problem with dMS-HRM, as the number of replicates required to achieve digital PCR will move non-converted cytosines into the background.

Conclusions dMS-HRM is a powerful tool for analysis of heterogeneous DNA methylation. It is readily performed by limiting dilution and the results are directly visualised by the melting profile. It can be used for counting methylated sequences and for estimating the extent of their methylation, all within a single-tube format. dMS-HRM can rapidly generate clonal templates ready for sequencing, eliminating the need for cloning into a vector. Used in combination with standard MS-HRM, it rapidly gives detailed information regarding the nature of the observed methylation, both at the individual allele and entire molecular population levels.

The invention claimed is:

1. A method for detecting the methylation status of a CpG-containing nucleic acid in a sample comprising the steps of:
   a) providing said sample comprising a CpG-containing nucleic acid,
   b) denaturing said CpG-containing nucleic acid, thereby producing denatured CpG-containing nucleic acid,
   c) treating said denatured CpG-containing nucleic acid with bisulphite which modifies at least one unmethylated cytosine in said CpG-containing nucleic acid, thereby producing treated CpG-containing nucleic acid,
   d) amplifying said treated CpG-containing nucleic acid by means of at least one methylation-independent oligonucleotide primer, which comprises within the first 10 nucleotides of the 5'-end, at least one CpG dinucleotide in a region which hybridizes to the CpG-containing nucleic acid, wherein said at least one methylation-independent oligonucleotide primer hybridizes to both methylated and unmethylated CpG-containing nucleic acids after modification, and
   e) analyzing the amplified CpG-containing nucleic acid by melting curve analysis.

2. The method according to claim 1, wherein said at least one methylation-independent oligonucleotide primer comprises at least two CpG dinucleotides.

3. The method according to claim 1, wherein said at least one CpG dinucleotide is located immediately after the first nucleotide of the 5'-end of said at least one methylation-independent oligonucleotide primer.

4. The method according to claim 1, wherein said unmethylated cytosine is modified to uracil.

5. The method according to claim 1, wherein said amplifying step is performed by a polymerisation reaction.

6. The method according to claim 5, wherein said polymerisation reaction is a polymerase chain reaction (PCR).

7. The method according to claim 6, wherein said PCR comprises the steps of:
   a) melting a CpG-containing nucleic acid template,
   b) annealing at least one methylation-independent oligonucleotide primer to said CpG-containing nucleic acid template, and
   c) elongating said at least one methylation-independent oligonucleotide primer.

8. The method according to claim 1, wherein said amplifying step is achieved by means of at least two methylation-independent oligonucleotide primers.

9. The method according to claim 1, wherein said sample is selected from the group consisting of breast tissue, ovarian tissue, uterine tissue, colon tissue, prostate tissue, lung tissue, renal tissue, thymus tissue, testis tissue, hematopoietic tissue, bone marrow, urogenital tissue, expiration air, stem cells, body fluids, sputum, urine, blood and sweat.

10. The method according to claim 1, wherein said sample is selected from the group consisting of breast tissue, ovarian tissue, uterine tissue, colon tissue, prostate tissue and lung tissue.

11. The method according to claim 1, wherein the at least one methylation-independent oligonucleotide primer comprises between 10 and 200 nucleotides.

12. The method according to claim 1, wherein the at least one methylation-independent oligonucleotide primer comprises between 15 and 60 nucleotides.

13. The method according to claim 1, wherein said CpG-containing nucleic acid is amplified using a first oligonucleotide primer and a second oligonucleotide primer of a primer pair wherein the first primer is the at least one methylation-independent oligonucleotide primer which comprises within the first 10 nucleotides of the 5'-end at least one CpG dinucleotide in a region which hybridizes to the CpG-containing nucleic acid, and wherein the second primer comprises at least one CpG dinucleotide in a region which hybridizes to the CpG-containing nucleic acid and wherein the first and second primers are selected from the group consisting of SEQ ID NO.: 46-151.

14. The method according to claim 1, wherein said at least one methylation-independent oligonucleotide primer is selected from the group consisting of SEQ ID NO.: 185-250.

15. The method according to claim 13, wherein said first oligonucleotide primer is SEQ ID NO.: 136 and said second oligonucleotide primer is SEQ ID NO: 137.

16. The method according to claim 1, wherein said at least one methylation-independent oligonucleotide primers is SEQ ID NO.: 138 and 139.

17. The method according to claim 8, wherein said at least two methylation-independent oligonucleotide primers is SEQ ID NO.: 142 and 143.

18. The method according to claim 8, wherein said at least two methylation-independent oligonucleotide primers is SEQ ID NO.: 144 and 145.

19. The method according to claim 8, wherein said at least two methylation-independent oligonucleotide primers is SEQ ID NO.: 146 and 147.

20. The method according to claim 7, wherein the primer annealing temperature during amplification of said CpG-containing nucleic acid is between 40 and 75 degrees Celsius.

21. The method according to claim 7, wherein the primer annealing temperature during amplification of said CpG-containing nucleic acid is 60 degrees Celsius.

22. The method according to claim 7, wherein the primer annealing temperature during amplification of said CpG-containing nucleic acid is 64 degrees Celsius.

23. The method according to claim 1, wherein the presence of methylated CpG-containing nucleic acid is indicative of a disorder.

24. The method according to claim 1, wherein the absence of methylated CpG-containing nucleic acid is indicative of a disorder.

25. The method according to claim 23, wherein said disorder is selected from the group consisting of Alzheimer's disease, atherosclerosis, breast cancer, bladder cancer, ovarian cancer, melanoma, prostate cancer, lung cancer, renal cancer, colon cancer, gastric cancer, cervical cancer, leukaemia, low grade astrocytoma, anaplastic astrocytoma, glioblastoma, haematopoietic disorders, medulloblastoma, leukemia, metabolic disorders, endometrial cancer, neuroblastoma, diffuse large B-cell lymphoma, developmental disorders, Prader-Willi syndrome, Angelman syndrome and imprinting disorders.

26. The method according to claim 23, wherein said disorder is selected from the group consisting of breast cancer, bladder cancer, ovarian cancer, melanoma, prostate cancer, lung cancer, colon cancer, endometrial cancer and leukaemia.

27. The method according to claim 23, wherein said disorder is colon cancer.

28. The method according to claim 23, wherein said disorder is breast cancer

29. The method according to claim 1, wherein said at least one methylation-independent oligonucleotide primer hybridizes to a target CpG-containing nucleic acid sequence, wherein methylation of said target sequence is indicative of the presence of a disorder.

30. The method according to claim 1, wherein said at least one methylation-independent oligonucleotide primer hybridizes to a target CpG-containing nucleic acid sequence of a gene selected from the group consisting of PPP3CC, BNIP3, Methylguanine-DNA Methyltransferase (MGMT), SNRPN, GSTP1, RARB2, RASSF1A, TIMP3, APC, beta-Actin, PTGS2 and 14-3-3 sigma.

31. The method according to claim 1, wherein said at least one oligonucleotide primer hybridizes to a target CpG-containing nucleic acid sequence of a gene selected from the group consisting of CHD1, COX2, PRSS3, PYCARD, BIN1, BRCA1, LATS2, PITX2, BCL2, EYA4, GSK3B, MLH1, TIMP-3, MSH6, MTHFR, PTEN, SFN, CD109, ERS1, PCDH10, DAPK1, FHIT, P16ink4a, PRSS3, RASSF1, TMS1, CAGE-1, GPR150, ITGA8, PRDX2, SYK, ALX3, HOXD11, PTPRO, WWOX, ABHD9, CAV9, GPR78, GSTP1, HIC1, PTGS2, CSMD1, C10orf59, MGMT, BNIP3, PPP3CC CSMD1, MAP3k7, C10orf59 and GRIFK2.

32. The method according to claim 1, wherein said at least one oligonucleotide primer hybridizes to a target CpG-containing nucleic acid sequence of a gene selected from the group consisting of SEQ ID NO.: 1-45, or the complement thereof.

33. The method according to claim 1, wherein said at least one oligonucleotide primer hybridizes to a target CpG-containing nucleic acid sequence of a gene selected from the group consisting of SEQ ID NO.: 9-13, or the complement thereof.

34. The method according to claim 1, wherein said at least one oligonucleotide primer hybridizes to a target CpG-containing nucleic acid sequence of a gene selected from the group consisting of SEQ ID NO.: 5-8, or the complement thereof.

35. The method according to claim 1, wherein said at least one oligonucleotide primer hybridizes to a target CpG-containing nucleic acid sequence of a gene selected from the group consisting of SEQ ID NO.: 21-26, or the complement thereof.

36. The method according to claim 1, wherein said at least one oligonucleotide primer hybridizes to a target CpG-containing nucleic acid sequence as defined by SEQ ID NO.: 44 or 45, or the complement thereof.

37. The method according to claim 1, wherein said at least one oligonucleotide primer hybridizes to a target CpG-containing nucleic acid sequence as defined by SEQ ID NO.: 42, or the complement thereof.

38. The method according to claim 1, wherein said at least one methylation-independent oligonucleotide primer hybridizes with a CpG-containing nucleic acid sequence, which is at least 97% identical to the target sequence, or the complement thereof.

39. The method according to claim 1, wherein the relative amount of methylated CpG-containing nucleic acid in said sample is between 40-60%.

40. The method according to claim 1, wherein the relative amount of methylated CpG-containing nucleic acid in said sample is below 50%.

41. The method according to claim 1, wherein the relative amount of methylated CpG-containing nucleic acid in said sample is below 1%.

42. The method according to claim 1, wherein the relative amount of methylated CpG-containing nucleic acid in said sample is below 0.1%.

43. The method according to claim 1, comprising the primers according to SEQ ID NO.: 46 and 47 for the detection of methylation status of CHD1 as defined in SEQ ID NO.: 1, wherein the primer annealing temperature during amplification is 59 degrees Celsius and the presence of methylation is indicative of Bladder cancer.

44. The method according to claim 1, comprising the primers according to SEQ ID NO.: 60 and 61 for the detection of methylation status of PITX2 as defined in SEQ ID NO.: 8, wherein the primer annealing temperature during amplification is 60 degrees Celsius and the presence of methylation is indicative of Breast cancer.

45. The method according to claim 1, comprising the primers according to SEQ ID NO.: 68 and 69 for the detection of methylation status of MLH1 as defined in SEQ ID NO.: 12, wherein the primer annealing temperature during amplification is 62 degrees Celsius and the presence of methylation is indicative of Colon cancer.

46. The method according to claim 1, comprising the primers according to SEQ ID NO.: 72 and 73 for the detection of methylation status of MSH6 as defined in SEQ ID NO.: 14, wherein the primer annealing temperature during amplification is 59 degrees Celsius and the presence of methylation is indicative of Endometrial cancer.

47. The method according to claim 1, wherein said melting curve analysis comprise normalization of melting curves by calculation of the 'line of best fit' in between two normalization regions before and after a major fluorescence decrease.

48. The method according to claim 1, wherein a melting profile displays at least one peak melting temperature.

49. The method according to claim 1, wherein a melting profile displays at least two peak melting temperatures.

50. The method according to claim 1, wherein the relative amount of methylated CpG-containing nucleic acid is estimated by comparison with melting curve analysis of at least one standard sample comprising said CpG-containing nucleic acid.

51. The method according to claim 50, wherein a higher melting Temperature of the amplified nucleic acid sample than of the standard sample is indicative of a higher relative amount of methylated nucleic acid of that sample than of the standard sample.

52. The method according to claim 50, wherein a lower melting Temperature of the amplified nucleic acid sample than of the standard sample is indicative of a lower relative amount of methylated nucleic acid of that sample than of the standard sample.

53. The method according to claim 50, wherein said at least one standard sample comprise any combination of methylated and unmethylated CpG-containing nucleic acid.

54. The method according to claim 50, wherein said at least one standard sample comprise 100% methylated CpG-containing nucleic acid.

55. The method according to claim 50, wherein said at least one standard sample comprise 100% unmethylated CpG-containing nucleic acid.

56. The method according to claim 50, wherein said at least one standard sample comprise 50% methylated nucleic acid and 50% unmethylated CpG-containing nucleic acid.

57. The method according to claim 1, wherein said melting curve analysis is performed by measurement of fluorescence.

58. The method according to claim 57, wherein said fluorescence is Measured immediately after amplification.

59. The method according to claim 57, wherein said peak melting temperature corresponds to the highest level of the negative derivative of fluorescence (−dF/dT) over temperature versus temperature (T).

60. The method according to claim 1, wherein said melting curve analysis is performed by using a thermal cycler coupled to a fluorometer.

61. The method according to claim 1, wherein said melting curve analysis is performed by incubating the nucleic acid amplification product at increasing temperatures, from 70 to 95 degrees Celsius, wherein the temperature increases by 0.05 degrees per second.

* * * * *

UNITED STATES PATENT AND TRADEMARK OFFICE
CERTIFICATE OF CORRECTION

PATENT NO. : 8,911,937 B2
APPLICATION NO. : 12/219378
DATED : December 16, 2014
INVENTOR(S) : Tomasz Kazimierz Wojdacz et al.

It is certified that error appears in the above-identified patent and that said Letters Patent is hereby corrected as shown below:

In the claims

Column 275, line 27, Claim 3: Replace "one oligonucleotide" with --one methylation-independent oligonucleotide--;

Column 276, line 56, Claim 51: Replace "Temperature" with --temperature--;

Column 276, line 61, Claim 52: Replace "Temperature" with --temperature--;

Column 276, line 66, Claim 53: Replace "comprise" with --comprises--;

Column 277, line 2, Claim 54: Replace "comprise" with --comprises--;

Column 277, line 5, Claim 55: Replace "comprise" with --comprises--;

Column 277, line 8, Claim 56: Replace "comprise" with --comprises--; and

Column 277, line 13, Claim 58: Replace "Measured" with --measured--.

Signed and Sealed this
Twentieth Day of October, 2015

Michelle K. Lee
*Director of the United States Patent and Trademark Office*